United States Patent
DiMaio et al.

(10) Patent No.: US 12,060,388 B2
(45) Date of Patent: Aug. 13, 2024

(54) CELL-PENETRATING PEPTIDES AND METHODS OF USE THEREOF

(71) Applicant: YALE UNIVERSITY, New Haven, CT (US)

(72) Inventors: Daniel DiMaio, North Haven, CT (US); Pengwei Zhang, New Haven, CT (US); Gabriel Monteiro Da Silva, Ribeirao Preto (BR); Weiya Bai, Shanghai (CN)

(73) Assignee: YALE UNIVERSITY, New Haven, CT (US)

( * ) Notice: Subject to any disclaimer, the term of this patent is extended or adjusted under 35 U.S.C. 154(b) by 770 days.

(21) Appl. No.: 17/057,501

(22) PCT Filed: May 24, 2019

(86) PCT No.: PCT/US2019/033888
§ 371 (c)(1),
(2) Date: Nov. 20, 2020

(87) PCT Pub. No.: WO2019/226974
PCT Pub. Date: Nov. 28, 2019

(65) Prior Publication Data
US 2021/0206811 A1    Jul. 8, 2021

Related U.S. Application Data

(60) Provisional application No. 62/676,706, filed on May 25, 2018.

(51) Int. Cl.
| | | |
|---|---|---|
| C07K 14/005 | (2006.01) | |
| A61K 9/00 | (2006.01) | |
| A61K 38/00 | (2006.01) | |
| A61P 31/20 | (2006.01) | |
| C12N 7/00 | (2006.01) | |

(52) U.S. Cl.
CPC .......... C07K 14/005 (2013.01); A61K 9/0014 (2013.01); A61P 31/20 (2018.01); C12N 7/00 (2013.01); A61K 38/00 (2013.01); C07K 2319/33 (2013.01); C12N 2710/20022 (2013.01); C12N 2710/20033 (2013.01)

(58) Field of Classification Search
None
See application file for complete search history.

(56) References Cited

U.S. PATENT DOCUMENTS

| 9,738,687 B2 | 8/2017 | Guay et al. | |
|---|---|---|---|
| 2008/0317761 A1* | 12/2008 | Cines | A61K 38/37 |
| | | | 424/159.1 |

OTHER PUBLICATIONS

Zhang et al. "Cell-penetrating Peptide Mediates Intracellular Membrane Passage of Human Papillomavirus L2 Protein to Trigger Retrograde Trafficking" Cell 174:1465-1476. (Year: 2018).*
International Search Report and Written Opinion issued on Nov. 21, 2019, for International Application No. PCT/2019/033888.
Fux, et al. "Rusa alfredi papillomavirus 1—a novel deltapapillomavirus inducing endemic papillomatosis in the endangered Visayan spotted deer." Journal of General Virology 97.1 (2016): 128-133.
Erdelyi, et al. Minor Capsid Protein L2, Partial [Cervus elaphus papillomavirus KE-2008]. National Center for Biotechnology Information. Gen bank Entry. Jul. 10, 2008 [retrieved on Oct. 4, 2019]; Retrieved from the Internet: <URL: https://www.ncbi.nlm.nih.gov/protein/AC123488>; p. 1.
Supplementary Partial European Search Report issued on Feb. 4, 2022, for European Patent Application No. EP 19807970.9.
Popa, et al. "Direct binding of retromer to human papillomavirus type 16 minor capsid protein L2 mediates endosome exit during viral infection." PLoS pathogens 11.2 (2015): e1004699.
Regberg, et al. "Applications of cell-penetrating peptides for tumor targeting and future cancer therapies." Pharmaceuticals 5.9 (2012): 991-1007.

* cited by examiner

*Primary Examiner* — Sudhakar Katakam
*Assistant Examiner* — Zachary J Miknis
(74) *Attorney, Agent, or Firm* — Saul Ewing LLP; Kathryn Doyle; Justin W. Crotty

(57) ABSTRACT

In various aspects and embodiments the invention provides compositions and methods for facilitating cell penetration of a cargo molecule. In another aspect, the invention provides a method of preventing viral infection in a subject in need thereof, the method comprising providing to the subject a therapeutically effective amount of a polypeptide comprising a cell-penetrating peptide and a retromer binding site.

15 Claims, 32 Drawing Sheets
Specification includes a Sequence Listing.

A

| | | |
|---|---|---|
| WT | Alexa488-CSPQYTIIADAGDFYLHPSYYMLRKRRKR | SEQ ID NO: 533 |
| 6A | Alexa488-CSPQYTIIADAGDFYLHPSYYMLAAAAAA | SEQ ID NO: 556 |
| 3R | Alexa488-CSPQYTIIADAGDFYLHPSYYMLRRR | SEQ ID NO: 557 |

B

| | | |
|---|---|---|
| WT | His6-GFP-linker-PQYTIIADAGDFYLHPSYYMLRKRRKR | SEQ ID NO: 530 |
| 6A | His6-GFP-linker-PQYTIIADAGDFYLHPSYYMLAAAAAA | SEQ ID NO: 558 |
| 3R | His6-GFP-linker-PQYTIIADAGDFYLHPSYYMLRRR | SEQ ID NO: 559 |

C

D

WT   Bio-CSPQYTIIADAGDFYLHPSYYMLRKRRKR SEQ ID NO: 560
3R   Bio-CSPQYTIIADAGDFYLHPSYYMLRRR SEQ ID NO: 561
DM   Bio-CSPQYTIIADAGDAAAHPSAAAARKRRKR SEQ ID NO: 562

A L2-GFP11-CPP
L2-CPP-GFP11
B
| HPV16 | HPV16-GFP11-CPP | HPV16-CPP-GFP11 |
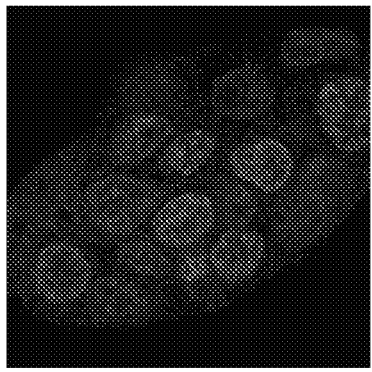 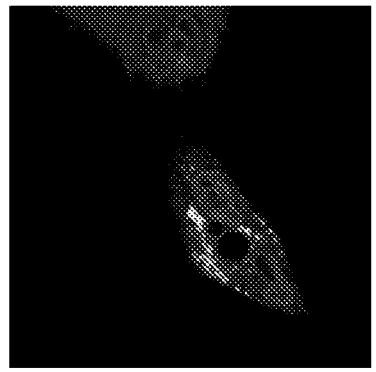 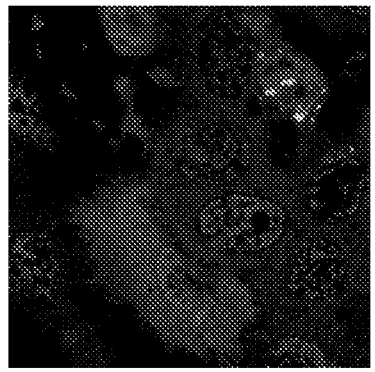
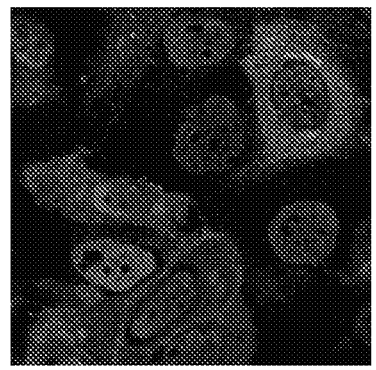 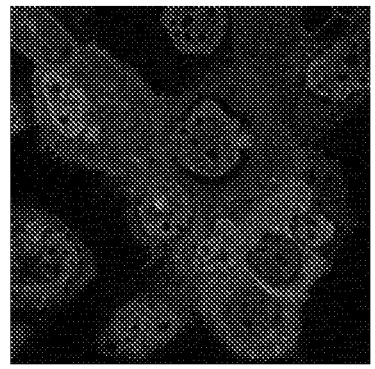
FIGS. 6A-6B GFP-21P-CPP His6-GFP-linker-PQYTIIADAGDFYLHPSYYMLRKRRKR(SEQ ID NO: 530)
GFP-CPP   His6-GFP-linker-RKRRKR(SEQ ID NO: 529)

GFP-21P-CPP His6-GFP-linker-PQYTIIADAGDFYLHPSYYMLRKRRKR(SEQ ID NO: 530)
GFP-HPV16 L2 His6-GFP-linker-PQYTIIADAGDFYLHPSYYMLRKRRKRLPYF FSDVSLAA(SEQ ID NO: 531)

GFP-HPV5 L2 His6-GFP-linker-IPVVIIHPHDSTGDFYLHPSLHRRKRKRKYL(SEQ ID NO: 532)

GFP11x7-L2-CPP His6-(GFP11-linker)$_7$-PQYTIIADAGDFYLHPSYYMLRKRRKR (SEQ ID NO: 530)

L2-C B-SPQYTIIADAGDFYLHPSYYMLRKRRKR-Am (SEQ ID NO: 533),

SEQUENCE LISTING

<160> NUMBER OF SEQ ID NOS: 569

<210> SEQ ID NO 1
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 1

Lys Arg Arg Lys Arg
1               5

<210> SEQ ID NO 2
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 2

Arg Lys Arg Arg Lys Arg
1               5

<210> SEQ ID NO 3
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 3

Lys Arg Lys Arg Lys Arg
1               5

<210> SEQ ID NO 4
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 4

Arg Arg Lys Arg Lys Arg
1               5

<210> SEQ ID NO 5
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 5

Arg Arg Arg Arg Lys Arg
1               5

<210> SEQ ID NO 6
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 6

Lys Lys Arg Lys Arg
1               5

```
<210> SEQ ID NO 7
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 7

Arg Arg Arg Lys Arg Lys Arg
1               5

<210> SEQ ID NO 8
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 8

Arg Lys Arg Lys Arg
1               5

<210> SEQ ID NO 9
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 9

Lys Arg Arg Lys Arg Lys Arg
1               5

<210> SEQ ID NO 10
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 10

Arg Lys Lys Arg Lys Arg
1               5

<210> SEQ ID NO 11
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 11

Arg Lys Arg Lys Arg Lys Arg
1               5

<210> SEQ ID NO 12
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 12

Arg Arg Arg Arg Arg Lys Arg
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 13

Arg Lys Arg Arg Lys Arg Lys
1               5

<210> SEQ ID NO 14
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 14

Arg Lys Arg Arg Arg
1               5

<210> SEQ ID NO 15
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 15

Arg Arg Arg Arg Lys Arg Lys
1               5

<210> SEQ ID NO 16
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 16

Lys Lys Arg Lys Arg Lys
1               5

<210> SEQ ID NO 17
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 17

Arg Lys Arg Lys Lys Arg Lys
1               5

<210> SEQ ID NO 18
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 18

Arg Lys Arg Lys Arg Arg
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 19

Arg Lys Arg Arg Lys
1               5

<210> SEQ ID NO 20
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 20

Arg Arg Arg Lys Arg Lys Arg Lys
1               5

<210> SEQ ID NO 21
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 21

Arg Arg Arg Arg Lys Arg Lys Arg
1               5

<210> SEQ ID NO 22
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 22

Arg Arg Arg Arg Lys Arg Arg
1               5

<210> SEQ ID NO 23
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 23

Lys Arg Arg Lys Arg Lys
1               5

<210> SEQ ID NO 24
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 24

Lys Arg Arg Arg Lys Arg
1               5

<210> SEQ ID NO 25
```

<211> LENGTH: 7
<212> TYPE: PRT
<213> ORGANISM: Artificial Sequence
<220> FEATURE:
<223> OTHER INFORMATION: cell penetrating peptide

<400> SEQUENCE: 25

Arg Lys Lys Arg Lys Arg Lys
1               5

<210> SEQ ID NO 26
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 26

Arg Lys Arg Lys Arg Lys
1               5

<210> SEQ ID NO 27
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 27

Arg Lys Arg Arg Arg Lys Arg
1               5

<210> SEQ ID NO 28
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 28

Arg Arg Lys Lys Arg Lys Arg
1               5

<210> SEQ ID NO 29
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 29

Arg Arg Arg Arg Lys
1               5

<210> SEQ ID NO 30
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 30

Arg Arg Arg Arg Arg Arg Arg Arg Arg Arg
1               5                   10

<210> SEQ ID NO 31
<211> LENGTH: 5

```
<212> TYPE: PRT
<213> ORGANISM: Artificial Sequence
<220> FEATURE:
<223> OTHER INFORMATION: cell penetrating peptide

<400> SEQUENCE: 31

Lys Lys His Lys Arg
1               5

<210> SEQ ID NO 32
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 32

Lys Lys Arg Lys Lys
1               5

<210> SEQ ID NO 33
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 33

Lys Lys Arg Lys Arg Lys Arg
1               5

<210> SEQ ID NO 34
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 34

Lys Arg His Lys His Lys
1               5

<210> SEQ ID NO 35
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 35

Lys Arg Lys Lys Arg Arg
1               5

<210> SEQ ID NO 36
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 36

Lys Arg Lys Arg Arg Lys Arg Lys
1               5

<210> SEQ ID NO 37
<211> LENGTH: 6
<212> TYPE: PRT
```

<213> ORGANISM: Artificial Sequence
<220> FEATURE:
<223> OTHER INFORMATION: cell penetrating peptide

<400> SEQUENCE: 37

Lys Arg Lys Arg Arg Arg
1               5

<210> SEQ ID NO 38
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 38

Lys Arg Leu Lys Arg Lys Arg Lys
1               5

<210> SEQ ID NO 39
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 39

Lys Arg Arg Lys Arg Lys Arg Lys
1               5

<210> SEQ ID NO 40
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 40

Lys Arg Arg Arg Arg Lys Arg
1               5

<210> SEQ ID NO 41
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 41

Arg Lys His Lys His Lys
1               5

<210> SEQ ID NO 42
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 42

Arg Lys Lys Arg Arg Arg
1               5

<210> SEQ ID NO 43
<211> LENGTH: 8
<212> TYPE: PRT
<213> ORGANISM: Artificial Sequence

```
<220> FEATURE:
<223> OTHER INFORMATION: cell penetrating peptide

<400> SEQUENCE: 43

Arg Lys Arg Lys Arg Lys Arg Lys
1               5

<210> SEQ ID NO 44
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 44

Arg Lys Arg Arg Lys Arg Lys Arg
1               5

<210> SEQ ID NO 45
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 45

Arg Lys Arg Arg Arg Lys Arg Lys
1               5

<210> SEQ ID NO 46
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 46

Arg Arg Lys Arg Lys Arg Lys
1               5

<210> SEQ ID NO 47
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 47

Arg Arg Lys Arg Lys Arg Lys Arg
1               5

<210> SEQ ID NO 48
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 48

Arg Arg Lys Arg Arg
1               5

<210> SEQ ID NO 49
<211> LENGTH: 8
<212> TYPE: PRT
<213> ORGANISM: Artificial Sequence
<220> FEATURE:
```

<223> OTHER INFORMATION: cell penetrating peptide

<400> SEQUENCE: 49

Arg Arg Arg Arg Arg Lys Arg Lys
1               5

<210> SEQ ID NO 50
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 50

Arg Arg Arg Arg Arg Arg Arg Arg
1               5

<210> SEQ ID NO 51
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 51

Lys Gly Lys Arg Arg Lys Lys Arg
1               5

<210> SEQ ID NO 52
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 52

Lys His Arg Lys Arg Lys Arg Lys
1               5

<210> SEQ ID NO 53
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 53

Lys Lys Gly Lys Lys Arg Lys
1               5

<210> SEQ ID NO 54
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 54

Lys Lys His Lys
1

<210> SEQ ID NO 55
<211> LENGTH: 6
<212> TYPE: PRT
<213> ORGANISM: Artificial Sequence
<220> FEATURE:
<223> OTHER INFORMATION: cell penetrating peptide

```
<400> SEQUENCE: 55

Lys Lys His Lys His Lys
1               5

<210> SEQ ID NO 56
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 56

Lys Lys Lys Gly Lys Lys
1               5

<210> SEQ ID NO 57
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 57

Lys Lys Lys Lys
1

<210> SEQ ID NO 58
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 58

Lys Lys Lys Lys Lys Arg
1               5

<210> SEQ ID NO 59
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 59

Lys Lys Lys Lys Lys Ser Lys
1               5

<210> SEQ ID NO 60
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 60

Lys Lys Lys Lys Arg Lys Arg Lys
1               5

<210> SEQ ID NO 61
<211> LENGTH: 8
<212> TYPE: PRT
<213> ORGANISM: Artificial Sequence
<220> FEATURE:
<223> OTHER INFORMATION: cell penetrating peptide
```

```
<400> SEQUENCE: 61

Lys Lys Lys Lys Ser Lys Val Arg
1               5

<210> SEQ ID NO 62
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 62

Lys Lys Lys Arg Lys Lys Lys Arg
1               5

<210> SEQ ID NO 63
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 63

Lys Lys Lys Arg Lys Arg
1               5

<210> SEQ ID NO 64
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 64

Lys Lys Lys Arg Arg
1               5

<210> SEQ ID NO 65
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 65

Lys Lys Lys Arg Arg Lys Arg
1               5

<210> SEQ ID NO 66
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 66

Lys Lys Lys Arg Arg Arg
1               5

<210> SEQ ID NO 67
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 67
```

```
Lys Lys Leu Arg Lys Lys Arg Lys Arg Arg
1               5                   10

<210> SEQ ID NO 68
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 68

Lys Lys Arg Lys
1

<210> SEQ ID NO 69
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 69

Lys Lys Arg Lys Arg Lys Arg Lys
1               5

<210> SEQ ID NO 70
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 70

Lys Lys Arg Arg Lys Arg Lys Arg
1               5

<210> SEQ ID NO 71
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 71

Lys Lys Arg Arg Arg
1               5

<210> SEQ ID NO 72
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 72

Lys Arg Cys Arg Arg Lys Arg Arg
1               5

<210> SEQ ID NO 73
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 73
```

```
Lys Arg Lys Cys Lys Arg Lys
1               5

<210> SEQ ID NO 74
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 74

Lys Arg Lys Lys Arg Lys
1               5

<210> SEQ ID NO 75
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 75

Lys Arg Lys Arg
1

<210> SEQ ID NO 76
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 76

Lys Arg Lys Arg Lys
1               5

<210> SEQ ID NO 77
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 77

Lys Arg Lys Arg Lys Arg Lys
1               5

<210> SEQ ID NO 78
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 78

Lys Arg Lys Arg Lys Arg Lys Arg Lys
1               5

<210> SEQ ID NO 79
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 79

Lys Arg Lys Arg Lys Arg Arg
```

```
1               5

<210> SEQ ID NO 80
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 80

Lys Arg Lys Arg Arg Lys
1               5

<210> SEQ ID NO 81
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 81

Lys Arg Lys Arg Arg Lys Arg
1               5

<210> SEQ ID NO 82
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 82

Lys Arg Lys Arg Arg Arg Lys Arg
1               5

<210> SEQ ID NO 83
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 83

Lys Arg Lys Arg Arg Arg Arg Arg
1               5

<210> SEQ ID NO 84
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 84

Lys Arg Arg Lys Lys
1               5

<210> SEQ ID NO 85
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 85

Lys Arg Arg Lys Lys Arg Lys
1               5
```

<210> SEQ ID NO 86
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 86

Lys Arg Arg Arg
1

<210> SEQ ID NO 87
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 87

Lys Arg Arg Arg Lys
1               5

<210> SEQ ID NO 88
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 88

Lys Arg Arg Arg Arg
1               5

<210> SEQ ID NO 89
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 89

Lys Arg Arg Arg Arg Arg
1               5

<210> SEQ ID NO 90
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 90

Lys Arg Arg Arg Arg Arg Arg
1               5

<210> SEQ ID NO 91
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 91

Lys Arg Arg Arg Arg Arg Arg Arg Lys
1               5

```
<210> SEQ ID NO 92
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 92

Lys Arg Arg Arg Arg Arg Arg Thr Arg Arg
1               5                   10

<210> SEQ ID NO 93
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 93

Lys Ser Arg Lys Arg Lys
1               5

<210> SEQ ID NO 94
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 94

Lys Thr Arg Lys Arg Lys Arg Lys
1               5

<210> SEQ ID NO 95
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 95

Lys Trp Lys Lys Arg Lys Arg
1               5

<210> SEQ ID NO 96
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 96

Arg Gly Arg Lys Arg Lys Arg Arg
1               5

<210> SEQ ID NO 97
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 97

Arg His Arg Arg Lys Arg Arg
1               5
```

```
<210> SEQ ID NO 98
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 98

Arg His Arg Arg Arg Lys Arg
1               5

<210> SEQ ID NO 99
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 99

Arg Lys Phe Lys Arg Arg Arg Lys
1               5

<210> SEQ ID NO 100
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 100

Arg Lys His Arg His Lys
1               5

<210> SEQ ID NO 101
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 101

Arg Lys Lys Lys Lys Lys
1               5

<210> SEQ ID NO 102
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 102

Arg Lys Lys Lys Lys Arg Lys
1               5

<210> SEQ ID NO 103
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 103

Arg Lys Lys Lys Arg
1               5

<210> SEQ ID NO 104
```

```
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 104

Arg Lys Lys Arg Lys
1               5

<210> SEQ ID NO 105
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 105

Arg Lys Lys Arg Arg
1               5

<210> SEQ ID NO 106
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 106

Arg Lys Lys Arg Arg Lys
1               5

<210> SEQ ID NO 107
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 107

Arg Lys Lys Arg Arg Lys Arg
1               5

<210> SEQ ID NO 108
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 108

Arg Lys Lys Arg Arg Lys Arg Lys
1               5

<210> SEQ ID NO 109
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 109

Arg Lys Lys Arg Arg Arg Arg
1               5

<210> SEQ ID NO 110
<211> LENGTH: 9
```

```
<212> TYPE: PRT
<213> ORGANISM: Artificial Sequence
<220> FEATURE:
<223> OTHER INFORMATION: cell penetrating peptide

<400> SEQUENCE: 110

Arg Lys Arg Phe Lys Arg Lys Arg Lys
1               5

<210> SEQ ID NO 111
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 111

Arg Lys Arg Lys
1

<210> SEQ ID NO 112
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 112

Arg Lys Arg Lys His Lys
1               5

<210> SEQ ID NO 113
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 113

Arg Lys Arg Lys Lys Arg Arg
1               5

<210> SEQ ID NO 114
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 114

Arg Lys Arg Lys Arg Lys Tyr Arg
1               5

<210> SEQ ID NO 115
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 115

Arg Lys Arg Lys Arg Arg Arg Lys
1               5

<210> SEQ ID NO 116
<211> LENGTH: 4
<212> TYPE: PRT
```

```
<213> ORGANISM: Artificial Sequence
<220> FEATURE:
<223> OTHER INFORMATION: cell penetrating peptide

<400> SEQUENCE: 116

Arg Lys Arg Arg
1

<210> SEQ ID NO 117
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 117

Arg Lys Arg Arg Lys Lys
1               5

<210> SEQ ID NO 118
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 118

Arg Lys Arg Arg Lys Arg Arg
1               5

<210> SEQ ID NO 119
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 119

Arg Lys Arg Arg Arg Arg Arg Lys Arg
1               5

<210> SEQ ID NO 120
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 120

Arg Lys Arg Arg Arg Arg Arg Arg Arg Arg
1               5                   10

<210> SEQ ID NO 121
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 121

Arg Leu Lys Arg Lys Arg Lys
1               5

<210> SEQ ID NO 122
<211> LENGTH: 8
<212> TYPE: PRT
<213> ORGANISM: Artificial Sequence
```

```
<220> FEATURE:
<223> OTHER INFORMATION: cell penetrating peptide

<400> SEQUENCE: 122

Arg Leu Lys Arg Lys Arg Lys Arg
1               5

<210> SEQ ID NO 123
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 123

Arg Leu Lys Arg Arg Arg Arg Arg
1               5

<210> SEQ ID NO 124
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 124

Arg Leu Arg Lys Arg Arg Lys Arg Arg
1               5

<210> SEQ ID NO 125
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 125

Arg Leu Arg Arg Lys Arg
1               5

<210> SEQ ID NO 126
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 126

Arg Leu Arg Arg Lys Arg Lys Arg
1               5

<210> SEQ ID NO 127
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 127

Arg Arg Lys Lys Arg Lys Arg Lys
1               5

<210> SEQ ID NO 128
<211> LENGTH: 5
<212> TYPE: PRT
<213> ORGANISM: Artificial Sequence
<220> FEATURE:
```

<223> OTHER INFORMATION: cell penetrating peptide

<400> SEQUENCE: 128

Arg Arg Lys Arg Lys
1               5

<210> SEQ ID NO 129
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 129

Arg Arg Lys Arg Lys Lys Arg Lys Arg
1               5

<210> SEQ ID NO 130
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 130

Arg Arg Lys Arg Lys Lys Arg Lys Arg Arg
1               5                   10

<210> SEQ ID NO 131
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 131

Arg Arg Lys Arg Lys Arg Arg
1               5

<210> SEQ ID NO 132
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 132

Arg Arg Lys Arg Arg Lys Arg Lys Arg
1               5

<210> SEQ ID NO 133
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 133

Arg Arg Lys Arg Arg Lys Arg Arg
1               5

<210> SEQ ID NO 134
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 134

Arg Arg Lys Arg Arg Arg
1               5

<210> SEQ ID NO 135
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 135

Arg Arg Lys Arg Arg Arg Arg Gly Arg Arg
1               5                   10

<210> SEQ ID NO 136
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 136

Arg Arg Lys Arg Arg Arg Arg Lys Arg
1               5

<210> SEQ ID NO 137
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 137

Arg Arg Lys Arg Arg Arg Arg Arg Lys
1               5

<210> SEQ ID NO 138
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 138

Arg Arg Lys Arg Arg Arg Arg Arg Arg Lys Arg
1               5                   10

<210> SEQ ID NO 139
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 139

Arg Arg Leu Arg Arg Lys Arg Lys
1               5

<210> SEQ ID NO 140
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 140

Arg Arg Arg Gly Arg Lys Arg Lys Arg
1               5

<210> SEQ ID NO 141
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 141

Arg Arg Arg Lys Arg Ile Lys
1               5

<210> SEQ ID NO 142
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 142

Arg Arg Arg Lys Arg Lys
1               5

<210> SEQ ID NO 143
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 143

Arg Arg Arg Lys Arg Arg
1               5

<210> SEQ ID NO 144
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 144

Arg Arg Arg Lys Arg Arg Lys Arg Arg
1               5

<210> SEQ ID NO 145
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 145

Arg Arg Arg Arg
1

<210> SEQ ID NO 146
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 146

Arg Arg Arg Arg Ala Arg Arg
1               5

<210> SEQ ID NO 147
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 147

Arg Arg Arg Arg Lys Arg Lys Arg Arg
1               5

<210> SEQ ID NO 148
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 148

Arg Arg Arg Arg Lys Arg Arg Arg
1               5

<210> SEQ ID NO 149
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 149

Arg Arg Arg Arg Arg Lys
1               5

<210> SEQ ID NO 150
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 150

Arg Arg Arg Arg Arg Lys Arg Arg Arg
1               5

<210> SEQ ID NO 151
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 151

Arg Arg Arg Arg Arg Arg
1               5

<210> SEQ ID NO 152
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 152

```
Arg Arg Arg Arg Arg Arg Lys Arg
1               5
```

<210> SEQ ID NO 153
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 153

```
Arg Arg Arg Arg Arg Arg Arg
1               5
```

<210> SEQ ID NO 154
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 154

```
Arg Arg Arg Arg Arg Arg Arg Arg Lys
1               5
```

<210> SEQ ID NO 155
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 155

```
Arg Arg Arg Arg Arg Arg Arg Arg Arg Lys
1               5                   10
```

<210> SEQ ID NO 156
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 156

```
Arg Ser Lys Lys Arg Lys Arg Lys
1               5
```

<210> SEQ ID NO 157
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 157

```
Arg Ser Arg Lys Arg Lys Arg
1               5
```

<210> SEQ ID NO 158
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 158

```
Arg Thr Lys Arg Arg Lys Arg Lys
1               5
```

```
1               5

<210> SEQ ID NO 159
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 159

Arg Val Lys Lys Arg Arg
1               5

<210> SEQ ID NO 160
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 160

Arg Trp Lys Lys Arg Lys Arg Lys
1               5

<210> SEQ ID NO 161
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 161

Arg Trp Arg Lys Arg Lys Arg
1               5

<210> SEQ ID NO 162
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 162

Arg Trp Arg Lys Arg Lys Arg Lys
1               5

<210> SEQ ID NO 163
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 163

Arg Trp Arg Arg Lys Arg Arg Arg Arg
1               5

<210> SEQ ID NO 164
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 164

Arg Trp Arg Arg Arg Lys Arg Lys
1               5
```

<210> SEQ ID NO 165
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 165

Asp Gly Asp Ile Ser Leu Thr Asp Leu Asn Tyr Arg Gln Tyr Phe Leu
1               5                   10                  15

His Pro Ser Leu Met Lys Gly Lys Arg Arg Lys Lys Arg Val Ser Gly
            20                  25                  30

<210> SEQ ID NO 166
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 166

Pro Ile Ser Pro Pro Leu Pro Phe Asp Ser Val Thr Ala Thr Phe Asp
1               5                   10                  15

Leu His Pro Gly Leu Lys His Arg Lys Arg Lys Arg Lys His His Gly
            20                  25                  30

Leu Thr

<210> SEQ ID NO 167
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 167

Leu Asp Pro Ala Ile Leu Ile Asp Val Ala Ser Asp Thr Tyr Tyr Ile
1               5                   10                  15

His Pro Ser Leu Leu Lys Lys Gly Lys Lys Arg Lys Tyr Ser Asp Ile
            20                  25                  30

Phe

<210> SEQ ID NO 168
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 168

Pro Asp Ile Ile Leu Asn Phe Glu Asp Asp Thr Ala Thr Phe Phe Leu
1               5                   10                  15

His Pro Ser Leu Leu Lys Lys His Lys His Asn Lys His Trp Phe Leu
            20                  25                  30

<210> SEQ ID NO 169
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 169

```
Pro Ala Ile Ile Ile Asp Phe Asp Glu Asp Thr Ala Thr Phe Phe Leu
1               5                   10                  15

His Pro Ser Leu Leu Lys Lys His Lys His Lys His Trp Phe Phe
            20                  25                  30
```

<210> SEQ ID NO 170
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 170

```
Pro Tyr Ser Ile Tyr Ile Val Gly Ser Asp Tyr Tyr Leu Phe Pro Ser
1               5                   10                  15

Tyr Ile Phe Phe Pro Lys Lys His Lys Arg Leu His Tyr Phe Phe Thr
            20                  25                  30

Asp Gly Tyr Val Ala Ala Trp
            35
```

<210> SEQ ID NO 171
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 171

```
Pro Tyr Ala Ile Tyr Val Val Gly Thr Asp Phe Tyr Leu Phe Pro Ser
1               5                   10                  15

Tyr Ile Phe Phe Pro Lys Lys His Lys Arg Ile His Tyr Ser Phe Thr
            20                  25                  30

Asp Gly Tyr Val Ala Ala Trp
            35
```

<210> SEQ ID NO 172
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 172

```
Ile Leu Thr Asp Ser Asp Ala Gly Phe Phe Trp Asn Thr Phe Leu His
1               5                   10                  15

Pro Ser Leu Leu Ser Lys Lys Lys Gly Lys Lys Thr Phe
            20                  25
```

<210> SEQ ID NO 173
<211> LENGTH: 58
<212> TYPE: PRT
<213> ORGANISM: Artificial Sequence
<220> FEATURE:
<223> OTHER INFORMATION: cell penetrating peptide

<400> SEQUENCE: 173

```
Gln Pro Ser Phe Gly Val Asp Val Tyr Ser Asp Asp Phe Tyr Leu His
1               5                   10                  15

Pro Gly Leu Tyr His Lys Lys Lys Lys Glu Thr Asn Arg Ile Phe Leu
            20                  25                  30

Met Phe Cys Arg Cys Pro Tyr Gly Cys Arg Pro Leu Glu Asn Cys Ile
            35                  40                  45
```

Phe His Leu Lys Ser Gln Leu Leu Lys Cys
        50                  55

<210> SEQ ID NO 174
<211> LENGTH: 43
<212> TYPE: PRT
<213> ORGANISM: Artificial Sequence
<220> FEATURE:
<223> OTHER INFORMATION: cell penetrating peptide

<400> SEQUENCE: 174

Thr Pro Ala Val Val Ile Asp Leu Leu Gly Gly Thr Asp Phe Tyr Leu
1               5                   10                  15

His Pro Ala Leu Phe Lys Lys Lys Lys Arg Leu Phe Cys Asp Phe
            20                  25                  30

Phe Ala Asp Gly Gly Val Ala Ser Cys Thr Glu
        35                  40

<210> SEQ ID NO 175
<211> LENGTH: 44
<212> TYPE: PRT
<213> ORGANISM: Artificial Sequence
<220> FEATURE:
<223> OTHER INFORMATION: cell penetrating peptide

<400> SEQUENCE: 175

Pro Ser Thr Ala Asn Ser Leu Asp Ala Ser Tyr Ser Tyr Tyr Leu His
1               5                   10                  15

Pro Ser Leu Asn Asn Lys Lys Lys Lys Ser Lys Gly Leu Arg Gly
            20                  25                  30

Gly Trp Trp Phe Val Ala Asp Asp Leu Leu Ala Thr
        35                  40

<210> SEQ ID NO 176
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 176

Thr Pro Thr Val Val Ile Arg Phe Gly Glu Ala Gly Thr Asp Tyr Tyr
1               5                   10                  15

Leu His Pro Ser Leu Lys Lys Lys Arg Lys Arg Lys Tyr Leu
            20                  25                  30

<210> SEQ ID NO 177
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 177

Gly Ile Val Ile Asp Leu Ser Asp Asp Tyr Tyr Arg His Tyr Tyr Leu
1               5                   10                  15

His Pro Ser Leu Leu Lys Lys Lys Lys Ser Lys Val Arg Lys Leu Trp
            20                  25                  30

Tyr Ala

<210> SEQ ID NO 178
<211> LENGTH: 31
<212> TYPE: PRT

```
<213> ORGANISM: Artificial Sequence
<220> FEATURE:
<223> OTHER INFORMATION: cell penetrating peptide

<400> SEQUENCE: 178

Ile Pro Val Ser Pro Ala Val Ser Leu Gly Gly Ala Asn Tyr Trp Leu
1               5                   10                  15
Glu Pro Ser Leu Ile Lys Lys Lys Arg Lys Lys Arg Leu Ile
            20                  25                  30

<210> SEQ ID NO 179
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 179

Gln Pro Pro Thr Val Ile Leu Asp Leu Phe Ser Asp Asp Tyr Phe Leu
1               5                   10                  15
His Pro Ser Tyr Leu Lys Lys Lys Arg Lys Arg Ser Asp Ile Phe
            20                  25                  30

<210> SEQ ID NO 180
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 180

Thr Ile Leu Ile Asp Phe Gln Ser Ser Tyr Gly Asp Phe Phe Leu His
1               5                   10                  15
Pro Ser Leu Ile Pro Lys Lys Lys Arg Arg Leu Gly Leu Phe Thr Asp
            20                  25                  30
Glu Tyr Val Val Thr Glu
        35

<210> SEQ ID NO 181
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 181

Thr Pro Val Ile Val Leu Asp Trp Gln Gln Ser Asn Asp Phe Phe Leu
1               5                   10                  15
His Pro Ser Leu Ile Lys Lys Lys Arg Arg Lys Arg Ser Ala Ala Phe
            20                  25                  30
Phe

<210> SEQ ID NO 182
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 182

Ile Gly Pro Ser Tyr Tyr Val Gly Val Asp Asn Asp Phe Tyr Leu His
1               5                   10                  15
Pro Ser Leu Ile Pro Lys Lys Lys Arg Arg Arg Leu Asp Tyr Phe
```

<210> SEQ ID NO 183
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 183

Pro Ile Arg Pro Gly Leu Asp Val Tyr Asp Ser Ile Asp Phe Tyr Leu
1               5                   10                  15

His Pro Ser Leu Gly Lys Lys Leu Arg Lys Lys Arg Lys Arg Arg Phe
            20                  25                  30

Tyr

<210> SEQ ID NO 184
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 184

Thr Phe Ala Ile Thr Ile Tyr Gly Ser Asn Tyr Tyr Leu Leu Pro Leu
1               5                   10                  15

Leu Phe Phe Leu Leu Lys Lys Arg Lys His Leu Pro Tyr Phe Phe Thr
            20                  25                  30

Asp Gly Ile Val Ala Ser
        35

<210> SEQ ID NO 185
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 185

Pro Trp Val Val Asp Gly Asp Gly Gly Ser Gly Tyr Trp Ile Asp Pro
1               5                   10                  15

Ser Leu Leu Thr Asn Lys Lys Arg Lys Lys His Phe His
            20                  25

<210> SEQ ID NO 186
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 186

Val His Pro Ala Tyr Ser Val Thr Phe Ser Met Leu Ser Glu Leu Asp
1               5                   10                  15

Asp Pro Phe Leu Thr Lys Lys Arg Lys Lys Cys Phe Ala Asp Gly Cys
            20                  25                  30

Leu Asp Thr Phe Tyr
        35

<210> SEQ ID NO 187
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 187

Thr Gln Tyr Ile Gly Ile His Gly Thr His Tyr Tyr Leu Trp Pro Leu
1               5                   10                  15

Tyr Tyr Phe Ile Pro Lys Lys Arg Lys Arg Val Pro Tyr Phe Phe Ala
            20                  25                  30

Asp Gly Phe Val Ala Ala
        35

<210> SEQ ID NO 188
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 188

Thr Tyr Ala Ile Thr Ile Gln Gly Ser Asn Tyr Tyr Leu Leu Pro Leu
1               5                   10                  15

Leu Tyr Phe Phe Leu Lys Lys Arg Lys Arg Ile Pro Tyr Phe Phe Ser
            20                  25                  30

Asp Gly Tyr Val Ala Val
        35

<210> SEQ ID NO 189
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 189

Thr Thr Tyr Ile Gly Ile His Gly Thr Gln Tyr Tyr Leu Trp Pro Trp
1               5                   10                  15

Tyr Tyr Tyr Phe Pro Lys Lys Arg Lys Arg Ile Pro Tyr Phe Phe Ala
            20                  25                  30

Asp Gly Phe Val Ala Ala
        35

<210> SEQ ID NO 190
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 190

Thr Val Ala Ile Ala Ile Gln Gly Ser Asn Tyr Tyr Leu Leu Pro Leu
1               5                   10                  15

Leu Tyr Tyr Phe Leu Lys Lys Arg Lys Arg Ile Pro Tyr Phe Phe Thr
            20                  25                  30

Asp Gly Phe Val Ala Val
        35

<210> SEQ ID NO 191
<211> LENGTH: 38
<212> TYPE: PRT
<213> ORGANISM: Artificial Sequence
<220> FEATURE:
<223> OTHER INFORMATION: cell penetrating peptide

```
<400> SEQUENCE: 191

Pro Ser Ser Phe Ile Val Tyr Gly Thr Glu Tyr Tyr Leu Met Pro Ser
1               5                   10                  15

Tyr Ile Phe Phe Pro Lys Lys Arg Lys Arg Val His Tyr Phe Phe Ala
            20                  25                  30

Asp Gly Phe Val Ala Ala
        35

<210> SEQ ID NO 192
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 192

Ile Gln Ser Val Phe Ile Asp Gly Thr Asp Tyr Tyr Leu Leu Pro Asn
1               5                   10                  15

Tyr Ile Phe Phe Pro Lys Lys Arg Lys Arg Val His Tyr Ser Phe Ala
            20                  25                  30

Asp Gly Tyr Val Ala Ala Trp
        35

<210> SEQ ID NO 193
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 193

Pro Tyr Ala Ile Tyr Ile Leu Gly Ser Asp Tyr Tyr Leu Leu Pro Asn
1               5                   10                  15

Tyr Ile Phe Phe Pro Lys Lys Arg Lys Arg Val Pro Tyr Ser Phe Ser
            20                  25                  30

Asp Gly Phe Val Ala Ala Trp
        35

<210> SEQ ID NO 194
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 194

Thr His Ser Val Val Leu Gln Gly Thr Asn Tyr Tyr Leu Trp Pro Asn
1               5                   10                  15

Tyr Tyr Phe Ile Phe Lys Lys Arg Lys Arg Val Pro Tyr Phe Leu Thr
            20                  25                  30

Asp Gly Phe Val Ala Phe
        35

<210> SEQ ID NO 195
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 195

Pro Gly Ser Val Leu Val Asn Gly Ser Thr Tyr Tyr Leu Leu Pro Pro
```

```
1               5                   10                  15
Leu Gly Leu Leu Pro Lys Lys Arg Lys Arg Phe Pro Tyr Phe Phe Ala
            20                  25                  30

Asp Gly Asn Val Glu Ala
        35

<210> SEQ ID NO 196
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 196

Thr His Tyr Ile Gly Ile Asn Gly Thr His Tyr Tyr Leu Trp Pro Leu
1               5                   10                  15

Tyr Tyr Phe Leu Pro Lys Lys Arg Lys Arg Val Pro Tyr Phe Phe Ala
            20                  25                  30

Asp Gly Leu Leu Ala Ala
        35

<210> SEQ ID NO 197
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 197

Ser Gln Ser Val Phe Val Asp Gly Thr Asp Tyr Phe Leu Leu Pro Asn
1               5                   10                  15

Tyr Leu Phe Phe Pro Lys Lys Arg Lys Arg Val His Tyr Ser Phe Ala
            20                  25                  30

Asp Gly Phe Val Ala Thr Trp
        35

<210> SEQ ID NO 198
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 198

Thr Ile Val Ile Glu Ala Phe Asp Ser Ser Gly Gly Phe Tyr Leu His
1               5                   10                  15

Pro Ser Phe Val Gly Lys Lys Arg Lys Arg Leu Tyr Phe Leu
            20                  25                  30

<210> SEQ ID NO 199
<211> LENGTH: 43
<212> TYPE: PRT
<213> ORGANISM: Artificial Sequence
<220> FEATURE:
<223> OTHER INFORMATION: cell penetrating peptide

<400> SEQUENCE: 199

Val Pro Ile Ile Val Val Asp Ala Thr Ser Gln Asp Phe Tyr Leu His
1               5                   10                  15

Pro Tyr Leu Gln His Lys Lys Arg Lys Arg Lys His Phe Val Tyr Met
            20                  25                  30

Phe Ala Asp Gly Ser Val Ala Ser Glu Tyr Gln
```

```
<210> SEQ ID NO 200
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 200

Val Ala Pro Ala Val His Val Glu Ala Phe Gly Ser Asn Tyr Tyr Leu
1               5                   10                  15

His Pro Ser Leu Leu Lys Lys Arg Lys Arg Lys Tyr Leu Asp Val Phe
            20                  25                  30

<210> SEQ ID NO 201
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 201

Pro Ala Ile Val Ile Asp Ile Leu Asp Ser Ser Ala Asp Tyr Tyr Leu
1               5                   10                  15

His Pro Ser Leu Ile Lys Lys Arg Lys Arg Lys His Phe Phe Phe
            20                  25                  30

<210> SEQ ID NO 202
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 202

Pro Ala Ile Leu Ile Glu Ile Trp Asp Ser Gly Ser Asn Tyr Ser Leu
1               5                   10                  15

His Pro Ser Leu Leu Lys Lys Arg Lys Arg Lys Leu Leu Phe Leu
            20                  25                  30

<210> SEQ ID NO 203
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 203

Leu Pro Ala Val Val Ile His Ile Tyr Asp Asp Ser Gly Asp Phe Tyr
1               5                   10                  15

Leu His Pro Ser Leu Lys Lys Arg Lys Arg Lys Arg Ala Tyr Leu
            20                  25                  30

<210> SEQ ID NO 204
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 204

Gly Pro Ser Ile Leu Ile Asp Glu Phe Ser Ser Glu Asp Phe Val Leu
1               5                   10                  15
```

His Pro Ser Leu Ser Lys Lys Arg Lys Arg Lys Arg Leu Tyr Ser Asp
                20                  25                  30
Phe

<210> SEQ ID NO 205
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 205

Thr Pro Thr Val Val Ile Lys Phe Ala Glu Ala Gly Gly Arg Phe Leu
1               5                   10                  15

Phe Thr Pro Ser Leu Lys Lys Arg Lys Arg Lys Arg Lys Tyr Leu
                20                  25                  30

<210> SEQ ID NO 206
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 206

Pro Phe Ile Pro Ser Thr Leu Gln Phe Asp Thr Phe Asp Tyr Asp Ile
1               5                   10                  15

His Pro Ser Ala Ile Lys Lys Arg Arg Lys Arg Lys Arg Ser Asp Phe
                20                  25                  30
Met

<210> SEQ ID NO 207
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 207

Val Ala Pro Ser Tyr Ile Pro Asp Tyr Tyr Ala Asp Phe Tyr Leu Tyr
1               5                   10                  15

Pro Ser Phe Leu Pro Lys Lys Arg Arg Arg Ile Asp Ile Val
                20                  25                  30

<210> SEQ ID NO 208
<211> LENGTH: 57
<212> TYPE: PRT
<213> ORGANISM: Artificial Sequence
<220> FEATURE:
<223> OTHER INFORMATION: cell penetrating peptide

<400> SEQUENCE: 208

Ser Ala Thr Pro Pro Thr Ser Thr Asp Thr Ala Gly Phe Ser Met Leu
1               5                   10                  15

Asp Pro Ser Leu Leu Lys Arg Cys Arg Arg Lys Arg Arg Ser Cys Phe
                20                  25                  30

Ala Asp Gly Ile Val Asp Ala Arg Gln Ser Glu Val Leu Ser Ala Pro
                35                  40                  45

Cys Ser Cys Asp Lys Gly Ala Gln Tyr
            50                  55

<210> SEQ ID NO 209

```
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 209

Pro Asp Ile Ile Ile Thr Phe Glu Glu Gly Thr Ala Thr Phe Phe Leu
1               5                   10                  15

His Pro Ser Leu Leu Lys Arg His Lys His Lys His Trp Phe Phe
            20                  25                  30

<210> SEQ ID NO 210
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 210

Pro Asp Ile Val Ile Asp Met Glu Glu Asp Thr Ala Thr Phe Thr Leu
1               5                   10                  15

His Pro Ser Leu Leu Lys Arg His Lys His Lys His Trp Phe Phe
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 211

Pro Thr Val Val Ile His Ile His Asp Thr Ser Gly Asp Tyr Tyr Leu
1               5                   10                  15

His Pro Ser Leu Gln Lys Arg Lys Cys Lys Arg Lys His Arg Tyr Leu
            20                  25                  30

<210> SEQ ID NO 212
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 212

Gly Pro Thr Ser Pro Val Ser Phe Tyr Ser Asp Asp Phe Tyr Leu His
1               5                   10                  15

Pro Ser Leu Phe Thr Lys Arg Lys Lys Arg Lys Tyr Tyr Asn Phe
            20                  25                  30

<210> SEQ ID NO 213
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 213

Ile Thr Asp Ser Gly Val Asp Gly Thr Tyr Phe Leu Asn Thr Tyr Leu
1               5                   10                  15

His Pro Ser Leu His Lys Arg Lys Lys Arg Arg Phe Ser
            20                  25
```

```
<210> SEQ ID NO 214
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 214

Ile Ile Asp Phe Ser Val Glu Gly Thr Tyr Phe Leu Asn Thr Tyr Ala
1               5                   10                  15

His Pro Ser Leu His Lys Arg Lys Arg Arg Leu Ser
            20                  25

<210> SEQ ID NO 215
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 215

Thr Pro Ile Ile Thr Gly Val Phe Val Ser Phe Asp Phe Trp Leu His
1               5                   10                  15

Pro Ser Gln Leu Leu Lys Arg Lys Arg Ser Pro Phe Tyr Leu Ala Asp
            20                  25                  30

Gly Ile Val Ala Ala
        35

<210> SEQ ID NO 216
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 216

Pro Tyr Ala Pro Ser Pro Ile Thr Val Phe Gly Asp Thr Phe Tyr Leu
1               5                   10                  15

Asn Pro Ser Leu Leu Lys Arg Lys Arg Lys Gln Tyr Phe Tyr
            20                  25                  30

<210> SEQ ID NO 217
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 217

Pro Ala Gly Pro Ile Tyr Ile Tyr Gly Ser Gly Phe Ile Leu His Pro
1               5                   10                  15

Ser Tyr Tyr Leu Leu Lys Arg Lys Arg Lys Arg Leu Ser Tyr Ser Phe
            20                  25                  30

Thr Asp Val Ala Thr Tyr
        35

<210> SEQ ID NO 218
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 218
```

-continued

```
Pro Ala Val Val Ile His Ile Ala Asp Ala Ser Gly Asp Phe Tyr Leu
1               5                   10                  15
His Pro Ser Leu Gln Lys Arg Lys Arg Lys Arg Ala Tyr Leu
            20                  25                  30

<210> SEQ ID NO 219
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 219

Glu Pro Ala Ile Ile Ile Asp Leu Glu Ser Ala Ser Asp Phe Phe Ile
1               5                   10                  15
His Pro Ser Leu Leu Lys Arg Lys Arg Lys Arg Pro Leu Leu
            20                  25                  30

<210> SEQ ID NO 220
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 220

Glu Pro Ala Ile Ile Ile Asp Leu Glu Ser Ala Asn Asp Phe Leu Ile
1               5                   10                  15
His Pro Ser Leu Leu Lys Arg Lys Arg Lys Arg Pro Leu Leu
            20                  25                  30

<210> SEQ ID NO 221
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 221

Glu Pro Ala Ile Val Ile Asp Leu Glu Ser Ala Ser Asp Phe Phe Ile
1               5                   10                  15
His Pro Ser Leu Leu Lys Arg Lys Arg Lys Arg Pro Leu Leu
            20                  25                  30

<210> SEQ ID NO 222
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 222

Ile Asn Pro Ser Leu Gly Ala Ser Val Ile Phe Asp Thr Tyr Asp Leu
1               5                   10                  15
His Pro Ser Leu Leu Lys Arg Lys Arg Lys Arg Pro Phe Phe
            20                  25                  30

<210> SEQ ID NO 223
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 223
```

Glu Pro Ala Ile Ile Ile Asp Val Asp Ser Ala Thr Asp Phe Leu Ile
1               5                   10                  15

His Pro Ser Leu Leu Lys Arg Lys Arg Lys Arg His Leu Leu
            20                  25                  30

<210> SEQ ID NO 224
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 224

Pro Leu Tyr Pro Thr Glu Val Thr Val Tyr Gly Asp Ser Phe Val Ile
1               5                   10                  15

Asp Pro Phe Phe Leu Lys Arg Lys Arg Lys Arg Tyr Thr Leu Tyr
            20                  25                  30

<210> SEQ ID NO 225
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 225

Thr Glu Pro His Leu Ile Ile Asp Leu Phe Ser Asp Asp Phe Tyr Leu
1               5                   10                  15

His Pro Gly Tyr Leu Lys Arg Lys Arg Lys Arg Ser Asp Ile Phe
            20                  25                  30

<210> SEQ ID NO 226
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 226

Ile Met Pro Gly Val Thr Ile Asp Ile Tyr Ser Ile Asp Tyr Asp Ile
1               5                   10                  15

His Pro Ser Leu Leu Lys Arg Lys Arg Lys Arg Ile Asp Tyr Val
            20                  25                  30

<210> SEQ ID NO 227
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 227

Glu Pro Ala Ile Ile Ile Asp Leu Glu Ser Ala Thr Asp Phe Leu Ile
1               5                   10                  15

His Pro Ser Leu Leu Lys Arg Lys Arg Lys Arg Asn Leu Leu
            20                  25                  30

<210> SEQ ID NO 228
<211> LENGTH: 30
<212> TYPE: PRT
<213> ORGANISM: Artificial Sequence
<220> FEATURE:
<223> OTHER INFORMATION: cell penetrating peptide

```
<400> SEQUENCE: 228

Ala Ile Val Ile Glu Ile Trp Gly Ser Gly Asn Ser Tyr Ser Leu His
1               5                   10                  15

Pro Ser Leu Leu Ser Lys Arg Lys Arg Lys Arg Leu Ser Leu
            20                  25                  30

<210> SEQ ID NO 229
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 229

His Ile Phe Val Tyr Ser Pro His Leu Thr Ser Phe Asp Phe Leu Pro
1               5                   10                  15

His Pro Ser Leu Leu Lys Arg Lys Arg Lys Arg Ser Leu Asp Asp
            20                  25                  30

Phe Thr Ile Leu Gln
        35

<210> SEQ ID NO 230
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 230

Ile Ile Asp Asn Glu Leu Ala Val Trp Phe His Ser Tyr Phe Leu His
1               5                   10                  15

Pro Ser Lys Leu Gly Lys Arg Lys Arg Lys Arg Ser Asp Ser Ser Val
            20                  25                  30

<210> SEQ ID NO 231
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 231

Ile Ile Asp Gly Asn Thr Ile Asp Leu Tyr Ser Ser Asn Phe Thr Leu
1               5                   10                  15

His Pro Ser Leu Leu Lys Arg Lys Arg Lys Arg Lys His Ala
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 232

Pro Thr Val Val Ile His Ile Ser Asp Thr Ser Gly Asp Tyr Tyr Leu
1               5                   10                  15

His Pro Ser Leu Gln Lys Arg Lys Arg Lys Arg Lys Arg Lys Tyr Leu
            20                  25                  30

<210> SEQ ID NO 233
<211> LENGTH: 30
<212> TYPE: PRT
```

```
<213> ORGANISM: Artificial Sequence
<220> FEATURE:
<223> OTHER INFORMATION: cell penetrating peptide

<400> SEQUENCE: 233

Pro Thr Ile Ile Val Thr Lys Glu Thr Gly Val Thr Tyr Asp Leu His
1               5                   10                  15

Pro Ser Leu Phe Gly Lys Arg Lys Arg Lys Arg Ser Leu
            20                  25                  30

<210> SEQ ID NO 234
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 234

Thr Val Leu Ile Asn Val Tyr Asp Glu Gly Leu Asp Phe Leu Leu His
1               5                   10                  15

Pro Ser Met Phe Pro Lys Arg Lys Arg Arg Lys Leu Ala Phe Leu
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 235

Pro Gly Ile Leu Ile Glu Val Leu Asp Ser Ser Gly Asp Phe Tyr Leu
1               5                   10                  15

His Pro Ser Leu Leu Lys Arg Lys Arg Arg Lys Arg Pro Ser Phe
            20                  25                  30

<210> SEQ ID NO 236
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 236

Pro Thr Val Val Ile His Ile Ala Asp Thr Ser Gly Asp Tyr Tyr Leu
1               5                   10                  15

His Pro Ser Leu Gln Lys Arg Lys Arg Arg Lys Arg Lys Tyr Leu
            20                  25                  30

<210> SEQ ID NO 237
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 237

Pro Val Val Ile Ile Tyr Pro His Asp Asn Thr Gly Asp Phe Tyr Leu
1               5                   10                  15

His Pro Ser Leu His Lys Arg Lys Arg Arg Lys Arg Lys Tyr Phe
            20                  25                  30

<210> SEQ ID NO 238
<211> LENGTH: 31
```

```
<212> TYPE: PRT
<213> ORGANISM: Artificial Sequence
<220> FEATURE:
<223> OTHER INFORMATION: cell penetrating peptide

<400> SEQUENCE: 238

Pro Ala Pro His Thr Val Ser Asp Ile Asn Asp Asp Tyr Tyr Leu Tyr
1               5                   10                  15

Pro Ser Leu Tyr Pro Lys Arg Lys Arg Arg Leu Asp Phe Phe
            20                  25                  30

<210> SEQ ID NO 239
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 239

Pro Leu Glu Pro Ala Asn Ala Ile Glu Val Tyr Tyr Asp Phe Phe Leu
1               5                   10                  15

His Pro Ala Leu Gln Lys Arg Lys Arg Arg Leu Asp Val Phe
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 240

Asp Gly Asn Ile Asn Leu Gln Glu Val Leu Tyr Arg Gln Tyr Phe Leu
1               5                   10                  15

His Pro Ser Leu Met Lys Arg Lys Arg Arg Lys Arg Leu Phe Gly
            20                  25                  30

<210> SEQ ID NO 241
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 241

Arg Pro Pro Ile Tyr Ile Gly Ser Ser Pro Gly Val Asp Tyr Tyr Leu
1               5                   10                  15

His Pro Ser Leu Tyr Lys Arg Lys Arg Arg Arg Arg His Ser Tyr
            20                  25                  30

Leu

<210> SEQ ID NO 242
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 242

Pro Val Val Ile Ile His Thr Tyr Asp Thr Ser Gly Asp Phe Tyr Leu
1               5                   10                  15

His Pro Ser Leu Thr Lys Arg Leu Lys Arg Lys Arg Lys Tyr Leu
            20                  25                  30
```

```
<210> SEQ ID NO 243
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 243

Pro Val Val Ile Ile His Thr Tyr Asp Thr Ser Gly Asp Phe Tyr Leu
1               5                   10                  15

His Pro Ser Leu His Lys Arg Leu Lys Arg Lys Arg Lys Tyr Leu
            20                  25                  30

<210> SEQ ID NO 244
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 244

Ser Thr Pro Leu Tyr Pro Pro Arg His Val Phe Phe Ser Asp Leu Asp
1               5                   10                  15

Asp Pro Ile Met Phe Lys Arg Arg Lys Lys Cys Phe Ala Asp Gly Cys
            20                  25                  30

Val Asp Ala Phe Tyr
        35

<210> SEQ ID NO 245
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 245

Pro Pro Thr Val Ile Val Tyr Asp Tyr Asp Asp Ser Val Asp Phe Tyr
1               5                   10                  15

Leu His Pro Ser Leu Lys Arg Arg Lys Lys Arg Lys Tyr Ile Val Tyr
            20                  25                  30

<210> SEQ ID NO 246
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 246

Pro Ser Ser Val Tyr Ile Phe Gly Gly Asp Tyr Tyr Leu Met Pro Ser
1               5                   10                  15

Tyr Val Leu Trp Pro Lys Arg Arg Lys Arg Val His Tyr Phe Phe Ala
            20                  25                  30

Asp Gly Phe Val Ala Ala
        35

<210> SEQ ID NO 247
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 247
```

-continued

```
Leu Pro Ala Ile Val Val His Gly Asp Asn Tyr Tyr Leu Trp Pro Tyr
1               5                   10                  15

Ile Tyr Leu Ile His Lys Arg Arg Lys Arg Met Pro Tyr Phe Phe Ser
            20                  25                  30

Asp Gly Phe Val Ala Tyr
        35

<210> SEQ ID NO 248
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 248

Pro Ser Ser Val Tyr Ile Phe Gly Gly Asp Tyr Tyr Leu Leu Pro Ser
1               5                   10                  15

Tyr Ile Leu Trp Pro Lys Arg Arg Lys Arg Val Asn Tyr Phe Phe Ala
            20                  25                  30

Asp Gly Phe Val Ala Ala
        35

<210> SEQ ID NO 249
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 249

Pro Ser Ser Val Tyr Ile Val Gly Gly Asp Tyr Tyr Leu Leu Pro Ser
1               5                   10                  15

Tyr Val Leu Trp Pro Lys Arg Arg Lys Arg Val His Tyr Phe Phe Ala
            20                  25                  30

Asp Gly Tyr Val Ala Ala
        35

<210> SEQ ID NO 250
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 250

Pro His Ser Ile Tyr Ile Gln Gly Ser Asp Phe Tyr Leu Leu Pro Ala
1               5                   10                  15

Tyr Val Phe Phe Pro Lys Arg Arg Lys Arg Val Pro Tyr Ser Phe Ser
            20                  25                  30

Asp Gly Phe Val Ala Ala Trp
        35

<210> SEQ ID NO 251
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 251

Pro His Ser Ile Tyr Val Glu Gly Phe Asp Phe Tyr Leu Leu Pro Ala
1               5                   10                  15
```

```
Tyr Ile Phe Phe Pro Lys Arg Arg Lys Arg Val Pro Tyr Ser Phe Ala
            20                  25                  30

Asp Gly Phe Val Ala Ala Trp
        35
```

<210> SEQ ID NO 252
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 252

```
Pro Tyr Ser Val Tyr Ile Gln Gly Ser Asp Tyr Tyr Leu Leu Pro Asn
1               5                   10                  15

Tyr Ile Phe Phe Pro Lys Arg Arg Lys Arg Val Pro Tyr Ser Phe Ser
            20                  25                  30

Asp Gly Phe Val Ala Ala Trp
        35
```

<210> SEQ ID NO 253
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 253

```
Pro Ser Ala Val Ser Ile Tyr Gly Thr Asp Phe Tyr Leu His Pro Ser
1               5                   10                  15

Leu Leu His Phe Gly Lys Arg Arg Lys Arg Ile Ser Tyr Phe Phe Ala
            20                  25                  30

Asp Asn Tyr Val Ala Ala
        35
```

<210> SEQ ID NO 254
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 254

```
Pro Tyr Ala Ile Tyr Ile Val Gly Ser Asp Tyr Tyr Leu Leu Pro Asn
1               5                   10                  15

Tyr Ile Phe Phe Pro Lys Arg Arg Lys Arg Val Pro Tyr Ser Phe Ser
            20                  25                  30

Asp Gly Phe Val Ala Ala Trp
        35
```

<210> SEQ ID NO 255
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 255

```
Gln His Ser Ile Tyr Val His Gly Thr Asp Phe Tyr Leu Leu Pro Gly
1               5                   10                  15

Tyr Leu Phe Val Pro Lys Arg Arg Lys Arg Phe Ile Tyr Ser Phe Ala
            20                  25                  30
```

Asp Gly Tyr Val Ala Ala
        35

<210> SEQ ID NO 256
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 256

Gln Pro Ser Ala Ala Ile Ser Ile Phe Ala Ser Asp Phe Tyr Leu His
1               5                   10                  15

Pro Ser Tyr Ile Leu Lys Arg Arg Lys Arg Val Pro Tyr Thr Phe Phe
            20                  25                  30

Ala Asp Gly Ile Val Ala Ser
        35

<210> SEQ ID NO 257
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 257

Ala Pro Pro Ala Ser Val Thr Val Val Ser Gly Asp Phe Val Leu His
1               5                   10                  15

Pro Ser Tyr Phe Trp Lys Arg Arg Lys Arg Val Ser Tyr Phe Phe Ala
            20                  25                  30

Asp Gly Val Val Ala Ala
        35

<210> SEQ ID NO 258
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 258

Val Ile Pro Ala Ala Val Thr Ile Tyr Ala Gly Asp Phe Phe Leu His
1               5                   10                  15

Pro Ser Tyr Ile Trp Lys Arg Arg Lys Arg Val Ser Tyr Phe Leu Ala
            20                  25                  30

Asp Gly Ile Val Ala Ala
        35

<210> SEQ ID NO 259
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 259

Pro Val Ile Val Ile His Gly Val Tyr Phe Ser Val Asp Phe Tyr Leu
1               5                   10                  15

His Pro His Leu Leu Lys Arg Arg Lys Arg Phe His Phe
            20                  25

<210> SEQ ID NO 260

```
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 260

Pro Gln Ser Val Ser Ile His Gly Thr Asp Phe Tyr Leu His Pro Ser
1               5                   10                  15

Leu Trp His Leu Gly Lys Arg Arg Lys Arg Phe Ser Tyr Phe Phe Thr
            20                  25                  30

Asp Asn Tyr Val Ala Ala
        35

<210> SEQ ID NO 261
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 261

Ile Gly His Val Val His Gly Gly Asp Phe Tyr Leu His Pro Ser
1               5                   10                  15

Tyr Tyr Thr Leu His Lys Arg Arg Lys Arg Met Pro Arg Phe Leu Ala
            20                  25                  30

Asp Val Ser Val Ala Ala
        35

<210> SEQ ID NO 262
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 262

Pro Gln Ala Ile Tyr Ile Gln Gly Thr Asp Phe Tyr Leu Val Pro Asn
1               5                   10                  15

Tyr Val Phe Phe Pro Lys Arg Arg Lys Arg Val Pro Tyr Ser Phe Ala
            20                  25                  30

Asp Gly Phe Val Ala Ala Trp
        35

<210> SEQ ID NO 263
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 263

Tyr Thr Pro Val Ile Tyr Ile Asp Pro Phe Gly Ser Asp Phe Tyr Leu
1               5                   10                  15

His Pro Ala Leu Leu Lys Arg Arg Lys Arg Lys Tyr Ser Glu Ile Phe
            20                  25                  30

<210> SEQ ID NO 264
<211> LENGTH: 32
<212> TYPE: PRT
<213> ORGANISM: Artificial Sequence
<220> FEATURE:
<223> OTHER INFORMATION: cell penetrating peptide
```

```
<400> SEQUENCE: 264

Leu Ile Pro Gly Arg Ser Val Asp Val Tyr Ser Asn Asp Phe Ile Ile
1               5                   10                  15

His Pro Ser Val Leu Lys Arg Arg Lys Arg Lys Leu Ser Asp Ser Phe
            20                  25                  30

<210> SEQ ID NO 265
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 265

Ile Ser Pro Ala Val Leu Ile Asp Ala Phe Ser Ala Asp Tyr Tyr Leu
1               5                   10                  15

His Pro Ser Leu Met Lys Arg Arg Lys Arg Lys Tyr Ser Glu Ile Phe
            20                  25                  30

<210> SEQ ID NO 266
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 266

Thr Pro Thr Val Ile Ile His Thr Glu Asp Tyr Ser Gly Asp Tyr Tyr
1               5                   10                  15

Leu His Pro Ser Leu Lys Arg Arg Lys Arg Lys Arg Ala Tyr Leu
            20                  25                  30

<210> SEQ ID NO 267
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 267

Pro Val Gly Pro Ser Ser Ser Val Asp Ile Phe Tyr Tyr Asp Tyr Asp
1               5                   10                  15

Leu His Pro Ser Leu Lys Arg Arg Lys Arg Lys Arg Asn Met Phe
            20                  25                  30

<210> SEQ ID NO 268
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 268

Pro Ile Gly Pro Ser Asn Ser Val Glu Ile Phe Tyr Tyr Asp Tyr Asp
1               5                   10                  15

Leu His Pro Ser Leu Lys Arg Arg Lys Arg Lys Arg Asn Val Phe
            20                  25                  30

<210> SEQ ID NO 269
<211> LENGTH: 31
<212> TYPE: PRT
<213> ORGANISM: Artificial Sequence
<220> FEATURE:
<223> OTHER INFORMATION: cell penetrating peptide
```

<400> SEQUENCE: 269

Pro Ala Ile Ile Leu Glu Ile Trp Gly Ser Gly Glu Asn Tyr Ser Leu
1               5                   10                  15

His Pro Ser Leu Leu Lys Arg Arg Lys Arg Lys Arg Leu Ile Leu
            20                  25                  30

<210> SEQ ID NO 270
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 270

Asp Val Pro Ser Ser Ser Asp Ser Val Ser Ser Thr Phe Asp Leu
1               5                   10                  15

His Pro Ser Leu Leu Lys Arg Arg Lys Arg Lys Arg Gly Asp Ile
            20                  25                  30

<210> SEQ ID NO 271
<211> LENGTH: 45
<212> TYPE: PRT
<213> ORGANISM: Artificial Sequence
<220> FEATURE:
<223> OTHER INFORMATION: cell penetrating peptide

<400> SEQUENCE: 271

Leu Glu Pro Pro Ile Leu Leu Asp Tyr Leu Gly Ser Gly Tyr Tyr Leu
1               5                   10                  15

His Pro Ser Leu Trp Lys Arg Arg Lys Arg Lys Arg Ser Asp Thr Tyr
            20                  25                  30

Asn Ser Phe Thr Asp Gly Ile Val Asp Ala Thr Glu Trp
            35                  40                  45

<210> SEQ ID NO 272
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 272

Thr Pro Thr Val Val Ile Asn Phe Glu Asp Ala Gly Gly Asp Tyr Tyr
1               5                   10                  15

Leu His Pro Ser Leu Lys Arg Arg Lys Arg Lys Arg Lys Tyr Leu
            20                  25                  30

<210> SEQ ID NO 273
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 273

Ile Thr Pro Ala Val Tyr Leu Asp Ala Phe Ser Ser Asp Tyr Tyr Leu
1               5                   10                  15

His Pro Ala Leu Met Lys Arg Arg Lys Arg Lys Arg Lys Tyr Leu Glu
            20                  25                  30

Val Phe

```
<210> SEQ ID NO 274
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 274

Ser Glu Gln Pro Leu Phe Val Leu Asp Tyr Ser Asp Tyr Asp Leu His
1               5                   10                  15

Pro Gly Leu Leu Pro Lys Arg Arg Arg Ile Asp Tyr Phe
            20                  25

<210> SEQ ID NO 275
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 275

Ile Phe Ser Thr Pro Tyr Tyr Glu Tyr Asn Tyr Ile Leu Asp Pro Ser
1               5                   10                  15

Ile Leu Phe Leu Leu Lys Arg Arg Arg Lys Leu Phe Val
            20                  25

<210> SEQ ID NO 276
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 276

Pro Gln Val Ser Ile Phe Val Asp Gly Gly Asp Phe Tyr Leu His Pro
1               5                   10                  15

Ser Tyr Tyr Met Leu Lys Arg Arg Lys Arg Val Ser Tyr Phe Phe
            20                  25                  30

Thr Asp Val Ser Val Ala Ala
        35

<210> SEQ ID NO 277
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 277

Pro Ile Tyr Ser Ile Ile Ala Asp Gly Gly Asp Phe Tyr Leu His Pro
1               5                   10                  15

Ser Tyr Tyr Leu Leu Lys Arg Arg Arg Lys Arg Ile Pro Tyr Phe Phe
            20                  25                  30

Ala Asp Val Ser Val Ala Val
        35

<210> SEQ ID NO 278
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 278
```

-continued

```
Ser His Ser Val Val Ala Gln Gly Gly Asn Tyr Tyr Leu Trp Pro Tyr
1               5                   10                  15

Ile Tyr Leu Ile His Lys Arg Arg Lys Arg Val Pro Cys Phe Phe
            20                  25                  30

Ser Asp Gly Leu Ala Ala Tyr
        35
```

<210> SEQ ID NO 279
<211> LENGTH: 41
<212> TYPE: PRT
<213> ORGANISM: Artificial Sequence
<220> FEATURE:
<223> OTHER INFORMATION: cell penetrating peptide

<400> SEQUENCE: 279

```
Pro Ser Phe Asp Trp Pro Met Thr Asp Leu Asp Ala Asp Phe Val Leu
1               5                   10                  15

His Pro Ser Leu Leu Lys Arg Arg Arg Arg Phe Tyr Trp Ser Phe Ala
            20                  25                  30

Asp Gly Gly Leu Ala Ser Arg Thr Lys
        35                  40
```

<210> SEQ ID NO 280
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 280

```
Asp Thr Thr His Asp Val Val Ile Gln Gly Ser Thr Phe Ala Leu Trp
1               5                   10                  15

Pro Val Tyr Phe Leu Lys Arg Arg Arg Lys Arg Ile Pro Tyr Phe
            20                  25                  30

Leu Ala Asp Gly Gly Val Ala Ala
        35                  40
```

<210> SEQ ID NO 281
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 281

```
Asp Val Thr His Asp Val Tyr Ile Gln Gly Ala Thr Phe Ala Leu Trp
1               5                   10                  15

Pro Val Tyr Phe Phe Lys Arg Arg Arg Lys Arg Ile Pro Tyr Phe
            20                  25                  30

Phe Ala Asp Gly Asp Val Ala Ala
        35                  40
```

<210> SEQ ID NO 282
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 282

```
Pro Ile Val Ile Ile Asp Leu Thr Ser Thr Ser Ile Asp Tyr Phe Leu
1               5                   10                  15
```

His Pro Ser Leu Ala Lys Arg Arg Arg Arg Ala His Trp Ser Phe
            20                  25                  30

Leu Ala Asp Val Gly Leu Ala Thr
            35                  40

<210> SEQ ID NO 283
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 283

Pro Asp Ile Ile Ile Asp Phe Leu Thr Pro Gly Asp Thr Phe Tyr Leu
1               5                   10                  15

His Pro Ser His Phe Lys Arg Arg Arg Arg Arg Tyr Gln Leu Phe
            20                  25                  30

Phe Phe

<210> SEQ ID NO 284
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 284

Val Ile Val Asp Val Glu Arg Gly Ser Gly Ser Asp Tyr Tyr Leu His
1               5                   10                  15

Pro Ser Leu Ser Leu Lys Arg Arg Arg Arg Arg Arg Lys Ser Leu
            20                  25                  30

<210> SEQ ID NO 285
<211> LENGTH: 35
<212> TYPE: PRT
<213> ORGANISM: Artificial Sequence
<220> FEATURE:
<223> OTHER INFORMATION: cell penetrating peptide

<400> SEQUENCE: 285

Ile Thr Ala Ile Pro Ala Gly Gly Gln Ser Ile Asp Phe Leu Leu His
1               5                   10                  15

Pro Gly Leu Phe Pro Lys Arg Arg Arg Arg Arg Thr Arg Arg His
            20                  25                  30

Ser Tyr Leu
        35

<210> SEQ ID NO 286
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 286

Ile Thr Pro Leu Ile Gln Ile Asp Pro Phe Gly Pro Asp Phe Tyr Leu
1               5                   10                  15

His Pro Ala Leu Met Lys Ser Arg Lys Arg Lys Tyr Leu Glu Val Phe
            20                  25                  30

<210> SEQ ID NO 287
<211> LENGTH: 31
<212> TYPE: PRT

<213> ORGANISM: Artificial Sequence
<220> FEATURE:
<223> OTHER INFORMATION: cell penetrating peptide

<400> SEQUENCE: 287

```
Thr Pro Thr Val Val Ile Asn Phe Glu Glu Ala Gly Gly Asp Tyr Tyr
1               5                   10                  15

Leu His Pro Ser Leu Lys Thr Arg Lys Arg Lys Arg Lys Tyr Leu
            20                  25                  30
```

<210> SEQ ID NO 288
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 288

```
Thr Pro Thr Val Ile Ile His Thr Glu Asp Phe Ser Gly Asp Tyr Tyr
1               5                   10                  15

Leu His Pro Ser Leu Lys Trp Lys Lys Arg Lys Arg Ala Tyr Leu
            20                  25                  30
```

<210> SEQ ID NO 289
<211> LENGTH: 44
<212> TYPE: PRT
<213> ORGANISM: Artificial Sequence
<220> FEATURE:
<223> OTHER INFORMATION: cell penetrating peptide

<400> SEQUENCE: 289

```
Pro Gln Pro Pro Thr Tyr Glu Gly Pro Ser Ser Gly Val Thr Tyr Tyr
1               5                   10                  15

Leu His Pro Ser Leu Arg Gly Arg Lys Arg Lys Arg Arg Asn Leu His
            20                  25                  30

Val Arg Phe Ser Ile Pro Asp Gly Ile Leu Ala Ser
            35                  40
```

<210> SEQ ID NO 290
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 290

```
Val Met Pro Pro Ile Ile Phe Asp Pro Glu Thr Ser Thr Phe Asp Leu
1               5                   10                  15

His Pro Ser Leu His Arg His Arg Arg Lys Arg Arg His Ile Gly Leu
            20                  25                  30
```

<210> SEQ ID NO 291
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 291

```
Thr His Tyr Val Tyr Ile Asp Gly Gly Asp Phe Tyr Leu Trp Pro Val
1               5                   10                  15

Thr Phe His Phe Ser Arg His Arg Arg Arg Lys Arg Val Ser Tyr Phe
            20                  25                  30
```

```
Phe Ala Asp Gly Thr Leu Ala Leu
        35                  40

<210> SEQ ID NO 292
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 292

Pro Val Val Ile Ile His Thr Phe Asp Thr Ser Gly Asp Phe Tyr Leu
1               5                   10                  15

His Pro Ser Leu Ser Arg Lys Phe Lys Arg Arg Lys Tyr Leu
            20                  25                  30

<210> SEQ ID NO 293
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 293

Pro Thr Val Ile Ile Asp Phe Glu Asp Gly Ser Ala Thr Phe Phe Leu
1               5                   10                  15

His Pro Ser Leu Leu Arg Lys His Lys His Lys His Trp Phe Phe
            20                  25                  30

<210> SEQ ID NO 294
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 294

Pro Glu Ile Val Ile Asp Phe Glu Glu Asn Thr Ala Thr Phe Tyr Leu
1               5                   10                  15

His Pro Ser Leu Leu Arg Lys His Lys His Lys His Trp Phe Phe
            20                  25                  30

<210> SEQ ID NO 295
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 295

Pro Asp Ile Ile Val Asn Leu Glu Glu Asn Thr Ala Thr Phe Phe Leu
1               5                   10                  15

His Pro Ser Leu Leu Arg Lys His Arg His Lys His Trp Phe Phe
            20                  25                  30

<210> SEQ ID NO 296
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 296

Pro Leu Val Ile Ile Asp Pro Val Gly Thr Gly Ala Asn Tyr Phe Leu
1               5                   10                  15
```

```
His Pro Ser Leu Leu Arg Lys Lys Lys Lys Leu Ile Phe His
            20                  25                  30
```

<210> SEQ ID NO 297
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 297

```
Glu Val Val Ile Val Gln Glu Gly Asn Asn Ser Gly Thr Phe Tyr Leu
1               5                   10                  15

His Pro Ser Leu Leu Arg Lys Lys Lys Arg Lys Tyr Val Phe
            20                  25                  30
```

<210> SEQ ID NO 298
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 298

```
Trp Tyr Pro Thr Ile Leu Ser Glu Leu Ser Ser Ser Asp Phe Ile Phe
1               5                   10                  15

His Pro Ser Leu Trp Arg Lys Lys Arg Phe Pro Phe Leu Ser
            20                  25                  30

Asp Gly Ile Val Ala Ala
        35
```

<210> SEQ ID NO 299
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 299

```
Val Ile Val Glu Asp Asp Thr Ala Ala Tyr Asp Tyr Trp Phe Asp Leu
1               5                   10                  15

Tyr Leu His Leu Pro Arg Lys Lys Arg Lys Trp Cys Ser Phe Cys Ser
            20                  25                  30

Leu Thr Asp Gly Ile Val Asp Thr
        35                  40
```

<210> SEQ ID NO 300
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 300

```
Pro Thr Thr His Val Val Val Tyr Gly Gly Asp Phe Tyr Leu His Pro
1               5                   10                  15

Ser Tyr Phe Pro Val Arg Lys Lys Arg Lys Arg Val His Arg Phe Leu
            20                  25                  30

Ser Asp Val Ile Val Ala Ala
        35
```

<210> SEQ ID NO 301

```
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 301

Leu Glu Pro Ala Leu Leu Ser Asp Ile Phe Ser Thr Asp Phe Val Tyr
1               5                   10                  15

Arg Pro Ser Leu Tyr Arg Lys Lys Arg Lys Arg Leu Glu Met Phe
            20                  25                  30

<210> SEQ ID NO 302
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 302

Leu Glu Pro Pro Phe Phe Ser Glu Phe Tyr Ser Ser Asp Phe Val Tyr
1               5                   10                  15

Arg Pro Ser Leu Tyr Arg Lys Lys Arg Lys Arg Ser Asp Ile Phe
            20                  25                  30

<210> SEQ ID NO 303
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 303

Pro Leu Lys Pro Ala Leu Leu Thr Asp Phe Tyr Ser Asp Phe Thr Tyr
1               5                   10                  15

Tyr Pro Ser Leu Tyr Arg Lys Lys Arg Lys Arg Ser Asp Leu Phe
            20                  25                  30

<210> SEQ ID NO 304
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 304

Pro Leu Ile Val Leu Phe Glu Pro Gly Phe Gly Pro Ser Phe Tyr Leu
1               5                   10                  15

His Pro Ser Leu Leu Arg Lys Lys Arg Lys Arg Val Phe Tyr
            20                  25                  30

<210> SEQ ID NO 305
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 305

Pro Phe Ile Phe Phe Leu Phe Ser His Gly Asp Pro Ser Phe Phe Leu
1               5                   10                  15

His Pro Ser Leu Leu Arg Lys Lys Arg Lys Arg Val Phe Tyr
            20                  25                  30
```

```
<210> SEQ ID NO 306
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 306

Arg Pro Ser Ile Leu Ile Asp Asp Phe Ala Ser Asn Asp Phe Val Leu
1               5                   10                  15

His Pro Ser Leu Asn Arg Lys Lys Arg Lys Arg Lys Gln Val His Phe
            20                  25                  30

Leu

<210> SEQ ID NO 307
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 307

Pro Thr Val Val Ile His Ile Asn Asp Thr Ser Gly Asp Tyr Tyr Leu
1               5                   10                  15

His Pro Ser Leu Gln Arg Lys Lys Arg Lys Arg Lys Tyr Leu
            20                  25                  30

<210> SEQ ID NO 308
<211> LENGTH: 42
<212> TYPE: PRT
<213> ORGANISM: Artificial Sequence
<220> FEATURE:
<223> OTHER INFORMATION: cell penetrating peptide

<400> SEQUENCE: 308

Val Gly Pro Ser Tyr Val Glu Ser Thr Asp Ser Phe Pro Tyr Trp Leu
1               5                   10                  15

Ala Pro Ser Leu Gln Arg Lys Lys Arg Lys Arg Lys Thr Val Ser Phe
            20                  25                  30

Cys Ser Leu Ala Asp Gly Cys Met Asp Ser
        35                  40

<210> SEQ ID NO 309
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 309

Ile Asn Trp Phe Pro Leu Phe Asp Ser Tyr Ser Asp Phe Ala Leu Asp
1               5                   10                  15

Pro Phe Phe Ile Pro Arg Lys Lys Arg Arg Leu Asp Ile Leu
            20                  25                  30

<210> SEQ ID NO 310
<211> LENGTH: 42
<212> TYPE: PRT
<213> ORGANISM: Artificial Sequence
<220> FEATURE:
<223> OTHER INFORMATION: cell penetrating peptide

<400> SEQUENCE: 310

Ile Ser Pro Val Phe Ile Phe Glu Gly Asn Ala Asp Gly Thr Tyr Tyr
```

```
                1               5                  10                  15
Leu Glu Glu Pro Leu Arg Lys Lys Arg Arg Lys Ser Ile Phe Leu Leu
                20                  25                  30

Ala Asp Gly Ser Val Ala Val Tyr Ala Glu
                35                  40

<210> SEQ ID NO 311
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 311

Pro Ala Ile Ser Phe Asp Ile Tyr Gly Asp Gly Leu Asn Phe Tyr Leu
1               5                  10                  15

His Pro Ser Leu Leu Arg Lys Lys Arg Arg Lys Arg Tyr Phe Tyr
                20                  25                  30

<210> SEQ ID NO 312
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 312

Ala Pro Ala Val Val Ile His Thr Leu Asp Lys Ser Phe Asp Tyr Tyr
1               5                  10                  15

Leu His Pro Ser Leu Arg Lys Lys Arg Arg Lys Arg Lys Tyr Leu
                20                  25                  30

<210> SEQ ID NO 313
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 313

Thr Pro Ala Phe Tyr Leu Asp Ile Tyr Asn Asp Phe Asn Leu His Pro
1               5                  10                  15

Ala Leu Leu Pro Pro Arg Lys Lys Arg Arg Arg Leu Asp Ile Phe
                20                  25                  30

<210> SEQ ID NO 314
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 314

Leu Thr Pro Ser Ile Ile Thr Ser Ser Tyr Asn Asn Phe Tyr Leu Glu
1               5                  10                  15

Pro Phe Tyr Val Pro Arg Lys Lys Arg Arg Arg Leu Asp Met Phe
                20                  25                  30

<210> SEQ ID NO 315
<211> LENGTH: 30
<212> TYPE: PRT
<213> ORGANISM: Artificial Sequence
<220> FEATURE:
<223> OTHER INFORMATION: cell penetrating peptide
```

```
<400> SEQUENCE: 315

Pro Asn Ile Asn Val Tyr Ser Leu Asp Asp Thr Gly Gly Gln Phe Arg
1               5                  10                  15

Phe Trp His Phe Leu Arg Lys Lys Arg Arg Arg Arg Tyr Leu
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 316

Leu Pro Val Val Ile Ile His Thr Tyr Asp Thr Ser Gly Asp Phe Tyr
1               5                  10                  15

Leu His Pro Ser Leu Arg Lys Arg Phe Lys Arg Lys Arg Lys Tyr Leu
            20                  25                  30

<210> SEQ ID NO 317
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 317

Val Val Val Ile Ser Tyr Thr Ala Asp Val Ser Ile Phe Ser Leu Phe
1               5                  10                  15

Glu Pro Ser Leu Tyr Arg Lys Arg Lys Tyr Ser Tyr Leu Tyr
            20                  25                  30

<210> SEQ ID NO 318
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 318

Pro Glu Ile Val Ile Asp Phe Gly Glu Ser Thr Ala Ser Phe Ser Leu
1               5                  10                  15

His Pro Ser Leu Leu Arg Lys Arg Lys His Lys His Trp Phe Phe
            20                  25                  30

<210> SEQ ID NO 319
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 319

Ile Ile Asp Gly His Thr Val Asp Leu Tyr Ser Ser Asn Tyr Thr Leu
1               5                  10                  15

His Pro Ser Leu Leu Arg Lys Arg Lys Lys Arg Lys His Ala
            20                  25                  30

<210> SEQ ID NO 320
<211> LENGTH: 30
<212> TYPE: PRT
<213> ORGANISM: Artificial Sequence
<220> FEATURE:
```

<223> OTHER INFORMATION: cell penetrating peptide

<400> SEQUENCE: 320

Ile Ile Asp Gly His Thr Val Asp Leu Tyr Ser Asn Asn Tyr Ser Leu
1               5                   10                  15

His Pro Ser Leu Leu Arg Lys Arg Lys Lys Arg Lys His Ala
            20                  25                  30

<210> SEQ ID NO 321
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 321

Ile Ile Asp Gly His Thr Ile Asp Leu Tyr Ser Asn Asn Tyr Ser Leu
1               5                   10                  15

His Pro Ser Leu Leu Arg Lys Arg Lys Lys Arg Lys His Ala
            20                  25                  30

<210> SEQ ID NO 322
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 322

Ile Ile Asp Gly His Ile Val Asp Leu Tyr Ser Arg Asn Tyr Ser Leu
1               5                   10                  15

His Pro Ser Leu Tyr Arg Lys Arg Lys Lys Arg Lys His Ala
            20                  25                  30

<210> SEQ ID NO 323
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 323

Asp Tyr Ser Tyr Asp Gln Ser Ala Gly Pro Ser Phe Thr Leu Asp Pro
1               5                   10                  15

Ser Leu Leu Gln Leu Arg Lys Arg Lys Lys Arg Arg Tyr Tyr
            20                  25                  30

<210> SEQ ID NO 324
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 324

Ser Gly Pro Ile Tyr Ile Tyr Gly Ser Asp Phe Ile Leu His Pro Ser
1               5                   10                  15

Leu Tyr Val Ile Pro Arg Lys Arg Lys Arg Leu Ser Tyr Phe Phe Ala
            20                  25                  30

Asp Val Ala Thr Tyr
        35

<210> SEQ ID NO 325

```
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 325

Thr Gly Asp Val Leu Val His Gly Ser Thr Tyr Tyr Leu Leu Pro Ser
1               5                   10                  15

Tyr Val Leu Leu Pro Arg Lys Arg Lys Arg Phe Pro Ser Phe Phe Ala
            20                  25                  30

Asp Gly Ile Val Glu Ala
        35

<210> SEQ ID NO 326
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 326

Ile Gln Ser Ile Asn Ile Glu Gly Thr Asn Tyr Phe Leu Trp Pro Ile
1               5                   10                  15

Tyr Tyr Phe Leu Pro Arg Lys Arg Lys Arg Val Pro Tyr Phe Phe Thr
            20                  25                  30

Asp Gly Ser Met Ala Phe
        35

<210> SEQ ID NO 327
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 327

Pro Tyr Ala Ile Tyr Ile Gln Gly Ser Asp Tyr Tyr Leu Leu Pro Asn
1               5                   10                  15

Tyr Ile Phe Phe Pro Arg Lys Arg Lys Arg Val His Tyr Ser Phe Ser
            20                  25                  30

Asp Gly Phe Val Ala Ala Trp
        35

<210> SEQ ID NO 328
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 328

Gly Asn Ile Asn Val Ser Met Glu Tyr Phe Arg His Tyr Tyr Leu His
1               5                   10                  15

Pro Ser Leu Leu Gly Arg Lys Arg Lys Arg Leu Phe Gly
            20                  25

<210> SEQ ID NO 329
<211> LENGTH: 30
<212> TYPE: PRT
<213> ORGANISM: Artificial Sequence
<220> FEATURE:
<223> OTHER INFORMATION: cell penetrating peptide
```

```
<400> SEQUENCE: 329

Pro Ser Val Val Asp Ser Phe Val Thr Ser Thr Thr Phe Tyr Leu
1               5                   10                  15

His Pro Gly Leu Ser Arg Lys Arg Lys Arg Ser His Met Phe
                20                  25              30

<210> SEQ ID NO 330
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 330

Gln Pro Ser Phe Ala Ile Asp Val Asp Asn Ser Thr Phe Asp Ile His
1               5                   10                  15

Pro Ser Leu Leu Pro Arg Lys Arg Lys Arg Pro Ser Phe
                20                  25

<210> SEQ ID NO 331
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 331

Leu Gly Pro Ala Val Gly Leu Thr Val Asn Phe Asp Phe Asp Leu
1               5                   10                  15

His Pro Ser Leu Leu Arg Lys Arg Lys Arg Ser Ile Leu
                20                  25

<210> SEQ ID NO 332
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 332

Leu Gly Pro Ser Gln Gly Leu Thr Val Asp Phe Tyr Asp Phe Asp Leu
1               5                   10                  15

His Pro Ser Leu Leu Arg Lys Arg Lys Arg Ser Ile Phe
                20                  25

<210> SEQ ID NO 333
<211> LENGTH: 28
<212> TYPE: PRT
<213> ORGANISM: Artificial Sequence
<220> FEATURE:
<223> OTHER INFORMATION: cell penetrating peptide

<400> SEQUENCE: 333

Pro Leu Ile Thr Ile Arg Ile Asp Asn Ser Thr Gly Asp Tyr Asp Val
1               5                   10                  15

Asp Pro Ser Leu Leu Arg Lys Arg Lys Arg Val Phe
                20                  25

<210> SEQ ID NO 334
<211> LENGTH: 30
<212> TYPE: PRT
<213> ORGANISM: Artificial Sequence
<220> FEATURE:
<223> OTHER INFORMATION: cell penetrating peptide
```

```
<400> SEQUENCE: 334

Ile Ser Pro Ala Phe Trp Asn Met Ser Tyr Ser Thr Phe Tyr Leu His
1               5                   10                  15

Pro Gly Tyr Leu Ala Arg Lys Arg Lys Arg Lys Val Leu Thr
            20                  25                  30

<210> SEQ ID NO 335
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 335

Ile Pro Ala Arg Thr Val Ile Tyr Phe Asp Asp Phe Ala Asp Phe Tyr
1               5                   10                  15

Leu His Pro Ser Leu Arg Lys Arg Lys Arg Lys His Val Ile Arg
            20                  25                  30

<210> SEQ ID NO 336
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 336

Pro Gly Ala Asp Val Val Val Pro Glu Asp Ser Val Asp Tyr Tyr
1               5                   10                  15

Leu His Pro Ser Leu Arg Lys Arg Lys Arg Lys Tyr Val Phe His
            20                  25                  30

<210> SEQ ID NO 337
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 337

Ile Pro Leu Ser Ser Pro Asp Tyr Gly Ser Val Thr Phe Asp Leu His
1               5                   10                  15

Pro Gly Leu Ile His Arg Lys Arg Lys Arg Gly Ser Val
            20                  25                  30

<210> SEQ ID NO 338
<211> LENGTH: 42
<212> TYPE: PRT
<213> ORGANISM: Artificial Sequence
<220> FEATURE:
<223> OTHER INFORMATION: cell penetrating peptide

<400> SEQUENCE: 338

Pro Phe Glu Pro Pro Thr Glu Pro Asp Pro Ala Glu Thr Gly Gly Asn
1               5                   10                  15

Phe Glu Pro Ser Leu Arg Lys Arg Lys Arg Lys Arg Val Glu Val Ala
            20                  25                  30

Ser Arg Thr Tyr Ser Leu Arg Arg Lys Arg
            35                  40

<210> SEQ ID NO 339
<211> LENGTH: 32
```

```
<212> TYPE: PRT
<213> ORGANISM: Artificial Sequence
<220> FEATURE:
<223> OTHER INFORMATION: cell penetrating peptide

<400> SEQUENCE: 339

Thr Pro Ser Ile Leu Val Asp Gly Phe Ser Ser Thr Asp Phe Ile Leu
1               5                   10                  15

His Pro Ser His Thr Arg Lys Arg Lys Arg Lys Arg Ser Asp Tyr Phe
            20                  25                  30

<210> SEQ ID NO 340
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 340

Asp Asn Thr Pro Leu Leu Val Leu Asp Leu Thr Ser Asp Asp Tyr Phe
1               5                   10                  15

Leu His Pro Ser Leu Arg Lys Arg Lys Arg Lys Arg Ser Asp Val Phe
            20                  25                  30

<210> SEQ ID NO 341
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 341

Pro Ala Ile Val Ile Glu Val Trp Ala Ser Gly Ala Thr Tyr Ser Leu
1               5                   10                  15

His Pro Ser Leu Leu Arg Lys Arg Lys Arg Lys Arg Ile Ser Leu
            20                  25                  30

<210> SEQ ID NO 342
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 342

Pro Ala Ile Val Ile Asp Ile Trp Glu Ser Gly Asn Ser Tyr Ser Leu
1               5                   10                  15

His Pro Ser Leu Leu Arg Lys Arg Lys Arg Lys Arg Leu Phe Leu
            20                  25                  30

<210> SEQ ID NO 343
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 343

Ile Pro Ile Val Val Ile His Thr His Asp Ser Ser Gly Asp Phe Tyr
1               5                   10                  15

Leu His Pro Ser Leu Arg Lys Arg Lys Arg Lys Arg Lys Tyr Leu
            20                  25                  30

<210> SEQ ID NO 344
```

<211> LENGTH: 31
<212> TYPE: PRT
<213> ORGANISM: Artificial Sequence
<220> FEATURE:
<223> OTHER INFORMATION: cell penetrating peptide

<400> SEQUENCE: 344

Ala Pro Ser Val Val Phe His Ile Thr Asp Thr Ser Gly Asp Phe Tyr
1               5                   10                  15

Leu His Pro Ser Leu Arg Lys Arg Lys Arg Lys Arg Lys Tyr Leu
            20                  25                  30

<210> SEQ ID NO 345
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 345

Pro Ala Ser Thr Val Ile Ser Val Asp Asp Phe Ala Asp Phe Tyr
1               5                   10                  15

Leu His Pro Ser Leu Arg Lys Arg Lys Arg Lys Tyr Arg Ile Tyr
            20                  25                  30

<210> SEQ ID NO 346
<211> LENGTH: 52
<212> TYPE: PRT
<213> ORGANISM: Artificial Sequence
<220> FEATURE:
<223> OTHER INFORMATION: cell penetrating peptide

<400> SEQUENCE: 346

Ser Val Phe Val Phe Thr Phe Ser Met Asn Gly Leu Phe Asp Leu His
1               5                   10                  15

Pro Ser Leu His Pro Arg Lys Arg Lys Arg Arg Tyr Asn Cys Cys Phe
            20                  25                  30

Ala Asp Gly Phe Leu Asp Asn Glu Gln Thr Thr Pro Val Pro Thr Pro
                35                  40                  45

Gln Ser Arg Leu
        50

<210> SEQ ID NO 347
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 347

Pro Phe Val Ile Val Asp Ser Phe Ile Ser Ser Asp Thr Phe Tyr Leu
1               5                   10                  15

His Pro Ser Leu Val Arg Lys Arg Lys Arg Arg Asp Leu Val
            20                  25                  30

<210> SEQ ID NO 348
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 348

Gln Pro Pro Asp Gly Val Leu Val Asp Asp Asn Asp Tyr Tyr Leu His

```
                 1               5                  10                 15
Pro Gly Leu Tyr Ser Arg Lys Arg Lys Arg Arg Val Leu
                20                 25
```

<210> SEQ ID NO 349
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 349

```
Thr Val Pro Val Leu Glu Tyr Asp Phe Thr Ser Ala Asp Phe Thr Leu
1               5                   10                  15
His Pro Ser Leu Ser Arg Lys Arg Lys Arg Arg Pro Ser Phe
                20                  25                  30
```

<210> SEQ ID NO 350
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 350

```
Asp Thr Pro Val Ile Thr Ile Asp Ile Trp Ser Ser Asp Phe Tyr Leu
1               5                   10                  15
His Pro Ser Leu Ser Arg Lys Arg Lys Arg Arg Lys Phe Val Phe
                20                  25                  30
Val Tyr
```

<210> SEQ ID NO 351
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 351

```
Ile Pro Thr Glu Pro His Lys Lys Gly Lys Pro Ile His Val His Arg
1               5                   10                  15
Lys Arg Arg Cys Ile Lys Arg Arg Gly Lys Arg Cys Val Lys Tyr Ser
                20                  25                  30
Leu
```

<210> SEQ ID NO 352
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 352

```
Pro Thr Gly Pro Val Phe Ile Asn Gly Ser Thr Phe Tyr Leu Tyr Pro
1               5                   10                  15
Ser Trp Tyr Phe Ala Arg Lys Arg Arg Lys His Val Pro Leu Phe Phe
                20                  25                  30
Thr Asp Val Ala Ala
                35
```

<210> SEQ ID NO 353
<211> LENGTH: 39

<212> TYPE: PRT
<213> ORGANISM: Artificial Sequence
<220> FEATURE:
<223> OTHER INFORMATION: cell penetrating peptide

<400> SEQUENCE: 353

Pro Ser Phe Asp Ser Val Met Val Leu Gly Trp Asp Phe Ile Leu His
1               5                   10                  15

Pro Ser Tyr Met Trp Arg Lys Arg Arg Lys Pro Val Pro Tyr Phe Phe
            20                  25                  30

Ala Asp Val Arg Val Ala Ala
        35

<210> SEQ ID NO 354
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 354

Pro Gln Gly His Ile Thr Val Leu Gly Gly Ala Phe Tyr Trp His Pro
1               5                   10                  15

Ser Trp Tyr Thr Ala Arg Lys Arg Arg Lys Leu Val Pro Asn Phe Leu
            20                  25                  30

Ala Asp Val Ser Val Ala Ala
        35

<210> SEQ ID NO 355
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 355

Ile Pro Leu Ile Ile His Leu Asp Asn Ser Thr Gly Asp Tyr Asp
1               5                   10                  15

Leu His Pro Ser Leu Arg Lys Arg Arg Lys Leu Val His Ile
            20                  25                  30

<210> SEQ ID NO 356
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 356

Pro Ile Pro Ala Val Leu Phe Asn Val Leu Ser Ser Asp Leu Leu
1               5                   10                  15

Asp Pro Ser Leu Leu Arg Lys Arg Arg Lys Lys Tyr Gly Val Phe Ser
            20                  25                  30

<210> SEQ ID NO 357
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 357

Pro Thr Ala Arg Ile Ile Val Tyr Gly Gly Asp Phe Tyr Leu His Pro
1               5                   10                  15

Ser Tyr Phe Gly Ile Arg Lys Arg Arg Lys Arg Val His His Ser Phe
                20                  25                  30

Ala Asp Val Phe Val Ala Ala
        35

<210> SEQ ID NO 358
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 358

Ile Pro Ala Ile Ser Val Leu Ile Arg Gly Thr Asp Tyr Tyr Leu Asn
1               5                   10                  15

Pro Ala Tyr Tyr Phe Arg Lys Arg Arg Lys Arg Ile Leu Ala Tyr
                20                  25                  30

<210> SEQ ID NO 359
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 359

Pro Thr Gly Pro Val Phe Ile Thr Ala Ser Gly Phe Tyr Leu Tyr Pro
1               5                   10                  15

Thr Trp Tyr Phe Thr Arg Lys Arg Arg Lys Arg Val Ser Leu Phe Phe
                20                  25                  30

Thr Asp Val Ala Ala
        35

<210> SEQ ID NO 360
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 360

Pro Gln Tyr Thr Ile Ile Ala Asp Ala Gly Asp Phe Tyr Leu His Pro
1               5                   10                  15

Ser Tyr Tyr Met Leu Arg Lys Arg Arg Lys Arg Leu Pro Tyr Phe Phe
                20                  25                  30

Ser Asp Val Ser Leu Ala Ala
        35

<210> SEQ ID NO 361
<211> LENGTH: 36
<212> TYPE: PRT
<213> ORGANISM: Artificial Sequence
<220> FEATURE:
<223> OTHER INFORMATION: cell penetrating peptide

<400> SEQUENCE: 361

Ile Pro Ala Ile Ser Val Leu Ile His Gly Thr Asp Tyr Tyr Leu His
1               5                   10                  15

Pro Ala Tyr Tyr Leu Arg Lys Arg Arg Lys Arg Ile Leu Ala His Gln
                20                  25                  30

Tyr Val Ala Thr
        35

<210> SEQ ID NO 362
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 362

Pro Thr Gly Pro Val Phe Ile Ser Gly Ala Ala Phe Tyr Leu Tyr Pro
1               5                   10                  15

Thr Trp Tyr Phe Ala Arg Lys Arg Lys Arg Val Ser Leu Phe Phe
            20                  25                  30

Ala Asp Val Ala Ala
        35

<210> SEQ ID NO 363
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 363

Thr Lys His Ser Ile Val Ile Leu Gly Gly Asp Tyr Tyr Leu Trp Pro
1               5                   10                  15

Tyr Thr His Leu Leu Arg Lys Arg Arg Lys Arg Ile Pro Tyr Phe Phe
            20                  25                  30

Thr Asp Gly Ile Val Ala His
        35

<210> SEQ ID NO 364
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 364

Pro Gln Thr Pro Ile Ala Val Asn Gly Gly Asp Phe Tyr Leu His Pro
1               5                   10                  15

Ser Tyr Thr Tyr Val Arg Lys Arg Arg Lys Arg Phe Pro Tyr Phe Leu
            20                  25                  30

Ala Asp Gly Tyr Val Ala Ala
        35

<210> SEQ ID NO 365
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 365

Thr Gln His Ala Ile Val Ile Gln Gly Gly Asp Tyr Tyr Leu Trp Pro
1               5                   10                  15

Tyr Thr Tyr Leu Leu Arg Lys Arg Arg Lys Arg Ile Pro Tyr Phe Phe
            20                  25                  30

Ala Asp Gly Phe Val Ala Tyr
        35

<210> SEQ ID NO 366

```
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 366

Pro Thr Ser His Val Val Tyr Gly Gly Asp Phe Tyr Leu His Pro
1               5                   10                  15

Ser Tyr Tyr Thr Ile Arg Lys Arg Arg Lys Arg Val His Arg Phe Leu
            20                  25                  30

Ser Asp Val Leu Val Ala Ala
        35

<210> SEQ ID NO 367
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 367

Pro Ser Ser His Ile Val Val Tyr Gly Gly Asp Phe Tyr Leu His Pro
1               5                   10                  15

Ala Tyr Tyr Pro Thr Arg Lys Arg Arg Lys Arg Met His Arg Phe Leu
            20                  25                  30

Ser Asp Val Leu Val Ala Ala
        35

<210> SEQ ID NO 368
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 368

Pro Ile Thr Pro Ile Phe Ile Ser Gly Ser Gln Phe Tyr Leu His Pro
1               5                   10                  15

Ser Leu Tyr Leu Ala Arg Lys Arg Arg Lys Arg Val Ser Leu Phe Phe
            20                  25                  30

Ala Asp Val Ala Ala
        35

<210> SEQ ID NO 369
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 369

Val Val Pro Ser Met Ser Val Thr Val Phe Ser Gly Asp Tyr Phe Leu
1               5                   10                  15

His Pro Ser Tyr Phe Arg Lys Arg Arg Lys Arg Val Ser Tyr Phe Phe
            20                  25                  30

Ala Asp Gly Ile Val Ala Ala
        35

<210> SEQ ID NO 370
<211> LENGTH: 30
<212> TYPE: PRT
<213> ORGANISM: Artificial Sequence
```

```
<220> FEATURE:
<223> OTHER INFORMATION: cell penetrating peptide

<400> SEQUENCE: 370

Pro Leu Ile Ile Ile Glu Val Leu Asp Gly Ser Gly Asp Tyr Phe Leu
1               5                   10                  15

His Pro Ser Leu Phe Arg Lys Arg Arg Lys Arg Pro Phe Phe
            20                  25                  30

<210> SEQ ID NO 371
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 371

Thr Pro Leu Val Ile Ile Ala Leu Asn Asn Ser Thr Gly Asp Phe Glu
1               5                   10                  15

Leu His Pro Ser Leu Arg Lys Arg Arg Lys Arg Ala Tyr Val
            20                  25                  30

<210> SEQ ID NO 372
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 372

Pro Thr Gly Pro Val Phe Ile Thr Gly Ser Gly Phe Tyr Leu His Pro
1               5                   10                  15

Ala Trp Tyr Phe Ala Arg Lys Arg Arg Lys Arg Ile Pro Leu Phe Phe
            20                  25                  30

Ser Asp Val Ala Ala
        35

<210> SEQ ID NO 373
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 373

Pro Val Val Val Ile His Thr His Asp Thr Ser Gly Asp Phe Tyr Leu
1               5                   10                  15

His Pro Ser Leu Ser Arg Lys Arg Arg Lys Arg Lys Tyr Leu
            20                  25                  30

<210> SEQ ID NO 374
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 374

Val Trp Ile His Thr His Asp Ala Thr Gly Asp Phe Tyr Leu His Pro
1               5                   10                  15

Ser Leu Thr Leu Arg Lys Arg Arg Lys Arg Lys Tyr Leu
            20                  25
```

```
<210> SEQ ID NO 375
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 375

Ile Gly Pro Ser Tyr Asp Val Ala Ala Thr Asn Ser Asp Phe Ile Tyr
1               5                   10                  15

Asp Pro Asp Leu Phe Arg Lys Arg Arg Lys Arg Lys Leu Ser Ala Phe
            20                  25                  30

<210> SEQ ID NO 376
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 376

Leu Lys Pro Ala Leu Gly Leu Tyr Thr Leu Gly Glu Asp Phe Ile Phe
1               5                   10                  15

Asp Pro Asp Leu Phe Arg Lys Arg Arg Lys Arg Lys Tyr Ser Asp Val
            20                  25                  30

<210> SEQ ID NO 377
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 377

Val Val Ile Ile His Thr His Asp Thr Thr Gly Asp Phe Tyr Leu His
1               5                   10                  15

Pro Ser Leu Thr Leu Arg Lys Arg Arg Lys Arg Lys Tyr Leu
            20                  25                  30

<210> SEQ ID NO 378
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 378

Ala Gly Pro Ser Ile Asp Val Gly Asp Val Gly Ile Asp Tyr Phe Leu
1               5                   10                  15

Asp Pro Tyr Leu Phe Arg Lys Arg Arg Lys Arg Lys Arg Phe Phe Ser
            20                  25                  30

Phe Ala Asp Asp His Val Asp Ser
            35                  40

<210> SEQ ID NO 379
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 379

Pro Thr Val Asp Leu Ser Asp Phe Glu Leu Ser Met Thr Phe Asp Leu
1               5                   10                  15
```

His Pro Ser Leu Leu Arg Lys Arg Arg Lys Arg Lys Arg Thr Phe Leu
            20                  25                  30

<210> SEQ ID NO 380
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 380

Arg Pro Pro Ala Leu Gly Gly Phe Pro Gly Thr Asp Tyr Tyr Leu His
1               5                   10                  15

Pro Gly Leu Ser His Arg Lys Arg Arg Lys Arg Arg Pro Phe Trp Phe
            20                  25                  30

Leu Leu

<210> SEQ ID NO 381
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 381

Val Glu Pro Ser Leu Ile Ile Thr Asp Ser His Asp Phe Glu Leu His
1               5                   10                  15

Pro Ala Leu Trp Pro Arg Lys Arg Arg Arg Leu Asp Leu Phe
            20                  25                  30

<210> SEQ ID NO 382
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 382

Ile Leu Pro Gln Tyr Val Ile Glu Thr Phe His Asp Phe Phe Leu Thr
1               5                   10                  15

Pro Asp Leu Tyr Pro Arg Lys Arg Arg Arg Ile Asp Phe Phe
            20                  25                  30

<210> SEQ ID NO 383
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 383

Pro Trp Tyr Ser Ile Ile Glu Arg Asn Phe Ala Asp Phe Val Leu Asp
1               5                   10                  15

Pro Ala Phe Ile Pro Arg Lys Arg Arg Arg Leu Glu Ile Leu
            20                  25                  30

<210> SEQ ID NO 384
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 384

Pro Gly Val Leu Ile Ser Tyr Asp Gly Ser Met Asp Pro Ser Leu Tyr
1               5                   10                  15

Tyr Leu Leu Phe Tyr Arg Lys Arg Arg Leu His Arg Leu Phe Tyr
            20                  25                  30

Arg

<210> SEQ ID NO 385
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 385

Asn Pro Gly Ile Pro Ile Ala Tyr Tyr Asp Asn Leu Asp Pro Ser Leu
1               5                   10                  15

Ile Trp Trp Tyr Leu Arg Lys Arg Arg Leu Gln His Leu Phe Tyr
            20                  25                  30

Arg

<210> SEQ ID NO 386
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 386

Thr His Tyr Val Tyr Ile Asp Gly Gly Asp Tyr Phe Leu Trp Pro Val
1               5                   10                  15

Thr Phe Pro Val Ser Arg Lys Arg Arg Lys Arg Leu Ser Tyr Phe
            20                  25                  30

Leu Ala Asp Gly Phe Val Ala Leu
        35                  40

<210> SEQ ID NO 387
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 387

Thr His Tyr Val Tyr Ile Asp Gly Gly Asn Phe Tyr Leu Trp Pro Val
1               5                   10                  15

Thr Phe Ser Val Ser Arg Lys Arg Arg Lys Arg Leu Ser Tyr Phe
            20                  25                  30

Phe Ala Asp Gly Thr Val Ala Leu
        35                  40

<210> SEQ ID NO 388
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 388

Ile Pro Ser Ile Leu Ile Asp Gly Phe Ser Ser Asp Asp Phe Val Leu
1               5                   10                  15

His Pro Ser His Ser Arg Lys Arg Arg Arg Lys Arg Thr Pro Leu Leu
            20                  25                  30

<210> SEQ ID NO 389
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 389

Ile Pro Val Val Val Ile His Thr His Asp Tyr Ser Gly Asp Phe Tyr
1               5                   10                  15

Leu His Pro Ser Leu Arg Lys Arg Arg Arg Lys Arg Lys Tyr Leu
            20                  25                  30

<210> SEQ ID NO 390
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 390

Thr Val Val Ile His Ile Ser Asp Thr Ser Gly Asp Tyr Tyr Leu His
1               5                   10                  15

Pro Ser Leu Gln Thr Arg Lys Arg Arg Arg Lys Arg Lys Tyr Leu
            20                  25                  30

<210> SEQ ID NO 391
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 391

Pro Pro Thr Val Val Val Gly Ser Phe Gly Gly Val Asp Tyr Ser Leu
1               5                   10                  15

His Pro Ser Leu Leu Arg Lys Arg Arg Arg Arg Arg Lys Arg Tyr Ile
            20                  25                  30

Ser

<210> SEQ ID NO 392
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 392

Leu Val Ile Ala Asp Ile Thr Met Gly Glu Gly Thr Asp Tyr Tyr Leu
1               5                   10                  15

His Pro Ser Leu Thr Arg Lys Arg Arg Arg Arg Arg Arg Arg Ser
            20                  25                  30

Leu

<210> SEQ ID NO 393
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 393

```
Pro Thr Val Val Ile Arg Thr Ser Asp Ser Ser Gly Asp Phe Tyr Leu
1               5                   10                  15

His Pro Ser Leu Leu Arg Leu Lys Arg Lys Arg Lys Tyr Leu
            20                  25                  30
```

<210> SEQ ID NO 394
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 394

```
Glu Pro Leu Pro Pro Ala Ile Val Glu Leu Asp Asn Phe Asp Tyr Asp
1               5                   10                  15

Leu His Pro Ser Leu Arg Leu Lys Arg Lys Arg Lys Arg Thr Asp Leu
            20                  25                  30

Val
```

<210> SEQ ID NO 395
<211> LENGTH: 36
<212> TYPE: PRT
<213> ORGANISM: Artificial Sequence
<220> FEATURE:
<223> OTHER INFORMATION: cell penetrating peptide

<400> SEQUENCE: 395

```
Asn Asp Thr Pro Ala Val Tyr Ile Asp Pro Phe Ser Ala Asp Tyr Tyr
1               5                   10                  15

Leu His Pro Ser Leu Arg Leu Lys Arg Arg Arg Arg Gly Gln Phe
            20                  25                  30

Val Tyr Val Tyr
            35
```

<210> SEQ ID NO 396
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 396

```
Thr Pro Glu Ile Ile Val Thr Phe Leu Asp Ser Ser Tyr Thr Val Ala
1               5                   10                  15

Asp Pro Ser Leu Phe Arg Leu Arg Lys Arg Arg Lys Arg Arg Phe His
            20                  25                  30
```

<210> SEQ ID NO 397
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 397

```
Pro Phe Val Val Leu His Phe Ser Gly Gly Gly Thr Ser Phe Phe Leu
1               5                   10                  15

His Pro Ser Leu Leu Arg Leu Arg Arg Lys Arg Val Phe Tyr
            20                  25                  30
```

<210> SEQ ID NO 398
<211> LENGTH: 40
<212> TYPE: PRT

<213> ORGANISM: Artificial Sequence
<220> FEATURE:
<223> OTHER INFORMATION: cell penetrating peptide

<400> SEQUENCE: 398

Ile Met Phe Pro Gln Ala Ser His Ile Ser Ser Phe Asp Phe Leu Leu
1               5                   10                  15

His Pro Ser Ala Leu Arg Leu Arg Arg Lys Arg Lys Arg Ser Val His
            20                  25                  30

Asp Asp Asp Gly Thr Ile Ile Glu
        35                  40

<210> SEQ ID NO 399
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 399

Pro Leu Pro Pro Thr Phe Val Asp Phe Asp Asn Phe Asp Tyr Asp Ile
1               5                   10                  15

His Pro Gly Leu Leu Arg Arg Lys Lys Arg Lys Arg Thr Asp Leu Val
            20                  25                  30

<210> SEQ ID NO 400
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 400

Lys Pro Thr Val Thr Phe Asp Ala Leu Asp Ile Gly Gly Gly Phe Tyr
1               5                   10                  15

Leu His Pro Tyr Ile Arg Arg Lys Lys Arg Lys Arg Met Tyr Leu
            20                  25                  30

<210> SEQ ID NO 401
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 401

Leu Gln Pro Val Ile Val Val Ser Pro Phe Glu Ser Phe Asp Tyr Asn
1               5                   10                  15

Leu His Pro Ser Leu Arg Arg Lys Lys Arg Lys Arg Pro Tyr Phe Phe
            20                  25                  30

<210> SEQ ID NO 402
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 402

Gly Pro Ala Ile Ile Gln Ser Pro Thr His Ser Ser Phe Asp Tyr Tyr
1               5                   10                  15

Leu His Pro Ser Leu Arg Arg Lys Lys Arg Lys Arg Lys Tyr Leu
            20                  25                  30

```
<210> SEQ ID NO 403
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 403

Leu Thr Pro Ser Phe Ser Ile Asp Val Asn Tyr Ser Asp Tyr Asn Ile
1               5                   10                  15

His Pro Ala Asn Ile Arg Arg Lys Arg Lys His Ser Ser Ser Leu Tyr
            20                  25                  30

Phe

<210> SEQ ID NO 404
<211> LENGTH: 43
<212> TYPE: PRT
<213> ORGANISM: Artificial Sequence
<220> FEATURE:
<223> OTHER INFORMATION: cell penetrating peptide

<400> SEQUENCE: 404

Pro Tyr Ile Val Val Asp Leu Tyr Ser Gly Ser Met Asp Tyr Asp Ile
1               5                   10                  15

His Pro Ser Leu Leu Arg Arg Lys Arg Lys Lys Arg Lys Arg Val Tyr
            20                  25                  30

Phe Ser Asp Gly Arg Val Ala Ser Arg Pro Lys
        35                  40

<210> SEQ ID NO 405
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 405

Ser Asn Ala Ser Asp Thr Thr Ser Asp Phe Ile Ser Val Thr Phe Asp
1               5                   10                  15

Leu His Pro Ser Leu Arg Arg Lys Arg Lys Lys Arg Lys Arg Arg Tyr
            20                  25                  30

Ile

<210> SEQ ID NO 406
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 406

Pro His Gly His Val Val Val Phe Gly Gly Asp Phe Leu Trp His Pro
1               5                   10                  15

Ser Trp Tyr Ser Pro Arg Arg Lys Arg Lys Arg Leu Pro Thr Phe Phe
            20                  25                  30

Ala Asp Val Ser Val Ala Ala
        35

<210> SEQ ID NO 407
<211> LENGTH: 39
<212> TYPE: PRT
<213> ORGANISM: Artificial Sequence
```

```
<220> FEATURE:
<223> OTHER INFORMATION: cell penetrating peptide

<400> SEQUENCE: 407

Pro Gln Gly His Val Tyr Val Ser Gly Gly Asp Phe Leu Trp His Pro
1               5                   10                  15

Ser Leu Tyr Thr Pro Arg Arg Lys Arg Lys Arg Val His Thr Phe Phe
                20                  25                  30

Ala Asp Val Ser Val Ala Ala
                35

<210> SEQ ID NO 408
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 408

Pro Ser Ala His Ile Ile Leu Tyr Gly Gly Asp Phe Tyr Leu His Pro
1               5                   10                  15

Ser Tyr Leu Gly Ile Arg Arg Lys Arg Lys Arg Met His Asn Phe Phe
                20                  25                  30

Ser Asp Val Tyr Val Ala Ala
                35

<210> SEQ ID NO 409
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 409

Pro Ala Val Val Ile His Phe Gly Glu Pro Gly Gly Asp Phe Tyr Leu
1               5                   10                  15

His Pro Asp Leu Gln Arg Arg Lys Arg Lys Arg Ala Tyr Leu
                20                  25                  30

<210> SEQ ID NO 410
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 410

Asp Gly Asn Ile Ile Ile Tyr Ser Thr Tyr Phe Lys His Tyr Tyr Leu
1               5                   10                  15

His Pro Ser Leu Tyr Arg Arg Lys Arg Lys Arg Leu Leu Asp
                20                  25                  30

<210> SEQ ID NO 411
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 411

Asp Gly Ser Ile Ala Leu Ser Leu Glu Tyr Phe Arg His Tyr Tyr Leu
1               5                   10                  15

His Pro Ser Leu Leu Arg Arg Lys Arg Lys Arg Asn Pro Ile Phe Ile
```

```
                   20                  25                  30

<210> SEQ ID NO 412
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 412

Asp Gly Asp Ile Ser Leu Ser Val Glu Tyr Phe Arg His Tyr Tyr Leu
1               5                   10                  15

His Pro Ser Leu Leu Arg Arg Lys Arg Lys Arg Leu Phe Asn
            20                  25                  30

<210> SEQ ID NO 413
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 413

Pro Gly Thr Pro Glu Val Val Ile Asp Ile Tyr Pro His Thr Pro Leu
1               5                   10                  15

Ala Phe Leu His His Arg Arg Lys Arg Lys Arg Gly Ser Ser Val Phe
            20                  25                  30

Phe Ala Asp Val Leu Leu Ala Phe
        35                  40

<210> SEQ ID NO 414
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 414

Pro Ser Ile Leu Ile Asn Glu Ser Ser Ser Asp Asp Phe Val Leu His
1               5                   10                  15

Pro Ser His Ile Pro Arg Arg Lys Arg Lys Arg Ala Tyr Pro Phe
            20                  25                  30

<210> SEQ ID NO 415
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 415

Val Val Pro Gly Phe Asp Ile Asn Val Glu Ala Ser Asp Phe Asn Ile
1               5                   10                  15

His Pro Ser Val Leu Arg Arg Lys Arg Lys Arg Ser Met Phe
            20                  25                  30

<210> SEQ ID NO 416
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 416
```

```
Pro Ser Ile Leu Leu Phe Tyr Pro Asp Ser Ser Pro Ser Phe Tyr Leu
1               5                   10                  15

His Pro Ser Leu Leu Arg Arg Lys Arg Lys Arg Val Phe Tyr
            20                  25                  30
```

<210> SEQ ID NO 417
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 417

```
Pro Ser Ile Leu Ile Asp Glu Phe Ser Ser Asp Phe Val Leu His
1               5                   10                  15

Pro Ser His Ile Pro Arg Arg Lys Arg Lys Arg Ile Asp Ser Leu
            20                  25                  30
```

<210> SEQ ID NO 418
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 418

```
Pro Ala Val Val Ile His Phe Gly Glu Ser Gly Ala Asp Tyr Tyr Leu
1               5                   10                  15

His Pro His Leu Gln Arg Arg Lys Arg Lys Arg Ala Tyr Leu
            20                  25                  30
```

<210> SEQ ID NO 419
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 419

```
Asp Gly Asn Ile Ile Ile Tyr Ser Thr Tyr Leu Arg His Tyr Tyr Leu
1               5                   10                  15

His Pro Ser Leu Tyr Arg Arg Lys Arg Lys Arg Leu Leu Asp
            20                  25                  30
```

<210> SEQ ID NO 420
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 420

```
Pro Val Val Ile Ile His Pro His Asp Ser Thr Gly Asp Phe Tyr Leu
1               5                   10                  15

His Pro Ser Leu His Arg Arg Lys Arg Lys Arg Lys Tyr Leu
            20                  25                  30
```

<210> SEQ ID NO 421
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 421

Asp Asp Pro Asp Ile Thr Leu Ala Ile Phe Gly Thr Asp Phe Tyr Leu
1               5                   10                  15

His Pro Gly Leu Leu Arg Arg Lys Arg Lys Arg Lys Asn Phe Ser Val
            20                  25                  30

<210> SEQ ID NO 422
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 422

Glu Pro Pro Ile Val Val Asp Gly Phe Asp Ala Phe Asp Thr Phe Tyr
1               5                   10                  15

Leu His Pro Ser His Arg Arg Lys Arg Lys Arg Lys Ser Gly Phe
            20                  25                  30

<210> SEQ ID NO 423
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 423

Pro Ser Ile Leu Ile Asp Gly Phe Ser Ser Asp Phe Val Leu His
1               5                   10                  15

Pro Ser His Ile Pro Arg Arg Lys Arg Lys Arg Lys Arg Ser Leu
            20                  25                  30

<210> SEQ ID NO 424
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 424

Asp Asp Thr Leu Asp Thr Phe Gln Asn Tyr Asn Asp Tyr Asp Leu His
1               5                   10                  15

Pro Ser Leu Leu Pro Arg Arg Lys Arg Lys Arg Arg Ile Leu
            20                  25                  30

<210> SEQ ID NO 425
<211> LENGTH: 49
<212> TYPE: PRT
<213> ORGANISM: Artificial Sequence
<220> FEATURE:
<223> OTHER INFORMATION: cell penetrating peptide

<400> SEQUENCE: 425

Asp Val Ile Ile Glu Tyr Pro Glu Ala Gly Gly Ser Tyr Phe Leu His
1               5                   10                  15

Pro Thr Ala Pro Cys Arg Arg Lys Arg Arg Tyr Cys Phe Ala Asp Gly
            20                  25                  30

Leu Leu Asp Ala Gly Gln Ser Glu Val Leu Ser Pro Pro Cys Ala Cys
                35                  40                  45

Tyr

<210> SEQ ID NO 426
<211> LENGTH: 38

```
<212> TYPE: PRT
<213> ORGANISM: Artificial Sequence
<220> FEATURE:
<223> OTHER INFORMATION: cell penetrating peptide

<400> SEQUENCE: 426

Thr Thr Pro His Ala Gly Val Tyr Val Ser Val Asp Phe Trp Leu His
1               5                   10                  15

Pro Gly Leu Leu Ser Arg Arg Lys Arg Arg Phe Pro Phe Leu Phe Thr
            20                  25                  30

Asp Gly Ile Val Ala Ala
        35

<210> SEQ ID NO 427
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 427

Pro Pro Tyr Ile Ile Asp Phe Asn Asp Asn Ser Ala Thr Phe Tyr Leu
1               5                   10                  15

His Pro Ser Leu Ile Arg Arg Lys Arg Lys Arg Lys Arg Ile Phe
            20                  25                  30

Ser

<210> SEQ ID NO 428
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 428

Pro Val Ile Ile Asp Phe Gly Thr Ser Gly Ala Thr Phe Tyr Leu His
1               5                   10                  15

Pro Ser Leu Phe Leu Arg Arg Lys Arg Lys Arg Arg Phe Leu
            20                  25                  30

<210> SEQ ID NO 429
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 429

His Pro Pro Ile Tyr Val Gly Ser Val Pro Gly Val Asp Tyr Tyr Leu
1               5                   10                  15

His Pro Ser Leu Ser Arg Arg Lys Arg Arg Arg His Ser Tyr Leu
            20                  25                  30

<210> SEQ ID NO 430
<211> LENGTH: 34
<212> TYPE: PRT
<213> ORGANISM: Artificial Sequence
<220> FEATURE:
<223> OTHER INFORMATION: cell penetrating peptide

<400> SEQUENCE: 430

Pro Ile Ile Ile Val Asp Val Ala Val Gly Ala Gly Thr Asp Tyr Tyr
1               5                   10                  15
```

Leu His Pro Ser Leu Arg Arg Lys Arg Arg Arg Gly Arg His
            20                  25                  30

Phe Met

<210> SEQ ID NO 431
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 431

Gly Ile Ile Ile Asp Leu Ser Glu Glu Leu Phe Lys His Tyr Tyr Leu
1               5                   10                  15

His Glu Ser Leu Leu Arg Arg Lys Arg Arg Arg Lys Arg Leu Tyr
            20                  25                  30

Ala

<210> SEQ ID NO 432
<211> LENGTH: 35
<212> TYPE: PRT
<213> ORGANISM: Artificial Sequence
<220> FEATURE:
<223> OTHER INFORMATION: cell penetrating peptide

<400> SEQUENCE: 432

Ser Asp Thr Pro Ile Val Thr Leu Asp Ile Trp Ser Asp Phe Tyr
1               5                   10                  15

Leu His Pro Ser Leu Arg Arg Lys Arg Arg Arg Arg Lys Tyr Val
            20                  25                  30

Phe Val Tyr
        35

<210> SEQ ID NO 433
<211> LENGTH: 35
<212> TYPE: PRT
<213> ORGANISM: Artificial Sequence
<220> FEATURE:
<223> OTHER INFORMATION: cell penetrating peptide

<400> SEQUENCE: 433

Pro Arg Pro Asp Val Val Ile Tyr Tyr Tyr Gly Gly Val Asp Tyr Ser
1               5                   10                  15

Leu His Pro Ser Leu Arg Arg Lys Arg Arg Arg Arg Arg Lys Arg
            20                  25                  30

Val Ser Phe
        35

<210> SEQ ID NO 434
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 434

Pro Ile Val Val Ile His Pro His Asp Asn Ser Gly Asp Phe Tyr Leu
1               5                   10                  15

His Pro Ser Leu Thr Arg Arg Leu Arg Arg Lys Arg Lys Tyr Leu
            20                  25                  30

<210> SEQ ID NO 435

```
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 435

Pro Asp Ile Ile Leu Asp Ile Tyr Thr Pro Gly Ser Thr Phe Tyr Leu
1               5                   10                  15

His Pro Ser His Tyr Arg Arg Arg Gly Arg Lys Arg Lys Arg Thr Val
            20                  25                  30

Phe

<210> SEQ ID NO 436
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 436

Pro Leu Val Ile Ile Asp Val Leu Gly Ser Gly Asp Phe Leu Leu His
1               5                   10                  15

Pro Ser Leu Leu Gln Arg Arg Arg Lys Arg Ile Lys Ser Val Phe
            20                  25                  30

<210> SEQ ID NO 437
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 437

Pro Gly Thr Glu Ile Val Phe Ile Pro Glu Asp Ser Ile Asp Phe Tyr
1               5                   10                  15

Leu His Pro Ser Leu Arg Arg Arg Lys Arg Lys Tyr Phe Val Arg
            20                  25                  30

<210> SEQ ID NO 438
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 438

Leu Pro Thr Val Ile Ile His Thr Ala Asp Thr Ser Gly Asp Phe Tyr
1               5                   10                  15

Leu His Pro Ser Leu Arg Arg Arg Lys Arg Lys Arg Thr Tyr Leu
            20                  25                  30

<210> SEQ ID NO 439
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 439

Leu Pro Ala Val Val Ile His Thr Ser Asp Thr Ser Gly Asp Phe Tyr
1               5                   10                  15

Leu His Pro Ser Leu Arg Arg Arg Lys Arg Lys Arg Ala Tyr Leu
            20                  25                  30
```

<210> SEQ ID NO 440
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 440

Leu Pro Ala Val Val Ile His Thr Ser Asp Thr Ser Gly Asp Phe Tyr
1               5                   10                  15

Leu His Pro Ser Leu Arg Arg Arg Lys Arg Lys Arg Ala Tyr Leu
            20                  25                  30

<210> SEQ ID NO 441
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 441

Thr Pro Thr Ile Ile Ile His Thr Glu Asp Phe Ser Gly Asp Tyr Tyr
1               5                   10                  15

Leu His Pro Ser Leu Arg Arg Arg Lys Arg Lys Arg Ala Tyr Leu
            20                  25                  30

<210> SEQ ID NO 442
<211> LENGTH: 41
<212> TYPE: PRT
<213> ORGANISM: Artificial Sequence
<220> FEATURE:
<223> OTHER INFORMATION: cell penetrating peptide

<400> SEQUENCE: 442

Arg Pro Gly Val Gly Leu Val Asp Asn Ala Phe Met Phe Ala Trp Gly
1               5                   10                  15

Pro Gln Tyr Ile Leu Arg Arg Arg Lys Arg Lys Arg Pro Leu Pro Pro
            20                  25                  30

Leu Phe Ala Asp Gly Phe Val Ala Ala
            35                  40

<210> SEQ ID NO 443
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 443

Ile Ile Gln Pro Ala Met Ala Val Asp Val Tyr Asp Asp Phe Tyr Leu
1               5                   10                  15

His Pro His Leu Leu Arg Arg Arg Lys Arg Lys Arg Leu Asp Phe Phe
            20                  25                  30

<210> SEQ ID NO 444
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 444

Pro Ile Gly Pro Ser Ala Ala Leu Asp Val Glu Tyr Tyr Asp Phe Asp

```
1               5                   10                  15
Leu His Pro Ser Leu Arg Arg Arg Lys Arg Lys Arg Asn Met Phe
        20                  25                  30
```

<210> SEQ ID NO 445
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 445

```
Thr Pro Ser Ile Leu Ile Asp Glu Phe Ser Ser Asp Asp Phe Ile Leu
1               5                   10                  15
His Pro Ser His Ile Arg Arg Arg Lys Arg Lys Arg Leu Asn Ser Leu
                20                  25                  30
```

<210> SEQ ID NO 446
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 446

```
Pro Leu Gln Pro Pro Tyr Glu Ala Glu Val Val Phe Asp Thr Phe Asp
1               5                   10                  15
Leu His Pro Ser Leu Arg Arg Arg Lys Arg Lys Arg Ser Ser Phe
                20                  25                  30
```

<210> SEQ ID NO 447
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 447

```
Pro Tyr Ala Pro Pro Leu Leu Tyr Asp Phe Glu Ser His Asp Phe Ile
1               5                   10                  15
Leu His Pro Ser His Arg Arg Arg Lys Arg Lys Arg Ile Ala Met Phe
                20                  25                  30
```

<210> SEQ ID NO 448
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 448

```
Gly Val Asp Ile Asn Val Gly Ser Ile Tyr Pro Ser Val Asp Tyr Tyr
1               5                   10                  15
Leu His Pro Ser Leu Arg Arg Arg Lys Arg Lys Arg Thr Leu His
                20                  25                  30
```

<210> SEQ ID NO 449
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 449

-continued

Gly Thr Thr His Ile Val Gly Ser Glu Phe Ser Val Asp Tyr Tyr
1               5                   10                  15

Leu His Pro Ser Leu Arg Arg Arg Lys Arg Lys Arg Asn Phe His
                20                  25                  30

<210> SEQ ID NO 450
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 450

Leu Pro Val Val Ile Ile His Thr His Asp Asn Ser Gly Asp Phe Phe
1               5                   10                  15

Leu His Pro Ser Leu Arg Arg Arg Lys Arg Lys Arg Lys Tyr Leu
                20                  25                  30

<210> SEQ ID NO 451
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 451

Ile Pro Val Val Val Ile His Thr His Asp Asn Ser Gly Asp Phe Tyr
1               5                   10                  15

Leu His Pro Ser Leu Arg Arg Arg Lys Arg Lys Arg Lys Tyr Leu
                20                  25                  30

<210> SEQ ID NO 452
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 452

Leu Pro Val Val Val Ile His Thr His Asp Asn Ser Gly Asp Phe Tyr
1               5                   10                  15

Leu His Pro Ser Leu Arg Arg Arg Lys Arg Lys Arg Lys Tyr Leu
                20                  25                  30

<210> SEQ ID NO 453
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 453

Gly Pro Ala Ile Val Gln Ser Leu Thr His Thr Ser Leu Asp Tyr Tyr
1               5                   10                  15

Leu His Pro Ser Leu Arg Arg Arg Lys Arg Lys Arg Lys Tyr Leu
                20                  25                  30

<210> SEQ ID NO 454
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 454

Ile Ile Ile Leu Val Asp Ser Pro Asp Thr Ser Gly Val Phe Asp Leu
1               5                   10                  15

His Pro Ser Leu Leu Arg Arg Arg Lys Arg Arg Tyr Met Trp Asn
            20                  25                  30

<210> SEQ ID NO 455
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 455

Val Pro Pro Leu Pro Gly Tyr Ser Asn Tyr Gly Gly Pro Asp Phe Tyr
1               5                   10                  15

Leu His Pro Ser Leu Arg Arg Arg Lys Arg Arg Lys Arg Arg Tyr Leu
            20                  25                  30

Ser Ser Phe Val Phe
        35

<210> SEQ ID NO 456
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 456

Arg Pro His Val Ile Tyr Arg Gly Tyr Asn Gly Thr Asp Tyr Tyr Leu
1               5                   10                  15

His Pro Ser Leu Ser Arg Arg Arg Arg Asn Ser Arg His Ile Tyr Phe
            20                  25                  30

Ser Asp Gly Val Leu Ala Ala
        35

<210> SEQ ID NO 457
<211> LENGTH: 36
<212> TYPE: PRT
<213> ORGANISM: Artificial Sequence
<220> FEATURE:
<223> OTHER INFORMATION: cell penetrating peptide

<400> SEQUENCE: 457

Pro Gly Val Leu Val Gly Tyr Asn Asp Phe Ala Lys Asp Pro Ser Leu
1               5                   10                  15

Tyr Trp Trp Phe Ile Arg Arg Arg Arg Ala Arg Arg Phe His Pro Tyr
            20                  25                  30

Ser Arg Ser Arg
        35

<210> SEQ ID NO 458
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 458

Pro Gln Gly Asn Phe Val Met Val Ser Gly Trp Asp Phe Ile Leu His
1               5                   10                  15

Pro Ser Tyr Phe Trp Arg Arg Arg Arg Lys Pro Val Pro Tyr Phe Phe
            20                  25                  30

Ala Asp Val Arg Val Ala Ala
        35

<210> SEQ ID NO 459
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 459

Pro Ser Ser His Val Val Tyr Gly Gly Asp Phe Tyr Leu His Pro
1               5                   10                  15

Ser Tyr Tyr Pro Val Arg Arg Arg Lys His Met Pro Arg Phe Leu
            20                  25                  30

Ser Asp Val Val Val Ala Ala
        35

<210> SEQ ID NO 460
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 460

Met Ile Pro Trp Ile Ile Ile Gly Thr Gln Gly Ser Asp Tyr Asp Leu
1               5                   10                  15

His Pro Ser Leu Leu Arg Arg Arg Arg Lys Leu Ser Phe Leu
            20                  25                  30

<210> SEQ ID NO 461
<211> LENGTH: 37
<212> TYPE: PRT
<213> ORGANISM: Artificial Sequence
<220> FEATURE:
<223> OTHER INFORMATION: cell penetrating peptide

<400> SEQUENCE: 461

Pro Thr Gly Pro Val Phe Ile Thr Gly Ser Asp Phe Tyr Leu His Pro
1               5                   10                  15

Thr Trp Tyr Phe Ala Arg Arg Arg Arg Lys Arg Ile Pro Leu Phe Phe
            20                  25                  30

Thr Asp Val Ala Ala
        35

<210> SEQ ID NO 462
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 462

Asp Gly Asn Ile Val Ile Tyr Ser Thr Tyr Leu Lys His Tyr Tyr Leu
1               5                   10                  15

His Pro Ser Leu Tyr Arg Arg Arg Arg Lys Arg Leu Leu Asp
            20                  25                  30

<210> SEQ ID NO 463
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 463

Pro Phe Asp Thr Ile Val Val Asp Gly Ala Asp Phe Val Leu His Pro
1               5                   10                  15

Ser Tyr Phe Ile Leu Arg Arg Arg Arg Lys Arg Phe Pro Tyr Phe Phe
            20                  25                  30

Thr Asp Val Arg Val Ala Ala
        35

<210> SEQ ID NO 464
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 464

Pro Ser Thr Ser Ile Ile Val Asp Gly Thr Asp Phe Ile Leu His Pro
1               5                   10                  15

Ser Tyr Phe Leu Leu Arg Arg Arg Arg Lys Arg Phe Pro Tyr Phe Phe
            20                  25                  30

Thr Asp Val Arg Val Ala Ala
        35

<210> SEQ ID NO 465
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 465

Pro Phe Asn Thr Ile Ile Val Asp Gly Ala Asp Phe Met Leu His Pro
1               5                   10                  15

Ser Tyr Phe Ile Leu Arg Arg Arg Arg Lys Arg Phe Pro Tyr Phe Phe
            20                  25                  30

Ala Asp Val Arg Val Ala Ala
        35

<210> SEQ ID NO 466
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 466

Ser Pro Phe Asn Asn Val Leu Val Tyr Gly Ser Asp Phe Ile Leu His
1               5                   10                  15

Pro Ser Tyr Phe Leu Arg Arg Arg Arg Lys Arg Phe Pro Tyr Phe Phe
            20                  25                  30

Ala Asp Val Arg Val Ala Ala
        35

<210> SEQ ID NO 467
<211> LENGTH: 39
<212> TYPE: PRT
<213> ORGANISM: Artificial Sequence
<220> FEATURE:
<223> OTHER INFORMATION: cell penetrating peptide

```
<400> SEQUENCE: 467

His Tyr Val Tyr Val Asp Gly Gly Asp Phe Tyr Leu Trp Pro Ile Thr
1               5                   10                  15

Phe Tyr Val Ser His Arg Arg Arg Lys Arg Val Ser Tyr Phe Phe
                20                  25                  30

Thr Asp Gly Thr Val Ala Thr
            35

<210> SEQ ID NO 468
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 468

Gln Tyr Val Tyr Ile Asp Gly Gly Asp Phe Tyr Leu Trp Pro Val Thr
1               5                   10                  15

Phe Ser Leu Phe Gly Arg Arg Arg Lys Arg Leu Ser Tyr Phe Phe
                20                  25                  30

Ala Asp Gly Thr Val Ala Leu
            35

<210> SEQ ID NO 469
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 469

Pro Ser Ala Asp Ile Ile Val Asn Gly Gly Asp Phe Tyr Leu His Pro
1               5                   10                  15

Ser Tyr Leu Ser Leu Arg Arg Arg Lys Arg Met His Arg Phe Phe
                20                  25                  30

Ala Asp Val Leu Val Ala Ala
            35

<210> SEQ ID NO 470
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 470

Pro Thr Ala His Ile Val Val His Gly Gly Asp Phe Tyr Leu His Pro
1               5                   10                  15

Ser Tyr Leu Tyr Val Arg Arg Arg Lys Arg Leu His His Phe Phe
                20                  25                  30

Thr Asp Val Tyr Val Ala Ala
            35

<210> SEQ ID NO 471
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 471

Gly Gly Asp Arg Glu Val Val Val Asn Met Tyr Pro Tyr Ser Ile Met
```

```
                1               5                  10                 15
Ser Phe Leu His Tyr Arg Arg Arg Lys Arg Gly Tyr Val Tyr Phe
                20                 25                 30
Ser Asp Val Ile Leu Ala Ile
                35
```

<210> SEQ ID NO 472
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 472

```
Pro Glu Phe Pro Glu Ile Val Ile Asp Gly Tyr Gly Leu Ser Ala Leu
1               5                  10                 15
Thr Phe Val Leu His Arg Arg Arg Lys Arg Gly Ser His Leu Tyr
                20                 25                 30
Phe Ser Asp Val Leu Leu Ala Val
                35                 40
```

<210> SEQ ID NO 473
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 473

```
Pro Ala Ile Ile Ile Asp Phe Thr Asp Ser Thr Ala Thr Phe Tyr Leu
1               5                  10                 15
His Pro Ser Leu Met Arg Arg Arg Arg Lys Arg His Ile Phe
                20                 25                 30
```

<210> SEQ ID NO 474
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 474

```
Ala Val Val Ile His Thr Glu Asp Ser Ser Gly Asp Phe Tyr Leu His
1               5                  10                 15
Pro Ser Leu Leu Gln Arg Arg Arg Arg Lys Arg Lys Tyr Leu
                20                 25                 30
```

<210> SEQ ID NO 475
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 475

```
Val Val Ile Ile His Thr Tyr Asp Thr Ser Gly Asp Phe Tyr Leu His
1               5                  10                 15
Pro Ser Leu Thr Thr Arg Arg Arg Arg Lys Arg Lys Tyr Leu
                20                 25                 30
```

<210> SEQ ID NO 476
<211> LENGTH: 30
<212> TYPE: PRT

<213> ORGANISM: Artificial Sequence
<220> FEATURE:
<223> OTHER INFORMATION: cell penetrating peptide

<400> SEQUENCE: 476

Val Val Ile His Val Glu Asp Ser Ser Gly Asp Tyr Tyr Leu His Pro
1               5                   10                  15

Ser Leu Arg Val Thr Arg Arg Arg Lys Arg Lys Tyr Leu
            20                  25                  30

<210> SEQ ID NO 477
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 477

Asp Ala Pro Leu Val Thr Ile Asn Ala Leu Gly Ser Asp Tyr Asp Leu
1               5                   10                  15

His Pro Ser Tyr Leu Arg Arg Arg Lys Arg Lys Tyr Ser Glu Ile
            20                  25                  30

Phe

<210> SEQ ID NO 478
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 478

Gly Thr Ile Thr Pro Ser Phe Ser Phe Asn Asn Ser Gly Asp Phe Val
1               5                   10                  15

Leu His Pro Ser Leu Arg Arg Arg Lys Arg Lys Phe Val Phe
            20                  25                  30

<210> SEQ ID NO 479
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 479

Asp Ile Ile Ile His Asp Val Gly Ser Ser Val Asp Tyr Ile Leu His
1               5                   10                  15

Pro Gly Leu Leu Pro Arg Arg Arg Lys Arg Lys Arg Ser Tyr
            20                  25                  30

<210> SEQ ID NO 480
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 480

Ser Glu Pro Asp Ile Arg Leu Asp Trp Phe Ser Pro Asp Tyr Asp Leu
1               5                   10                  15

His Pro Ser Leu Leu Arg Arg Arg Arg Lys Arg Lys Arg Asn Met Phe
            20                  25                  30

```
<210> SEQ ID NO 481
<211> LENGTH: 46
<212> TYPE: PRT
<213> ORGANISM: Artificial Sequence
<220> FEATURE:
<223> OTHER INFORMATION: cell penetrating peptide

<400> SEQUENCE: 481

Pro Leu Glu Pro Pro Ile Ile Leu Asp Phe Gln Ser Ser Thr Tyr Tyr
1               5                   10                  15

Leu His Pro Ser Leu Arg Arg Arg Arg Lys Arg Lys Arg Ser Asp Ile
            20                  25                  30

Tyr Asp Phe Leu Ser Asp Gly Ser Val Asp Thr Pro Glu Trp
        35                  40                  45

<210> SEQ ID NO 482
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 482

Gly Pro Asp Leu Ile Ile Asn Leu Tyr Gly Asn Asp Tyr Ser Leu His
1               5                   10                  15

Pro Ser Tyr Leu Leu Arg Arg Arg Arg Lys Arg Lys Arg Phe His Val
            20                  25                  30

Leu

<210> SEQ ID NO 483
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 483

Asp Ala Pro Asp Leu Thr Ser Ser Glu Tyr Leu Ser Val Thr Phe Asp
1               5                   10                  15

Leu His Pro Ser Leu Arg Arg Arg Arg Lys Arg Lys Arg Tyr Ile
            20                  25                  30

<210> SEQ ID NO 484
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 484

Pro Ser Val Val Ile Leu Ser Thr Asp Asp Phe Gly Asp Met Phe Arg
1               5                   10                  15

Phe Trp His Leu Leu Arg Arg Arg Arg Lys Arg Lys Arg Tyr Leu
            20                  25                  30

<210> SEQ ID NO 485
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 485

Pro Asp Val Val Ile Tyr Ser Thr Asp Asp Phe Gly Tyr Met Phe Arg
```

```
                1               5                  10                  15
Phe Trp His Phe Leu Arg Arg Arg Arg Lys Arg Arg Tyr Leu
                20                  25                  30

<210> SEQ ID NO 486
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 486

Pro His Val Val Ile Tyr Tyr Thr Asp Asp Tyr Gly Asp Met Phe Arg
1               5                  10                  15

Phe Trp His Leu Leu Arg Arg Arg Arg Lys Arg Arg Tyr Leu
                20                  25                  30

<210> SEQ ID NO 487
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 487

Pro His Val Asn Ile Tyr Tyr Thr Asp Glu Phe Gly Asp Met Phe Arg
1               5                  10                  15

Phe Trp His Phe Leu Arg Arg Arg Arg Lys Arg Arg Tyr Leu
                20                  25                  30

<210> SEQ ID NO 488
<211> LENGTH: 35
<212> TYPE: PRT
<213> ORGANISM: Artificial Sequence
<220> FEATURE:
<223> OTHER INFORMATION: cell penetrating peptide

<400> SEQUENCE: 488

Arg Pro Ala Pro Ser Asp Asp Thr Val Tyr Tyr Ser Ala Gly Val Leu
1               5                  10                  15

Asp Pro Ser Leu Leu Arg Arg Arg Arg Lys Arg Arg Arg Ser Val Ala
                20                  25                  30

Tyr Gly Phe
        35

<210> SEQ ID NO 489
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 489

Asp Thr Thr His Asp Val Val Ile His Gly Ser Thr Phe Ala Leu Trp
1               5                  10                  15

Pro Val Tyr Phe Leu Arg Arg Arg Arg Arg Lys His Val Pro Tyr Phe
                20                  25                  30

Leu Ala Asp Gly Gly Val Ala Ala
        35                  40

<210> SEQ ID NO 490
<211> LENGTH: 40
<212> TYPE: PRT
```

```
<213> ORGANISM: Artificial Sequence
<220> FEATURE:
<223> OTHER INFORMATION: cell penetrating peptide

<400> SEQUENCE: 490

Thr His Tyr Val Tyr Ile Asp Gly Gly Asp Phe Tyr Leu Trp Pro Val
1               5                   10                  15

Thr Phe Phe Leu Pro Arg Arg Arg Arg Lys Arg Val Ser Tyr Phe
            20                  25                  30

Leu Ala Asp Gly Thr Val Ala Leu
        35                  40

<210> SEQ ID NO 491
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 491

Thr His Tyr Val Tyr Ile Asp Gly Gly Asp Phe Tyr Leu Trp Pro Val
1               5                   10                  15

Thr Leu Phe Val Pro Arg Arg Arg Arg Lys Arg Leu Ser Tyr Phe
            20                  25                  30

Leu Ala Asp Gly Thr Val Ala Leu
        35                  40

<210> SEQ ID NO 492
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 492

Asp Val Thr His Asp Val Tyr Ile Gln Gly Ser Ser Phe Ala Leu Trp
1               5                   10                  15

Pro Val Tyr Phe Phe Arg Arg Arg Arg Lys Arg Ile Pro Tyr Phe
            20                  25                  30

Phe Ala Asp Gly Asp Val Ala Ala
        35                  40

<210> SEQ ID NO 493
<211> LENGTH: 29
<212> TYPE: PRT
<213> ORGANISM: Artificial Sequence
<220> FEATURE:
<223> OTHER INFORMATION: cell penetrating peptide

<400> SEQUENCE: 493

Thr His Tyr Val Tyr Ile Asp Gly Gly Asp Phe Tyr Leu Trp Pro Val
1               5                   10                  15

Thr Phe Tyr Leu Ser Arg Arg Arg Arg Lys Arg Val
            20                  25

<210> SEQ ID NO 494
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 494
```

Thr His Tyr Val Tyr Ile Asn Gly Gly Asp Phe Tyr Leu Trp Pro Val
1               5                   10                  15

Thr Phe Pro Leu Ser Arg Arg Arg Arg Lys Arg Val Ser Tyr Phe
            20                  25                  30

Phe Thr Asp Gly Thr Leu Ala Pro
        35                  40

<210> SEQ ID NO 495
<211> LENGTH: 40
<212> TYPE: PRT
<213> ORGANISM: Artificial Sequence
<220> FEATURE:
<223> OTHER INFORMATION: cell penetrating peptide

<400> SEQUENCE: 495

Thr His Tyr Val Tyr Ile Asp Gly Ala Asp Phe Tyr Leu Trp Pro Val
1               5                   10                  15

Ala Leu Phe Val Pro Arg Arg Arg Arg Lys Arg Ile Ser Tyr Phe
            20                  25                  30

Leu Ala Asp Gly Thr Val Ala Leu
        35                  40

<210> SEQ ID NO 496
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 496

Pro Ala Val Val Ile His Thr Tyr Asp Asn Ser Gly Asp Phe Tyr Leu
1               5                   10                  15

His Pro Ser Leu Leu Arg Arg Arg Arg Lys Arg Lys Tyr Leu
            20                  25                  30

<210> SEQ ID NO 497
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 497

Pro Val Val Val Ile His Thr His Asp Asn Ser Gly Asp Phe Tyr Leu
1               5                   10                  15

His Pro Ser Leu Phe Arg Arg Arg Arg Lys Arg Lys Tyr Leu
            20                  25                  30

<210> SEQ ID NO 498
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 498

Pro Arg Val Val Val Phe Tyr Tyr Gly Gly Val Asp Tyr Ser Leu His
1               5                   10                  15

Pro Ser Leu Leu Phe Arg Arg Arg Arg Lys Arg Arg His Ala
            20                  25                  30

Phe

-continued

```
<210> SEQ ID NO 499
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 499

Phe Pro Ser Gly Val Asp Ile Asn Val Thr Asp Pro Ser Leu Tyr Trp
1               5                   10                  15

Leu Arg Trp Trp Leu Arg Arg Arg Arg Arg Gly Tyr Leu Leu Phe
            20                  25                  30

Arg

<210> SEQ ID NO 500
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 500

Pro Thr Val Val Val Gly Tyr Phe Gly Gly Val Asp Tyr Ser Leu His
1               5                   10                  15

Pro Ser Leu Met Phe Arg Arg Arg Arg Arg Lys Arg Tyr Ile Ser
            20                  25                  30

<210> SEQ ID NO 501
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 501

Ser Asp Val Val Ile Tyr Ser Thr Asp Asp Phe Gly Asp Met Phe Arg
1               5                   10                  15

Phe Trp His Phe Leu Arg Arg Arg Arg Arg Arg Tyr Leu
            20                  25                  30

<210> SEQ ID NO 502
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 502

Ile Ile Val Asp Val Ala Ser Gly Ala Gly Thr Asp Tyr Tyr Leu His
1               5                   10                  15

Pro Ser Leu Gln Ala Arg Arg Arg Arg Arg Arg His Phe Met
            20                  25                  30

<210> SEQ ID NO 503
<211> LENGTH: 38
<212> TYPE: PRT
<213> ORGANISM: Artificial Sequence
<220> FEATURE:
<223> OTHER INFORMATION: cell penetrating peptide

<400> SEQUENCE: 503

Ala Pro Val Ser Tyr Gly Gly Leu Val Ser Met Asp Pro Asn Ser Leu
1               5                   10                  15

Phe Trp Phe Leu Leu Arg Arg Arg Arg Arg Arg Arg Thr Thr Lys
```

```
                    20                  25                  30

Arg Ile Leu Leu Asn Arg
            35

<210> SEQ ID NO 504
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 504

Ile Ile Val Asp Val Glu Arg Gly Ser Gly Ser Asp Tyr Tyr Leu His
1               5                   10                  15

Pro Ser Leu Thr Leu Arg Arg Arg Arg Arg Arg Arg Arg Lys Ser Leu
            20                  25                  30

<210> SEQ ID NO 505
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 505

Ile Val Asp Val Ala Arg Gly Pro Ser Ser Asp Tyr Phe Leu His Pro
1               5                   10                  15

Ser Leu Tyr Ala Thr Arg Arg Arg Arg Arg Arg Arg Arg Lys His
            20                  25                  30

Ile

<210> SEQ ID NO 506
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 506

Ile Ile Ile Val Asp Val Ile Gly Ala Ser Gly Ser Asp Tyr Tyr Leu
1               5                   10                  15

His Pro Ala Leu Ser Arg Arg Arg Arg Arg Arg Arg Arg Arg Ser
            20                  25                  30

Leu

<210> SEQ ID NO 507
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 507

Val Ile Ile Val Asp Val Ser Val Gly Ser Ser Thr Asp Tyr Tyr Leu
1               5                   10                  15

His Pro Ser Leu Ala Arg Arg Arg Arg Arg Arg Arg Arg Arg Ser
            20                  25                  30

Leu

<210> SEQ ID NO 508
<211> LENGTH: 33
<212> TYPE: PRT
```

```
<213> ORGANISM: Artificial Sequence
<220> FEATURE:
<223> OTHER INFORMATION: cell penetrating peptide

<400> SEQUENCE: 508

Ile Ile Ile Val Asp Ile Ile Gly Gly Ala Gly Ser Asp Tyr Tyr Leu
1               5                   10                  15

His Pro Ser Leu Ser Arg Arg Arg Arg Arg Arg Arg Arg Arg Arg Ser
            20                  25                  30

Gln

<210> SEQ ID NO 509
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 509

Ala Pro Ala Val Val Ile His Val Glu Asp Ser Ser Gly Asp Phe Tyr
1               5                   10                  15

Leu His Pro Ser Leu Arg Ser Lys Lys Arg Lys Arg Lys Tyr Leu
            20                  25                  30

<210> SEQ ID NO 510
<211> LENGTH: 32
<212> TYPE: PRT
<213> ORGANISM: Artificial Sequence
<220> FEATURE:
<223> OTHER INFORMATION: cell penetrating peptide

<400> SEQUENCE: 510

Pro Ser Ser Leu Gln Pro Thr Asn Tyr Phe Asp Tyr Trp Gln Leu Phe
1               5                   10                  15

Glu Pro Ser Leu Trp Arg Ser Arg Lys Arg Lys Arg Asn Val Tyr Tyr
            20                  25                  30

<210> SEQ ID NO 511
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 511

Ile Pro Ala Val Ile Val His Ile Ile Asp Thr Ser Phe Asp Tyr Tyr
1               5                   10                  15

Leu His Pro Ser Leu Arg Thr Lys Arg Arg Lys Arg Lys Tyr Leu
            20                  25                  30

<210> SEQ ID NO 512
<211> LENGTH: 39
<212> TYPE: PRT
<213> ORGANISM: Artificial Sequence
<220> FEATURE:
<223> OTHER INFORMATION: cell penetrating peptide

<400> SEQUENCE: 512

Pro Tyr Trp Pro Gly Glu Gly Trp Pro Pro His Phe Glu Phe Ser
1               5                   10                  15

Asp Pro Ser Leu Tyr Arg Val Lys Lys Arg Arg Trp Asp Asp Cys Ile
            20                  25                  30

Ala Ile Met Ile Thr Val Thr
```

<210> SEQ ID NO 513
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 513

Val Pro Ala Val Ile Val His Ile Thr Asp Thr Ser Gly Asp Phe Tyr
1               5                   10                  15

Leu His Pro Ser Leu Arg Trp Lys Lys Arg Lys Arg Lys Tyr Leu
            20                  25                  30

<210> SEQ ID NO 514
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 514

Thr Pro Val Val Val Ile His Thr Glu Asp Asn Thr Gly Asp Phe Tyr
1               5                   10                  15

Leu His Pro Ser Leu Arg Trp Arg Lys Arg Lys Arg His Tyr Leu
            20                  25                  30

<210> SEQ ID NO 515
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 515

Ile Pro Val Val Ile His Thr His Asp Asn Thr Gly Asp Phe Tyr
1               5                   10                  15

Leu His Pro Ser Leu Arg Trp Arg Lys Arg Lys Arg Lys Tyr Leu
            20                  25                  30

<210> SEQ ID NO 516
<211> LENGTH: 33
<212> TYPE: PRT
<213> ORGANISM: Artificial Sequence
<220> FEATURE:
<223> OTHER INFORMATION: cell penetrating peptide

<400> SEQUENCE: 516

Gly Gln Pro Ser Leu Leu Trp Asp Pro Ser Thr Gly Thr Phe Asp Leu
1               5                   10                  15

His Pro Gly Leu Leu Arg Trp Arg Arg Lys Arg Arg Arg His Asp
            20                  25                  30

Leu

<210> SEQ ID NO 517
<211> LENGTH: 31
<212> TYPE: PRT
<213> ORGANISM: Artificial Sequence
<220> FEATURE:
<223> OTHER INFORMATION: cell penetrating peptide

<400> SEQUENCE: 517

Ile Pro Thr Val Val Ile His Val Ala Asp Ser Ser Gly Asp Phe Tyr

```
              1               5                  10                 15
            Leu His Pro Ser Leu Arg Trp Arg Arg Arg Lys Arg Lys Tyr Leu
                            20                 25                 30
```

<210> SEQ ID NO 518
<211> LENGTH: 473
<212> TYPE: PRT
<213> ORGANISM: Artificial Sequence
<220> FEATURE:
<223> OTHER INFORMATION: minor capsid protein of a papillomavirus

<400> SEQUENCE: 518

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
```

340                 345                 350
Ser His Ala Ala Ser Pro Thr Ser Ile Asn Asn Gly Leu Tyr Asp Ile
            355                 360                 365

Tyr Ala Asp Asp Phe Ile Thr Asp Thr Ser Thr Thr Pro Val Pro Ser
370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
            405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
            435                 440                 445

His Pro Ser Tyr Tyr Met Leu Arg Lys Arg Arg Lys Arg Leu Pro Tyr
        450                 455                 460

Phe Phe Ser Asp Val Ser Leu Ala Ala
465                 470

<210> SEQ ID NO 519
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 519

Arg Lys Lys Arg Arg Gln Arg Arg Arg
1               5                   10

<210> SEQ ID NO 520
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 520

Pro Leu Ser Ser Ile Phe Ser Arg Ile Asp Gly
1               5                   10

<210> SEQ ID NO 521
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 521

Ala Ala Val Leu Leu Pro Val Leu Leu Ala Ala Pro
1               5                   10

<210> SEQ ID NO 522
<211> LENGTH: 10
<212> TYPE: PRT
<213> ORGANISM: Artificial Sequence
<220> FEATURE:
<223> OTHER INFORMATION: nuclear export signal (NES) sequence

<400> SEQUENCE: 522

Leu Pro Pro Leu Glu Arg Leu Thr Leu Asp
1               5                   10

```
<210> SEQ ID NO 523
<211> LENGTH: 16
<212> TYPE: PRT
<213> ORGANISM: Artificial Sequence
<220> FEATURE:
<223> OTHER INFORMATION: GFP11

<400> SEQUENCE: 523

Arg Asp His Met Val Leu His Glu Tyr Val Asn Ala Ala Gly Ile Thr
1               5                   10                  15

<210> SEQ ID NO 524
<211> LENGTH: 5
<212> TYPE: PRT
<213> ORGANISM: Artificial Sequence
<220> FEATURE:
<223> OTHER INFORMATION: linker sequence

<400> SEQUENCE: 524

Gly Gly Ser Gly Gly
1               5

<210> SEQ ID NO 525
<211> LENGTH: 171
<212> TYPE: PRT
<213> ORGANISM: Artificial Sequence
<220> FEATURE:
<223> OTHER INFORMATION: GFP11-CD8-CIMPR

<400> SEQUENCE: 525

Met Ala Leu Pro Val Thr Ala Leu Leu Leu Pro Leu Ala Leu Leu Leu
1               5                   10                  15

His Ala Ala Arg Pro Arg Asp His Met Val Leu His Glu Tyr Val Asn
                20                  25                  30

Ala Ala Gly Ile Thr Gly Gly Ser Gly Gly Arg Asp His Met Val Leu
            35                  40                  45

His Glu Tyr Val Asn Ala Ala Gly Ile Thr Gly Gly Ser Gly Gly Arg
    50                  55                  60

Asp His Met Val Leu His Glu Tyr Val Asn Ala Ala Gly Ile Thr Gly
65                  70                  75                  80

Gly Ser Gly Gly Arg Asp His Met Val Leu His Glu Tyr Val Asn Ala
                85                  90                  95

Ala Gly Ile Thr Gly Gly Ser Gly Gly Arg Asp His Met Val Leu His
            100                 105                 110

Glu Tyr Val Asn Ala Ala Gly Ile Thr Gly Gly Ser Gly Gly Arg Asp
        115                 120                 125

His Met Val Leu His Glu Tyr Val Asn Ala Ala Gly Ile Thr Gly Gly
    130                 135                 140

Ser Gly Gly Arg Asp His Met Val Leu His Glu Tyr Val Asn Ala Ala
145                 150                 155                 160

Gly Ile Thr Gly Gly Lys Ser Gln Phe Arg Val
                165                 170

<210> SEQ ID NO 526
<211> LENGTH: 161
<212> TYPE: PRT
<213> ORGANISM: Artificial Sequence
<220> FEATURE:
<223> OTHER INFORMATION: CD8-CIMPR-GFP11

<400> SEQUENCE: 526

Asp Asp Ser Asp Glu Asp Leu Leu His Val Gly Ser Ser Gly Ser Ser
```

```
                1               5                  10                  15
Arg Asp His Met Val Leu His Glu Tyr Val Asn Ala Ala Gly Ile Thr
                                20                  25                  30
Gly Gly Ser Gly Gly Arg Asp His Met Val Leu His Glu Tyr Val Asn
                35                  40                  45
Ala Ala Gly Ile Thr Gly Gly Ser Gly Gly Arg Asp His Met Val Leu
        50                  55                  60
His Glu Tyr Val Asn Ala Ala Gly Ile Thr Gly Gly Ser Gly Gly Arg
65                  70                  75                  80
Asp His Met Val Leu His Glu Tyr Val Asn Ala Ala Gly Ile Thr Gly
                        85                  90                  95
Gly Ser Gly Gly Arg Asp His Met Val Leu His Glu Tyr Val Asn Ala
                100                 105                 110
Ala Gly Ile Thr Gly Gly Ser Gly Gly Arg Asp His Met Val Leu His
            115                 120                 125
Glu Tyr Val Asn Ala Ala Gly Ile Thr Gly Gly Ser Gly Gly Arg Asp
        130                 135                 140
His Met Val Leu His Glu Tyr Val Asn Ala Ala Gly Ile Thr Gly Gly
145                 150                 155                 160
Lys

<210> SEQ ID NO 527
<211> LENGTH: 174
<212> TYPE: PRT
<213> ORGANISM: Artificial Sequence
<220> FEATURE:
<223> OTHER INFORMATION: L2-GFP11-CPP

<400> SEQUENCE: 527

Phe Tyr Leu His Pro Ser Tyr Tyr Met Leu Arg Asp His Met Val Leu
1               5                   10                  15
His Glu Tyr Val Asn Ala Ala Gly Ile Thr Gly Gly Ser Gly Gly Arg
                20                  25                  30
Asp His Met Val Leu His Glu Tyr Val Asn Ala Ala Gly Ile Thr Gly
            35                  40                  45
Gly Ser Gly Gly Arg Asp His Met Val Leu His Glu Tyr Val Asn Ala
    50                  55                  60
Ala Gly Ile Thr Gly Gly Ser Gly Gly Arg Asp His Met Val Leu His
65                  70                  75                  80
Glu Tyr Val Asn Ala Ala Gly Ile Thr Gly Gly Ser Gly Gly Arg Asp
                85                  90                  95
His Met Val Leu His Glu Tyr Val Asn Ala Ala Gly Ile Thr Gly Gly
            100                 105                 110
Ser Gly Gly Arg Asp His Met Val Leu His Glu Tyr Val Asn Ala Ala
        115                 120                 125
Gly Ile Thr Gly Gly Ser Gly Gly Arg Asp His Met Val Leu His Glu
    130                 135                 140
Tyr Val Asn Ala Ala Gly Ile Thr Gly Gly Lys Phe Arg Lys Arg Arg
145                 150                 155                 160
Lys Arg Leu Pro Tyr Phe Phe Ser Asp Val Ser Leu Ala Ala
                165                 170

<210> SEQ ID NO 528
<211> LENGTH: 180
<212> TYPE: PRT
<213> ORGANISM: Artificial Sequence
```

<220> FEATURE:
<223> OTHER INFORMATION: L2-CPP-GFP11

<400> SEQUENCE: 528

```
Tyr Tyr Met Leu Arg Lys Arg Arg Lys Arg Leu Pro Tyr Phe Phe Ser
1               5                   10                  15

Asp Val Ser Leu Ala Ala Asp Ala Ser Gly Ser Ser Gly Ser Ser Arg
            20                  25                  30

Asp His Met Val Leu His Glu Tyr Val Asn Ala Ala Gly Ile Thr Gly
        35                  40                  45

Gly Ser Gly Gly Arg Asp His Met Val Leu His Glu Tyr Val Asn Ala
    50                  55                  60

Ala Gly Ile Thr Gly Gly Ser Gly Gly Arg Asp His Met Val Leu His
65                  70                  75                  80

Glu Tyr Val Asn Ala Ala Gly Ile Thr Gly Gly Ser Gly Gly Arg Asp
                85                  90                  95

His Met Val Leu His Glu Tyr Val Asn Ala Ala Gly Ile Thr Gly Gly
            100                 105                 110

Ser Gly Gly Arg Asp His Met Val Leu His Glu Tyr Val Asn Ala Ala
        115                 120                 125

Gly Ile Thr Gly Gly Ser Gly Gly Arg Asp His Met Val Leu His Glu
    130                 135                 140

Tyr Val Asn Ala Ala Gly Ile Thr Gly Gly Ser Gly Gly Arg Asp His
145                 150                 155                 160

Met Val Leu His Glu Tyr Val Asn Ala Ala Gly Ile Thr Gly Gly Lys
                165                 170                 175

Phe Pro Arg Leu
            180
```

<210> SEQ ID NO 529
<211> LENGTH: 6
<212> TYPE: PRT
<213> ORGANISM: Artificial Sequence
<220> FEATURE:
<223> OTHER INFORMATION: synthetic peptide

<400> SEQUENCE: 529

```
Arg Lys Arg Arg Lys Arg
1               5
```

<210> SEQ ID NO 530
<211> LENGTH: 27
<212> TYPE: PRT
<213> ORGANISM: Artificial Sequence
<220> FEATURE:
<223> OTHER INFORMATION: synthetic peptide

<400> SEQUENCE: 530

```
Pro Gln Tyr Thr Ile Ile Ala Asp Ala Gly Asp Phe Tyr Leu His Pro
1               5                   10                  15

Ser Tyr Tyr Met Leu Arg Lys Arg Arg Lys Arg
            20                  25
```

<210> SEQ ID NO 531
<211> LENGTH: 39
<212> TYPE: PRT
<213> ORGANISM: Artificial Sequence
<220> FEATURE:
<223> OTHER INFORMATION: synthetic peptide

<400> SEQUENCE: 531

```
Pro Gln Tyr Thr Ile Ile Ala Asp Ala Gly Asp Phe Tyr Leu His Pro
1               5                   10                  15

Ser Tyr Tyr Met Leu Arg Lys Arg Arg Lys Arg Leu Pro Tyr Phe Phe
                20                  25                  30

Ser Asp Val Ser Leu Ala Ala
                35

<210> SEQ ID NO 532
<211> LENGTH: 31
<212> TYPE: PRT
<213> ORGANISM: Artificial Sequence
<220> FEATURE:
<223> OTHER INFORMATION: synthetic peptide

<400> SEQUENCE: 532

Ile Pro Val Val Ile Ile His Pro His Asp Ser Thr Gly Asp Phe Tyr
1               5                   10                  15

Leu His Pro Ser Leu His Arg Arg Lys Arg Lys Arg Lys Tyr Leu
                20                  25                  30

<210> SEQ ID NO 533
<211> LENGTH: 28
<212> TYPE: PRT
<213> ORGANISM: Artificial Sequence
<220> FEATURE:
<223> OTHER INFORMATION: synthetic peptide

<400> SEQUENCE: 533

Ser Pro Gln Tyr Thr Ile Ile Ala Asp Ala Gly Asp Phe Tyr Leu His
1               5                   10                  15

Pro Ser Tyr Tyr Met Leu Arg Lys Arg Arg Lys Arg
                20                  25

<210> SEQ ID NO 534
<211> LENGTH: 19
<212> TYPE: DNA
<213> ORGANISM: Artificial Sequence
<220> FEATURE:
<223> OTHER INFORMATION: primer

<400> SEQUENCE: 534
gcacccagag catgagaat                                                   19

<210> SEQ ID NO 535
<211> LENGTH: 19
<212> TYPE: DNA
<213> ORGANISM: Artificial Sequence
<220> FEATURE:
<223> OTHER INFORMATION: primer

<400> SEQUENCE: 535
tcgtaggtgg tggttctct                                                   19

<210> SEQ ID NO 536
<211> LENGTH: 20
<212> TYPE: DNA
<213> ORGANISM: Artificial Sequence
<220> FEATURE:
<223> OTHER INFORMATION: primer

<400> SEQUENCE: 536
aatgtttcag gacccacagg                                                  20
```

```
<210> SEQ ID NO 537
<211> LENGTH: 21
<212> TYPE: DNA
<213> ORGANISM: Artificial Sequence
<220> FEATURE:
<223> OTHER INFORMATION: primer

<400> SEQUENCE: 537
ctcacgtcgc agtaactgtt g                                              21

<210> SEQ ID NO 538
<211> LENGTH: 22
<212> TYPE: DNA
<213> ORGANISM: Artificial Sequence
<220> FEATURE:
<223> OTHER INFORMATION: primer

<400> SEQUENCE: 538
ctgctgtcac cttcaccgtt cc                                             22

<210> SEQ ID NO 539
<211> LENGTH: 20
<212> TYPE: DNA
<213> ORGANISM: Artificial Sequence
<220> FEATURE:
<223> OTHER INFORMATION: primer

<400> SEQUENCE: 539
agtactccgt gtggatcggc                                                20

<210> SEQ ID NO 540
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 540

Ala Asp Ala Gly Asp Phe Tyr Leu His Pro Ser Tyr Tyr Met Leu Arg
1               5                   10                  15

Lys Arg Arg Lys Arg Leu Pro Tyr Phe Phe Ser Asp Val Ser Leu Ala
            20                  25                  30

Ala

<210> SEQ ID NO 541
<211> LENGTH: 22
<212> TYPE: PRT
<213> ORGANISM: Artificial Sequence
<220> FEATURE:
<223> OTHER INFORMATION: C-terminus of the L2 protein of HPV

<400> SEQUENCE: 541

Asp Ser Thr Gly Asp Phe Tyr Leu His Pro Ser Leu His Arg Arg Lys
1               5                   10                  15

Arg Lys Arg Lys Tyr Leu
            20

<210> SEQ ID NO 542
<211> LENGTH: 31
<212> TYPE: PRT
<213> ORGANISM: Artificial Sequence
<220> FEATURE:
<223> OTHER INFORMATION: C-terminus of the L2 protein of HPV

<400> SEQUENCE: 542
```

Ile Thr Gly Ser Gly Phe Tyr Leu His Pro Ala Trp Tyr Phe Ala Arg
1               5                   10                  15

Lys Arg Arg Lys Arg Ile Pro Leu Phe Phe Ser Asp Val Ala Ala
                20                  25                  30

<210> SEQ ID NO 543
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 543

Ile His Gly Thr His Tyr Tyr Leu Trp Pro Leu Tyr Tyr Phe Ile Pro
1               5                   10                  15

Lys Lys Arg Lys Arg Val Pro Tyr Phe Phe Ala Asp Gly Phe Val Ala
                20                  25                  30

Ala

<210> SEQ ID NO 544
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 544

Val Asp Gly Ala Asp Phe Val Leu His Pro Ser Tyr Phe Ile Leu Arg
1               5                   10                  15

Arg Arg Arg Lys Arg Phe Pro Tyr Phe Phe Thr Asp Val Arg Val Ala
                20                  25                  30

Ala

<210> SEQ ID NO 545
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 545

Ala Asp Ala Gly Asp Phe Tyr Leu His Pro Ser Tyr Tyr Met Leu Arg
1               5                   10                  15

Lys Arg Arg Lys Arg Leu Pro Tyr Phe Phe Ser Asp Val Ser Leu Ala
                20                  25                  30

Ala

<210> SEQ ID NO 546
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 546

Ala Asp Ala Gly Asp Phe Tyr Leu His Pro Ser Tyr Tyr Met Leu Ala
1               5                   10                  15

Ala Ala Ala Ala Ala Leu Pro Tyr Phe Phe Ser Asp Val Ser Leu Ala
                20                  25                  30

Ala

```
<210> SEQ ID NO 547
<211> LENGTH: 36
<212> TYPE: PRT
<213> ORGANISM: Artificial Sequence
<220> FEATURE:
<223> OTHER INFORMATION: C-terminus of the L2 protein of HPV

<400> SEQUENCE: 547

Ala Asp Ala Gly Asp Phe Tyr Leu His Pro Ser Tyr Tyr Met Leu Arg
1               5                   10                  15

Lys Lys Arg Arg Gln Arg Arg Arg Leu Pro Tyr Phe Phe Ser Asp Val
            20                  25                  30

Ser Leu Ala Ala
        35

<210> SEQ ID NO 548
<211> LENGTH: 39
<212> TYPE: PRT
<213> ORGANISM: Artificial Sequence
<220> FEATURE:
<223> OTHER INFORMATION: C-terminus of the L2 protein of HPV

<400> SEQUENCE: 548

Ala Asp Ala Gly Asp Phe Tyr Leu His Pro Ser Tyr Tyr Met Leu Pro
1               5                   10                  15

Leu Ser Ser Ile Phe Ser Arg Ile Gly Asp Pro Leu Pro Tyr Phe Phe
            20                  25                  30

Ser Asp Val Ser Leu Ala Ala
        35

<210> SEQ ID NO 549
<211> LENGTH: 39
<212> TYPE: PRT
<213> ORGANISM: Artificial Sequence
<220> FEATURE:
<223> OTHER INFORMATION: C-terminus of the L2 protein of HPV

<400> SEQUENCE: 549

Ala Asp Ala Gly Asp Phe Tyr Leu His Pro Ser Tyr Tyr Met Leu Ala
1               5                   10                  15

Ala Val Leu Leu Pro Val Leu Leu Ala Ala Pro Leu Pro Tyr Phe Phe
            20                  25                  30

Ser Asp Val Ser Leu Ala Ala
        35

<210> SEQ ID NO 550
<211> LENGTH: 30
<212> TYPE: PRT
<213> ORGANISM: Artificial Sequence
<220> FEATURE:
<223> OTHER INFORMATION: C-terminus of the L2 protein of HPV

<400> SEQUENCE: 550

Ala Asp Ala Gly Asp Phe Tyr Leu His Pro Ser Tyr Tyr Met Leu Arg
1               5                   10                  15

Arg Arg Leu Pro Tyr Phe Phe Ser Asp Val Ser Leu Ala Ala
            20                  25                  30

<210> SEQ ID NO 551
<211> LENGTH: 31
<212> TYPE: PRT
<213> ORGANISM: Artificial Sequence
<220> FEATURE:
<223> OTHER INFORMATION: C-terminus of the L2 protein of HPV
```

```
<400> SEQUENCE: 551

Ala Asp Ala Gly Asp Phe Tyr Leu His Pro Ser Tyr Tyr Met Leu Arg
1               5                   10                  15

Arg Arg Arg Leu Pro Tyr Phe Phe Ser Asp Val Ser Leu Ala Ala
            20                  25                  30

<210> SEQ ID NO 552
<211> LENGTH: 32
<212> TYPE: PRT
<213> ORGANISM: Artificial Sequence
<220> FEATURE:
<223> OTHER INFORMATION: C-terminus of the L2 protein of HPV

<400> SEQUENCE: 552

Ala Asp Ala Gly Asp Phe Tyr Leu His Pro Ser Tyr Tyr Met Leu Arg
1               5                   10                  15

Arg Arg Arg Arg Leu Pro Tyr Phe Phe Ser Asp Val Ser Leu Ala Ala
            20                  25                  30

<210> SEQ ID NO 553
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 553

Ala Asp Ala Gly Asp Phe Tyr Leu His Pro Ser Tyr Tyr Met Leu Arg
1               5                   10                  15

Arg Arg Arg Arg Arg Leu Pro Tyr Phe Phe Ser Asp Val Ser Leu Ala
            20                  25                  30

Ala

<210> SEQ ID NO 554
<211> LENGTH: 34
<212> TYPE: PRT
<213> ORGANISM: Artificial Sequence
<220> FEATURE:
<223> OTHER INFORMATION: C-terminus of the L2 protein of HPV

<400> SEQUENCE: 554

Ala Asp Ala Gly Asp Phe Tyr Leu His Pro Ser Tyr Tyr Met Leu Arg
1               5                   10                  15

Arg Arg Arg Arg Arg Arg Leu Pro Tyr Phe Phe Ser Asp Val Ser Leu
            20                  25                  30

Ala Ala

<210> SEQ ID NO 555
<211> LENGTH: 33
<212> TYPE: PRT
<213> ORGANISM: Artificial Sequence
<220> FEATURE:
<223> OTHER INFORMATION: C-terminus of the L2 protein of HPV

<400> SEQUENCE: 555

Ala Asp Ala Gly Asp Phe Tyr Leu His Pro Ser Tyr Tyr Met Leu Lys
1               5                   10                  15

Lys Lys Lys Lys Lys Leu Pro Tyr Phe Phe Ser Asp Val Ser Leu Ala
            20                  25                  30

Ala
```

<210> SEQ ID NO 556
<211> LENGTH: 28
<212> TYPE: PRT
<213> ORGANISM: Artificial Sequence
<220> FEATURE:
<223> OTHER INFORMATION: synthetic peptide

<400> SEQUENCE: 556

Ser Pro Gln Tyr Thr Ile Ile Ala Asp Ala Gly Asp Phe Tyr Leu His
1               5                   10                  15

Pro Ser Tyr Tyr Met Leu Ala Ala Ala Ala Ala Ala
            20                  25

<210> SEQ ID NO 557
<211> LENGTH: 25
<212> TYPE: PRT
<213> ORGANISM: Artificial Sequence
<220> FEATURE:
<223> OTHER INFORMATION: synthetic peptide

<400> SEQUENCE: 557

Ser Pro Gln Tyr Thr Ile Ile Ala Asp Ala Gly Asp Phe Tyr Leu His
1               5                   10                  15

Pro Ser Tyr Tyr Met Leu Arg Arg Arg
            20                  25

<210> SEQ ID NO 558
<211> LENGTH: 27
<212> TYPE: PRT
<213> ORGANISM: Artificial Sequence
<220> FEATURE:
<223> OTHER INFORMATION: synthetic peptide

<400> SEQUENCE: 558

Pro Gln Tyr Thr Ile Ile Ala Asp Ala Gly Asp Phe Tyr Leu His Pro
1               5                   10                  15

Ser Tyr Tyr Met Leu Ala Ala Ala Ala Ala Ala
            20                  25

<210> SEQ ID NO 559
<211> LENGTH: 24
<212> TYPE: PRT
<213> ORGANISM: Artificial Sequence
<220> FEATURE:
<223> OTHER INFORMATION: synthetic peptide

<400> SEQUENCE: 559

Pro Gln Tyr Thr Ile Ile Ala Asp Ala Gly Asp Phe Tyr Leu His Pro
1               5                   10                  15

Ser Tyr Tyr Met Leu Arg Arg Arg
            20

<210> SEQ ID NO 560
<211> LENGTH: 29
<212> TYPE: PRT
<213> ORGANISM: Artificial Sequence
<220> FEATURE:
<223> OTHER INFORMATION: synthetic peptide

<400> SEQUENCE: 560

Cys Ser Pro Gln Tyr Thr Ile Ile Ala Asp Ala Gly Asp Phe Tyr Leu
1               5                   10                  15

His Pro Ser Tyr Tyr Met Leu Arg Lys Arg Arg Lys Arg
            20                  25

```
<210> SEQ ID NO 561
<211> LENGTH: 26
<212> TYPE: PRT
<213> ORGANISM: Artificial Sequence
<220> FEATURE:
<223> OTHER INFORMATION: synthetic peptide

<400> SEQUENCE: 561

Cys Ser Pro Gln Tyr Thr Ile Ile Ala Asp Ala Gly Asp Phe Tyr Leu
1               5                   10                  15

His Pro Ser Tyr Tyr Met Leu Arg Arg Arg
            20                  25

<210> SEQ ID NO 562
<211> LENGTH: 29
<212> TYPE: PRT
<213> ORGANISM: Artificial Sequence
<220> FEATURE:
<223> OTHER INFORMATION: synthetic peptide

<400> SEQUENCE: 562

Cys Ser Pro Gln Tyr Thr Ile Ile Ala Asp Ala Gly Asp Ala Ala Ala
1               5                   10                  15

His Pro Ser Ala Ala Ala Ala Arg Lys Arg Arg Lys Arg
            20                  25

<210> SEQ ID NO 563
<211> LENGTH: 32
<212> TYPE: PRT
<213> ORGANISM: Artificial Sequence
<220> FEATURE:
<223> OTHER INFORMATION: synthetic peptide

<400> SEQUENCE: 563

Cys Ser Pro Gln Tyr Thr Ile Ile Ala Asp Ala Gly Asp Phe Tyr Leu
1               5                   10                  15

His Pro Ser Tyr Tyr Met Leu Arg Arg Gln Arg Lys Lys Arg Arg Arg
            20                  25                  30

<210> SEQ ID NO 564
<211> LENGTH: 29
<212> TYPE: PRT
<213> ORGANISM: Artificial Sequence
<220> FEATURE:
<223> OTHER INFORMATION: synthetic peptide

<400> SEQUENCE: 564

Cys Ser Pro Gln Tyr Thr Ile Ile Ala Asp Ala Gly Asp Phe Tyr Leu
1               5                   10                  15

His Pro Ser Tyr Tyr Met Leu Lys Arg Arg Arg Lys Arg
            20                  25

<210> SEQ ID NO 565
<211> LENGTH: 29
<212> TYPE: PRT
<213> ORGANISM: Artificial Sequence
<220> FEATURE:
<223> OTHER INFORMATION: synthetic peptide

<400> SEQUENCE: 565

Cys Ser Pro Gln Tyr Thr Ile Ile Ala Asp Ala Gly Asp Phe Tyr Leu
1               5                   10                  15

His Pro Ser Tyr Tyr Met Leu Ala Ala Ala Ala Ala Ala
```

```
                    20                  25

<210> SEQ ID NO 566
<211> LENGTH: 26
<212> TYPE: PRT
<213> ORGANISM: Artificial Sequence
<220> FEATURE:
<223> OTHER INFORMATION: synthetic peptide

<400> SEQUENCE: 566

Cys Ser Pro Gln Tyr Thr Ile Ile Ala Asp Ala Gly Asp Phe Tyr Leu
1               5                   10                  15

His Pro Ser Tyr Tyr Met Leu Arg Arg Arg
            20                  25

<210> SEQ ID NO 567
<211> LENGTH: 38
<212> TYPE: PRT
<213> ORGANISM: Artificial Sequence
<220> FEATURE:
<223> OTHER INFORMATION: synthetic peptide

<400> SEQUENCE: 567

Gln Tyr Thr Ile Ile Ala Asp Ala Gly Asp Phe Tyr Leu His Pro Ser
1               5                   10                  15

Tyr Tyr Met Leu Arg Lys Arg Arg Lys Arg Leu Pro Tyr Phe Phe Ser
            20                  25                  30

Asp Val Ser Leu Ala Ala
        35

<210> SEQ ID NO 568
<211> LENGTH: 27
<212> TYPE: PRT
<213> ORGANISM: Artificial Sequence
<220> FEATURE:
<223> OTHER INFORMATION: synthetic peptide

<400> SEQUENCE: 568

Ile Ile His Pro His Asp Ser Thr Gly Asp Phe Tyr Leu His Pro Ser
1               5                   10                  15

Leu His Arg Arg Lys Arg Lys Arg Lys Tyr Leu
            20                  25

<210> SEQ ID NO 569
<211> LENGTH: 24
<212> TYPE: PRT
<213> ORGANISM: Artificial Sequence
<220> FEATURE:
<223> OTHER INFORMATION: synthetic peptide

<400> SEQUENCE: 569

His Leu Gly Leu Thr Ala Gln Pro Glu Leu Tyr Leu Leu Asn Thr Met
1               5                   10                  15

Asp Ala Asp Ser Leu Val Ser Arg
            20
```

CELL-PENETRATING PEPTIDES AND METHODS OF USE THEREOF

CROSS-REFERENCE TO RELATED APPLICATIONS

The present application is a 35 U.S.C. § 371 national phase application from, and claiming priority to, International Application No. PCT/US2019/033888, filed May 24, 2019, which claims priority under 35 U.S.C. § 119(e) to U.S. Provisional Patent Application No. 62/676,706, filed May 25, 2018, which are hereby incorporated by reference in their entireties herein.

STATEMENT REGARDING FEDERALLY SPONSORED RESEARCH OR DEVELOPMENT

This invention was made with government support under CA016038 and AI102876 awarded by National Institutes of Health. The government has certain rights in the invention.

BACKGROUND OF THE INVENTION

Cell-penetrating peptides as vectors for cell entry show great promise as research tools or for drug delivery. However, the majority of cell-penetrating peptides and thus the associated cargo molecules are sequestered in endosomes and eventually degraded.

There is a need in the art for cell-penetrating peptides that allow for transport of attached cargo into the cell, and yet avoid endosome sequestration and consequent degradation of the cargo. The present disclosure addresses this need.

SUMMARY OF THE INVENTION

In one aspect, the invention provides a method of delivering a cargo molecule to the cytoplasm of at least one cell, the method comprising contacting the cell with a transport construct comprising the cargo molecule and at least one cell-penetrating peptide selected from the group consisting of SEQ ID NOs: 1-164, or a salt or solvate thereof.

In another aspect, the invention provides a method of promoting endosomal escape for a cargo molecule, the method comprising contacting at least one cell with a transport construct comprising the cargo molecule and at least one cell-penetrating peptide selected from the group consisting of SEQ ID NOs: 1-164, or a salt or solvate thereof.

In various embodiments, the cell-penetrating peptide is SEQ ID NO: 2.

In various embodiments, the transport construct further comprises at least one selected from the group consisting of an activity modulating flanking sequence, a temperature modulating flanking sequence, and a pH modulating flanking sequence.

In various embodiments, the transport construct further comprises a linker connecting the cargo molecule and the cell-penetrating peptide.

In various embodiments, the cargo molecule is at least one selected from the group consisting of a nucleic acid; peptide; protein; peptide-nucleic acid; oligosaccharide; lipid; glycolipid; lipoprotein; small molecule compound; therapeutic drug; UV-vis, fluorescent or radioactive label; imaging agent; diagnostic agent; prophylactic agent; liposome; and virus.

In various embodiments, the at least one cell is human.

In various embodiments, the at least one cell is in a human subject.

In various embodiments, the contacting comprises administering a pharmaceutical composition comprising an effective amount of the transport construct and at least one pharmaceutically acceptable carrier to the human subject.

In another aspect, the invention provides an isolated transport construct comprising a cargo molecule and at least one cell-penetrating peptide selected from the group consisting of SEQ ID NOs: 165-517, or a salt or solvate thereof.

In various embodiments, the cell-penetrating peptide is SEQ ID NO: 2.

In various embodiments, the transport construct further comprises at least one selected from the group consisting of an activity modulating flanking sequence, a temperature modulating flanking sequence, and a pH modulating flanking sequence.

In various embodiments, the transport construct further comprises a linker connecting the cargo molecule and the cell-penetrating peptide.

In various embodiments, the cargo molecule is at least one selected from the group consisting of a nucleic acid; peptide; protein; peptide nucleic acid; oligosaccharide; lipid; glycolipid; lipoprotein; small molecule compound; therapeutic drug; UV-vis, fluorescent or radioactive label; imaging agent; diagnostic agent; prophylactic agent; liposome; and virus.

In various embodiments, the invention provides a pharmaceutical composition comprising the transport construct and at least one pharmaceutically acceptable excipient.

In another aspect, the invention provides a method of preventing viral infection in a subject in need thereof, the method comprising providing to the subject a therapeutically effective amount of a polypeptide comprising a cell-penetrating peptide and a retromer binding site.

In various embodiments, the viral infection is papillomavirus, hepatitis C virus, influenza virus or human immunodeficiency virus (HIV).

In various embodiments, the therapeutically effective amount of the polypeptide is formulated for topical administration.

In various embodiments, the polypeptide comprises at least one cell-penetrating peptide selected from the group consisting of SEQ ID NOS: 165-517.

In various embodiments, the polypeptide comprises a retromer binding site comprising the sequence FYL.

BRIEF DESCRIPTION OF THE DRAWINGS

The following detailed description of preferred embodiments of the invention will be better understood when read in conjunction with the appended drawings. For the purpose of illustrating the invention, certain embodiments are shown in the drawings. It should be understood, however, that the invention is not limited to the precise arrangements and instrumentalities of the embodiments shown in the drawings.

FIG. 1A depicts the amino acid sequence of the C-terminus of the L2 protein of various HPV types. Basic amino acids downstream of the FYL major retromer binding motif are shown. Numbers indicate the amino acid position in the 473-residue HPV16 L2 protein. The membrane-destabilizing sequence in HPV33 L2 is underlined. FIG. 1B depicts the sequence of the C-terminus of wild-type and mutant HPV16 L2 proteins. In FIGS.

1C-1D HeLa S3 cells were infected with wild-type (WT) or mutant HPV16 pseudovirus (PsV) stocks containing equal numbers of the HcRed reporter plasmid (corresponding to multiplicity of infection (MOI) of one for wild-type). Forty-eight hours post-infection (h.p.i.), infectivity was measured by using flow cytometry to determine the fraction of fluorescent cells. The results were normalized to the fraction of cells infected by wild-type. The mean results and standard deviation of three or more independent experiments for each sample are shown. *p<0.05; **p<0.01. In FIG. 1E, HeLa S3 cells were transfected with a RISC-free control siRNA (black bars) or siRNA targeting retromer subunit Vps29 (grey bars), followed by infection at MOI of one with wild-type or L2-Tat HPV16 PsV. Infectivity was measured (n=3) and displayed as in FIG. 1C. In FIG. 1F HeLa S3 cells were left untreated (black bars) or pretreated with 250 nM γ-secretase inhibitor XXI for one h at 37° C. (grey bars), and then infected at MOI of one with wild-type or L2-Tat HPV16 PsV. Infectivity was measured (n=3) and displayed as described in FIG. 1C. See also FIGS. 7A-7B and Table 1.

FIG. 2A depicts the amino acid sequence of HPV16 L2 C-terminal peptides containing the wild-type (WT) basic sequence or the six alanine (6A) or three arginine (3R) mutations conjugated to Alexa Fluor 488. 293T cells were mock-treated or incubated with fluorescent peptides for three h at 37° C. and examined by confocal microscopy. FIG. 2B: Schematic diagram and C-terminal sequences of GFP-L2 fusion proteins containing the wild-type or mutant L2 C-terminal sequence. FIG. 2C: HaCaT and HeLa S3 cells were incubated with GFP-L2 fusion proteins for five h. Cells were examined by confocal microscopy, then treated for 10-15 min with 0.04% trypan blue (+TB) to quench extracellular fluorescence, and the same fields were re-imaged. FIG. 2D: HeLa S3 and HaCaT cells were incubated with GFP-L2 fusion proteins for various times. Cells were then treated with trypsin, and fluorescence was measured by flow cytometry. Mean fluorescent intensity (MFI) was plotted at the indicated time periods.

FIG. 3A: HeLa-sen2 cells were mock-infected or incubated at 4° C. for two h at MOI of 20 with wild-type, 6A, or 3R HPV16 PsV. Non-permeabilized cells were stained with anti-L1 antibody (green) and examined by confocal microscopy. FIG. 3B: HeLa-sen2 cells were treated as described in FIG. 3A, detached with 0.5 mM EDTA for 10 min, and stained with rabbit polyclonal anti-L1 antibody. MFI of the cells was measured by flow cytometry and normalized to cells incubated with wild-type HPV16 PsV. Mean results and standard deviation are shown (n=3). ***p<0.001; ns, not significant. FIG. 3C: HeLa cells were treated as described in FIG. 3A. After two h, cells were washed, lysed, and bound virus was assessed by SDS-polyacrylamide gel electrophoresis and blotting for L1 (top panel). GAPDH was used as a loading control (bottom panel). FIG. 3D: HeLa-sen2 cells were treated and processed as described in FIG. 3C with PsV containing wild-type or 6A mutant L2 or with L1-only PsV lacking L2. FIG. 3E: HeLa cells-sen2 were mock-infected or infected at MOI of 20 at 4° C. for two h with wild-type, 6A or 3R HPV16 PsV and then washed and shifted to 37° C. for six or 16 h to allow internalization. Permeabilized cells were stained with anti-L1 antibody (green) and examined by confocal microscopy. FIG. 3F: HeLa-sen2 cells were infected as described in FIG. 3E, and 6 h after shift to 37° C. harvested by trypsinization. Permeabilized cells were stained with anti-L1 antibody and subjected to flow cytometry. MFI of the cell populations was normalized to cells infected with wild-type HPV16 PsV. Mean results and standard deviation are shown (n=3). *p<0.05. See also FIG. 11B.

FIG. 4A: HeLa-sen2 cells were mock-infected or infected at 37° C. at MOI of 100 with wild-type, 3R or retromer binding site (DM) mutant HPV16 PsV. At eight and 16 h.p.i., PLA was performed with anti-L1 antibody and either an EEA1 (FIG. 4A) or a TGN46 (FIG. 4B) antibody. PLA signal is green. Multiple images obtained as in left panels were processed with BlobFinder software to determine the fluorescence intensity per cell. The graphs in the right panels show mean results and standard deviation (n=3), in which the results for the EEA1/L1 samples and the TGN46/L1 samples were normalized to those of cells infected with wild-type HPV16 PsV at eight and 16 h.p.i., respectively. Black bars, 8 h.p.i.; grey bars, 16 h.p.i. p<0.01; *p<0.001.

FIG. 5A: HeLa-sen2 cells were infected as in FIG. 4A. At eight and 16 h.p.i., PLA was performed with anti-L1 antibody and an antibody recognizing Vps35 to assess L1 in proximity to retromer. FIG. 5B: Multiple images obtained as in FIG. 5A were processed by using BlobFinder software to determine the fluorescence intensity per cell. The graph shows the mean intensity and standard deviation for the mutant samples normalized to that of cells infected with wild-type PsV at eight h.p.i. Black bars, wild-type; dark grey bars, 3R mutant; light grey bars, DM mutant. *p<0.05; p<0.01; *p<0.001. FIG. 5C: Retromer adsorbed to glutathione beads via GST-tagged Vps35 was incubated with purified GFP-L2 fusion proteins. After pull-down, proteins bound to retromer were separated by SDS-PAGE and detected by blotting with anti-GFP antibody (top panel). Bottom panel shows input GFP-L2 fusion proteins. FIG. 5D: Top portion shows sequences of wild-type and mutant biotinylated peptides from the C-terminus of L2. Bottom portion. Peptides were incubated with extracts of uninfected HeLa S3 cells, pulled-down with streptavidin, and separated by SDS-PAGE. Retromer associated with the peptide was detected by blotting for Vps35.

FIGS. 6A-6D show reconstitution of split GFP by infection with PsV containing L2-GFP11. FIG. 6A: Schematic diagrams of wild-type L2 protein and derivatives with GFP11 (green) inserted upstream of RKRRKR (L2-GFP11-CPP) or at the C-terminus of L2 (L2-CPP-GFP11). The bulk of the L2 protein is shown in blue; wild-type and mutant CPP in red; and retromer binding sites in purple. See FIGS. 8A-8F for sequences. FIG. 6B: Clonal HaCaT/GFP1-10NES cells were infected at MOI of 2000 with untagged HPV16 PsV or with a PsV containing GFP11-tagged L2. Three h.p.i., cells were examined by confocal microscopy for GFP fluorescence. FIG. 6C: Fluorescence of cells in images as in FIG. 6B was quantified for ~250 cells for each condition. Results show the fluorescence intensity of individual cells from three independent experiments. ***p<0.0001. FIG. 6D: Clonal HaCaT/GFP1-10NES cells were infected at MOI of 2000 with HPV16 or PsV containing L2-GFP11-CPP or L2-CPP-GFP11 with the wild-type L2 or the 3R mutation. Three h.p.i., cells were examined by confocal microscopy for GFP fluorescence. See FIGS. 8A-12B.

FIG. 7C: HeLa S3 (black bars) and HaCaT (grey bars) cells were infected with wild-type, 6A, or 3R mutant HPV16 PsV at MOI of one. Two days later, infection was measured by flow cytometry for HcRed expression and normalized to infection by wild-type. Average results±standard deviation are shown (n=3). Size bars in FIG. 7A are 50 nm. Numbers in FIG. 7B show molecular mass (in kDa) of size markers.

(FIG. 8A) Schematic diagram of GFP1-10 construct with a C-terminal nuclear export signal (blue). (FIG. 8B) Parental HaCaT cells and HaCaT cells expressing GFP1-10NES were analyzed by immunostaining with anti-GFP antibody (green) and confocal microscopy. (FIG. 8C) Schematic diagram of CD8-CIMPR and calnexin (CNX) fusion proteins used to validate the split GFP system. All proteins contain a transmembrane domain (TM). The GFP11 segment is in the luminal domain of GFP11-CD8-CIMPR and the cytoplasmic domain of the CD8-CIMPR-GFP11. Both proteins contain a WLM-to-AAA mutation that inactivates the retromer binding site in the cytoplasmic segment. The GFP1-10 segment is in the luminal domain of GFP1-10-CXN and the cytoplasmic domain of CXN-GFP1-10. (FIG. 8D) Cartoon showing cytoplasmic localization of the GFP11 segment in CD8-CIMPR-GFP11 reconstituting GFP fluorescence in HaCaT/GFP1-10NES cells, and luminal localization of the GFP11 segment in GFP11-CD8-CIMPR, reconstituting GFP fluorescence in cells expressing GFP1-10-CNX. (FIG. 8E) A plasmid expressing GFP11-CD8-CIMPR or CD8-CIMPR-GFP11 was transfected into clonal HaCaT/GFP1-10NES cells. Reconstituted GFP fluorescence is shown. (FIG. 8F) 293T cells were co-transfected with a plasmid expressing GFP11-CD8-CIMPR and a plasmid expressing GFP1-10 fused to the N-terminal luminal domain or the C-terminal cytoplasmic domain of calnexin (i.e., GFP1-10-CNX or CXN-GFP1-10, respectively). Reconstituted GFP fluorescence is shown.

FIG. 9A depicts the amino acid sequence of the C-terminus of wild-type and mutant HPV16 L2 proteins with inserted copies of GFP11. FIG. 9B depicts HeLa S3 cells were infected at MOI (determined by the number of encapsidated reporter genomes) of one with the indicated HPV16 PsV containing an hcRed reporter gene. After 48 h, the fraction of fluorescent cells was determined by flow cytometry and normalized to cells infected with wild-type PsV. Mean results±standard deviation are shown (n=3).

FIG. 11A depicts HaCaT cells mock-infected or infected at MOI of 200 with wild-type HPV16 PsV or GFP11-tagged PsV with a wild-type or 3R mutant CPP. Three h.p.i., cells were stained with mouse polyclonal anti-L1 antibody (BD Sciences, #554171) and examined by confocal microscopy. FIG. 11B: HaCaT cells were mock-infected or infected at an MOI of 200 with wild-type HPV16 PsV. Cells were stained with conformation-specific 33L1-7 antibody at the indicated times and examined by confocal microscopy.

FIG. 12A depicts HeLa S3 cells left untreated or treated with 6 μM aphidicolin. Twenty-four h later, cells were infected at MOI of one with wild-type HPV16 PsV or PsV containing L2-GFP11-CPP or L2-CPP-GFP11. Forty-eight h.p.i., the fraction of infected cells was determined by flow cytometry for HcRed fluorescence and normalized to untreated cells infected with wild-type HPV16 PsV. FIG. 12B depicts HaCaT/GFP1-10NES cells infected at an MOI of 2000 with wild-type HPV16 PsV or PsV containing GFP11-tagged L2 in the presence of absence of 6 μM aphidicolin. Three h.p.i., cells were examined by confocal microscopy for reconstituted GFP fluorescence. Fluorescence in individual cells (~250 for each condition) is plotted from two independent experiments. There were no statistically significant differences among samples infected with either GFP11-tagged PsV in the presence or absence of aphidocolin.

FIG. 18A (top) depicts sequences of L2 peptides. The top line shows wild-type P16/16 peptide with CPP segment and retromer binding site (RBS) highlighted. Amino acid substitutions in the CPP or RBS mutant peptides are shown in orange and blue, respectively. Bottom: RBS and flanking sequences of indicated HPV L2 proteins or DMT1-II. FIG. 18B depicts an inhibitory dose-response curve for P16/16 peptide. $5 \times 10^4$ HeLa-S3 in 24-well plates were pretreated with various concentrations of P16/16 for one hour prior to infection with HPV pseudovirus (PsV) at multiplicity of infection (MOI) of 1. Peptide was left in the medium for the duration of the experiment. Cells were assessed by flow cytometry to determine the fraction of cells expressing reporter protein HcRed at 48 hours post-infection (h.p.i.). Graph shows average results of three independent experiments, +/−standard deviation. FIG. 18C depicts $5 \times 10^4$ HeLa-S3 in 24-well plates were pretreated with 14 μM of the indicated peptide for one hour, followed by infection with HPV PSV at MOI of one. Peptides were left in the medium for the duration of the experiment. As a control, cells were incubated with the solution used to dissolve peptide. Forty-eight h.p.i., cells were assessed by flow cytometry to determine fraction of cells expressing reporter protein HcRed. Graph shows average results of three independent experiments, +/−standard deviation, normalized to infection of each PsV type in the absence of peptide. P16/16, P16/Tat, and P16/31 caused statistically significant (p<0.01) inhibition of all three PsV types. For the comparison of P16/16 to P16/6A, P16/3R, and PDM/16 for HPV16 PsV, , p<0.01; *, p<0.001. Similar levels of significance were achieved with these peptides and HPV18 and HPV5 PsV. FIG. 18D depicts inhibition of HPV infection of HaCaT cells. HaCaT keratinocytes were infected at MOI of 1 with HPV16 PsV in the presence and absence of 14 μM P16/16, and infectivity was assessed 48 h.p.i. by flow cytometry for HcRed fluorescence. FIG. 18E depicts inhibition of authentic HPV16. HeLa cells were infected with HPV16 harvested from organotypic cultures of human keratinocytes or with HPV16 PsV in the presence (grey bars) or absence (black bars) of P16/16. Successful infection by HPV16 and HPV16 PsV was assessed by quantitative reverse transcription-PCR (qRT-PCR) for expression of HPV early region and HcRed mRNA, respectively, and normalized to infection by the cognate virus in the absence of peptide. Background signal determined with non-cognate primers was <0.01%.

FIG. 19A depicts uninfected HeLa cells were incubated with 14 μM bP16/16 or bPDM/16 for three hours ("b" refers to peptides with an N-terminal biotin moiety). Cells were then fixed, permeabilized, and stained with AlexaFluor-streptavidin (green) and with anti-VPS35 (red). Overlapping signal is pseudo-colored yellow. Nuclei were stained blue with DAPI. Mander's correlation coefficients for overlap between streptavidin and VPS35 staining are shown at right, with each spot representing an individual cell. Approximately 100 cells were analyzed for each condition. FIG. 19B depicts $5 \times 10^4$ HeLa-S3 cells grown on glass coverslips for 16 hours were incubated for one hour with or without 14 μM P16/16 or PDM/16, followed by mock-infection or infection with HPV16 PsV at MOI of 200. At 8 or 16 (or both) h.p.i., cells were fixed and processed for PLA with anti-L1 antibody and an antibody recognizing retromer subunit VPS35. PLA signal is green and the nuclei are stained blue with DAPI. Images were acquired by a Leica SP5 confocal microscope. Approximately 200 cells in each sample were imaged. Images show results of a representative experiment. Images were processed by Fiji and quantitatively analyzed by BlobFinder software to measure total fluorescence intensity per cell in each sample. The PLA signal was normalized to that of cells infected with wild-type HPV16 PsV in the absence of peptide at 8 h.p.i. Graph shows the average of total fluorescence per cell, +/−standard deviation, from three independent experiments. n.s., not significant; , p<0.01; *p<0.001.

FIG. 22A depicts HeLa cells in 24-well plates infected with HPV16 PsV at MOI of 1. 14 μM P16/16 peptide was added at the time of infection (0) or at the indicated h.p.i., and cells were analyzed by flow cytometry 48 h.p.i. to determine reporter protein fluorescence as a measure of infection. FIG. 22B depicts HeLa-S3 in 24-well plates were incubated with 14 μM P16/16 or vehicle for one hour, followed by infection with HPV16 PSV at MOI of 1. Peptide was left in the medium for the duration of the experiment. Cells were analyzed by flow cytometry 48, 72, or 96 h.p.i. to determine fluorescence. Infectivity was normalized to that in the absence of peptide at each timepoint. ** p<0.0005. FIG. 22C depicts HeLa cells mock-infected (line A) or infected with HPV16 PsV at MOI of 1 in the absence of peptide (blue, Line B) or in the presence of P16/16. Virus was removed from all infected samples after 24 h. At this time, peptide was added back to some samples (Line C) or removed (Line D). Cells were harvested at various times and subjected to flow cytometry to measure HcRed fluorescence. Panels show histograms at the indicated h.p.i.

FIG. 26A depicts clonal HaCaT/GFP1-10NES cells expressing cytosolic GFP1-10 infected at MOI of 2000 with untagged HPV16 or with HPV16 PsV containing GFP11-tagged L2 in the absence or presence of 30 μM P16/16. Three h.p.i., cells were stained with Hoescht 33342 to visualize nuclei (blue) and examined by confocal microscopy for GFP fluorescence. FIG. 26B the corrected total cellular fluorescence (CTCF) of each cell was calculated and plotted in arbitrary units from three independent experiments. n.s., not significant. FIG. 26C depicts HaCaT/GFP-10NES cells infected as described in FIG. 26A with wild-type HPV16 PsV in the presence of 30 μM P16/16 or in its absence for three hours, followed by removal of PsV and incubation with medium containing peptide for an additional 48 hours. Cells were assessed by flow cytometry to determine reporter protein expression. Infectivity was normalized with that in the absence of peptide. **, p<0.01.

FIG. 27A depicts HeLa-S3 cells transfected with a plasmid expressing a GFP-DMT1-II fusion protein. Six hours later, cells were treated with 14 μM P16/16 or PDM/16 or vehicle. After ~20 hours, cells were fixed, permeabilized, and stained with anti-TGN46 antibody. Cells were stained with DAPI (blue) and imaged on a Leica SP5 inverted fluorescence microscope for GFP and anti-TGN46 fluorescence. Areas of colocalization are shown in yellow in the merge panels. FIG. 27B depicts Mander's coefficient for colocalization of staining was analyzed and plotted. ~100 cells were analyzed for each condition.

DETAILED DESCRIPTION OF THE INVENTION

Definitions

Figures 1A, 1B, 1C, 1D, 1E, 1F:
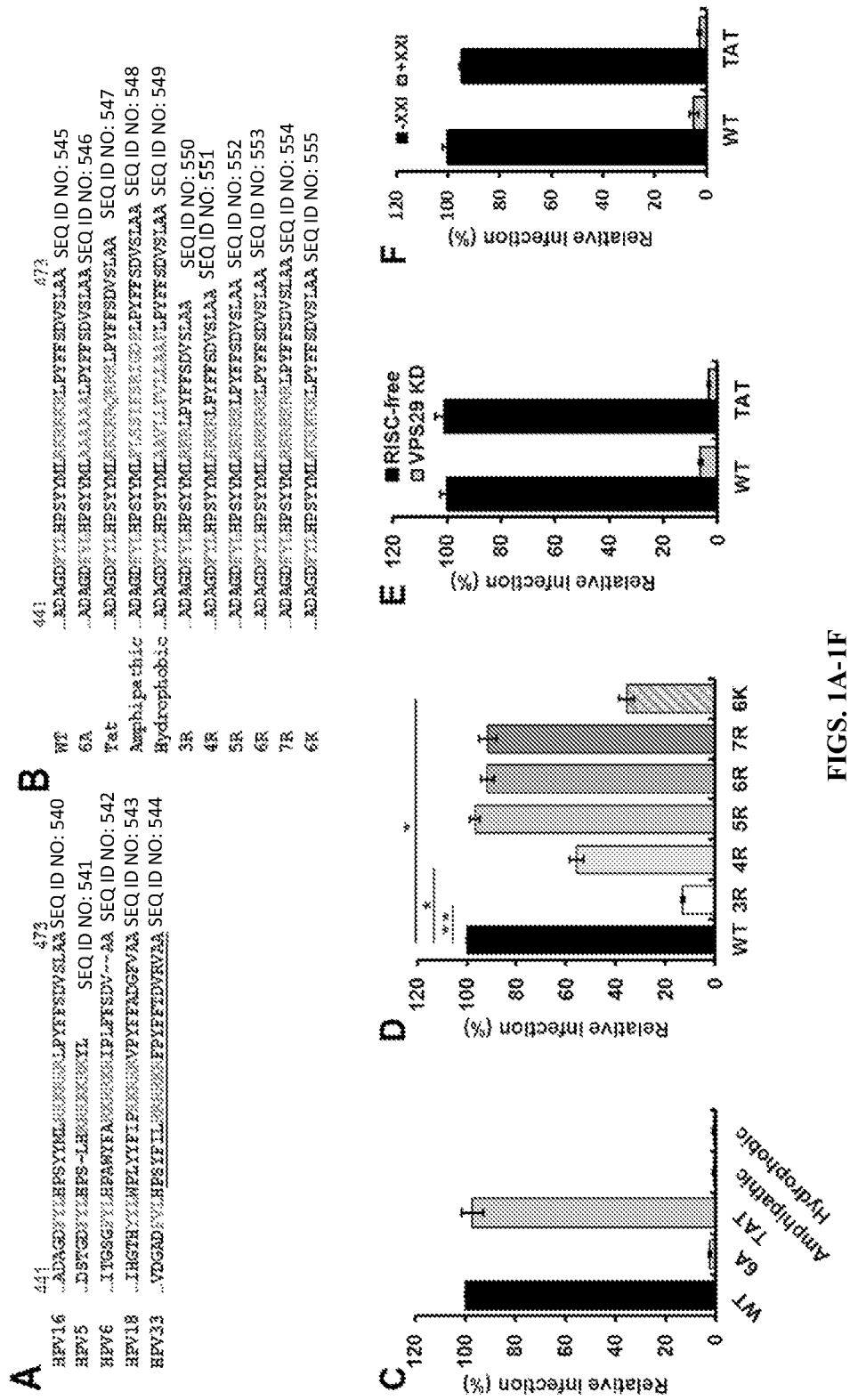
FIGS. 1A-1F show that the basic region of human papillomavirus (HPV) 16 L2 can be replaced by a cationic cell-penetrating motif.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, selected materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, subcutaneous, oral, aerosol, parenteral, ophthalmic, pulmonary and topical administration.

As used herein, the term "cell-penetrating peptide" or "CPP" refers to a cell-permeable peptide, which is defined as a peptide capable of permeating and/or crossing a cell membrane. CPPs are sometimes referred to as protein transduction domains (PTD)

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

"L2" as used herein, refers to the minor capsid protein of a papillomavirus, of which the HPV16 type has the amino acid sequence (SEQ ID NO. 518):

```
              10         20         30         40         50
       MRHKRSAKRT KRASATQLYK TCKQAGTCPP DIIPKVEGKT IAEQILQYGS
              60         70         80         90        100
       MGVFFGGLGI GTGSGTGGRT GYIPLGTRPP TATDTLAPVR PPLTVDPVGP
             110        120        130        140        150
       SDPSIVSLVE ETSFIDAGAP TSVPSIPPDV SGFSITTSTD TTPAILDINN
             160        170        180        190        200
       TVTTVTTHNN PTFTDPSVLQ PPTPAETGGH FTLSSSTIST HNYEEIPMDT
             210        220        230        240        250
       FIVSTNPNTV TSSTPIPGSR PVARLGLYSR TTQQVKVVDP AFVTTPTKLI
             260        270        280        290        300
```

```
TYDNPAYEGI DVDNTLYFSS NDNSINIAPD PDFLDIVALH RPALTSRRTG
        310        320        330        340        350
IRYSRIGNKQ TLRTRSGKSI GAKVHYYYDL STIDPAEEIE LQTITPSTYT
        360        370        380        390        400
TTSHAASPTS INNGLYDIYA DDFITDTSTT PVPSVPSTSL SGYIPANTTI
        410        420        430        440        450
PFGGAYNIPL VSGPDIPINI TDQAPSLIPI VPGSPQYTII ADAGDFYLHP
        460        470
SYYMLRKRRK RLPYFFSDVS LAA
```

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it can perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds can also be incorporated into the compositions. The "pharmaceutically acceptable carrier" can further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "polypeptide" refers to a polymer composed of amino acid residues, related naturally occurring structural variants, and synthetic non-naturally occurring analogs thereof linked via peptide (or amide) bonds. Synthetic polypeptides can be synthesized, for example, using an automated polypeptide synthesizer.

As used herein, the term "solvate" refers to a complex between a molecule and a solvent molecule, which can exist in solution or in solid phase. In certain embodiments, the solvent comprises at least one selected from the group consisting of water, methanol, ethanol, n-propanol, 2-propanol, DMSO, DMF, ethyl ether, acetone and pyridine.

As used herein, the term "transport construct" refers to a construct that crosses the cell membrane, wherein the construct comprises a cell-penetrating peptide and at least one heterologous cargo molecule, wherein the cargo molecule alone crosses the cell membrane at a lower rate or to a lower degree than the transport construct. In certain embodiments, the cargo molecule is selected from the group consisting of a nucleic acid; peptide; protein; peptide nucleic acid; oligosaccharide; lipid; glycolipid; lipoprotein; small molecule compound; therapeutic drug; UV-vis, fluorescent or radioactive label; imaging agent; diagnostic agent; prophylactic agent; liposome and virus. In other embodiments, the cargo molecule is linked to the transport peptide through a covalent or non-covalent linkage.

As used herein, "treating a disease or disorder" means reducing the frequency or severity with which a symptom of the disease or disorder is experienced by a patient. Disease and disorder are used interchangeably herein.

As used herein, the term "treatment" or "treating" encompasses prophylaxis and/or therapy. Accordingly the compositions and methods of the present invention are not limited to therapeutic applications and can be used in prophylactic ones. Therefore "treating" or "treatment" of a state, disorder or condition includes: (i) preventing or delaying the appearance of clinical symptoms of the state, disorder or condition developing in a subject that can be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Transport Constructs

The invention is based in part on the discovery that the human papillomavirus L2 protein C-terminal basic sequence acts as a cell-penetrating peptide that facilitates entry into the cell and escape from the endosome. These sequences are unlikely to be toxic because they naturally evolved to support infection by a non-lytic virus. There are a variety of analogous peptides found in various types of papillomavirus that can be fused to a cargo molecule and used for cell penetration and endosomal escape.

In one aspect, the invention provides an isolated transport construct comprising a cargo molecule and at least one cell-penetrating peptide selected from the group consisting of SEQ ID NO:1 to SEQ ID NO: 164, or a salt or solvate thereof. In various embodiments, the cell-penetrating peptide is SEQ ID NO: 2, which is RKRRKR. This is the basic sequence common to several papillomavirus L2 proteins including HPV16 and is evaluated in the examples described elsewhere herein. The sequences for other cell-penetrating peptides are shown in Table 1.

In various embodiments, the cargo molecule is selected from the group consisting of a nucleic acid; peptide; protein; peptide nucleic acid; oligosaccharide; lipid; glycolipid; lipoprotein; small molecule compound; therapeutic drug; UV-vis, fluorescent or radioactive label; imaging agent; diagnostic agent; prophylactic agent; liposome; and virus.

The cargo molecule can be combined with or linked to the cell-penetrating peptide to form the transport construct of the present invention. The cell-penetrating peptide and the cargo molecule are combined or linked in such a manner that they remain combined or linked under the conditions in which the transport construct is used (e.g., under conditions in which the transport construct is administered to an individual).

In certain embodiments, the cargo molecule is covalently linked to the cell-penetrating peptide through a linker or a chemical bond. In other embodiments, the linker comprises a disulfide bond, or the chemical bond between the cargo molecule and the transport peptide comprises a disulfide bond. In yet other embodiments, the cargo molecule comprises a peptide. In yet other embodiments, the transport peptide is covalently linked through an amide bond to the N-terminus of the peptide molecule of the cargo molecule. In yet other embodiments, the transport peptide is covalently linked through an amide bond to the C-terminus of the peptide of the cargo molecule. In yet other embodiments, the transport peptide is covalently linked through an amide bond to both the N-terminus and the C-terminus of the peptide of the cargo molecule.

Alternatively, the transport peptide and the cargo molecule are combined through a noncovalent linkage, such as electrostatic and/or hydrophobic interaction.

Figure 17:
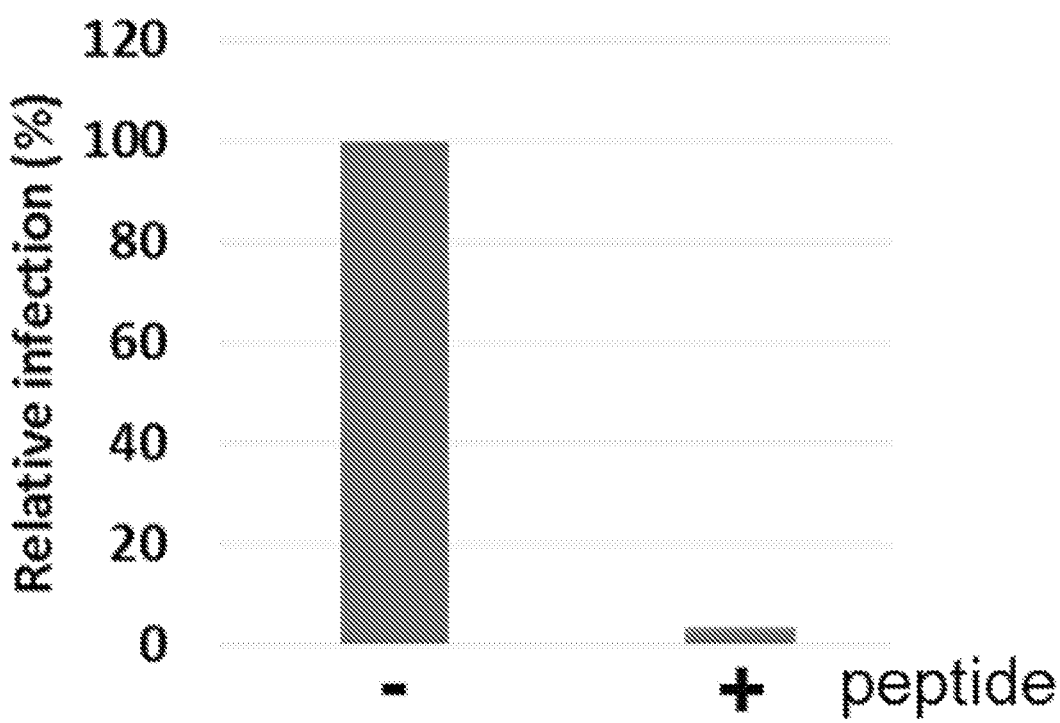
FIG. 17 shows that the HPV16 L2 CPP can deliver a peptide into cells that inhibits HPV16 infection. HeLa cells were treated at 37° C. with 4 μg L2-C, a peptide containing the HPV16 L2 retromer binding site and CPP or mock treated. B represents N terminal biotinylation and Am represents C-terminal amidation. Two hours later, the cells were infected for two hours at 37° C. with wild-type HPV16 pseudovirus. Cells were washed and medium was replenished with medium containing the peptide for 24 hours. Infectivity was tested 48 hours later by using flow cytometry to measure fluorescence of HcRed expressed from a plasmid encapsidated in the pseudovirus particle. Similar results were obtained in two independent experiments.

In various embodiments, the transport construct further comprises a linker connecting the cargo molecule and the cell-penetrating peptide. In various embodiments, the linker is a disulfide, a polyethylene glycol chain (PEG), a short polypeptide chain, or an amide, or other linkers that do not impair activity. In various embodiments, the cargo molecule can inhibit infection by papillomavirus. As shown in FIG. 17, HPV16 L2 CPP can deliver a peptide into cells that inhibits infection by HPV16 and other HPV types.

Figure 13:
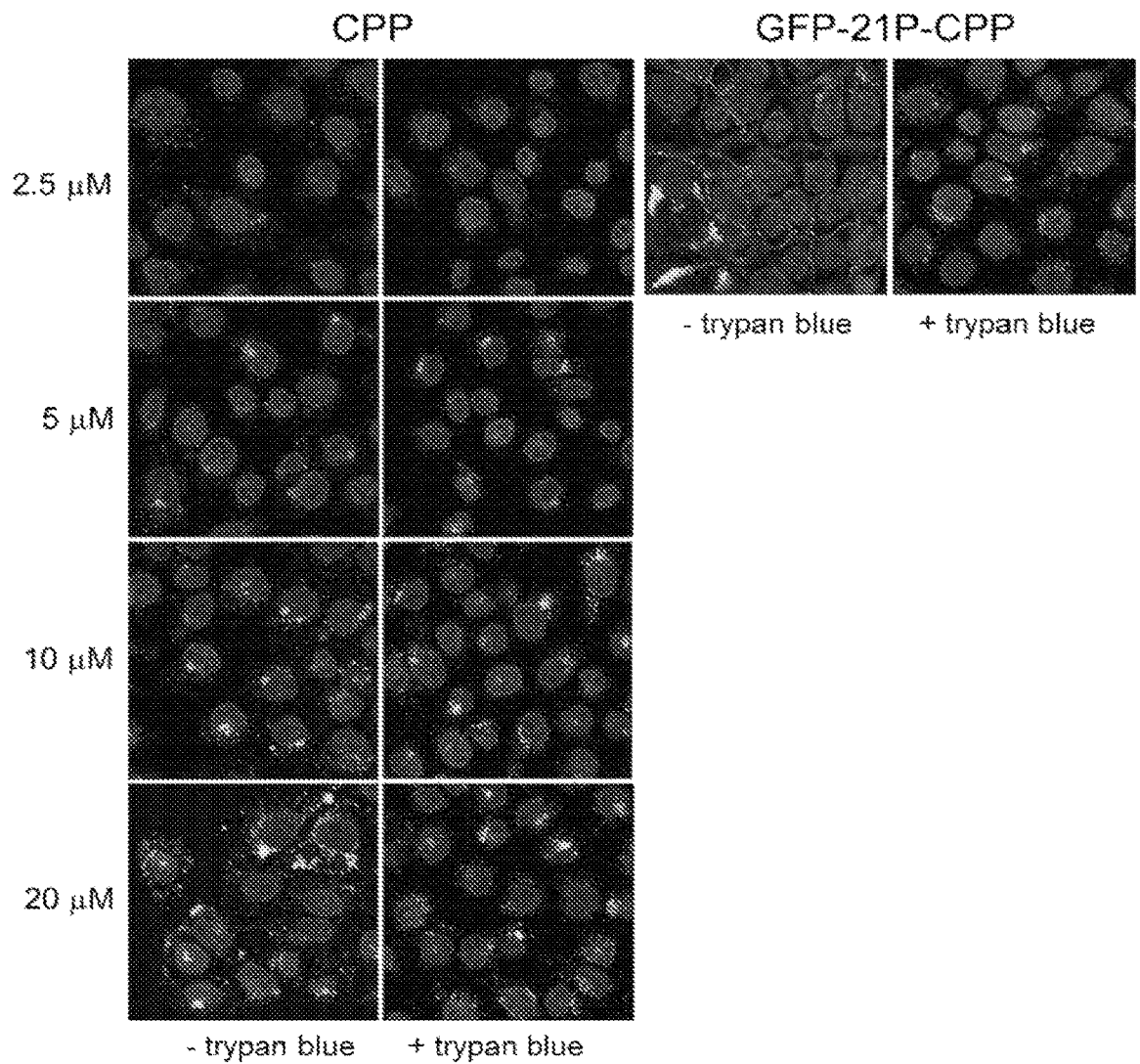
FIG. 13 shows that GFP fusion protein containing the HPV16 L2 CPP alone is active in cell binding and internalization, but is not as efficient at cell binding and internalization as a GFP fusion protein containing the HPV16 L2 CPP plus flanking upstream L2 sequences. HaCaT cells were incubated for three hours at 37° C. at pH 7 with the indicated concentration of GFP fusion protein containing only the HPV16 L2 CPP or the L2 CPP plus 21 flanking upstream amino acids from L2. The cells were then imaged in the presence or absence of trypan blue. Trypan blue quenches extracellular fluorescence. In the sequences of peptides below the images, the HPV16 L2 CPP (RKRRKR), SEQ ID NO: 2, and the retromer binding site (FYL) are shown in bold.

In various embodiments, the transport construct can include one or more flanking sequences that modulate the cell-penetrating activity or properties of the transport construct. In various embodiments, the flanking sequences can be an activity modulating flanking sequence, a flanking sequence that modulates temperature dependence, and/or a flanking sequence that modulates pH dependence, or a flanking sequence that modulates other aspects of cell penetration, such as lipid composition of the membrane. The term "flanking sequence" as used herein refers to a peptide fused to the transport construct that modulates the cell-penetrating activity of the transport construct. In various embodiments, the flanking sequence can modulate the cell-penetrating activity of the transport construct generally. As shown in FIG. 13, the activity modulating flanking sequence can be the 21 flanking upstream amino acids from L2, which improve the cell-penetrating activity of the construct relative to a transport construct with the cell-penetrating peptide alone.

Figure 14:
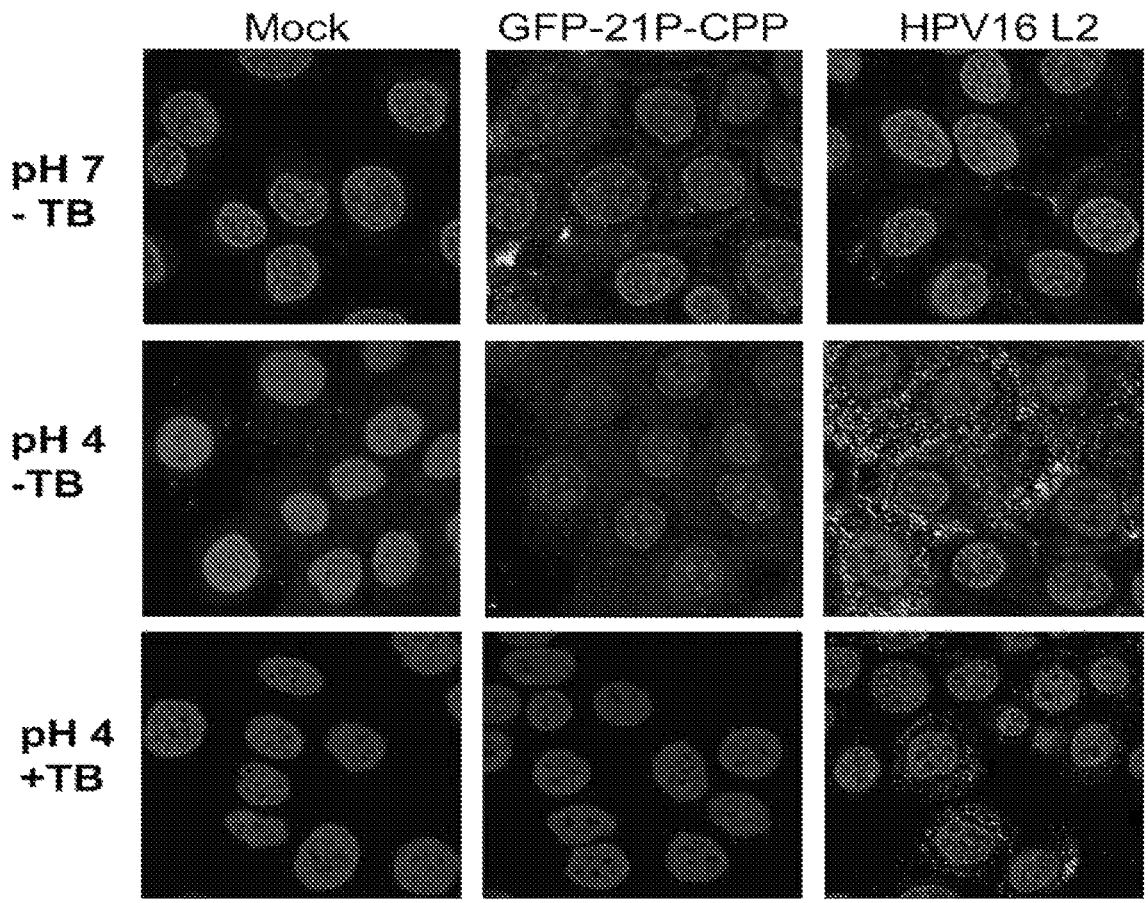
FIG. 14 shows that GFP fusion protein with full-length HPV16 C-terminus (HPV16 L2) binds and enters HaCaT cells poorly at pH 7 but well at pH 4. A GFP fusion protein lacking the C-terminal 12 amino acids of L2 (GFP-21P-CPP) binds at pH 7. HaCaT cells were incubated in the absence of GFP fusion protein (mock) or with the indicated GFP fusion protein for three hours at 37° C. at pH 7 or pH 4. The cells were then imaged in the presence or absence of trypan blue (TB). GFP-HPV16 L2 contains 12 amino acids from the end of the basic CPP to the C-terminus of the native protein. These 12 amino acids are not present in GFP-21P-CPP.
Figure 15:
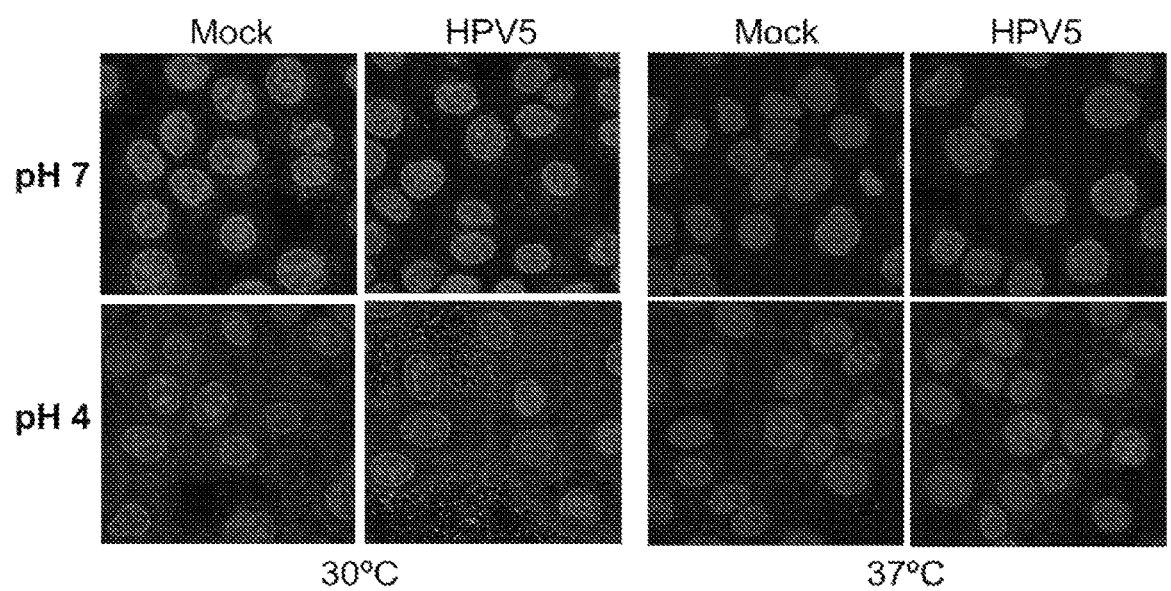
FIG. 15 shows that GFP fusion protein with HPV5 C-terminus binds HaCaT cells better at 30° C. than at 37° C. HaCaT cells were incubated for three hours at pH 7 or pH 4 at 30° C. or 37° C. in the absence of GFP fusion protein (mock) or with the GFP fusion protein containing the C-terminus of HPV5. HPV5 is a papillomavirus that infects skin, which is at a lower temperature than core body temperature of 37° C.
Figure 16:
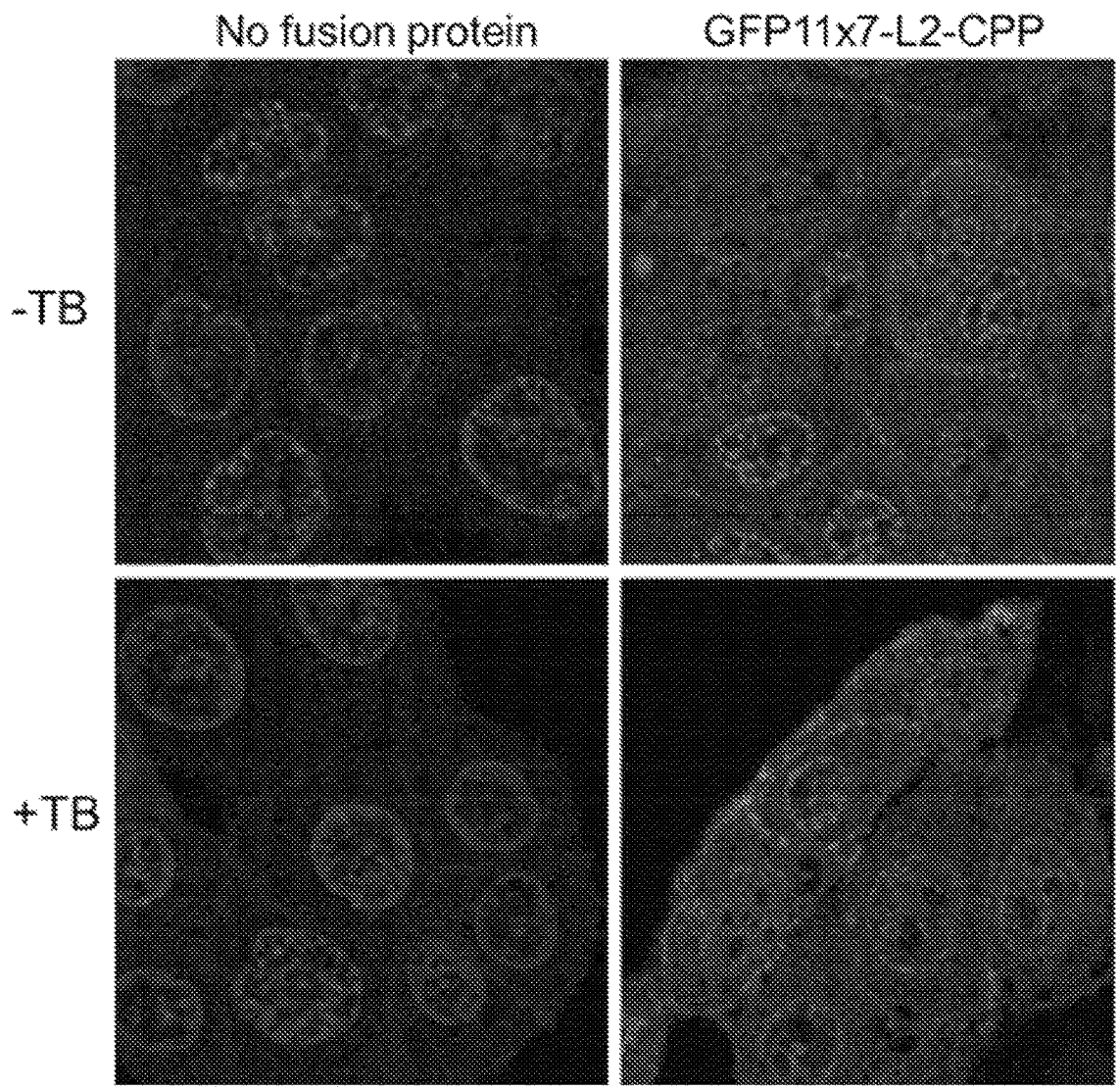
FIG. 16 shows that GFP11 fused to truncated HPV16 C-terminus reconstitutes cytoplasmic fluorescence in HaCaT/GFP1-10NES cells. HaCaT/GFP1-10NES cells were incubated for three hours at pH 7 at 37° C. in the absence of GFP fusion protein or with a short fusion protein consisting of seven tandem copies of GFP11 fused to the C-terminus of L2 terminating at the L2 CPP. The cells were then imaged in the presence or absence of trypan blue (TB). Reconstituted fluorescence is resistant to trypan blue, indicating the delivery of the C-terminus of L2 into the cytoplasm.

In various embodiments, the flanking sequence can be a certain portion of L2 from a form of papillomavirus selected to modulate the activity of the transport construct based on the characteristics of the papillomavirus. As shown in FIG. 14, addition of the 12 amino acids at the C-terminus of HPV16 L2 improves the cell-penetrating activity of the transport construct at pH 4. As a non-limiting example, HPV5 infects skin and therefore would require greater cell-penetrating activity at lower temperatures. As shown in FIG. 15, addition of the HPV5 C-terminus to the transport construct modulates the cell-penetrating activity such that it is higher at 30° C. than at 37° C..

In various embodiments, the invention provides a pharmaceutical composition comprising the transport construct as described herein and at least one pharmaceutically acceptable excipient.

Methods of Delivering a Cargo Molecule

In another aspect, the invention provides a method of delivering a cargo molecule to the cytoplasm of at least one cell by contacting the cell with a transport construct comprising the cargo molecule and at least one cell-penetrating peptide selected from the group consisting of SEQ ID NO: 1 to SEQ ID NO: 164, or a salt or solvate thereof.

In another aspect, the invention provides a method of promoting endosomal escape for a cargo molecule by contacting at least one cell with a transport construct comprising the cargo molecule and at least one cell-penetrating peptide selected from the group consisting of SEQ ID NO:1 to SEQ ID NO: 164. In various embodiments, the cell-penetrating peptide is SEQ ID NO: 2, or a salt or solvate thereof.

The cargo molecule can be any molecule intended for delivery to the cytoplasm and that can be covalently linked the cell-penetrating peptides of the invention. In various embodiments, the cargo molecule is at least one selected from the group consisting of a nucleic acid; peptide; protein; oligosaccharide; lipid; glycolipid; lipoprotein; small molecule compound; therapeutic drug; UV-vis, fluorescent or radioactive label; imaging agent; diagnostic agent; prophylactic agent; liposome; and virus.

The methods of the invention can be applied to deliver a cargo molecule to cells in vitro or to the cells of a subject. In various embodiments, the contacting step comprises administering a pharmaceutical composition comprising the transport construct and at least one pharmaceutically acceptable carrier to a subject. In various embodiments, the cell or cells are human. In various embodiments, the subject is human. Various suitable pharmaceutically acceptable carriers are described under administration/dosage/formulations.

In table 1, the left two columns list virus type and associated cell penetrating peptide. The right two columns compile the basic sequences found in the various virus-associated cell-penetrating peptides and their frequency.

TABLE 1

| Virus | Sequence | | Basic sequence | Frequency |
|---|---|---|---|---|
| RaIPV1 | ... DGDISLTDLNYRQYFLHPSLMKGKRRKKRVSG SEQ. ID NO: 165. | | SEQ. ID NO: 1. KRRKR | 17 |
| FcaPV4 | ... PISPPLPFDSVTATFDLHPGLKHRKRKRKHHGLT SEQ. ID NO: 166. | | SEQ. ID NO: 2. RKRRKR | 16 |
| HPV144 | ... LDPAILIDVASDTYYIHPSLKKKGKRKYSDIF SEQ. ID NO: 167. | | SEQ. ID NO: 3. KRKRKR | 14 |
| BPV4 | ... PDIILNFEDDTATFFLHPSLLKKHKHNKHWFL SEQ. ID NO: 168. | | SEQ. ID NO: 4. RRKRKR | 14 |
| BPV9 | ... PAIIIDFDEDTATFFLHPSLLKKHKHKHWFF SEQ. ID NO: 169. | | SEQ. ID NO: 5. RRRRKR | 13 |
| HPV62 | ... PYSIYIVGSDYYLFPSYIFFPKKHKRLHYFFTDGYVAAW SEQ. ID NO: 170. | | SEQ. ID NO: 6. KKRKR | 12 |
| HPV81 | ... PYAIYVVGTDFYLFPSYIFFPKKHKRIHYSFTDGYVAAW SEQ. ID NO: 171. | | SEQ. ID NO: 7. RRRKRKR | 12 |
| CePV1 | ... ILTDSDAGFFWNTFLHPSLLSKKKGKKTF SEQ. ID NO: 172. | | SEQ. ID NO: 8. RKRKR | 10 |
| HPV156 | ... QPSFGVDVYSDDFYLHPGLYHKKKKETNRIFLMFCRCPYGCRPLENC IFHLKSQLLKC SEQ. ID NO: 173. | | SEQ. ID NO: 9. KRKRKR | 6 |
| CcrPV1 | ... TPAVVIDLLGGTDFYLHPALFKKKKKRLFCDFFADGGVASCTE SEQ. ID NO: 174. | | SEQ. ID NO: 10. RKKRKR | 6 |
| EcPV8 | ... PSTANSLDASYSYYLHPSLNNKKKKKSKGLRGGWWFVADDLLAT SEQ. ID NO: 175. | | SEQ. ID NO: 11. RKRKRKR | 6 |
| HPV37 | ... TPTVVIRFGEAGTDYYLHPSLKKKKRKRKYL SEQ. ID NO: 176. | | SEQ. ID NO: 12. RRRRRKR | 6 |
| CdPV1 | ... GIVIDLSDDYYRHYYLHPSLLKKKKSKVRKLWYA SEQ. ID NO: 177. | | SEQ. ID NO: 13. RKRRKRK | 5 |
| OaPV3 | ... IPVSPAVSLGGANYWLEPSLIKKKRKKKRLI SEQ. ID NO: 178. | | SEQ. ID NO: 14. RKRRR | 5 |
| HPV162 | ... QPPTVILDLFSDDYFLHPSYLKKKRKRSDIF SEQ. ID NO: 179. | | SEQ. ID NO: 15. RRRRKRK | 5 |
| TmPV1 | ... TILIDFQSSYGDFFLHPSLIPKKKRRLGLFTDEYVVTE SEQ. ID NO: 180. | | SEQ. ID NO: 16. KKRKRK | 4 |
| AmPV4 | ... TPVIVLDWQQSNDFFLHPSLIKKKRRKRSAAFF SEQ. ID NO: 181. | | SEQ. ID NO: 17. RKRKKRK | 4 |
| HPV132 | ... IGPSYYVGVDNDFYLHPSLIPKKKRRRLDYF SEQ. ID NO: 182. | | SEQ. ID NO: 18. RKRRRR | 4 |
| BPV22 | ... PIRPGLDVYDSIDFYLHPSLGKKLRKKRKRRFY SEQ. ID NO: 183. | | SEQ. ID NO: 19. RKRRK | 4 |
| HPV68 | ... TFAITIYGSNYYLLPLLFFLLKKRKHLPYFFTDGIVAS SEQ. ID NO: 184. | | SEQ. ID NO: 20. RRRKRKRK | 4 |
| RrPV1 | ... PWVVDGDGGSGYWIDPSLLTNKKRKKHFH SEQ. ID NO: 185. | | SEQ. ID NO: 21. RRRRKRKR | 4 |
| CmPV1 | ... VHPAYSVTFSMLSELDDPFLTKKRKKCFADGCLDTFY SEQ. ID NO: 186. | | SEQ. ID NO: 22. RRRRKRR | 4 |
| HPV18 | ... TQYIGIHGTHYYLWPLYYFIPKKRKRVPYFFADGFVAA SEQ. ID NO: 187. | | SEQ. ID NO: 23. KRRKRK | 3 |
| HPV39 | ... TYAITIQGSNYYLLPLLYFFLKKRKRIPYFFSDGYVAV SEQ. ID NO: 188. | | SEQ. ID NO: 24. KRRRKR | 3 |
| HPV45 | ... TTYIGIHGTQYYLWPWYYFPKKRKRIPYFFADGFVAA SEQ. ID NO: 189. | | SEQ. ID NO: 25. RKKRKRK | 3 |
| HPV70 | ... TVAIAIQGSNYYLLPLLYYFLKKRKRIPYFFTDGFVAV SEQ. ID NO: 190. | | SEQ. ID NO: 26. RKRRKR | 3 |
| HPV71 | ... PSSFIVYGTEYYLMPSYIFFPKKRKRVHYFFADGFVAA SEQ. ID NO: 191. | | SEQ. ID NO: 27. RKRRRKR | 3 |
| HPV83 | ... IQSVFIDGTDYYLLPNYIFFPKKRKRVHYSFADGYVAAW SEQ. ID NO: 192. | | SEQ. ID NO: 28. RKKRKR | 3 |
| HPV84 | ... PYAIYILGSDYYLLPNYIFFPKKRKRVPYSFSDGYVAAW SEQ. ID NO: 193. | | SEQ. ID NO: 29. RRRRK | 3 |
| HPV85 | ... THSVVLQGTNYYLWPNYYFIFKKRKRVPYFLTDGFVAF SEQ. ID NO: 194. | | SEQ. ID NO: 30. RRRRRRRRR | 3 |
| HPV90 | ... PGSVLVNGSTYYLLPPLGLLPKKRKRFPYFFADGNVEA SEQ. ID NO: 195. | | SEQ. ID NO: 31. KKHKR | 2 |

TABLE 1-continued

| Virus | Sequence | Basic sequence | Frequency |
|---|---|---|---|
| HPV97 | ... THYIGINGTHYYLWPLYYFLPKKRKRVPYFFADGLLAA SEQ. ID NO: 196. | SEQ. ID NO: 32. KKRKK | 2 |
| HPV102 | ... SQSVFVDGTDYFLLPNYLFFPKKRKRVHYSFADGFVATW SEQ. ID NO: 197. | SEQ. ID NO: 33. KKRKRKR | 2 |
| EePV1 | ... TIVIEAFDSSGGFYLHPSFVGKKRKRLYFL SEQ. ID NO: 198. | SEQ. ID NO: 34. KRHKHK | 2 |
| EhPV1 | ... VPIIVVDATSQDFYLHPYLQHKKRKRKHFVYMFADGSVASEYQ SEQ. ID NO: 199. | SEQ. ID NO: 35. KRKKRR | 2 |
| HPV147 | ... VAPAVHVEAFGSNYYLHPSLLKKRKRKYLDVF SEQ. ID NO: 200. | SEQ. ID NO: 36. KRKRRKRK | 2 |
| CPV1 | ... PAIVIDILDSSADYYLHPSLIKKRKRKHFFF SEQ. ID NO: 201. | SEQ. ID NO: 37. KRKRRR | 2 |
| LrPV1 | ... PAILIEIWDSGSNYSLHPSLLKKRKRKLLFL SEQ. ID NO: 202. | SEQ. ID NO: 38. KRLKRKRK | 2 |
| HPV115 | ... LPAVVIHIYDDSGDFYLHPSLKKRKRKRAYL SEQ. ID NO: 203. | SEQ. ID NO: 39. KRKKRKRK | 2 |
| HPV170 | ... GPSILIDEFSSEDFVLHPSLSKKRKRKRLYSDF SEQ. ID NO: 204. | SEQ. ID NO: 40. KRRRRKR | 2 |
| HPV17 | ... TPTVVIKFAEAGGRFLFTPSLKKRKRKRKYL SEQ. ID NO: 205. | SEQ. ID NO: 41. RKHKHK | 2 |
| HPV158 | ... PFIPSTLQFDTFDYDIHPSAIKKRRRKRKRSDFM SEQ. ID NO: 206. | SEQ. ID NO: 42. RKKRRR | 2 |
| HPV148 | ... VAPSYIPDYYADFYLYPSFLPKKRRRIDIV SEQ. ID NO: 207. | SEQ. ID NO: 43. RKRKRKRK | 2 |
| EcPV4 | ... SATPPTSTDTAGFSMLDPSLLKRCRRKRRSCFADGIVDARQSEVLSAP CSCDKGAQY SEQ. ID NO: 208. | SEQ. ID NO: 44. RKRRKRKR | 2 |
| BPV3 | ... PDIIITFEEGTATFFLHPSLLKRHKHKHWFF SEQ. ID NO: 209. | SEQ. ID NO: 45. RKRRRKRK | 2 |
| BPV15 | ... PDIVIDMEEDTATFTLHPSLLKRHKHKWFF SEQ. ID NO: 210. | SEQ. ID NO: 46. RRKRKRK | 2 |
| HPV159 | ... PTVVIHIHDTSGDYYLHPSLQKRKCKRKHRYL SEQ. ID NO: 211. | SEQ. ID NO: 47. RRRKRKR | 2 |
| HPV135 | ... GPTSPVSFYSDDFYLHPSLFTKRKKRKYYNF SEQ. ID NO: 212. | SEQ. ID NO: 48. RRKKRR | 2 |
| BPV5 | ... ITDSGVDGTYFLNTYLHPSLHKRKKRRFS SEQ. ID NO: 213. | SEQ. ID NO: 49. RRRRKRK | 2 |
| BPV8 | ... IIDFSVEGTYFLNTYAHPSLHKRKKRRLS SEQ. ID NO: 214. | SEQ. ID NO: 50. RRRRRRR | 2 |
| AmPV2 | ... TPIITGVFVSFDFWLHPSQLLKRKRSPFYLADGIVAA SEQ. ID NO: 215. | SEQ. ID NO: 51. KGKRRKKR | 1 |
| HPV128 | ... PYAPSPITVFGDTFYLNPSLLKRKRKQYFY SEQ. ID NO: 216. | SEQ. ID NO: 52. KHRKRKRK | 1 |
| HPV73 | ... PAGPIYIYGSGFILHPSYYLLKRKRKRLSYSFTDVATY SEQ. ID NO: 217. | SEQ. ID NO: 53. KKGKKRK | 1 |
| HPV104 | ... PAVVIHIADASGDFYLHPSLQKRKRKRAYL SEQ. ID NO: 218. | SEQ. ID NO: 54. KKHK | 1 |
| HPV121 | ... EPAIIIDLESASDFFIHPSLLKRKRKRPLL SEQ. ID NO: 219. | SEQ. ID NO: 55. KKHKHK | 1 |
| HPV130 | ... EPAIIIDLESANDFLIHPSLLKRKRKRPLL SEQ. ID NO: 220. | SEQ. ID NO: 56. KKKGKK | 1 |
| HPV133 | ... EPAIVIDLESASDFFIHPSLLKRKRKRPLL SEQ. ID NO: 221. | SEQ. ID NO: 57. KKKK | 1 |
| HPV136 | ... INPSLGASVIFDTYDLHPSLLKRKRKRPFF SEQ. ID NO: 222. | SEQ. ID NO: 58. KKKKKR | 1 |
| HPV142 | ... EPAIIIDVDSATDFLIHPSLLKRKRKRHLL SEQ. ID NO: 223. | SEQ. ID NO: 59. KKKKKSK | 1 |
| HPV153 | ... PLYPTEVTVYGDSFVIDPFFLKRKRKRYTLY SEQ. ID NO: 224. | SEQ. ID NO: 60. KKKKRKRK | 1 |
| HPV166 | ... TEPHLIIDLFSDDFYLHPGYLKRKRKRSDIF SEQ. ID NO: 225. | SEQ. ID NO: 61. KKKKSKVR | 1 |
| HPV175 | ... IMPGVTIDIYSIDYDIHPSLLKRKRKRIDYV SEQ. ID NO: 226. | SEQ. ID NO: 62. KKKKKKR | 1 |
| HPV180 | ... EPAIIIDLESATDFLIHPSLLKRKRKRNLL SEQ. ID NO: 227. | SEQ. ID NO: 63. KKKRKR | 1 |
| UuPV1 | ... AIVIEIWGSGNSYSLHPSLLSKRKRKRLSL SEQ. ID NO: 228. | SEQ. ID NO: 64. KKKRR | 1 |
| TmPV3 | ... HIFVYSPHLTSFDFLPHPSLLKRKRKRSLDDDFTILQ SEQ. ID NO: 229. | SEQ. ID NO: 65. KKKRRKR | 1 |
| GcPV1 | ... IIDNELAVWFHSYFLHPSKLGKRKRKRSDSSV SEQ. ID NO: 230. | SEQ. ID NO: 66. KKKRRR | 1 |

TABLE 1-continued

| Virus | Sequence | Basic sequence | Frequency |
|---|---|---|---|
| BPV14 | ... IIDGNTIDLYSSNFTLHPSLLKRKRKRKHA SEQ. ID NO: 231. | SEQ. ID NO: 67. KKLRKKKRKRR | 1 |
| HPV111 | ... PTWVIHISDTSGDYYLHPSLQKRKRKRKYL SEQ. ID NO: 232. | SEQ. ID NO: 68. KKRK | 1 |
| MpPV1 | ... PTIIVTKETGVTYDLHPSLFGKRKRKRRSL SEQ. ID NO: 233. | SEQ. ID NO: 69. KKRKRKRK | 1 |
| RtiPV1 | ... TVLINVYDEGLDFLLHPSMFPKRKRRKLAFL SEQ. ID NO: 234. | SEQ. ID NO: 70. KKRRKRKR | 1 |
| EIPV1 | ... PGILIEVLDSSGDFYLHPSLLKRKRKRPSF SEQ. ID NO: 235. | SEQ. ID NO: 71. KKRRR | 1 |
| HPV122 | ... PTWVIHIADTSGDYYLHPSLQKRKRKRKYL SEQ. ID NO: 236. | SEQ. ID NO: 72. KRCRRKRR | 1 |
| CgPV2 | ... PWVIIYPHDNTGDFYLHPSLHKRKRRKRKYF SEQ. ID NO: 237. | SEQ. ID NO: 73. KRKCKRK | 1 |
| HPV165 | ... PAPHTVSDINDDYYLPSLYPKRKRRRLDFF SEQ. ID NO: 238. | SEQ. ID NO: 74. KRKKRK | 1 |
| HPV184 | ... PLEPANAIEVYYDFFLHPALQKRKRRRLDVF SEQ. ID NO: 239. | SEQ. ID NO: 75. KRKR | 1 |
| CcaPV1 | ... DGNINLQEVLYRQYFLHPSLMKRKRRRKRLFG SEQ. ID NO: 240. | SEQ. ID NO: 76. KRKRK | 1 |
| RnPV2 | ... RPPIYIGSSPGVDYYLHPSLYKRKRRRRHSYL SEQ. ID NO: 241. | SEQ. ID NO: 77. KRKRKRK | 1 |
| HPV20 | ... PVVIIHTYDTSGDFYLHPSLTKRLKRKRKYL SEQ. ID NO: 242. | SEQ. ID NO: 78. KRKRKRKRK | 1 |
| HPV14 | ... PVVIIHTYDTSGDFYLHPSLHKRLKRKRKYL SEQ. ID NO: 243. | SEQ. ID NO: 79. KRKRKRR | 1 |
| CcPV1 | ... STPLYPPRHVFFSDLDDPIMFKRRKKCFADGCVDAFY SEQ. ID NO: 244. | SEQ. ID NO: 80. KRKRRK | 1 |
| AsPV1 | ... PPTVIVYDYDDSVDFYLHPSLKRRKKRKYIVY SEQ. ID NO: 245. | SEQ. ID NO: 81. KRKRRKR | 1 |
| HPV2 | .. PSSVYIFGGDYYLMPSYVLWPKRRKRVHYFFADGFVAA SEQ. ID NO: 246. | SEQ. ID NO: 82. KRKRRRKR | 1 |
| HPV26 | ... LPAIVVHGDNYYLWPYIYLIHKRRKRMPYFFSDGFVAY SEQ. ID NO: 247. | SEQ. ID NO: 83. KRKRRRRR | 1 |
| HPV27 | ... PSSVYIFGGDYYLLPSYILWPKRRKRVNYFFADGFVAA SEQ. ID NO: 248. | SEQ. ID NO: 84. KRKKK | 1 |
| HPV57 | ... PSSVYIVGGDYYLLPSYVLWPKRRKRVHYFFADGYVAA SEQ. ID NO: 249. | SEQ. ID NO: 85. KRKKKRK | 1 |
| HPV61 | ... PHSIYIQGSDFYLLPAYVFFPKRRKRVPYSFSDGFVAAW SEQ. ID NO: 250. | SEQ. ID NO: 86. KRRR | 1 |
| HPV72 | ... PHSIYVEGFDFYLLPAYIFFPKRRKRVPYSFADGFVAAW SEQ. ID NO: 251. | SEQ. ID NO: 87. KRRRK | 1 |
| HPV87 | ... PYSVYIQGSDYYLLPNYIFFPKRRKRVPYSFSDGFVAAW SEQ. ID NO: 252. | SEQ. ID NO: 88. KRRRR | 1 |
| HPV91 | ... PSAVSIYGTDFYLHPSLLHFGKRRKRISYFFADNYVAA SEQ. ID NO: 253. | SEQ. ID NO: 89. KRRRRR | 1 |
| HPV114 | ... PYAIYIVGSDYYLLPNYIFFPKRRKRVPYSFSDGFVAAW SEQ. ID NO: 254. | SEQ. ID NO: 90. KRRRRRR | 1 |
| CgPV1 | ... QHSIYVHGTDFYLLPGYLFVPKRRKRFIYSFADGYVAA SEQ. ID NO: 255. | SEQ. ID NO: 91. KRRRRRRK | 1 |
| AgPV1 | ... QPSAAISIFASDFYLHPSYILKRRKRVPYTFFADGIVAS SEQ. ID NO: 256. | SEQ. ID NO: 92. KRRRRRRTRR | 1 |
| SscPV1 | ... APPASVTVVSGDFVLHPSYFWKRRKRVSYFFADGVVAA SEQ. ID NO: 257. | SEQ. ID NO: 93. KSRKRK | 1 |
| SscPV2 | ... VIPAAVTIYAGDFFLHPSYIWKRRKRVSYFLADGIVAA SEQ. ID NO: 258. | SEQ. ID NO: 94. KTRKRKRK | 1 |
| TePV1 | ... PVIVIHGVYFSVDFYLHPHLLKRRKRFHF SEQ. ID NO: 259. | SEQ. ID NO: 95. KWKKRKR | 1 |
| HPV43 | ... PQSVSIHGTDFYLHPSLWHLGKRRKRFSYFFTDNYVAA SEQ. ID NO: 260. | SEQ. ID NO: 96. RGRKRKRR | 1 |
| MfPV6 | ... IGHVVVHGGDFYLHPSYYTLHKRRKRMPRFLADVSVAA SEQ. ID NO: 261. | SEQ. ID NO: 97. RHRRKRR | 1 |

TABLE 1-continued

| Virus | Sequence | Basic sequence | Frequency |
|---|---|---|---|
| HPV89 | ... PQAIYIQGTDFYLVPNYVFFPKRRRKRVPYSFADGFVAAW SEQ. ID NO: 262. | SEQ. ID NO: 98. RHRRRKR | 1 |
| HPV112 | ... YTPVIYIDPFGSDFYLHPALLKRRRKRKYSEIF SEQ. ID NO: 263. | SEQ. ID NO: 99. RKFKRRRK | 1 |
| HPV172 | ... LIPGRSVDVYSNDFIIHPSVLKRRRKRKLSDSF SEQ. ID NO: 264. | SEQ. ID NO: 100. RKHRHK | 1 |
| HPV168 | ... ISPAVLIDAFSADYYLHPSLMKRRRKRKYSEIF SEQ. ID NO: 265. | SEQ. ID NO: 101. RKKKKK | 1 |
| HPV150 | ... TPTVIIHTEDYSGDYYLHPSLKRRRKRKRAYL SEQ. ID NO: 266. | SEQ. ID NO: 102. RKKKKRK | 1 |
| HPV169 | ... PVGPSSSVDIFYYDYDLHPSLKRRRKRKRNMF SEQ. ID NO: 267. | SEQ. ID NO: 103. RKKKR | 1 |
| HPV171 | ... PIGPSNSVEIFYYDYDLHPSLKRRRKRKRNVF SEQ. ID NO: 268. | SEQ. ID NO: 104. RKKRK | 1 |
| PcPV1 | ... PAIILEIWGSGENYSLHPSLLKRRRKRKRLIL SEQ. ID NO: 269. | SEQ. ID NO: 105. RKKRR | 1 |
| CPV17 | ... DVPSSSSDSVSSTFDLHPSLLKRRRKRKRGDI SEQ. ID NO: 270. | SEQ. ID NO: 106. RKKRRK | 1 |
| HPV197 | ... LEPPILLDYLGSGYYLHPSLWKRRRKRKRSDTYNSFTDGIVDATEW SEQ. ID NO: 271. | SEQ. ID NO: 107. RKKRRKR | 1 |
| HPV80 | ... TPTWVINFEDAGGDYYLHPSLKRRRKRKRKYL SEQ. ID NO: 272. | SEQ. ID NO: 108. RKKRRKRK | 1 |
| HPV164 | ... ITPAVYLDAFSSDYYLHPALMKRRRKRKRKYLEVF SEQ. ID NO: 273. | SEQ. ID NO: 109. RKKRRRR | 1 |
| HPV50 | ... SEQPLFVLDYSDYDLHPGLLPKRRRIDYF SEQ. ID NO: 274. | SEQ. ID NO: 110. RKRFKRKRK | 1 |
| MrPV1 | ... IFSTPYYEYNYILDPSILFLLKRRRKLFV SEQ. ID NO: 275. | SEQ. ID NO: 111. RKRK | 1 |
| HPV31 | ... PQVSIFVDGGDFYLHPSYYMLKRRRKRVSYFFTDVSVAA SEQ. ID NO: 276. | SEQ. ID NO: 112. RKRKHK | 1 |
| HPV35 | ... PIYSIIADGGDFYLHPSYYLLKRRRKRIPYFFADVSVAV SEQ. ID NO: 277. | SEQ. ID NO: 113. RKRKKRR | 1 |
| HPV69 | ... SHSVVAQGGNYYLWPYIYLIHKRRRKRVPCFFSDGLAAY SEQ. ID NO: 278. | SEQ. ID NO: 114. RKRKRKYR | 1 |
| EaPV1 | ... PSFDWPMTDLDADFVLHPSLLKRRRRFYWSFADGGLASRTK SEQ. ID NO: 279. | SEQ. ID NO: 115. RKRKRRRK | 1 |
| HPV53 | ... DTTHDVVIQGSTFALWPVYFLKRRRRKRIPYFLADGGVAA SEQ. ID NO: 280. | SEQ. ID NO: 116. RKRR | 1 |
| HPV66 | ... DVTHDVYIQGATFALWPVYFFKRRRRKRIPYFFADGDVAA SEQ. ID NO: 281. | SEQ. ID NO: 117. RKRRKK | 1 |
| TmPV2 | ... PIVIIDLTSTSIDYFLHPSLAKRRRRAHWSFLADVGLAT SEQ. ID NO: 282. | SEQ. ID NO: 118. RKRRKRR | 1 |
| RtPV2 | ... PDIIIDFLTPGDTFYLHPSHFKRRRRRRYQLFFF SEQ. ID NO: 283. | SEQ. ID NO: 119. RKRRRRKR | 1 |
| CPV3 | ... VIVDVERGSGSDYYLHPSLSLKRRRRRRRKSL SEQ. ID NO: 284. | SEQ. ID NO: 120. RKRRRRRRR | 1 |
| MscPV1 | ... ITAIPAGGQSIDFLLHPGLFPKRRRRRRRTRRH-SYL SEQ. ID NO: 285. | SEQ. ID NO: 121. RLKRKRK | 1 |
| HPV119 | ... ITPLIQIDPFGPDFYLHPALMKSRKRKYLEVF SEQ. ID NO: 286. | SEQ. ID NO: 122. RLKRKRKR | 1 |
| HPV15 | ... TPTVVINFEEAGGDYYLHPSLKTRKRKRKYL SEQ. ID NO: 287. | SEQ. ID NO: 123. RLKRRRR | 1 |
| HPV92 | ... TPTVIIHTEDFSGDYYLHPSLKWKRKRAYL SEQ. ID NO: 288. | SEQ. ID NO: 124. RLKRRKRR | 1 |
| PmPV1 | ... PQPPTYEGPSSGVTYYLHPSLRGRKRKRRNLHVRFSIPDGILAS SEQ. ID NO: 289. | SEQ. ID NO: 125. RLRRKR | 1 |
| FcaPV5 | ... VMPPIIFDPETSTFDLHPSLHRHRRKRRHIGL SEQ. ID NO: 290. | SEQ. ID NO: 126. RLRRKRKR | 1 |
| HPV10 | ... THYVYIDGGDFYLWPVTFHFSRHRRRKRVSYFFADGTLAL SEQ. ID NO: 291. | SEQ. ID NO: 127. RRKKRKK | 1 |
| HPV21 | ... PVVIIHTFDTSGDFYLHPSLSRKFKRRRKYL SEQ. ID NO: 292. | SEQ. ID NO: 128. RRKRK | 1 |
| BPV10 | ... PTVIIDFEDGSATFFLHPSLLRKHKHKHWFF SEQ. ID NO: 293. | SEQ. ID NO: 129. RRKRKKKR | 1 |
| BPV11 | ... PEIVIDFEENTATFYLHPSLLRKHKHKHWFF SEQ. ID NO: 294. | SEQ. ID NO: 130. RRKRKKRKR | 1 |

TABLE 1-continued

| Virus | Sequence | Basic sequence | Frequency |
|---|---|---|---|
| BPV6 | ... PDIIVNLEENTATFFLHPSLLRKHRHKHWFF SEQ. ID NO: 295. | SEQ. ID NO: 131. RRKRKRR | 1 |
| MscPV2 | ... PLVIIDPVGTGANYFLHPSLLRKKKKKLIFH SEQ. ID NO: 296. | SEQ. ID NO: 132. RRKRRKRKR | 1 |
| MsPV1 | ... EVVIVQEGNNSGTFYLHPSLLRKKKKRKYVF SEQ. ID NO: 297. | SEQ. ID NO: 133. RRKRRKRR | 1 |
| AmPV1 | ... WYPTILSELSSSDFIFHPSLWRKKKRFPPFFLSDGIVAA SEQ. ID NO: 298. | SEQ. ID NO: 134. RRKRRRR | 1 |
| RaPV1 | ... VIVEDDTAAYDYWFDLYLHLPRKKRKWCSFCSLTDGIVDT SEQ. ID NO: 299. | SEQ. ID NO: 135. RRKRRRRGRR | 1 |
| MfPV9 | ... PTTHVVVYGGDFYLHPSYFPVRKKRKRVHRFLSDVIVAA SEQ. ID NO: 300. | SEQ. ID NO: 136. RRKRRRRKR | 1 |
| HPV4 | ... LEPALLSDIFSTDFVYRPSLYRKKRKRLEMF SEQ. ID NO: 301. | SEQ. ID NO: 137. RRKRRRRRK | 1 |
| HPV65 | ... LEPPFFSEFYSSDFVYRPSLYRKKRKRSDIF SEQ. ID NO: 302. | SEQ. ID NO: 138. RRKRRRRRKR | 1 |
| HPV95 | ... PLKPALLTDFYSDFTYYPSLYRKKRKRSDLF SEQ. ID NO: 303. | SEQ. ID NO: 139. RRLRRKRK | 1 |
| PphPV1 | ... PLIVLFEPGFGPSFYLHPSLLRKKKRVFY SEQ. ID NO: 304. | SEQ. ID NO: 140. RRRGRKRK | 1 |
| TtPV5 | ... PFIFFLFSHGDPSFFLHPSLLRKKKRVFY SEQ. ID NO: 305. | SEQ. ID NO: 141. RRRKRIK | 1 |
| HPV134 | ... RPSILIDDFASNDFVLHPSLNRKKKRKQVHFL SEQ. ID NO: 306. | SEQ. ID NO: 142. RRRKRK | 1 |
| HPV9 | ... PTVVIHINDTSGDYYLHPSLQRKKKRKYL SEQ. ID NO: 307. | SEQ. ID NO: 143. RRRKRR | 1 |
| EhPV3 | ... VGPSYVESTDSFPYWLAPSLQRKKKRKTVSFCSLADGCMDS SEQ. ID NO: 308. | SEQ. ID NO: 144. RRRKRKRR | 1 |
| HPV48 | ... INWFPLFDSYSDFALDPFFIPRKKKRLDIL SEQ. ID NO: 309. | SEQ. ID NO: 145. RRRR | 1 |
| SfPV1 | ... ISPVFIFEGNADGTYYLEEPLRKKKRKSIFLLADGSVAVYAE SEQ. ID NO: 310. | SEQ. ID NO: 146. RRRRARR | 1 |
| CPV6 | .. PAISFDIYGDGLNFYLHPSLLRKKKRRKYFY SEQ. ID NO: 311. | SEQ. ID NO: 147. RRRRKRKR | 1 |
| HPV23 | ... APAVVIHTLDKSFDYYLHPSLRKKKRKYL SEQ. ID NO: 312. | SEQ. ID NO: 148. RRRKRRR | 1 |
| HPV127 | ... TPAFYLDIYNDFNLHPALLPPRKKRRLDIF SEQ. ID NO: 313. | SEQ. ID NO: 149. RRRRRK | 1 |
| HPV199 | ... LTPSIITSSYNNFYLEPFYVPRKKRRLDMF SEQ. ID NO: 314. | SEQ. ID NO: 150. RRRRKRRR | 1 |
| TtPV2 | ... PNINVYSLDDTGGQFRFWHFLRKKKRRRYL SEQ. ID NO: 315. | SEQ. ID NO: 151. RRRRRR | 1 |
| HPV19 | ... LPVVIHTYDTSGDFYLHPSLRKRFKRKRYL SEQ. ID NO: 316. | SEQ. ID NO: 152. RRRRRKR | 1 |
| BPV7 | ... VVVISYTADVSIFSLFEPSLYRKRKYSYLY SEQ. ID NO: 317. | SEQ. ID NO: 153. RRRRRRR | 1 |
| BPV23 | ... PEIVIDFGESTASFSLHPSLLRKRKHKHWFF SEQ. ID NO: 318. | SEQ. ID NO: 154. RRRRRRRK | 1 |
| BPV1 | ... IIDGHTVDLYSSNYTLHPSLLRKRKKRKHA SEQ. ID NO: 319. | SEQ. ID NO: 155. RRRRRRRRK | 1 |
| BPV2 | ... IIDGHTVDLYSNNYSLHPSLRKRKKRKHA SEQ. ID NO: 320. | SEQ. ID NO: 156. RSKKRKRK | 1 |
| BPV13 | ... IIDGHTIDLYSNNYSLHPSLRKRKKRKHA SEQ. ID NO: 321. | SEQ. ID NO: 157. RSRKRKR | 1 |
| BgPV1 | ... IIDGHIVDLYSRNYSLHPSLYRKRKKRKHA SEQ. ID NO: 322. | SEQ. ID NO: 158. RTKRRKRK | 1 |
| BPV16 | ... DYSYDQSAGPSFTLDPSLLQLRKRKKRRYY SEQ. ID NO: 323. | SEQ. ID NO: 159. RVKKRR | 1 |
| HPV34 | ... SGPIYIYGSDFILHPSLYVIPRKRKRLSYFFADVATY SEQ. ID NO: 324. | SEQ. ID NO: 160. RWKKRKRK | 1 |
| HPV106 | ... TGDVLVHGSTYYLLPSYVLLPRKRKRFPSFFADGIVEA SEQ. ID NO: 325. | SEQ. ID NO: 161. RWKRKR | 1 |
| HPV59 | ... IQSINIEGTNYFLWPIYYFLPRKRKRVPYFFTDGSMAF SEQ. ID NO: 326. | SEQ. ID NO: 162. RWKRKRK | 1 |
| HPV86 | ... PYAIYIQGSDYYLLPNYIFFPRKRKRVHYSFSDGFVAAW SEQ. ID NO: 327. | SEQ. ID NO: 163. RWRKRRR | 1 |
| AaPV1 | ... GNINVSMEYFRHYYLHPSLLGRKRKRLFG SEQ. ID NO: 328. | SEQ. ID NO: 164. RWRRRKRK | 1 |
| HPV103 | ... PSVVVDSFVTSTTFYLHPGLSRKRKRSHMF SEQ. ID NO: 329. | | |

TABLE 1-continued

| Virus | Sequence | Basic sequence | Frequency |
|---|---|---|---|
| HPV129 | ... QPSFAIDVDNSTFDIHPSLLPRKRKRPSF SEQ. ID NO: 330. | | |
| HPV140 | ... LGPAVGLTVNFDDFDLHPSLLRKRKRSIL SEQ. ID NO: 331. | | |
| HPV202 | ... LGPSQGLTVDFYDFDLHPSLLRKRKRSIF SEQ. ID NO: 332. | | |
| HPV204 | ... PLITIRIDNSTGDYDVDPSLLRKRKRVF SEQ. ID NO: 333. | | |
| PphPV4 | ... ISPAFWNMSYSTFYLHPGYLARKRRKVLT SEQ. ID NO: 334. | | |
| McPV2 | ... IPARTVIYFDDFADFYLHPSLRKRKRKHVIR SEQ. ID NO: 335. | | |
| MmiPV1 | ... PGADVVVVPEDSVDYYLHPSLRKRKRKYVFH SEQ. ID NO: 336. | | |
| CPV2 | ... IPLSSPDYGSVTFDLHPGLIHRKRKRKRGSV SEQ. ID NO: 337. | | |
| BpPV1 | ... PFEPPTEPDPAETGGNFEPSLRKRKRKRVEVASRTYSLRRKR SEQ. ID NO: 338. | | |
| HPV123 | ... TPSILVDGFSSTDFILHPSHTRKRKRKRSDYF SEQ. ID NO: 339. | | |
| HPV161 | ... DNTPLLVLDLTSDDYFLHPSLRKRKRKRSDVF SEQ. ID NO: 340. | | |
| FcaPV1 | ... PAIVIEVWASGATYSLHPSLLRKRKRKRISL SEQ. ID NO: 341. | | |
| PlpPV1 | ... PAIVIDIWESGNSYSLHPSLLRKRKRKRLFL SEQ. ID NO: 342. | | |
| HPV105 | ... IPIVVIHTHDSSGDFYLHPSLRKRKRKRKYL SEQ. ID NO: 343. | | |
| HPV113 | ... APSVVFHITDTSGDFYLHPSLRKRKRKRKYL SEQ. ID NO: 344. | | |
| MmuPV1 | ... PASTVISVDDDFADFYLHPSLRKRKRKYRIY SEQ. ID NO: 345. | | |
| EcPV2 | ... SVFVFTFSMNGLFDLHPSLHPRKRKRRYNCCFADGFLDNEQTTPVPTP QSRL SEQ. ID NO: 346. | | |
| HPV108 | ... PFVIVDSFISSDTFYLHPSLVRKRKRRDLV SEQ. ID NO: 347. | | |
| HPV137 | ... QPPDGVLVDDNDYYLHPGLYSRKRKRRVL SEQ. ID NO: 348. | | |
| HPV201 | ... TVPVLEYDFTSADFTLHPSLSRKRKRRPSF SEQ. ID NO: 349. | | |
| EsPV3 | ... DTPVITIDIWSSDFYLHPSLSRKRKRRRKFVFVY SEQ. ID NO: 350. | | |
| SaPV1 | ... IPTEPHKKGKPIHVHRKRRCIKRRGKRCVKYSL SEQ. ID NO: 351. | | |
| HPV74 | ... PTGPVFINGSTFYLYPSWYFARKRRKHVPLFFTDVAA SEQ. ID NO: 352. | | |
| HPV32 | ... PSFDSVMVLGWDFILHPSYMWRKRRKPVPYFFADVRVAA SEQ. ID NO: 353. | | |
| MfPV7 | ... PQGHITVLGGAFYWHPSWYTARKRRKLVPNFLADVSVAA SEQ. ID NO: 354. | | |
| HPV63 | ... IPLIIIHLDNSTGDYDLHPSLRKRRRKLVHI SEQ. ID NO: 355. | | |
| ChPV1 | ... PIPAVLFNVLSSDLLLDPSLLRKRRKKYGVFS SEQ. ID NO: 356. | | |
| PhPV1 | ... PTARIIVYGGDFYLHPSYFGIRKRRKRVHHSFADVFVAA SEQ. ID NO: 357. | | |
| HPV7 | ... IPAISVLIRGTDYYLNPAYYFRKRRKRILAY SEQ. ID NO: 358. | | |
| HPV13 | ... PTGPVFITASGFYLYPTWYFTRKRRKRVSLFFTDVAA SEQ. ID NO: 359. | | |
| HPV16 | ... PQYTIIADAGDFYLHPSYYMLRKRRKRLPYFFSDVSLAA SEQ. ID NO: 360. | | |
| HPV40 | ... IPAISVLIHGTDYYLHPAYYLRKRRKRILAHQYVAT SEQ. ID NO: 361. | | |
| HPV44 | ... PTGPVFISGAAFYLYPTWYFARKRRKRVSLFFADVAA SEQ. ID NO: 362. | | |

TABLE 1-continued

| Virus | Sequence | Basic sequence | Frequency |
|---|---|---|---|
| HPV51 | ... TKHSIVILGGDYYLWPYTHLLRKRRKRIPYFFTDGIVAH SEQ. ID NO: 363. | | |
| HPV54 | ... PQTPIAVNGGDFYLHPSYTYVRKRRKRFPYFLADGYVAA SEQ. ID NO: 364. | | |
| HPV82 | ... TQHAIVIQGGDYYLWPYTYLLRKRRKRIPYFFADGFVAY SEQ. ID NO: 365. | | |
| MfPV5 | ... PTSHVVVYGGDFYLHPSYYTIRKRRKRVHRFLSDVLVAA SEQ. ID NO: 366. | | |
| MfuPV1 | ... PSSHIVVYGGDFYLHPAYYPTRKRRKRMHRFLSDVLVAA SEQ. ID NO: 367. | | |
| PpPV1 | ... PITPIFISGSQFYLHPSLYLARKRRKRVSLFFADVAA SEQ. ID NO: 368. | | |
| SscPV3 | ... WVPSMSVTVFSGDYFLHPSYFRKRRKRVSYFFADGIVAA SEQ. ID NO: 369. | | |
| PlPV1 | ... PLIIIEVLDGSGDYFLHPSLFRKRRKRPFF SEQ. ID NO: 370. | | |
| HPV1 | ... TPLVIIALNNSTGDFELHPSLRKRRKRAYV SEQ. ID NO: 371. | | |
| HPV6 | ... PTGPVFITGSGFYLHPAWYFARKRRKRIPLFFSDVAA SEQ. ID NO: 372. | | |
| HPV118 | ... PVVVIHTHDTSGDFYLHPSLSRKRRKRKYL SEQ. ID NO: 373 | | |
| HPV124 | ... VWIHTHDATGDFYLHPSLTLRKRRKRKYL SEQ. ID NO: 374 | | |
| HPV146 | ... IGPSYDVAATNSDFIYDPDLFRKRRKRKLSAF SEQ. ID NO: 375 | | |
| HPV179 | ... LKPALGLYTLGEDFIFDPDLFRKRRKRKYSDV SEQ. ID NO: 376 | | |
| HPV152 | ... VVIIHTHDTTGDFYLHPSLTLRKRRKRKYL SEQ. ID NO: 377 | | |
| EhPV2 | ... AGPSIDVGDVGIDYFLDPYLFRKRRKRKRFFSFADDHVDS SEQ. ID NO: 378 | | |
| CPV13 | ... PTVDLSDFELSMTFDLHPSLLRKRRKRKRTFL SEQ. ID NO: 379 | | |
| AmPV3 | ... RPPALGGFPGTDYYLHPGLSHRKRRKRRPFWFLL SEQ. ID NO: 380 | | |
| HPV131 | ... VEPSLIITDSHDFELHPALWPRKRRKRLDLF SEQ. ID NO: 381 | | |
| HPV157 | ... ILPQYVIETFHDFFLTPDLYPRKRRKRIDFF SEQ. ID NO: 382 | | |
| HPV200 | ... PWYSIIERNFADFVLDPAFIPRKRRKRLEIL SEQ. ID NO: 383 | | |
| PaPV1 | ... PGVLISYDGSMDPSLYYLLFYRKRRKRLHRLFYR SEQ. ID NO: 384 | | |
| PaPV2 | ... NPGIPIAYYDNLDPSLIWWYLRKRRKRLQHLFYR SEQ. ID NO: 385 | | |
| HPV29 | ... THYVYIDGGDYFLWPVTFPVSRKRRKRLSYFLADGFVAL SEQ. ID NO: 386 | | |
| HPV77 | ... THYVYIDGGNFYLWPVTFSVSRKRRKRLSYFFADGTVAL SEQ. ID NO: 387 | | |
| HPV149 | ... IPSILIDGFSSDDFVLHPSHSRKRRKRKRTPLL SEQ. ID NO: 388 | | |
| HPV99 | ... IPVVVIHTHDYSGDFYLHPSLRKRRKRKRKYL SEQ. ID NO: 389 | | |
| HPV110 | ... TWIHISDTSGDYYLHPSLQTRKRRKRKYL SEQ. ID NO: 390 | | |
| CPV8 | ... PPTVVVGSFGGVDYSLHPSLLRKRRRRRKRYIS SEQ. ID NO: 391 | | |
| CPV5 | ... LVIADITMGEGTDYYLHPSLTRKRRRRRRRRSL SEQ. ID NO: 392 | | |
| MfPV2 | ... PTVVIRTSDSSGDFYLHPSLLRLRKRKRKYL SEQ. ID NO: 393 | | |
| HPV173 | ... EPLPPAIVELDNFDYDLHPSLRLKRRKRKRTDLV SEQ. ID NO: 394 | | |
| RfPV1 | ... NDTPAVYIDPFSADYYLHPSLRLKRRRRRGQFVYVY SEQ. ID NO: 395 | | |

TABLE 1-continued

| Virus | Sequence | Basic sequence | Frequency |
|---|---|---|---|
| PpuPV1 | ... TPEIIVTFLDSSYTVADPSLFRLRKRRKRRFH SEQ. ID NO: 396 | | |
| TtPV6 | ... PFVVLHFSGGGTSFFLHPSLLRLRRKRVFY SEQ. ID NO: 397 | | |
| TmPV4 | ... IMFPQASHISSFDFLLHPSALRLRRKRKRSVHDDDGTIIE SEQ. ID NO: 398 | | |
| HPV205 | ... PLPPTFVDFDNFDYDIHPGLLRRKKRKRTDLV SEQ. ID NO: 399 | | |
| PphPV2 | ... KPTVTFDALDIGGGFYLHPYIRKKRKRMYL SEQ. ID NO: 400 | | |
| VvPV1 | ... LQPVIVVSPFESFDYNLHPSLRKKRKRPYFF SEQ. ID NO: 401 | | |
| HPV22 | ... GPAIIQSPTHSSFDYYLHPSLRRKKRKRKYL SEQ. ID NO: 402 | | |
| HPV116 | ... LTPSFSIDVNYSDYNIHPANIRRKRKHSSSLYF SEQ. ID NO: 403 | | |
| HPV41 | ... PYIVVDLYSGSMDYDIHPSLLRRKKRKRKRVYFSDGRVASRPK SEQ. ID NO: 404 | | |
| CPV7 | ... SNASDTTSDFISVTFDLHPSLRRKRKKRRRYI SEQ. ID NO: 405 | | |
| MfPV8 | ... PHGHVVVFGGDFLWHPSWYSPRRKKRLPTFFADVSVAA SEQ. ID NO: 406 | | |
| MfPV11 | ... PQGHVYVSGGDFLWHPSLYTPRRKRKRVHTFFADVSVAA SEQ. ID NO: 407 | | |
| MmPV1 | ... PSAHIILYGGDFYLHPSYLGIRRKRKRMHNFFSDVYVAA SEQ. ID NO: 408 | | |
| HPV209 | ... PAVVIHFGEPGGDFYLHPDLQRRKRKRAYL SEQ. ID NO: 409 | | |
| OaPV1 | ... DGNIIIYSTYFKHYYLHPSLYRRKRKRLLD SEQ. ID NO: 410 | | |
| OvPV1 | ... DGSIALSLEYFRHYYLHPSLLRRKRKRNPIFI SEQ. ID NO: 411 | | |
| RtPV1 | ... DGDISLSVEYFRHYYLHPSLLRRKRKRLFN SEQ. ID NO: 412 | | |
| EcPV6 | ... PGTPEVVIDIYPHTPLAFLHHRRKRKRGSSVFFADVLLAF SEQ. ID NO: 413 | | |
| HPV109 | ... PSILINESSSDDFVLHPSHIPRRKRKRAYPF SEQ. ID NO: 414 | | |
| HPV154 | ... VVPGFDINVEASDFNIHPSVLRRKRKRSMF SEQ. ID NO: 415 | | |
| PsPV1 | ... PSILLFYPDSSPSFYLHPSLLRRKRKRVFY SEQ. ID NO: 416 | | |
| HPV138 | ... PSILIDEFSSDDFVLHPSHIPRRKRKRIDSL SEQ. ID NO: 417 | | |
| HPV107 | ... PAVVIHFGESGADYYLHPHLQRRKRKRAYL SEQ. ID NO: 418 | | |
| OaPV4 | ... DGNIIIYSTYLRHYYLHPSLYRRKRKRLLD SEQ. ID NO: 419 | | |
| HPV5 | ... PVVIIHPHDSTGDFYLHPSLRRKRKRKYL SEQ. ID NO: 420 | | |
| BPV21 | ... DDPDITLAIFGTDFYLHPGLLRRKRKRKNFSV SEQ. ID NO: 421 | | |
| HPV101 | ... EPPIVVDGFDAFDTFYLHPSHRRKRKRKRSGF SEQ. ID NO: 422 | | |
| HPV155 | ... PSILIDGFSSDDFVLHPSHIPRRKRKRKRSL SEQ. ID NO: 423 | | |
| EdPV1 | ... DDTLDTFQNYNDYDLHPSLLPRRKRKRRIL SEQ. ID NO: 424 | | |
| EcPV5 | ... DVIIEYPEAGGSYFLHPTAPCRRKRRYCFADGLLDAGQSEVLSPPCACY SEQ. ID NO: 425 | | |
| UmPV1 | ... TTPHAGVYVSVDFWLHPGLLSRRKRRFPPFLFTDGIVAA SEQ. ID NO: 426 | | |
| BPV17 | ... PPYIIDFNDNSATFYLHPSLIRRKRRKRKRIFS SEQ. ID NO: 427 | | |
| CePV2 | ... PVIIDFGTSGATFYLHPSLFLRRKRRKRRFL SEQ. ID NO: 428 | | |
| RnPV3 | ... HPPIYVGSVPGVDYYLHPSLSRRKRRRRHSYL SEQ. ID NO: 429 | | |
| CPV12 | ... PIIVDVAVGAGTDYYLHPSLRRKRRRRGRRHFM SEQ. ID NO: 430 | | |

TABLE 1-continued

| Virus | Sequence | Basic sequence | Frequency |
|---|---|---|---|
| CdPV2 | ... GIIIDLSEELFKHYYLHESLLRRKRRRRKRLYA SEQ. ID NO: 431 | | |
| EsPV1 | ... SDTPIVTLDIWSSDFYLHPSLRRKRRRRRKYVFVY SEQ. ID NO: 432 | | |
| CPV10 | ... PRPDVVIYYYGGVDYSLHPSLRRKRRRRRRKRVSF SEQ. ID NO: 433 | | |
| MfPV1 | ... PIVVIHPHDNSGDFYLHPSLTRRLRRKRKYL SEQ. ID NO: 434 | | |
| BPV20 | ... PDIILDIYTPGSTFYLHPSHYRRGRKRKRTVF SEQ. ID NO: 435 | | |
| SsPV2 | ... PLVIIDVLGSGDFLLHPSLLQRRKRIKSVF SEQ. ID NO: 436 | | |
| RnPV1 | ... PGTEIVFIPEDSIDFYLHPSLRRKRKYFVR SEQ. ID NO: 437 | | |
| HPV49 | ... LPTVIIHTADTSGDFYLHPSLRRKRKRTYL SEQ. ID NO: 438 | | |
| HPV75 | ... LPAVVIHTSDTSGDFYLHPSLRRKRKRAYL SEQ. ID NO: 439 | | |
| HPV76 | ... LPAVVIHTSDTSGDFYLHPSLRRKRKRAYL SEQ. ID NO: 440 | | |
| HPV96 | ... TPTIIIHTEDFSGDYYLHPSLRRKRKRAYL SEQ. ID NO: 441 | | |
| SsPV1 | ... RPGVGLVDNAFMFAWGPQYILRRRKRKRPLPPLFADGFVAA SEQ. ID NO: 442 | | |
| HPV60 | ... IIQPAMAVDVYDDFYLHPHLLRRRKRKRLDFF SEQ. ID NO: 443 | | |
| HPV126 | ... PIGPSAALDVEYYDFDLHPSLRRRKRKRNMF SEQ. ID NO: 444 | | |
| HPV139 | ... TPSILIDEFSSDDFILHPSHIRRRKRKRLNSL SEQ. ID NO: 445 | | |
| HPV141 | ... PLQPPYEAEVVFDTFDLHPSLRRRKRKRSSF SEQ. ID NO: 446 | | |
| HPV163 | ... PYAPPLLYDFESHDFILHPSHRRRKRKRIAMF SEQ. ID NO: 447 | | |
| MaPV1 | ... GVDINVGSIYPSVDYYLHPSLRRRKRKRTLH SEQ. ID NO: 448 | | |
| PsuPV1 | ... GTTHIVGSEFSSVDYYLHPSLRRRKRKRNFH SEQ. ID NO: 449 | | |
| HPV8 | ... LPVVIIHTHDNSGDFFLHPSLRRRKRKRKYL SEQ. ID NO: 450 | | |
| HPV12 | ... IPVVVIHTHDNSGDFYLHPSLRRRKRKRKYL SEQ. ID NO: 451 | | |
| HPV47 | ... LPVVVIHTHDNSGDFYLHPSLRRRKRKRKYL SEQ. ID NO: 452 | | |
| HPV151 | ... GPAIVQSLTHTSLDYYLHPSLRRRKRKRKYL SEQ. ID NO: 453 | | |
| EcPV1 | ... IIILVDSPDTSGVFDLHPSLLRRRKRRYMWN SEQ. ID NO: 454 | | |
| ZcPV1 | ... VPPLPGYSNYGGPDFYLHPSLRRKRKRKRRYLSSFVF SEQ. ID NO: 455 | | |
| MnPV1 | ... RPHVIYRGYNGTDYYLHPSLSRRRRNSRHIYFSDGVLAA SEQ. ID NO: 456 | | |
| FlPV1 | ... PGVLVGYNDFAKDPSLYWWFIRRRRARRFHPYSRSR SEQ. ID NO: 457 | | |
| HPV42 | ... PQGNFVMVSGWDFILHPSYFWRRRRKPVPYFFADVRVAA SEQ. ID NO: 458 | | |
| MfPV4 | ... PSSHVVVYGGDFYLHPSYYPVRRRRKHMPRFLSDVVVAA SEQ. ID NO: 459 | | |
| CcanPV1 | ... MIPWIIIGTQGSDYDLHPSLLRRRRKLSFL SEQ. ID NO: 460 | | |
| HPV11 | ... PTGPVFITGSDFYLHPTWYFARRRRKRIPLFFTDVAA SEQ. ID NO: 461 | | |
| OaPV2 | ... DGNIVIYSTYLKHYYLHPSLYRRRRKRLLD SEQ. ID NO: 462 | | |
| HPV33 | ... PFDTIVVDGADFVLHPSYFILRRRRKRFPYFFTDVRVAA SEQ. ID NO: 463 | | |
| HPV52 | ... PSTSIIVDGTDFILHPSYFLLRRRRKRFPYFFTDVRVAA SEQ. ID NO: 464 | | |

TABLE 1-continued

| Virus | Sequence | Basic sequence | Frequency |
|---|---|---|---|
| HPV58 | ... PFNTIIVDGADFMLHPSYFILRRRRKRFPYFFADVRVAA SEQ. ID NO: 465 | | |
| HPV67 | ... SPFNNVLVYGSDFILHPSYFLRRRRKRFPYFFADVRVAA SEQ. ID NO: 466 | | |
| HPV78 | ... HYVYVDGGDFYLWPITFYVSHRRRRKRVSYFFTDGTVAT SEQ. ID NO: 467 | | |
| HPV160 | ... QYVYIDGGDFYLWPVTFSLFGRRRRKRLSYFFADGTVAL SEQ. ID NO: 468 | | |
| MfPV3 | ... PSADIIVNGGDFYLHPSYLSLRRRRKRMHRFFADVLVAA SEQ. ID NO: 469 | | |
| MfPV10 | ... PTAHIVVHGGDFYLHPSYLYVRRRRKRLHHFFTDVYVAA SEQ. ID NO: 470 | | |
| EcPV3 | ... GGDREVVVNMYPYSIMSFLHYRRRRKRGYVYFSDVILAI SEQ. ID NO: 471 | | |
| EcPV7 | ... PEFPEIVIDGYGLSALTFVLHRRRRKRGSHLYFSDVLLAV SEQ. ID NO: 472 | | |
| BPV12 | ... PAIIIDFTDSTATFYLHPSLMRRRRKRHIF SEQ. ID NO: 473 | | |
| HPV24 | ... AVVIHTEDSSGDFYLHPSLLQRRRRKRKYL SEQ. ID NO: 474 | | |
| HPV25 | ... WVIIHTYDTSGDFYLHPSLTTRRRRKRKYL SEQ. ID NO: 475 | | |
| HPV145 | ... VVIHVEDSSGDYYLHPSLRVTRRRRKRKYL SEQ. ID NO: 476 | | |
| HPV167 | ... DAPLVTINALGSDYDLHPSYLRRRRKRKYSEIF SEQ. ID NO: 477 | | |
| OcPV1 | ... GTITPSFSFNNSGDFVLHPSLRRRRKRKFVF SEQ. ID NO: 478 | | |
| EsPV2 | ... DIIIHDVGSSVDYILHPGLLPRRRRKRKRSY SEQ. ID NO: 479 | | |
| HPV88 | ... SEPDIRLDWFSPDYDLHPSLLRRRRKRKRNMF SEQ. ID NO: 480 | | |
| HPV178 | ... PLEPPIILDFQSSTYYLHPSLRRRRKRKRSDIYDFLSDGSVDT PEW SEQ. ID NO: 481 | | |
| BPV19 | ... GPDLIINLYGNDYSLHPSYLLRRRRKRKRFHVL SEQ. ID NO: 482 | | |
| CPV19 | ... DAPDLTSSEYLSVTFDLHPSLRRRRKRKRRYI SEQ. ID NO: 483 | | |
| DdPV1 | ... PSVVILSTDDFGDMFRFWHLLRRRRKRRYL SEQ. ID NO: 484 | | |
| TtPV1 | ... PDVVIYSTDDFGYMFRFWHLRRRRKRRYL SEQ. ID NO: 485 | | |
| TtPV4 | ... PHVVIYYTDDYGDMFRFWHLLRRRRKRRYL SEQ. ID NO: 486 | | |
| TtPV7 | ... PHVNIYYTDEFGDMFRFWHFLRRRRKRRYL SEQ. ID NO: 487 | | |
| FcaPV2 | ... RPAPSDDTVYYSAGVLDPSLLRRRRKRRRSVAYGF SEQ. ID NO: 488 | | |
| HPV30 | ... DTTHDVVIHGSTFALWPVYFLRRRRRKHVPYFLADGGVAA SEQ. ID NO: 489 | | |
| HPV3 | ... THYVYIDGGDFYLWPVTFFLPRRRRRKRVSYFLADGTVAL SEQ. ID NO: 490 | | |
| HPV28 | ... THYVYIDGGDFYLWPVTLFVPRRRRRKRLSYFLADGTVAL SEQ. ID NO: 491 | | |
| HPV56 | ... DVTHDVYIQGSSFALWPVYFFRRRRRKRIPYFFADGDVAA SEQ. ID NO: 492 | | |
| HPV94 | ... THYVYIDGGDFYLWPVTFYLSRRRRRKV SEQ. ID NO: 493 | | |
| HPV117 | ... THYVYINGGDFYLWPVTFPLSRRRRRKRVSYFFTDGTLAP SEQ. ID NO: 494 | | |
| HPV125 | ... THYVYIDGADFYLWPVALFVPRRRRRKRISYFLADGTVAL SEQ. ID NO: 495 | | |

TABLE 1-continued

| Virus | Sequence | Basic sequence | Frequency |
|---|---|---|---|
| HPV93 | ... PAVVIHTYDNSGDFYLHPSLLRRRRRKRKYL SEQ. ID NO: 496 | | |
| HPV98 | ... PVVVIHTHDNSGDFYLHPSLFRRRRRKRKYL SEQ. ID NO: 497 | | |
| CPV15 | ... PRVVVFYYGGVDYSLHPSLLFRRRRRKRRRHAF SEQ. ID NO: 498 | | |
| FcPV1 | ... FPSGVDINVTDPSLYWLRWWLRRRRRRGYLLFR SEQ. ID NO: 499 | | |
| CPV14 | ... PTVVVGYFGGVDYSLHPSLMFRRRRRRKRYIS SEQ. ID NO: 500 | | |
| TtPV3 | ... SDWVIYSTDDFGDMFRFWHFLRRRRRRRYL SEQ. ID NO: 501 | | |
| CPV9 | ... IIVDVASGAGTDYYLHPSLQARRRRRRRRHFM SEQ. ID NO: 502 | | |
| PePV1 | .. APVSYGGLVSMDPNSLFWFLLRRRRRRRRTTKRILLNR SEQ. ID NO: 503 | | |
| CPV18 | ... IIVDVERGSGSDYYLHPSLTLRRRRRRRRKSL SEQ. ID NO: 504 | | |
| CPV4 | ... IVDVARGPSSDYFLHPSLYATRRRRRRRRRKHI SEQ. ID NO: 505 | | |
| CPV11 | ... IIIVDVIGASGSDYYLHPALSRRRRRRRRRRSL SEQ. ID NO: 506 | | |
| CPV16 | ... VIIVDVSVGSSTDYYLHPSLARRRRRRRRRRSL SEQ. ID NO: 507 | | |
| CPV20 | .. IIIVDIIGGAGSDYYLHPSLSRRRRRRRRRRSQ SEQ. ID NO: 508 | | |
| HPV174 | ... APAVVIHVEDSSGDFYLHPSLRSKKRKRKYL SEQ. ID NO: 509 | | |
| BPV18 | ... PSSLQPTNYFDYWQLFEPSLWRSRKRKRNVYY SEQ. ID NO: 510 | | |
| HPV120 | ... IPAVIVHIIDTSFDYYLHPSLRTKRRRKRKYL SEQ. ID NO: 511 | | |
| FgPV1 | ... PYWPGEGWPPPHFEFSDPSLYRVKKRRWDDCIAIMITVT SEQ. ID NO: 512 | | |
| HPV100 | ... VPAVIVHITDTSGDFYLHPSLRWKKRKRKYL SEQ. ID NO: 513 | | |
| HPV143 | ... TPVVVIHTEDNTGDFYLHPSLRWRKRKRHYL SEQ. ID NO: 514 | | |
| HPV36 | ... IPVVVIHTHDNTGDFYLHPSLRWRKRKRKYL SEQ. ID NO: 515 | | |
| FcaPV3 | ... GQPSLLWDPSTGTFDLHPGLLRWRRKRRRRHDL SEQ. ID NO: 516 | | |
| HPV38 | ... IPTVVIHVADSSGDFYLHPSLRWRRRKRKYL SEQ. ID NO: 517 | | |

Methods of Preventing Viral Infection

Without wishing to be limited by theory, it has now been found that delivering a peptide containing a retromer binding site to a cell in advance of or shortly after exposure to a virus prevents viral infection by sequestering retromer and interfering with the role this complex plays in the viral infection of the cell. Accordingly, in another aspect, the invention provides a method of preventing viral infection in a subject in need thereof, the method comprising providing to the subject a therapeutically effective amount of a polypeptide comprising a cell-penetrating peptide and a retromer binding site. In various embodiments, the viral infection is papillomavirus, hepatitis C virus, influenza virus or human immunodeficiency virus (HIV). The polypeptide is provided to the subject by a method appropriate for the viral infection to be prevented. In various embodiments, the polypeptide is formulated for topical administration.

The cell-penetrating peptide may be any cell-penetrating peptide known in the art including but not limited to the cell-penetrating peptides taught herein. In various embodiments, the polypeptide comprises at least one cell-penetrating peptide selected from the group consisting of SEQ ID NOS: 1-164. In various embodiments, the polypeptide comprises at least one cell-penetrating peptide selected from the group consisting of SEQ ID NOS: 165-517. In various embodiments, the polypeptide comprises a retromer binding site comprising the sequence FYL.

Administration/Dosage/Formulations

The regimen of administration can affect what constitutes an effective amount for the treatment of various diseases, depending on the nature of the cargo molecule. The therapeutic formulations can be administered to the subject either prior to or after the onset of diseases contemplated herein. Further, several divided dosages, as well as staggered dosages can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

Administration of the compositions of the present invention to a patient, preferably a mammal, more preferably a human, can be carried out using known procedures, at dosages and for periods of time effective to treat the disease in the patient. An effective amount of the therapeutic compound necessary to achieve a therapeutic effect can vary according to factors such as the state of the disease or disorder in the patient; the age, sex, and weight of the patient; and the ability of the therapeutic compound to treat the disease in the patient. Dosage regimens can be adjusted to provide the optimum therapeutic response. For example, several divided doses can be administered daily or the dose can be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention can be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of an inflammatory disease in a patient.

The carrier can be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration can be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of the disease in a patient.

Formulations can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents.

Routes of administration of any of the compositions of the invention include oral, nasal, rectal, intravaginal, parenteral, buccal, sublingual or topical. The compounds for use in the invention can be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use can be prepared according to any method known in the art and such compositions can contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets can be uncoated or they can be coated by known techniques for elegance or to delay the release of the active ingredients. Formulations for oral use can also be presented as hard gelatin capsules wherein the active ingredient is mixed with an inert diluent.

The present invention also includes a multi-layer tablet comprising a layer providing for the delayed release of one or more compounds of the invention, and a further layer providing for the immediate release of a medication for treatment of certain diseases or disorders. Using a wax/pH-sensitive polymer mix, a gastric insoluble composition can be obtained in which the active ingredient is entrapped, ensuring its delayed release.

Parenteral Administration

For parenteral administration, the compounds of the invention can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material which provides sustained release properties to the compounds. As such, the compounds for use the method of the invention can be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of an inflammatory disease in the patient being treated. The skilled artisan is able to determine appropriate dosages depending on these and other factors.

A suitable dose of a compound of the present invention can be in the range of from about 0.01 mg to about 5,000 mg per day, such as from about 0.1 mg to about 1,000 mg, for example, from about 1 mg to about 500 mg, such as about 5 mg to about 250 mg per day. The dose can be administered in a single dosage or in multiple dosages, for example from 1 to 4 or more times per day. When multiple dosages are used, the amount of each dosage can be the same or different. For example, a dose of 1 mg per day can be administered as two 0.5 mg doses, with about a 12-hour interval between doses.

It is understood that the amount of compound dosed per day can be administered, in non-limiting examples, every day, every other day, every 2 days, every 3 days, every 4 days, or every 5 days. For example, with every other day administration, a 5 mg per day dose can be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in practicing the following examples 1-9 are here described:

Cells, Plasmids, and Virus

HeLa S3 cervical carcinoma cells were obtained from the American Type Culture Collection (ATCC). HeLa-Sen2, a cloned strain of HeLa cells, infect efficiently with SV40 and HPV16 pseudovirus and were used for immunofluorescence experiments. HaCaT adult human keratinocyte cells were purchased from AddexBio. The HPV16 L2 C-terminal mutants were constructed in pHPV16sheLL by using the Phusion site-directed mutagenesis protocol (New England Biolabs, Ipswich, MA). This method was also used to replace the basic segment of the L2 protein with known CPPs: cationic (SEQ ID NO: 519 RKKRRRQRRR), amphipathic (SEQ ID NO: 520 PLSSIFSRIDG), and hydrophobic (SEQ ID NO: 521 AAVLLPVLLAAP), from HIV Tat, hepatitis B virus large surface antigen, and the K-fibroblast growth factor signal peptide, respectively. The L1 and L2 genes in each mutant were sequenced to verify mutations.

HPV PsVs were produced by co-transfecting 293TT cells with pCAG-HcRed (cat. #11152; Addgene, Cambridge, MA) and p16sheLL or p16L1-GFP with or without mutations or a FLAG tag at the C-terminus of L2. The packaged PsVs were purified by density gradient centrifugation in Opti Prep (cat. ##1114524; Axis-shield, Dundee, Scotland). Encapsidated HcRed genomes were quantified by qPCR as described. Briefly, purified PsVs were treated with DNase I (cat. #79254; Qiagen, Germantown, MD) to remove unencapsidated DNA associated with capsids. Reporter DNA genome was isolated using a DNA purification kit (Qiagen, #69504), and the copy number of encapsidated reporter plasmids was determined by qPCR using primers for the HcRed gene in comparison to a standard curve.

Characterization of Purified Pseudovirus

Five µl of pseudovirus solution was placed on freshly glow-discharged copper grids (formvar/carbon-coated, 200 mesh, Electron Microscopy Services, Hatfield, PA). After two min, the grids were rinsed twice with droplets of deionized water, stained by 2% aqueous uranyl acetate for two min, and then the excess staining solution was blotted off. The grids were allowed to air dry for 15 min. The samples were examined in a FEI Tecnai F20 transmission electron microscope at 200 kV. Images were acquired using a FEI Eagle CCD camera (4K×4K). Virus stocks containing ~1×10⁷ PsV genomes were analyzed by SDS-PAGE, followed by staining with Coomassie brilliant blue.

Infectivity $5 \times 10^4$ HeLa S3 or HaCaT cells in 12-well plates were incubated with PsVs at MOI of approximately one. The number of packaged reporter plasmids required to achieve this MOI as assessed by flow cytometry for reporter gene expression from wild-type PsV was quantified by qPCR, and an equivalent number of genomes in mutant PsV were used to infect cells. Approximately five-fold more virus was used to attain this MOI in HaCaT cells. Cells were analyzed by flow cytometry on a Stratedigm-12 flow cytometer to determine the fraction of cells displaying HcRed fluorescence 48 h.p.i. To measure dependence on retromer, $1 \times 10^5$ HeLa S3 cells in a 12-well plate were transfected 48 h.p.i. prior to infection with 10 pmol siRNAs targeting Vps29 (Dharmacon, Lafayette, CO; #D-009764-03) or Vps35 (Dharmacon, #D-010894-01) by using RNAiMAX (Thermo Fisher, Waltham, MA, #13778100) according to manufacturer's protocol. Cells transfected with a 10 pmol RISC-free siRNA were used as a control. Forty-eight h.p.i., infectivity was measured by flow cytometry for reporter gene expression. To measure dependence on γ-secretase, HeLa S3 cells were pretreated for one h with 250 nM γ-secretase inhibitor, compound XXI, which was retained in the medium for the duration of the experiment. Cells were infected at MOI of one. Forty-eight h.p.i., infectivity was measured by flow cytometry for HcRed expression. To measure the effect of aphidicolin, HeLa S3 cells were pretreated for 24 h with 6 µM aphidicolin, which was retained in the medium for the duration of the experiment. Cells were infected at MOI of one. Forty-eight h.p.i., infectivity was measured by flow cytometry for HcRed expression.

Immunofluorescence Microscopy and Proximity Ligation Assay

To measure cell binding, $5 \times 10^4$ HeLa-Sen2 cells grown on glass coverslips were infected with wild-type PsV at MOI of 20 or mutant PsV containing the same number of encapsidated reporter plasmids. Cells were incubated with PsVs at 4° C. for two h and then washed three times with phosphate-buffered saline (PBS). Cells were fixed for 15 min at room temperature with 4% Formalde-Fresh, washed with PBS and reacted with anti-L1 rabbit polyclonal serum (obtained from J. Schiller, NIH), followed by fluorescently-tagged donkey anti-rabbit secondary antibody. Images were acquired with a Leica SP5 inverted fluorescence microscope and processed with ImageJ.

For the internalization experiments, HeLa cells were incubated with PsV at MOI of 50 at 4° C. for two h, followed by extensive washing in PBS to remove loosely bound PsV. Cells were then shifted to 37° C. to initiate internalization. After six hours, samples were fixed, permeabilized and reacted with anti-L1 antibody (BD Biosciences, San Jose, CA, #554171), followed by donkey anti-rabbit secondary antibody. Cells were analyzed by fluorescence confocal microscopy. In the experiment shown in FIG. 11B, cells were infected with wild-type HPV16 PsV and stained with the antibody 33L1-7, which recognizes L1 after virus is internalized and capsid disassembly has begun.

For the proximity ligation assay, HeLa-Sen2 cells were infected with wild-type PsV at MOI of 100-to-200 or mutant PsV containing the same number of encapsidated reporter plasmids. Infected cells were fixed, permeabilized at various times post-infection, and incubated with pairs of antibodies, one recognizing L1 (#554171) and the other recognizing a cellular marker or a retromer subunit. PLA was performed with Duolink reagents from Olink Biosciences (Uppsala, Sweden) according to the manufacturer's directions. Briefly, cells were incubated in a humidified chamber with a pair of suitable PLA antibody probes diluted 1:5 and processed for ligation and amplification with fluorescent substrate at 37° C. Images were acquired as described above. Approximately 100 nuclei in each sample were imaged. The images were processed by ImageJ and quantitatively analyzed by BlobFinder software to measure total fluorescence intensity in each sample. The average fluorescence intensity per cell in each sample was normalized to the control sample as indicated in each experiment. Similar results were obtained in three independent experiments for each antibody pair.

In all fluorescence imaging experiments, cells were also stained with DAPI or Hoechst 33342 to visualize nuclei (blue), and a single confocal Z-plane is shown in each panel.

Flow Cytometry to Measure Binding and Internalization

To measure cell surface binding by wild-type and mutant PsV, $7.5 \times 10^5$ Hela cells in six-well plates were incubated with wild-type PsVs at MOI of 20 or mutant PsVs containing the same number of reporter plasmids at 4° C. for two h and then washed three times with PBS. Cells were harvested by treatment of 0.5 mM EDTA on ice for 15 min. Samples were fixed in ice-cold methanol and stained with mouse anti-L1 polyclonal IgG (BD Biosciences, #554171) and incubated with corresponding Alexa Fluor secondary antibodies. Fluorescence intensity was assayed on a Stratedigm-13 flow cytometer.

To measure internalization, $7.5 \times 10^5$ HeLa cells in six-well plates were incubated at 4° C. for two h with wild-type PsV at MOI of 20 or mutant PsV containing the same number of reporter plasmids and then washed three times with PBS, followed by additional incubation at 37° C. for six h to initiate internalization. Cells were then harvested by trypsinization to remove PsV on the cell surface. Samples were fixed in ice-cold methanol and stained with anti-L1 antibody #554171 and incubated with Alexa Fluor-labeled secondary antibody. Fluorescence intensity was assayed on a Stratedigm-13 flow cytometer.

Peptide and Fusion Protein Cellular Uptake Experiments $5 \times 10^4$ 293T cells grown on eight-chambered glass coverslips were incubated with 30 µM fluorescently-labeled peptides for three hours at 37° C. or mock-infected. $5 \times 10^4$ HaCaT and HeLa S3 cells grown on eight-chambered glass coverslips were incubated with 2.5 µM wild-type or mutant His-tagged GFP-L2 fusion proteins (see next section) for three h at 37° C. After treatment, cells were washed with PBS three times, stained with Hoechst 33342, and examined by confocal microscopy. To observe internalized fusion proteins, cells were treated for 10-15 min with 0.04% trypan blue, washed with PBS, and examined by confocal microscopy.

Fusion Protein and Peptide Pull-Down Experiments

For fusion protein pull-down experiments, individual human Vps26, Vps29, and GST-tagged Vps35 subunits were expressed individually in E. coli, and the assembled trimeric retromer complex was immobilized on GSH resin (GE Health Care Life Sciences, Pittsburgh, PA, #17075601). His6-GFP-L2 fusion proteins containing a C-terminal segment from wild-type or mutant HPV16 L2 (amino acids 435-461) were expressed in bacteria and purified using the His GraviTrap column (GE Healthcare, #11-0033-99). Purified proteins were exchanged into PBS buffer by dialysis and quantified by bicinchoninic acid protein assay. Ten µg fusion protein was incubated with assembled 15 µg retromer trimer immobilized on GSH resin for two h at 4° C. in 20 mM HEPES pH 8.0, 50 mM NaCl, 5 mM $MgCl_2$, 1 mM DTT, and 0.1% Triton X-100. Beads were centrifuged and washed twice in HEPES buffer, suspended in SDS loading buffer, boiled, and subjected to SDS-PAGE and anti-GFP immunoblotting.

For peptide pull-down experiments, N-terminal biotinylated L2 peptides (sequences shown in FIG. 2A) were purchased from ABClonal Science (Woburn, MA) at >95% purity. L2 wild-type was dissolved initially in 30% acetic acid and DMSO (~70 µl each), and then dissolved in sterile deionized water with 0.01% sodium azide. L2-6A, L2-3R and L2-DM were initially solubilized in a small amount of DMSO (~70-80 µl) and then dissolved in sterile deionized water with 0.01% sodium azide. Peptide stocks (5 mg/ml) were aliquoted and stored at −20° C. HeLa S3 cells plated in six-well plates were lysed at ~80% confluency with 500 µl RIPA-MOPS buffer (20 mM morpholinepropanesulfonic acid [pH 7.0], 150 mM NaCl, 1% Nonidet P-40, 1 mM EDTA, 1% deoxycholic acid, 0.1% sodium dodecyl sulfate [SDS]) supplemented with protease inhibitors (1×HALT protease and phosphatase inhibitor cocktail (Thermo Scientific, Waltham, MA; #78443)). The lysate was centrifuged at 14,000 rpm for 20 min, and the supernatant was incubated with 10 µg of a biotinylated peptide for two h at 4° C. Fifty µl of streptavidin agarose beads slurry (Pierce, Rockford, IL; #20349) was added, and the mixture was gently rocked for 45 min at 4° C. Beads were recovered by centrifugation and washed four times with RIPA-MOPS buffer supplemented with NaCl to a final concentration of 0.4M. Samples were analyzed by SDS-PAGE and immunoblotting with antibody recognizing Vps35 (Abcam, Cambridge, MA; ab57632).

Split GFP Assay

Plasmids. The full-length GFP gene in pLenti CMV GFP Puro (658-5) (Addgene, #17448) contained on a BamHI and SalI fragment was replaced with the DNA segment encoding GFP1-10 amplified from pCMV-mGFP1-10 to generate pLenti CMV.GFP1-10. To construct pLentiCMV.GFP1-10NES, oligonucleotides encoding the nuclear export signal (NES) sequence LPPLERLTLD (SEQ ID NO: 522) were inserted in-frame at the C-terminus of GFP1-10 in pLentiCMV.GFP1-10.

Plasmid pCD8-CIMPR expresses a CD8-CIMPR fusion protein containing the extracellular domain of CD8 fused to the transmembrane and mutant cytoplasmic domain of the cation-independent mannose phosphate receptor (CIMPR), which contains an endocytosis motif and three alanines replacing the WLM retromer binding site. The In-Fusion HD cloning Kit (TaKaRa Bio USA, Inc., Kusatsu, Shiga, Japan), #121416) was used to insert seven tandem copies of GFP11 (SEQ ID NO: 523 RDHMVLHEYVNAAGIT) in-frame into pCD8-CIMPR either immediately downstream of the CD8 signal peptide sequence or at the C-terminus of the fusion protein to generate pGFP11-CD8-CIMPR and pCD8-CIMPR-GFP11, respectively.

Each GFP11 repeat was separated by short GGSGG (SEQ ID NO: 524)linker sequences. The sequences of the relevant portions of the encoded CD8-CIMPR fusion proteins are as follows, with GFP11 and linker sequences in bold.

GFP11-CD8-CIMPR,
(SEQ ID NO: 525)
MALPVTALLLPLALLLHAARP(RDHMVLHEYVNAAGITGGSGG)₆**RDH
MVLHEYVNAAGITGGK**SQFRV...

CD8-CIMPR-GFP11,
(SEQ ID NO: 526)
...DDSDEDLLHVGSSGSS(RDHMVLHEYVNAAGITGGSGG)₆**RDHMV
LHEYVNAAGITGGK**.

Plasmids CNX-S1-10(N) and CNX-S1-10(C) were obtained from Bernard Moss (NIH) and designated here GFP1-10-CNX and CNX-GFP1-10, respectively.

To construct pHPV16sheLL-GFP11-CPP for producing PsVs containing GFP11 inserted into the HPV16 L2 protein immediately upstream of the basic segment, DNA encoding the tandem GFP11 repeats was amplified from pGFP11-CD8-CIMPR by using the In-Fusion HD cloning Kit and cloned in-frame into L2 in p16sheLL. pHPV16sheLL-CPP-GFP11 with the GFP11 repeats at the extreme C-terminus of L2 was constructed by first inserting NsiI and AvrII restriction sites immediately upstream of the L2 stop codon in p16sheLL. The DNA segment encoding the GFP11 repeats was then inserted into this plasmid between these sites. Site-directed mutagenesis of pHPV16sheLL-GFP11-CPP and pHPV16sheLL-CPP-GFP11 was used to construct pHPV16sheLL-GFP11-3R and pHPV16sheLL-3R-GFP11, respectively, both of which contain three arginines in place of the wild-type CPP. The sequences of the relevant portions of the encoded L2-GFP11 fusion proteins with wild-type CPP are as follows, with GFP11 and linker sequences in bold and L2 CPP underlined.

L2-GFP11-CPP,
(SEQ ID NO: 527)
...FYLHPSYYML(RDHMVLHEYVNAAGITGGSGG)₆**RDHMVLHEYVNAA
GITGGKF**<u>RKRRKR</u>LPYFFSDVSLAA.

L2-CPP-GFP11,
(SEQ ID NO: 528)
...YYML<u>RKRRKR</u>LPYFFSDVSLAADASGSSGSS(**RDHMVLHEYVNAAGI
TGGSGG)₆RDHMVLHEYVNAAGITGGKF**PRL.

Generation of stable cell lines. To generate stable cell lines expressing cytoplasmic GFP1-10NES, lentiviruses were produced by co-transfection of 293T cells in 100 mm dishes with 6 µg of pLentiCMV.GFP1-10NES, 4.5 µg of lentiviral packaging plasmid psPAX2 and 1.5 µg envelope plasmid pMD2.G. Forty-eight h later, the lentiviral supernatant was harvested, filtered and stored at −80° C. for later use. Cells stably expressing GFP1-10NES were constructed by infecting HaCaT cells with lentivirus for 48 h in medium containing 1 µg/mL puromycin. Single cells were then plated in a 96-well plate, and monoclonal cell lines were isolated and tested by infection of HPV16-CPP-GFP11 PsV at ~2000 MOI and monitoring fluorescence.

Immunofluorescence microscopy of GFP 1-10 expression. 5×10⁴ clonal HaCaT/GFP1-10NES stable cells grown on glass coverslips were fixed for 15 min at room temperature with 4% Formalde-Fresh, washed with PBS and incubated with anti-GFP mouse antibody (Santa Cruz, Dallas, TX, #SC-9996) and Alexa Fluor 488 donkey anti-mouse IgG (H&L) secondary antibody (Fisher, #A-21202). Images were acquired with a Leica SP5 inverted fluorescence microscope to identify cell lines expressing cytoplasmic GFP1-10NES.

Validation of the split GFP assay. 5×10⁴ clonal HaCaT/GFP1-10NES cells in eight-chambered glass slides were transfected with 0.25 µg of pGFP11-CD8-CIMPR or pCD8-CIMPR-GFP11. Twenty-four hours later, live cells were examined by fluorescence microscopy. To demonstrate the functionality of GFP11 in GFP11-CD8-CIMPR, 5×10⁴ 293T cells in eight-chambered glass slides were co-transfected with a plasmid expressing GFP11-CD8-CIMPR and a plasmid expressing a calnexin transmembrane fusion protein containing luminal GPF1-10 or cytoplasmic GFP1-10

Figures 8A, 8B, 8C, 8D, 8E, 8F:
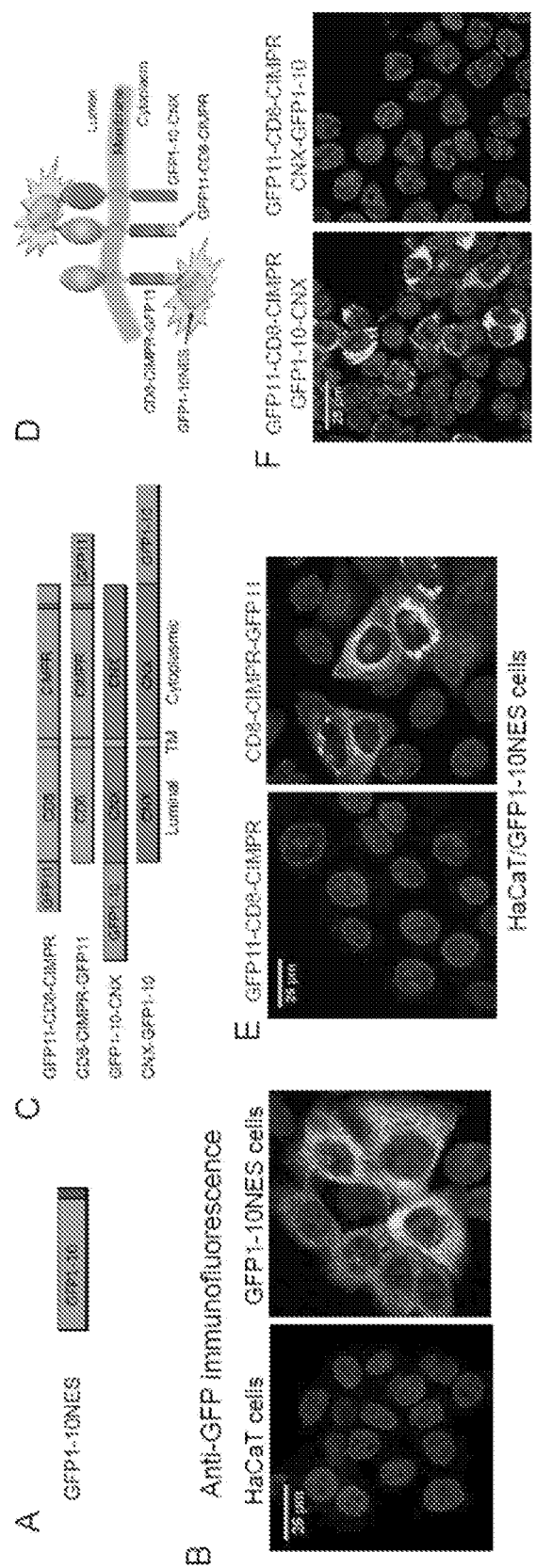
FIGS. 8A-8F depict the validation of the split GFP assay.

(GFP1-10-CNX and CNX-GFP1-10, respectively) (FIGS. 8C and 8D). Twenty-four h later, live cells were examined by fluorescence microscopy. As expected, fluorescence with GFP11-CD8-CIMPR was reconstituted only when the GFP1-10 segment was luminal (FIG. 8F).

Figures 12A, 12B:
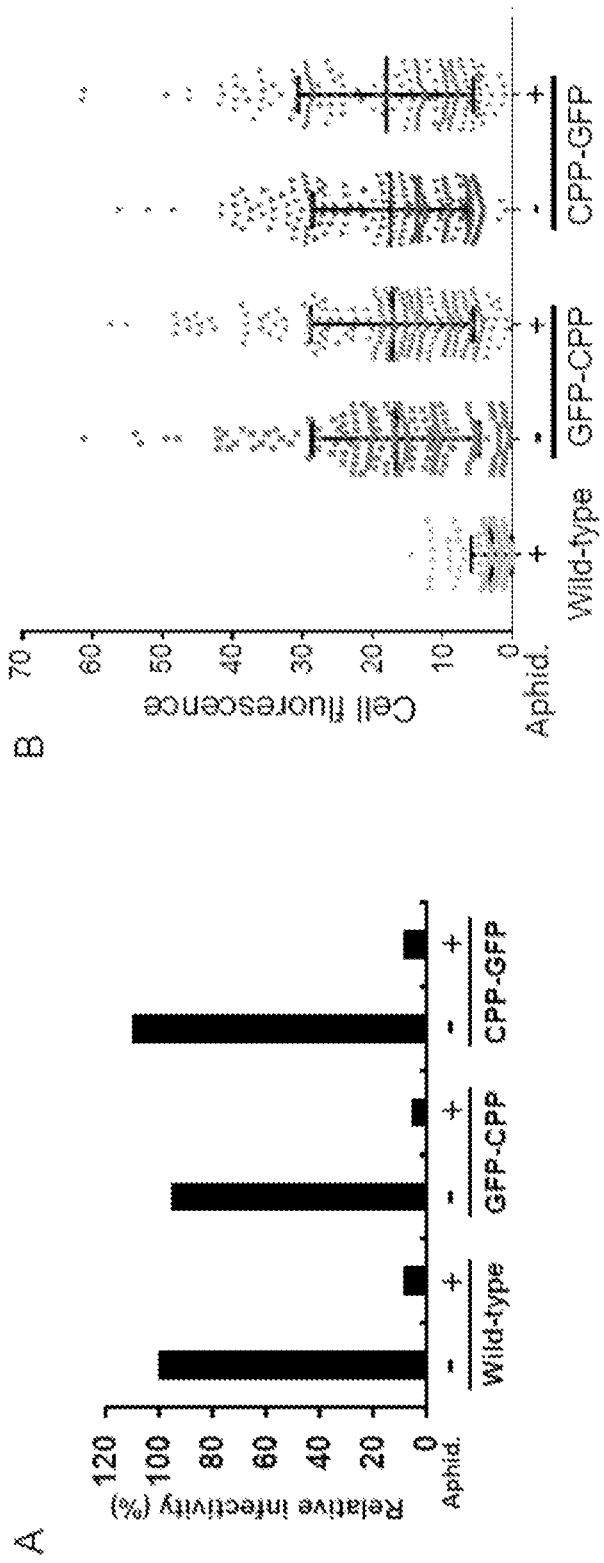
FIGS. 12A-12B show that cell cycle progression is required for HPV infection but not L2 protrusion.

Use of split GFP assay to demonstrate cytoplasmic protrusion of L2. $3 \times 10^4$ clonal HaCaT/GFP1-10NES cells seeded in eight-chambered glass slides were incubated for 1.5 or 3 h at MOI of ~2000 with HPV16 PsV containing wild-type L2 or L2 containing inserted GFP11 and a wild-type or 3R mutant CPP. Live cells were analyzed by a Leica SP5 inverted fluorescence microscope and processed with ImageJ. In the experiment shown in FIG. 12B, cells were pretreated with aphidocolin, which was left in the medium for the duration of the experiment (Santa Cruz, #201535).

Modulation of CPP Action by Flanking Sequences

Fusion proteins with various segments of the C-terminus of HPV16 or HPV5 L2 were added to HaCaT cells. The sequences used are as follows:

```
GFP- His6-GFP-linker CPP
                                        (SEQ ID NO: 529)
-RKRRKR GFP-21P-CPP His6-GFP-linker-
                                        (SEQ ID NO: 530)
PQYTIIADAGDFYLHPSYYMLRKRRKR GFP-HPV16 L2 His6-GFP-linker-
                                        (SEQ ID NO: 531)
PQYTIIADAGDFYLHPSYYMLRKRRKRLPYFFSDVSLAA GFP-HPV5 L2 His6-GFP-linker-
                                        (SEQ ID NO: 532)
IPVVIIHPHDSTGDFYLHPSLHRRKRKRKYL
```

In some cases, various concentrations of fusion proteins were added to assess efficacy. In other cases, the pH of the culture medium was physiological pH 7 or adjusted to acidic pH 4 prior to peptide addition, or the cells were incubated with peptide at physiological temperature of 37° C. or at 30° C. Activity was assessed by confocal microscopy for intracellular fluorescence. In some experiments, cell surface fluorescence was extinguished by treatment with the membrane-impermeable fluorescence quencher, trypan blue.

Peptide Inhibition Experiment

HeLa cells were left untreated or treated at 37° C. with 4 µg L2-C, a peptide containing the HPV16 L2 retromer binding site and CPP. The sequence of L2-C is as follows: B-SPQYTIIADAGDFYLHPSYYMLRKRRKR-Am, (SEQ ID NO: 533), where B represents N-terminal biotinylation and Am represents C-terminal amidation. Two hours later, the cells were infected for two hours at 37° C. with wild-type HPV16 pseudovirus. Cells were washed and medium was replenished with medium containing the peptide for 24 hours. Infectivity was tested 48 hours later by using flow cytometry to measure fluorescence of HcRed expressed from a reporter plasmid encapsidated in the pseudovirus particle, and normalized to infectivity of cells infected in the absence of peptide. Similar results were obtained in two independent experiments.

Figures 7A, 7B:
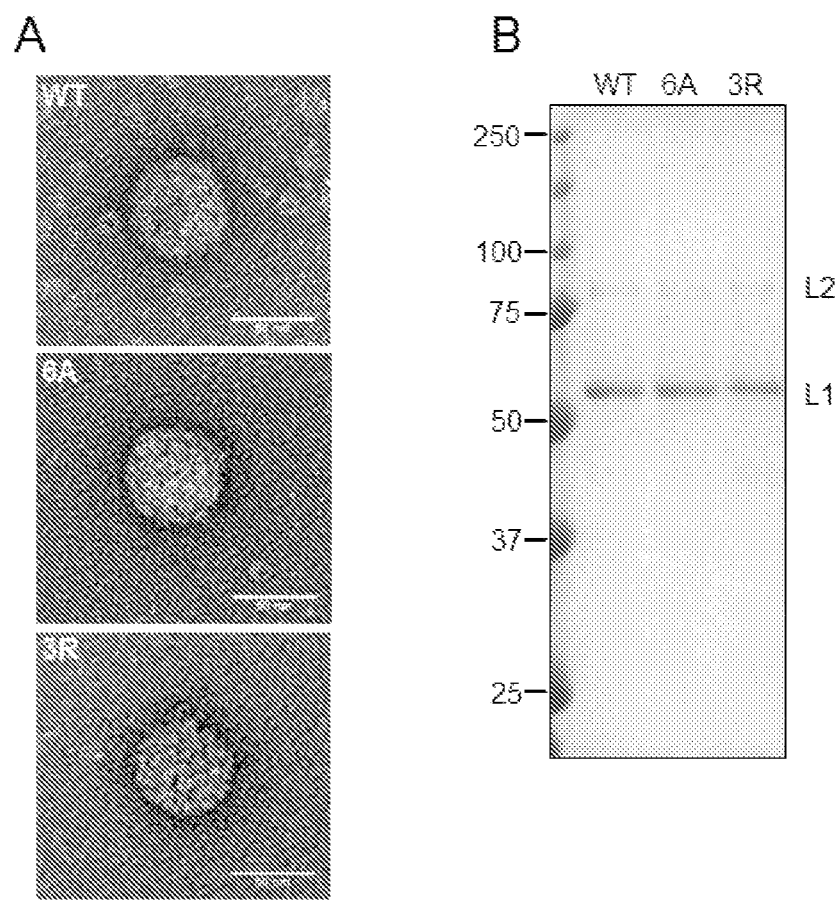
FIGS. 7A-7C show the assembly and infectivity of L2 CPP mutants. HPV16 PsV containing wild-type (WT) L2 or the six alanine (6A) or three arginine (3R) mutants were examined by (FIG. 7A) transmission electron microscopy or (FIG. 7B) SDS-PAGE and staining with coomassie blue.

Example 1: The C-Terminal Basic Sequence of L2 can be Replaced by a Cationic Cell-Penetrating Motif Direct binding of retromer to a carboxy-terminal segment of the HPV16 L2 protein is required for transport of the incoming virus from endosomes to the Golgi. To test whether the basic amino acids in the C-terminus of the L2 protein function as a CPP to transfer a segment of the L2 protein into the cytoplasm to allow a direct interaction with retromer, it was first tested whether mutations in this segment of L2 inhibited infectivity. For these experiments, pseudoviruses (PsVs) comprised of an HcRed reporter plasmid, wild-type HPV16 L1, and wild-type or mutant HPV16 L2 were used. PsV assembly was confirmed by electron microscopy, which showed no obvious morphologic differences between wild-type and mutant PsVs (FIG. 7A). Each PsV stock was normalized to the number of encapsidated reporter plasmids and analyzed by SDS-PAGE. Wild-type and mutant PsVs displayed comparable purity and contained similar levels of L1 and L2 (FIG. 7B).

Figure 7C:
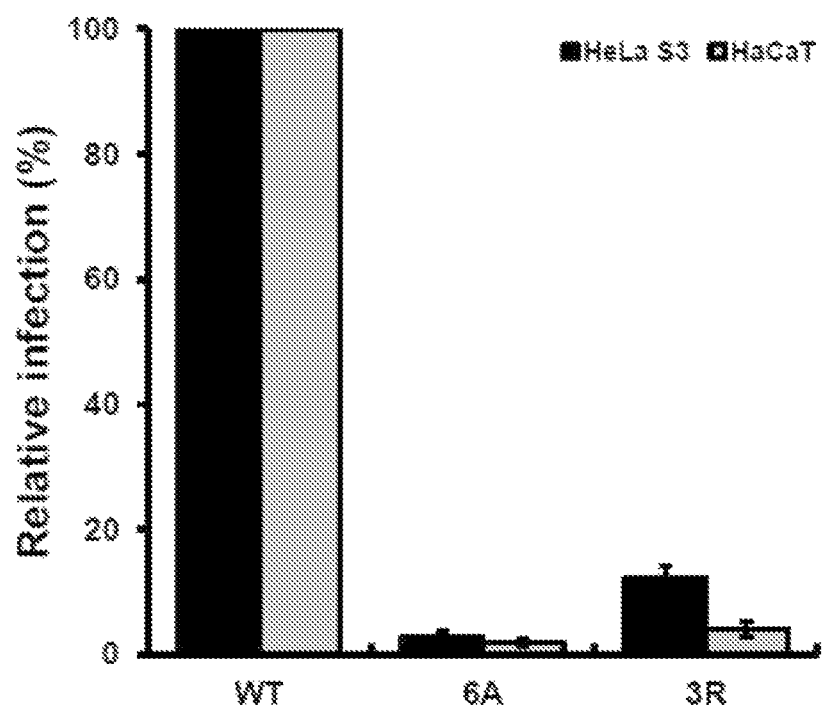

To determine if the L2 basic sequence is important for HPV16 infection, wild-type RKRRKR (SEQ ID NO: 2) was replaced with six alanines (6A mutant) (FIG. 1B). HeLa or HaCaT cells were infected with wild-type HPV16 PsV at multiplicity of infection (MOI) of one or with 6A mutant PsV containing an equivalent number of encapsidated reporter plasmids, and infection efficiency was measured two days later by flow cytometry for HcRed fluorescence. As shown in FIG. 1C and FIG. 7C, the 6A mutation abolished infectivity, indicating that the basic sequence is essential for HPV16 infection. Next, the basic sequence of L2 was replaced with the CPP domain of the HIV-1 Tat protein to generate L2-Tat (FIG. 1B). Strikingly, HPV16 PsV with the Tat sequence in place of the basic region infected cells as well as HPV16 PsV containing wild-type L2 (FIG. 1C). In contrast, an amphipathic or a hydrophobic CPP did not support infection. These results suggest that the basic region of L2 acts as a cationic CPP to deliver the C-terminus of L2 containing retromer binding sites through a membrane into the cytoplasm and that only the cationic class of CPP can support HPV infection.

RKRRKR (SEQ ID NO: 2) was then replaced with six consecutive lysines or with various numbers of arginines (FIG. 1B). A stretch of five or more arginines can act as efficient CPPs, whereas fewer arginines and polylysine were less effective. Infectivity of the mutant PsV with three arginines (3R) was minimal (~10%) and increased with the number of arginine residues, reaching a plateau with five arginines (FIG. 1D and FIGS. 7A-7C). The mutant with six lysines was ~40% as infectious as PsV containing five or more arginines. These results demonstrate that the basic region at the C-terminus of HPV16 L2 can be functionally replaced by arginine-rich sequences with known CPP activity, and that infectivity correlated with predicted CPP activity.

It was next tested if the HPV16 PsV containing L2-Tat utilized a similar entry pathway as wild-type HPV16 PsV. To determine if retromer was required for infection mediated by L2-Tat, cells transfected with siRNA that knocked down the Vps29 retromer subunit were infected.

Retromer knockdown dramatically inhibited infection by either wild-type or the L2-Tat PsV, indicating that the L2-Tat chimera requires retromer (FIG. 1E). γ-secretase is also required for proper trafficking by HPV16. To determine if γ-secretase was required for PsV containing L2-Tat, cells were treated with a chemical inhibitor of γ-secretase, compound XXI, and infectivity was measured. XXI caused near-complete inhibition of both wild-type and L2-Tat PsV infection, showing that the L2-Tat chimera also requires γ-secretase (FIG. 1F). Thus, the L2-Tat chimeric HPV16 PsV displays two of the key entry requirements as wild-type HPV16 PsV, namely dependence on retromer and γ-secretase. Taken together, these results provide strong genetic evidence that the basic segment of L2 acts as a CPP during HPV16 infection.

Figure 2A:
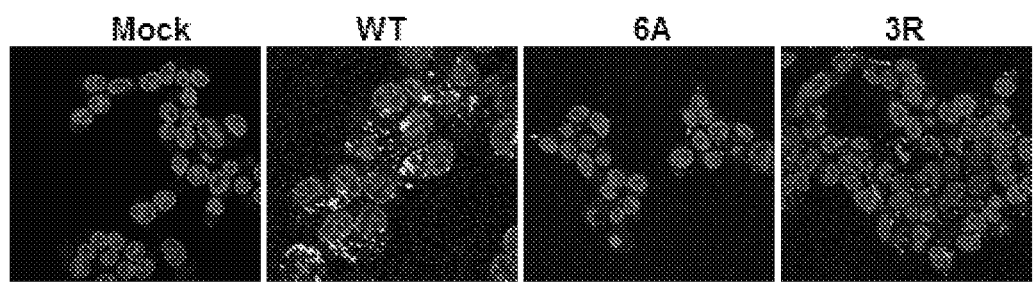
FIGS. 2A-2D show that the L2 basic sequence displays cell-penetrating activity.

Example 2: The Basic Sequence of L2 can Translocate Peptides and GFP Fusion Proteins into Cells Experiments were conducted to determine whether the basic sequence of L2 has intrinsic cell penetrating activity. First, Alexa Fluor 488 was conjugated onto the N-terminus of a 28-residue L2 peptide that terminates with the wild-type basic sequence or the corresponding L2 peptide with the 6A or the 3R mutation (FIG. 2A, top). As assessed by confocal microscopy, the wild-type peptide entered cells, but the peptide containing 6A mutation did not (FIG. 2A, bottom). The 3R peptide displayed less cell-associated fluorescence signal than wild-type, suggesting that the 3R peptide is partially impaired for cell penetration.

Figure 2B:
Figure 2C:
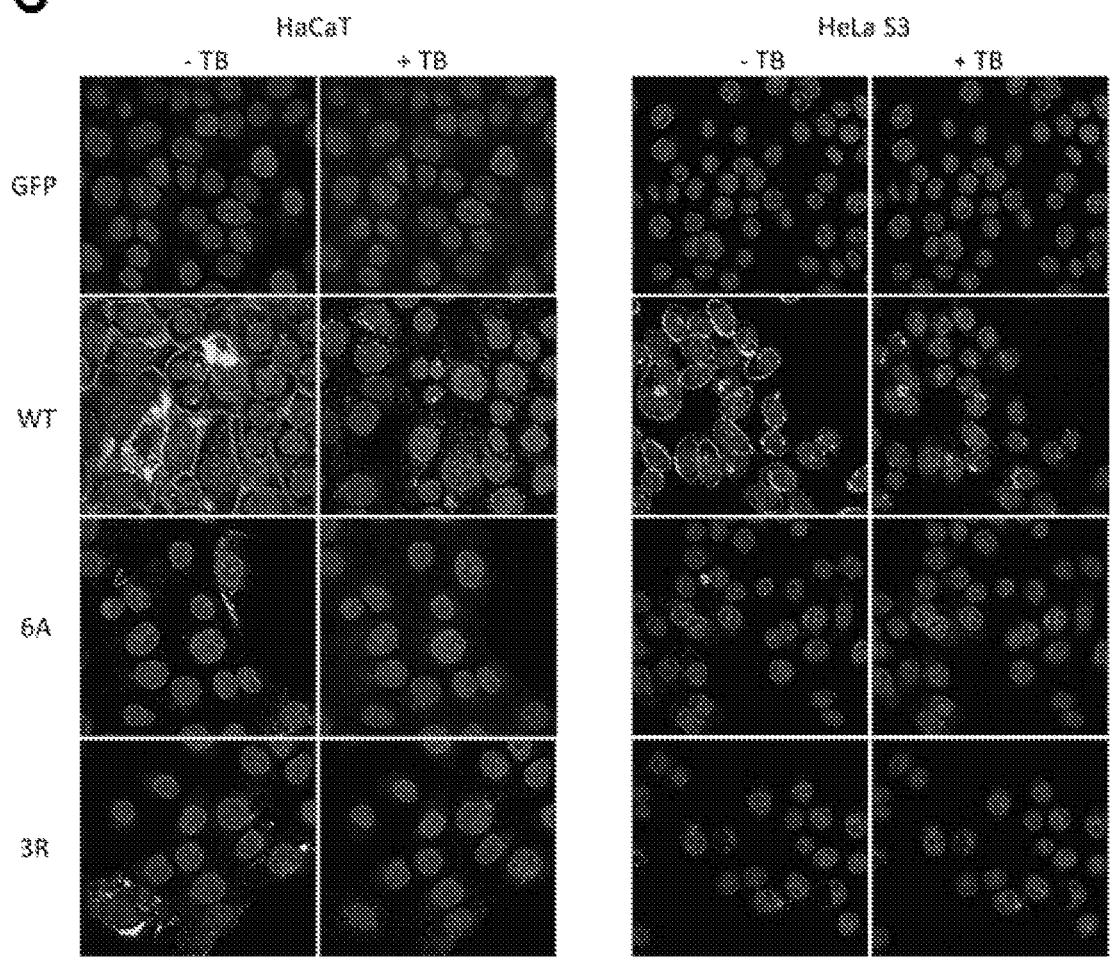
Figure 2D:
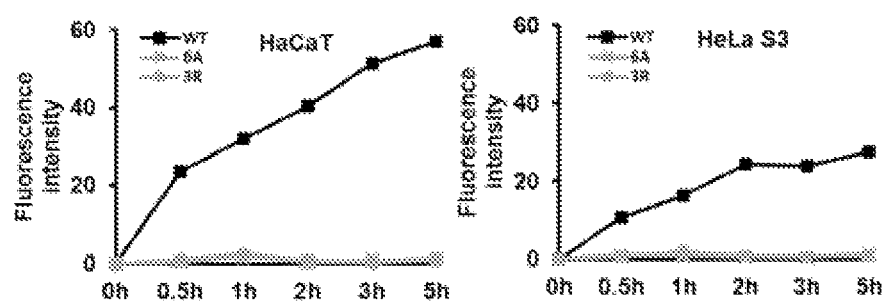

To confirm CPP activity of this L2 segment, GFP fusion proteins were expressed and purified from bacteria consisting of GFP fused in-frame to a 28-residue segment from the C-terminus of L2 terminating with either the wild-type basic segment or a mutant segment (FIG. 2B). Microscopic examination of HeLa and HaCaT cells incubated with medium containing L2-GFP fusion proteins showed that the protein with the wild-type L2 segment generated a strong punctate fluorescence signal inside cells and at the cell periphery (FIG. 2C). The 3R mutation greatly impaired cellular uptake and the 6A mutation abolished it. To show that the wild-type fusion protein was internalized, cells incubated with fusion protein were treated with 0.04% trypan blue, a cell membrane-impermeable agent that quenches cell-surface GFP fluorescence but not intracellular fluorescence. As shown in FIG. 2C, in cells incubated with the wild-type fusion protein, the signal at the cell periphery was eliminated by trypan blue, but the punctate signal persisted, demonstrating intracellular uptake of the protein. In contrast, the signal from the 3R mutant was largely eliminated. To quantify cellular fluorescence at 0.5 to 5 h post-incubation, flow cytometry was performed following trypsinization to remove any GFP fusion protein adsorbed to the cell surface. This experiment showed that the wild-type fusion protein translocated into cells rapidly (with >50% and >90% of maximum fluorescence observed in HaCaT cells and HeLa cells by two hours, respectively), whereas there was no internalization of 6A and 3R fusion proteins (FIG. 2D). Thus, the wild-type and mutant basic segments of L2 displayed cell penetration activity that correlated with the infectivity of PSV containing these segments. These results provide strong evidence that the membrane-penetration property of the L2 CPP is required for HPV entry.

Example 3: The L2 CPP is not Essential for Virus Binding and Internalization

Figure 3A:
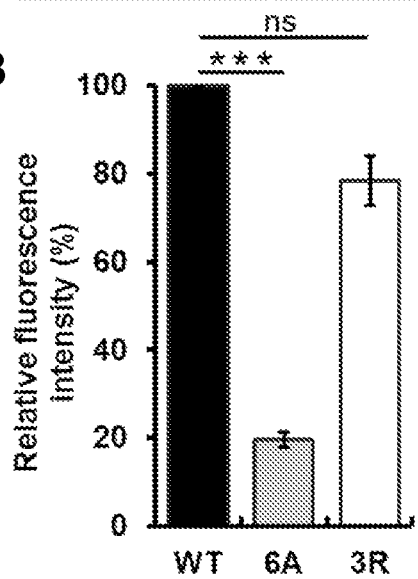
FIGS. 3A-3F show that the basic region of HPV16 L2 is not essential for virus binding and internalization.
Figure 3B:
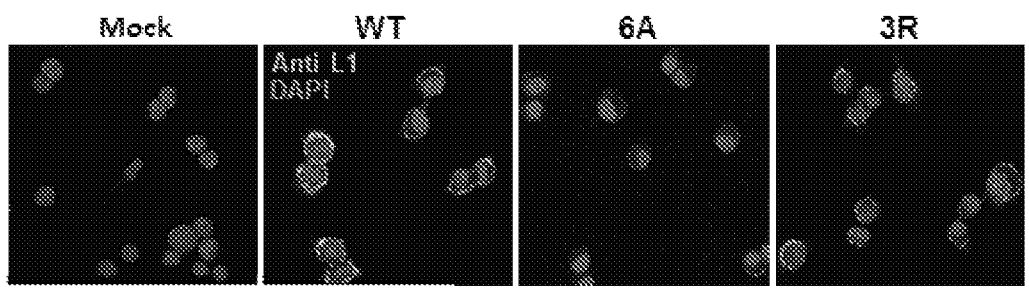
Figure 3C:
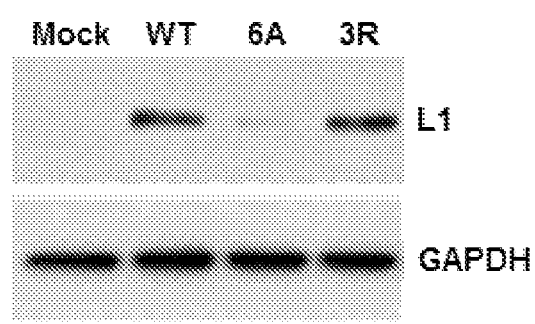
Figures 3D, 3E, 3F:
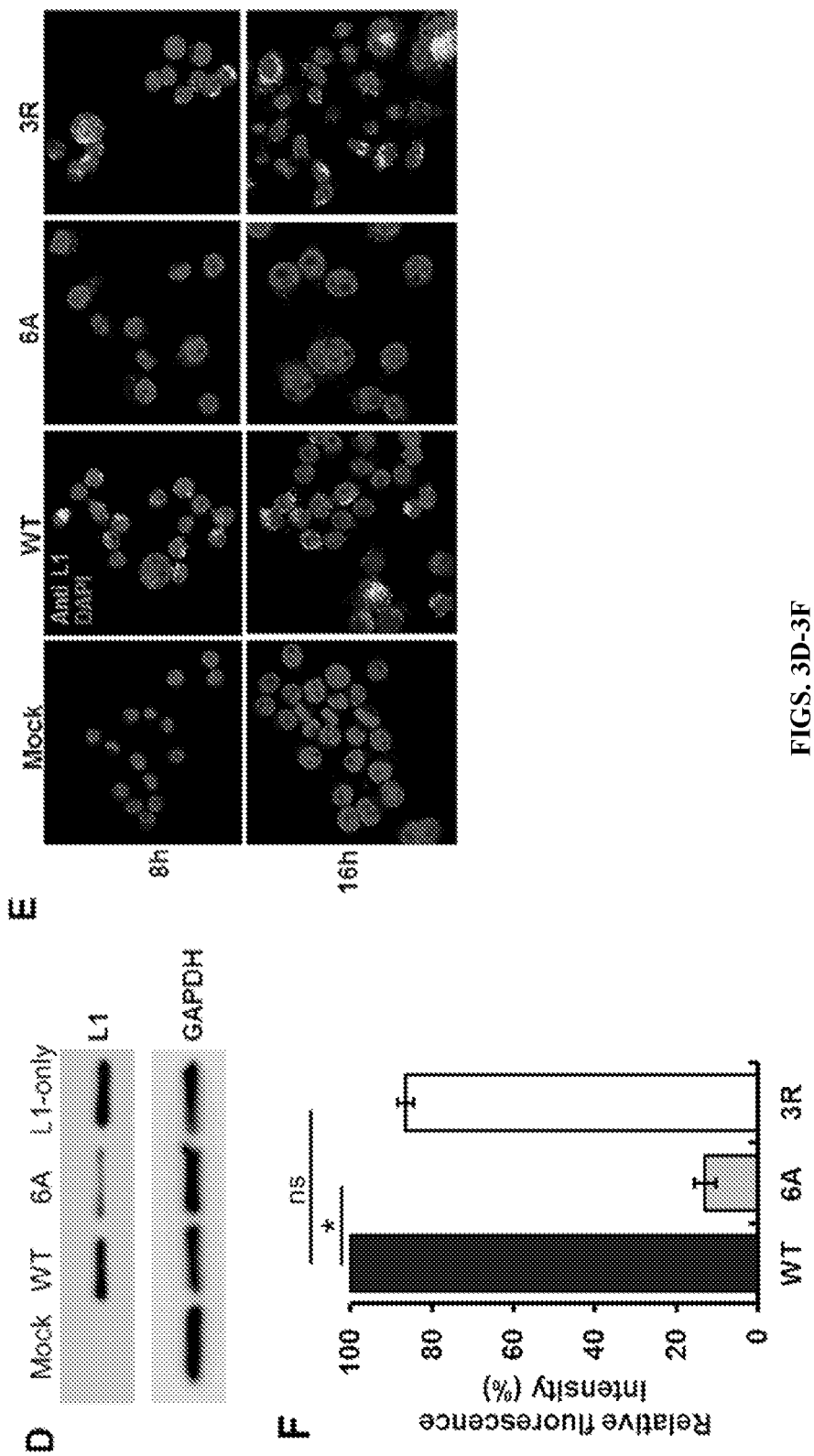

To determine the role of the L2 CPP in HPV infection, cell binding experiments were conducted. HeLa cells were incubated with either wild-type or mutant HPV16 PsV for two hours at 4° C., followed by washing to remove unbound viruses. Non-permeabilized cells were stained with an L1 antibody, and immunofluorescence was performed to detect viruses stably bound to cells. As shown in FIG. 3A, binding of wild-type PsV to cells was readily detectable, as was binding of the 3R mutant. Unexpectedly, the 6A mutation resulted in a dramatic reduction of cell binding. Similar results were obtained when cell binding was assessed by flow cytometry for L1 (FIG. 3B) or by western blotting (FIG. 3C) for L1 stably associated with cells incubated with HPV16 PsV at 4° C. Because the cell binding defect of the 6A mutant was in conflict with published studies showing efficient binding of capsids lacking L2, binding with PsV lacking L2 (L1-only PsV) was also tested. As shown in FIG. 3D, L1-only PsV bound cells to a similar level as complete PsV containing L1 plus wild-type L2, far better than PsV containing the 6A mutant. These results imply that the L2 CPP does not play a direct role in cell surface binding, but sequences in the C-terminus of L2 can modulate binding.

The role of the L2 CPP in virus internalization was examined next. After incubation of cells with HPV16 PsVs at 4° C., cells were shifted to 37° C. for six hours to allow internalization. Internalization was assessed by immunofluorescence and by flow cytometry. The 3R L2 mutant internalized into cells as well as wild-type, while the 6A mutant showed much less internalized L1, as expected because of its cell surface binding defect (FIGS. 3E and 3F). This result showed that the short basic segment of three arginines was able to support cell surface binding and virus internalization, even though it was not sufficient to restore infectivity. Thus, the L2 CPP is required for an intracellular event subsequent to cell binding and internalization.

Example 4: The 3R Mutant Accumulates in Endosomes and Fails to Reach the Golgi

Figures 4A, 4B:
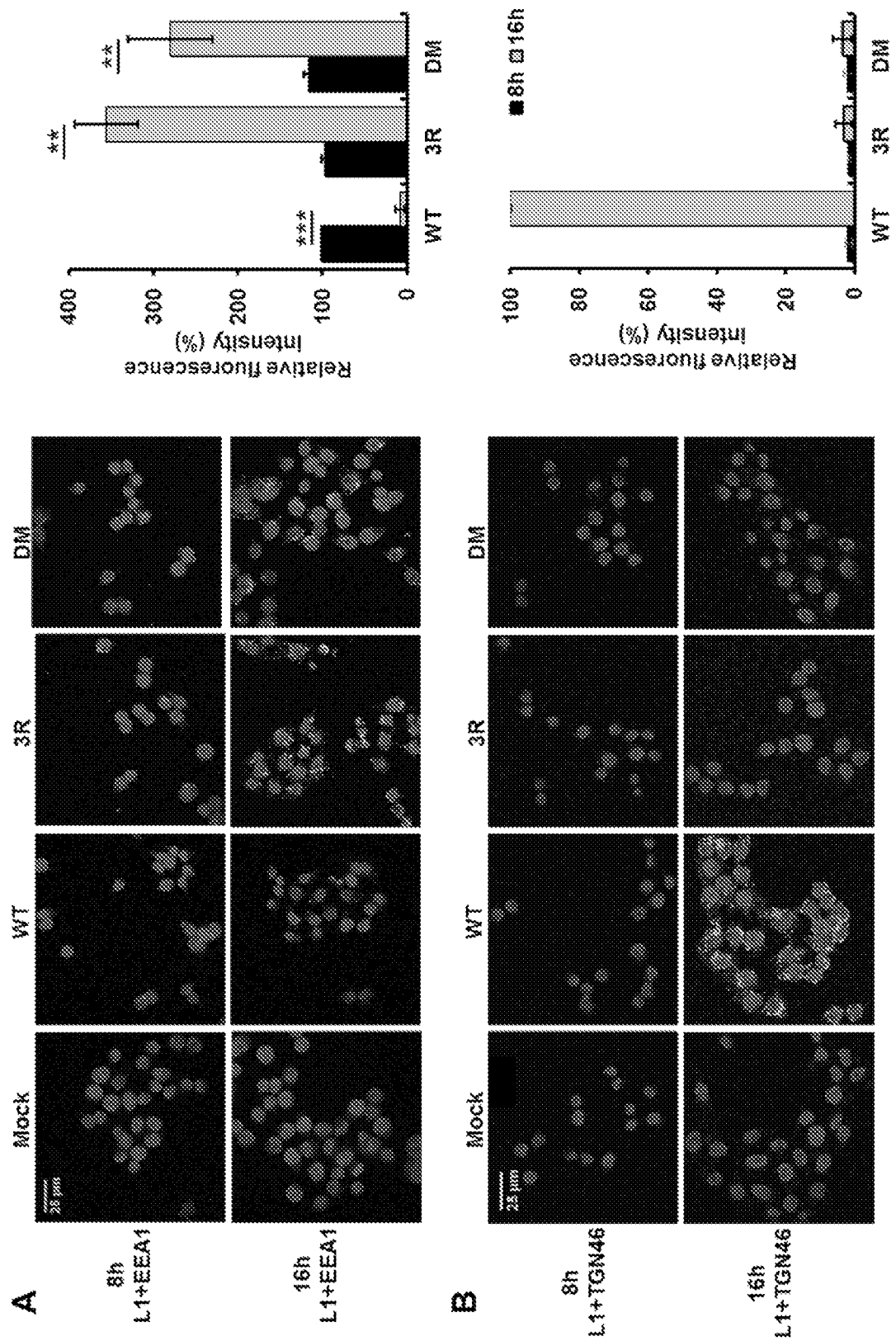
FIGS. 4A-4B show that the 3R mutant PsV accumulates in endosomes and does not reach trans-Golgi network (TGN).

To examine the post-internalization defect of the 3R mutant, proximity ligation assay (PLA) was used to determine the localization of incoming wild-type and 3R mutant HPV16 PsV. PLA is an immune-based assay used to test if two proteins of interest are within 40 nm. PLA was performed with an anti-L1 antibody and an antibody that recognizes either EEA1, a marker of the early endosome, or the trans-Golgi network (TGN) marker, TGN46. The L2 double mutant (DM), which lacks retromer binding sites, was used as a control. As shown in FIG. 4A, these antibodies did not generate a PLA signal in mock-infected cells. At eight hours post-infection, punctate intracellular EEA1/L1 PLA signal was observed in cells infected with wild-type L2 or either mutant and showed similar fluorescence intensity, confirming that the 3R mutant, like DM, efficiently entered cells and reached the endosome. At 16 hours post-infection, the EEA1/L1PLA signal of cells infected with wild-type PsV was significantly diminished, reflecting the departure of the incoming virion from the endosome, whereas the signal for the DM in the endosome was markedly increased, reflecting endosomal accumulation due to the absence of retromer binding sites (FIG. 4A). Notably, the EEA1/L1 PLA signal of the 3R mutant at 16 h.p.i. was increased ~3-fold compared to the eight-hour signal, similar to the increase seen with DM mutant. Thus, the 3R mutant and the DM accumulated in the endosome. As expected, little TGN46/L1 PLA signal was generated at eight hours after wild-type or mutant PsV infection (FIG. 4B). At 16 h.p.i., cells infected with wild-type displayed abundant TGN46 PLA signal, reflecting delivery of L1 to this distal site. In contrast, 3R and DM mutants showed a greatly reduced TGN46/L1 PLA signal, indicating that these mutants did not arrive at the TGN. These results indicate that 3R mutation leads to accumulation of the incoming virus particle in the endosome and prevents its arrival into the TGN, a phenotype similar to the mutant that cannot bind retromer. Together with the reduced infectivity of the 3R mutant and the impaired cell entry of 3R mutant fusion proteins, these data suggest that the trafficking defect displayed by 3R mutant is due to impaired endosomal membrane penetration and retromer association.

Figures 5A, 5B:
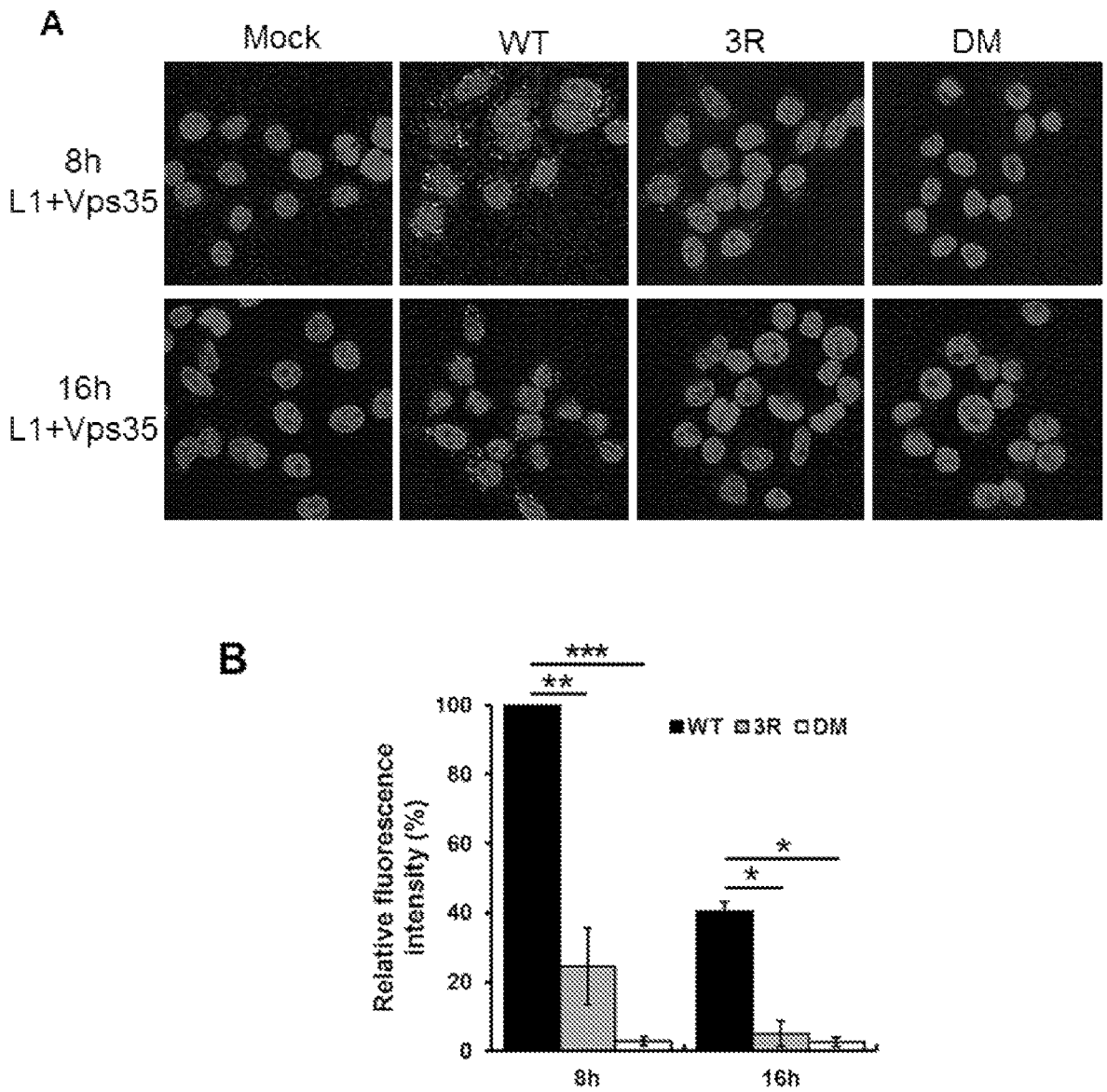
FIGS. 5A-5D show that the 3R mutant is defective in accessing retromer during HPV infection.

Example 5: The 3R Mutant is Defective in Accessing Retromer During HPV Infection but Binds Retromer In Vitro It was next tested whether the 3R mutation impaired association between the capsid and retromer in infected cells. HeLa cells were infected with either wild-type or mutant HPV16 PsV, and PLA was performed with an anti-L1 antibody and an antibody recognizing Vps35, a subunit of retromer. As shown in FIG. 5A, wild-type PsV generated abundant Vps35/L1 PLA signal at eight h.p.i., while the signal was diminished by 16 h.p.i., reflecting the exit of virus from endosomes and dissociation from retromer by this time. As expected, the PLA signal for DM mutant was very weak at both eight and 16 h.p.i., consistent with its lack of retromer binding sites. Interestingly, ~75% reduction of PLA signal was observed for the 3R mutant at eight hours, and this signal decreased further by 16 hours (FIGS. 5A-5B), despite the accumulation of the mutant at the endosome at this later timepoint.

Figure 5C:
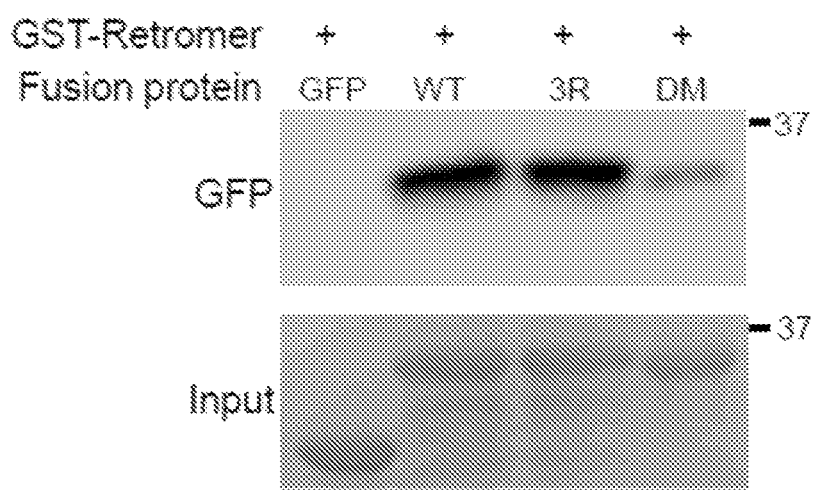
Figure 5D:
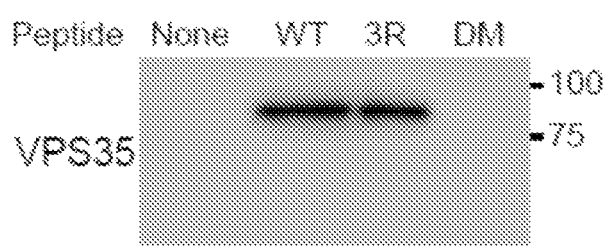

In certain embodiments, the 3R mutation can inhibit retromer association directly, by impinging on the retromer binding sites, or indirectly, by preventing the exposure of the binding sites in the cytoplasm. To determine if mutations in the L2 CPP directly inhibited binding to retromer, pull-down experiments were performed. GST-tagged retromer subunits were expressed in bacteria, assembled into the trimeric retromer complex, and bound to glutathione beads. The purified GFP-L2 fusion proteins containing a wild-type L2 segment, the 3R mutation, or the DM mutations in the retromer binding sites were incubated with the retromer beads at 4° C., pelleted, and subjected to western blotting with an anti-GFP antibody to detect the L2 fusion protein in the pellet. As expected, the wild-type protein bound retromer well and the DM fusion protein bound poorly (FIG. 5C). Notably, the 3R mutant L2 fusion protein also bound retromer well, demonstrating that this mutation did not inhibit the intrinsic ability of L2 to bind retromer. In addition, biotinylated, wild-type and mutant C-terminal L2 peptides were incubated with detergent lysates of uninfected HeLa cells and streptavidin pull-down experiments and western blotting were performed for Vps35. Similar to the results with purified fusion proteins, the 3R mutation did not affect retromer binding to the L2 peptide, whereas binding was abolished by the mutations in the retromer binding sites (FIG. 5D). Therefore, the 3R mutation does not directly interfere with retromer binding, and the 3R mutant displays impaired retromer association in infected cells because it cannot protrude through the endosomal membrane and access retromer in the cytoplasm.

Example 6: Split GFP Assay Detects CPP-Mediated Cytoplasmic Exposure of the C-Terminus of L2

To directly demonstrate membrane passage of the L2 C-terminus during virus entry, a split GFP imaging method was adapted. A protein consisting of GFP beta strands 1 to 10 (GFP1-10) does not fluoresce, nor does the 16-residue eleventh beta strand of GFP (GFP11). However, when GFP11 is in the same cellular compartment as GFP1-10, holo-GFP is reconstituted, generating a fluorescent signal. This approach has been used to demonstrate cytoplasmic delivery of soluble fusion proteins linked to CPPs.

To use this assay to assess L2 exposure, a clonal HaCaT cell line expressing GFP1-10 linked at its C-terminus to a nuclear export signal (NES) was constructed (FIG. 8A). Immunofluorescence experiments with an anti-GFP antibody confirmed cytoplasmic expression of GFP1-10NES (FIG. 8B). As expected, cells expressing this construct without GFP11 displayed minimal fluorescence (see FIG. 8E and FIG. 6B). Control experiments were then conducted to establish that GFP fluorescence in HaCaT/GFP1-10NES cells indicated the presence of GFP11 in the cytoplasm. CD8-cation-independent mannose phosphate receptor (CD8-CIMPR) fusion proteins consisting of the extracellular domain of CD8 fused to the transmembrane and cytoplasmic domains of CIMPR were used. Seven tandem copies of GFP11 were inserted at either the N-terminus or the C-terminus of CD8-CIMPR to generate GFP11-CD8-CIMPR and CD8-CIMPR-GFP11, respectively (FIG. 8C). When expressed, these proteins adopt a type 1 transmembrane orientation with the GFP11 segment located in the extracellular/luminal space for GFP11-CD8-CIMPR and in the cytoplasm for CD8-CIMPR-GFP11 (FIG. 8D). Neither construct fluoresced on its own when transfected into unmodified HaCaT cells. HaCaT/GFP1-10NES cells were then transfected with a plasmid expressing GFP11-CD8-CIMPR or CD8-CIMPR-GFP11 and fluorescence was assessed. As shown in FIG. 8E, bright cytoplasmic fluorescence was observed after expression of CD8-CIMPR-GFP11 (with cytoplasmic GFP11) but not after expression of GFP11-CD8-CIMPR. Additional control experiments showed that luminal GFP1-10 reconstituted fluorescence in cells expressing GFP11-CD8-CIMPR (see FIGS. 8C, 8D, and 8F). Taken together, these results validate the split GFP reporter system by showing that fluorescence is reconstituted in HaCaT/GFP1-10NES cells only when the GFP11 segment is in the cytoplasm and shows that GFP1-10NES does not access the luminal space.

Figures 6C, 6D:
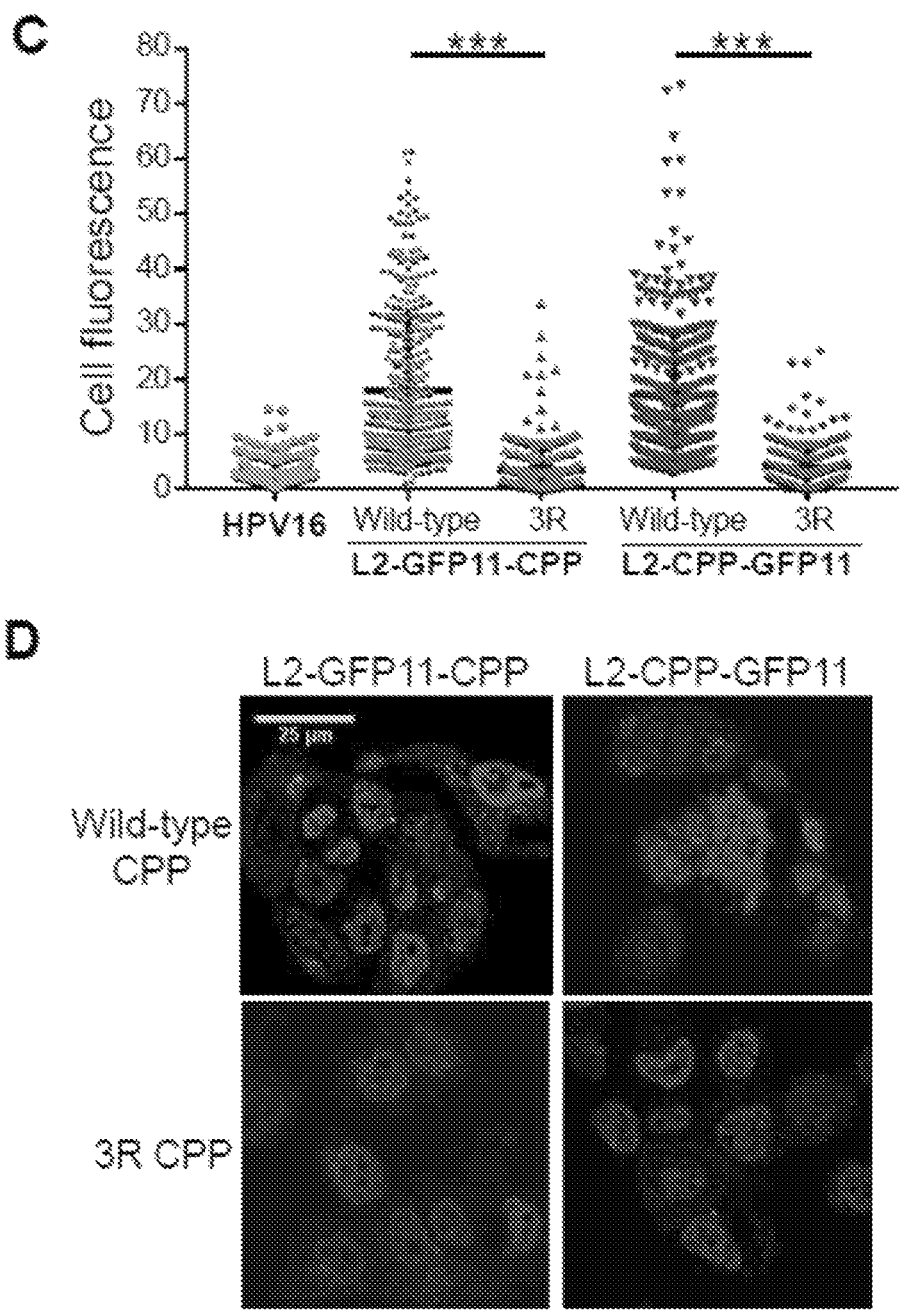
Figures 9A, 9B:
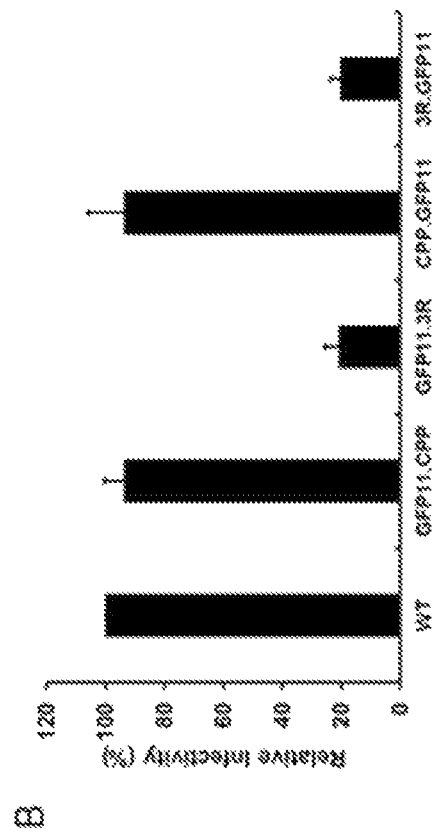
FIGS. 9A-9B depict infection by GFP11-tagged HPV16 pseudovirus.
Figure 10:
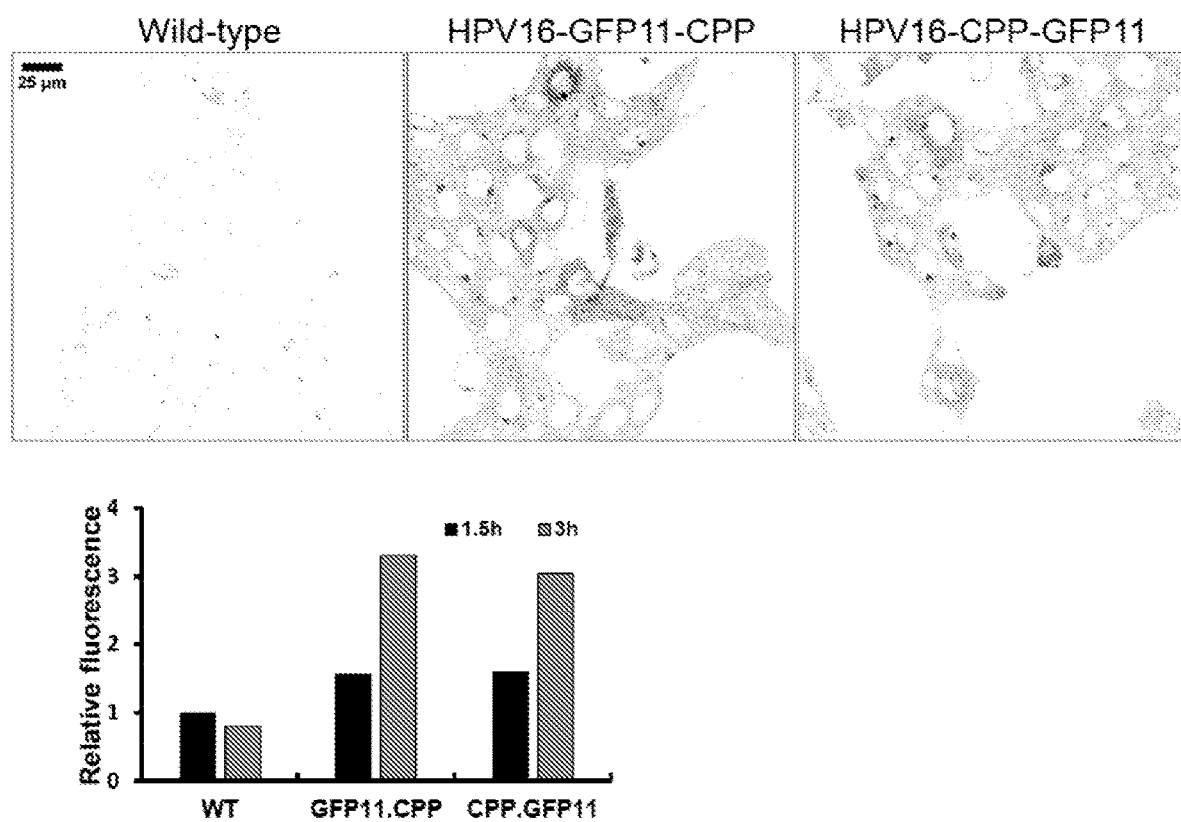
FIG. 10 depicts early reconstitution of GFP fluorescence in infected cells. Clonal HaCaT/GFP1-10NES cells were infected at MOI of 2000 with untagged HPV16 PsV (WT) or a PsV containing GFP11-tagged L2. Cells were examined by confocal microscopy for GFP fluorescence (pseudo-colored black) at three h.p.i. Graph shows quantitation of fluorescent signal at 1.5 (black bars) and three (grey bars) h.p.i. normalized to cells infected with HPV16 PsV containing untagged L2 at 1.5 h.p.i.

To assess cytoplasmic exposure of L2 during infection, seven tandem copies of GFP11 were inserted at two different positions in the C-terminus of the L2 protein: between the CPP and the retromer binding sites (L2-GFP11-CPP) or at the extreme C-terminus of L2 (L2-CPP-GFP11) (FIGS. 6A and 9A). Insertion of GFP11 into L2 did not impair HPV16 PsV infectivity (FIG. 9B). HaCaT/GFP1-10NES cells were then infected at high MOI with HPV16 PsV with or without GFP11-tagged L2 protein and the cells were examined by confocal microscopy. As shown in FIGS. 6B and 10, fluorescence was not detectable in HaCaT/GFP1-10NES cells infected with wild-type HPV16PsV lacking the GFP11 insert, confirming that the GFP1-10NES protein did not fluoresce on its own. Similarly, infection of unmodified HaCaT cells with HPV16 PsV containing GFP11-tagged L2 did not generate a fluorescent signal. Strikingly, however, infection of HaCaT/GFP1-10NES cells with the PsV containing GFP11 inserted at either C-terminal position in L2 resulted in reconstituted cytoplasmic fluorescence in ~60-90% of cells (FIGS. 6B, 6C, and 10). Reconstituted fluorescence showed either a punctate distribution or a more uniform distribution throughout the cytoplasm (or both) and was evident at a low level as early as 1.5 h.p.i., which increased by 3 h.p.i (FIGS. 6B and 10). Notably, reconstituted fluorescence did not display peripheral, cell-surface localization at any timepoint examined. This result demonstrates that early during HPV infection, the C-terminus of at least a fraction of L2 molecules was exposed in the cytoplasm.

Figure 11A:
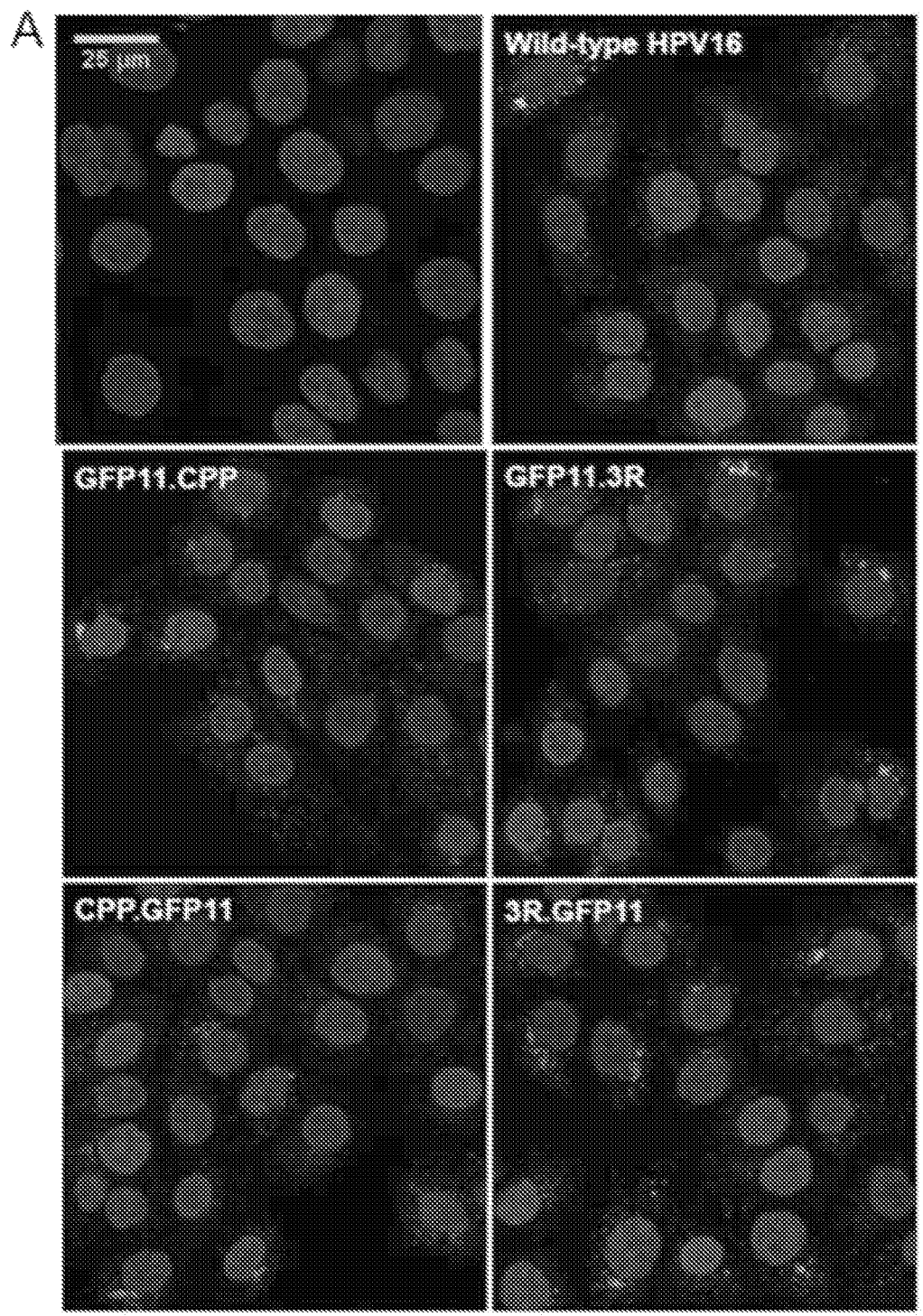
FIGS. 11A-11B depict the rapid internalization of HPV16 PsV.
Figure 11B:
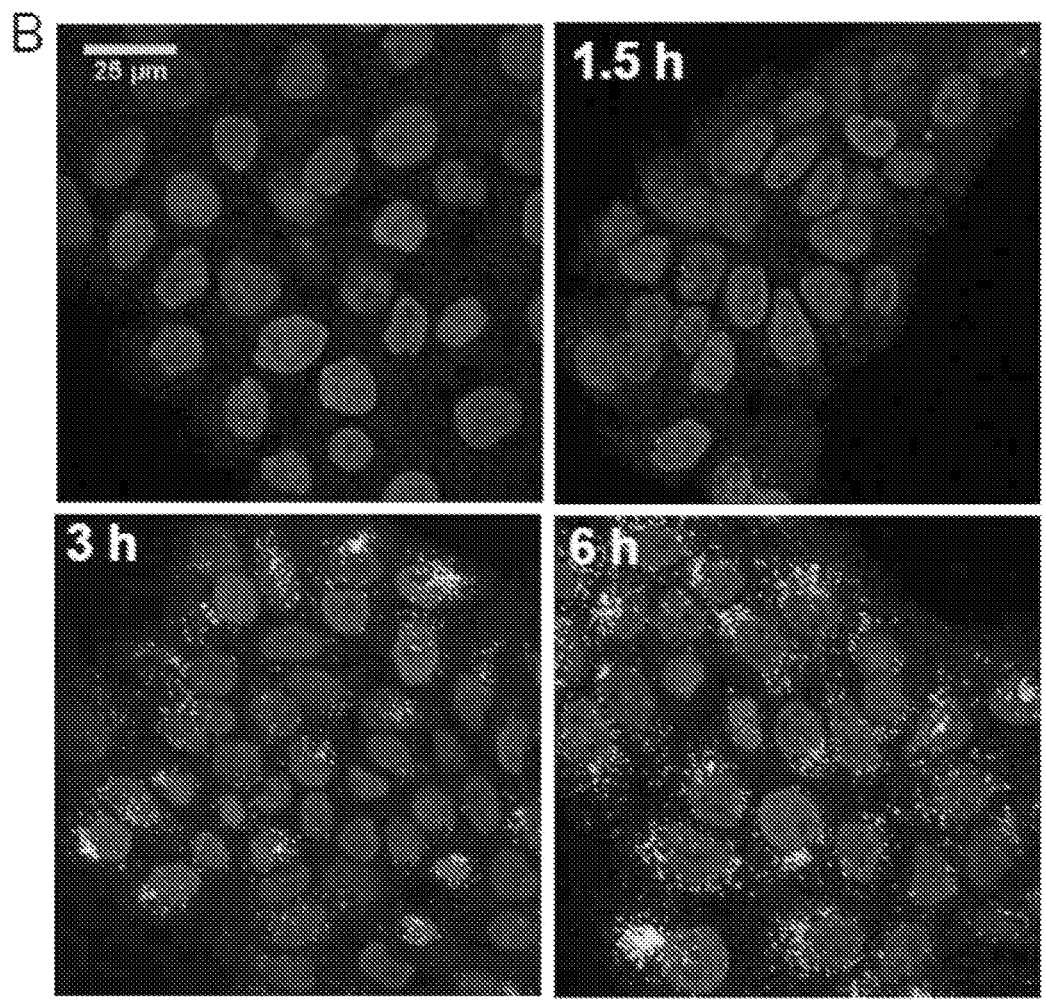

To test if the L2 CPP was required for membrane protrusion, the wild-type CPP in L2-GFP11-CPP and L2-CPP- GFP11 was replaced with three arginines (FIG. 9A). The 3R mutation inhibited infection but did not inhibit virus internalization (FIGS. 9B and 11A). In HaCaT/GFP1-10NES cells infected with these mutant PsVs, there was significantly less reconstituted fluorescence compared to cells infected with PsV with wild-type CPP (FIGS. 6C and 6D). This result provides direct evidence that the L2 CPP is required for cytoplasmic exposure of the L2 C-terminus during infection.

Example 7

To assess the effect of sequences flanking the core basic CPP, fusion proteins were constructed and purified with varying portions of the C-terminal segment of HPV16 and HPV5 L2. HPV16 typically infects genital and oral epithelia, at body core temperature of 37° C., whereas HPV5 is a virus that infects skin, which is several degrees cooler. The ability of these L2 segments to allow the fusion proteins to bind to cells and be delivered intracellularly was tested under a variety of conditions. In aggregate, these experiments show 1) that the 21 amino acids upstream of the HPV16 L2 CPP stimulates the ability of fusion proteins to enter cells (FIG. 13); 2) that the 12 amino acids downstream of the HPV16 L2 CPP allows the fusion protein to preferentially enter cells at low pH and apparently inhibits uptake at neutral pH (FIG. 14); and 3) sequences encompassing the HPV5 L2 CPP and flanking amino acids allow preferential cell binding at 30° C. (FIG. 15). Taken together, these results indicate that sequences flanking the CPP can modulate its ability to bind and enter cells, and that the behavior of fusion proteins containing HPV L2 segments may mimic the activity of the virus in vivo.

Example 8

A major long-term goal is to use CPPs to deliver bioactive peptides into cells as therapeutics. As an example of using the HPV L2 CPP to deliver a novel peptide-based inhibitor that blocks HPV infection. Intracellular delivery of peptides containing the retromer binding site (RBS) of HPV16 compete for retromer binding with the RBS on the L2 protein of the incoming virus particle protruding through the endosome membrane, and thus cause HPV to accumulate in the endosome. Cells were treated with peptide L2-C, comprised of a C-terminal segment of HPV16 L2 including the RBS and adjacent CPP. The CPP delivers the peptide across the plasma membrane into the cytoplasm where the RBS on the peptide will bind retromer and compete with the intact L2 protein on the incoming virion, thereby inhibiting infection. FIG. 17 shows that a wild-type peptide terminating at the end of the CPP causes a dramatic inhibition of infection by HPV16 PsV, as measured by expression of a reporter gene packaged into the virus particle. Therefore, the CPP delivers the peptide into the cytoplasm where it competes with the incoming virus particle for binding to the essential cellular trafficking factor retromer, thereby inhibiting infection.

Example 9

In order to traffic to the nucleus, papillomaviruses rely on cellular retrograde transport, but it was not clear how the incoming virion in the endosomal lumen enters the retrograde pathway. Here, these data show that a short sequence of basic amino acids near the C-terminus of the L2 protein acts as a CPP to transfer a segment of the L2 protein into the cytoplasm where adjacent sequences can bind retromer for transport to the TGN. First, it was shown that the basic region of L2 is required for efficient infection of epithelial cells and can be replaced with the cationic CPP from HIV-1 Tat. Like wild-type HPV16 PsV, PsV containing the Tat CPP required retromer and γ-secretase for infection. Five or more consecutive arginine residues restored full infectivity, whereas fewer arginines and six lysines were less effective, consistent with the known cell-penetrating activities of these sequences. Peptide and protein transduction assays were used to demonstrate that the basic segment of L2 did in fact display CPP activity. Importantly, a truncated sequence of three arginines was defective for CPP activity and failed to support infection. The preferential uptake of the 3R peptide compared to the 3R fusion protein may reflect the much higher concentration of molecules used in the peptide experiments. Taken together, these experiments demonstrated that L2 CPP activity was required for HPV infection.

The presence of a C-terminal basic region in all papillomavirus L2 proteins implies that the essential role of the L2 CPP has been maintained since the papillomaviruses first emerged more than 250 million years ago. The amino acid sequence of the basic segment is variable, consistent with the relatively relaxed sequence requirements for CPPs. The 353 sequenced L2 proteins in the papillomavirus PaVe sequence database (pave dot niaid dot nih dot gov/ #home) contain 164 different C-terminal basic sequences, including a 10-residue poly-arginine stretch in three canine viruses (Table 1). RKRRKR (SEQ ID NO: 2) present in HPV16 L2 is one of the most common, being found in 16 diverse human and animal papillomaviruses, and many more CPPs are likely to exist in the papillomavirus virome because most of these different basic sequences have been identified in only a single virus type (Table 1). In addition, sequences flanking the core basic amino acids may influence membrane penetration activity. The multitude of papillomavirus types thus represents the results of a mutational analysis carried out over evolutionary time, revealing hundreds of different, presumably non-toxic sequences that can have cargo-carrying activity.

HPV16 PsV containing a mutant CPP consisting of three arginines was internalized, showing the L2 CPP was not required for endocytosis, but the mutant was defective for retromer engagement, exit of the virus from the endosome, and trafficking to the TGN. The same phenotype is caused by retromer binding site mutations. However, the CPP mutation did not directly impair the ability of L2 to bind retromer, implying that during infection the retromer binding sites were not in the same cellular compartment as retromer.

To directly assay the cytoplasmic exposure of L2, a split GFP assay was developed, in which fluorescence is reconstituted when a segment of GFP at the C-terminus of L2 encounters GFP1-10 in the cytoplasm. Cytoplasmic exposure of L2 was detectable early during infection and was impaired by replacing the CPP with three arginines. These findings show that the L2 CPP mediates passage of the C-terminus of the L2 protein into the cytoplasm so that it can engage retromer and enter the retrograde trafficking pathway. In some cells, reconstituted fluorescence is fairly uniform throughout the cytoplasm (FIGS. 6B and 10), suggesting that the C-terminal segment of L2 can be cleaved from the virion after protrusion through the membrane or that retrograde transport vesicles containing virions rapidly distribute through the cytoplasm.

The rapid generation of reconstituted GFP fluorescent signal is consistent with the fact that the L2 protein binds to the cytoplasmic protein SNX17 as early as two h.p.i. In addition, by one and a half to three h.p.i., intracellular L1 is detectable by immunofluorescence with the 33L1-7 conformation-specific antibody (FIG. 11B) and by western blotting, providing additional evidence that HPV internalization can occur quite rapidly. To determine if L2 protrusion also required cell cycle progression, aphidocolin, which causes S-phase arrest and blocks HPV infection by inhibiting translocation of the incoming virus into the nucleus late during entry, was used. As shown in FIG. 12, aphidocolin inhibited infection but did not decrease the reconstituted GFP signal, showing that cell cycle progression and nuclear membrane breakdown are not required for L2 exposure. Thus, GFP reconstitution indicates the protrusion of L2 molecules into the cytoplasm to engage the retrograde trafficking machinery in the first place. The split GFP assay should be useful in investigating the action of additional chemicals and mutations that inhibit HPV trafficking.

The physiological role of most CPPs is not known. Naturally-occurring CPPs are usually studied as small peptide fragments removed from their protein of origin, and in many cases cell-penetrating activity may be the fortuitous consequence of basic sequences with no natural role in membrane penetration. These results show that CPP-driven membrane penetration by L2 plays an important role in HPV infection and that the L2 CPP of endocytosed virus protrudes through the endosomal membrane into the cytoplasm. The bulk of L2 then passes through the membrane, possibly assisted by endosomal acidification, until it is arrested by its N-terminal transmembrane domain in a type 1 transmembrane orientation with its N-terminus in the endosomal lumen and most of the protein exposed in the cytoplasm. The exposed C-terminus then binds to essential entry factors, including retromer, which sorts the virus into retrograde transport vesicles that later fuse with more distal retrograde compartments. The effect of the L2 CPP on the membrane is relatively subtle and localized, in contrast to the more drastic membrane disruption events caused by other non-enveloped viruses, which are deposited into the cytoplasm. This allows the residual HPV virion, including viral DNA, to be retained in transport vesicles and presumably contributes to the relatively low immunogenicity of these viruses during cell entry by sequestering them from cytoplasmic immune sensors. The L2 protein may protrude into the cytoplasm in a sequential fashion, with the C-terminus being exposed prior to the middle of the protein. Thus, cellular proteins may bind L2 sequentially, first retromer to the C-terminus of L2 and later proteins such as SNX17 to the middle portion of L2. Such ordered binding may be important for the assembly of the protein complexes necessary for proper trafficking. It also is important to note that each capsid contains up to 72 L2 proteins. The presence of multiple L2 molecules in each virion ensures a high local concentration of CPPs upon infection even at low MOI, which may be important for membrane penetration activity. However, it is possible that not all L2 molecules insert into membranes or bind retromer or other cytoplasmic factors.

The experiments reported here show that the L2 protein is an inducible transmembrane protein. In the intact capsid, which lacks membranes, L2 cannot have any transmembrane character. However, once the L2 CPP inserts into the membrane and protrudes into the cytoplasm, the L2 protein adopts a transmembrane existence. Thus, CPPs can not only transport molecules into cells or between compartments, but can also transform a soluble protein into a transmembrane one. Cellular and other viral proteins may also transition from a soluble to a transmembrane state, with important consequences for their biological activities. These results suggest that the primary role of CPPs in biology may not be to transfer proteins into cells in a paracrine fashion but rather to act intracellularly to mediate the transfer of proteins or protein segments between cellular compartments and to convert soluble proteins into transmembrane proteins.

The Materials and Methods employed in Example 10 are here described.

Cells, Plasmids, and Virus

HeLa-S3 cells were obtained from the American Type Culture Collection (ATCC). HaCaT cells purchased from AddexBio Technologies are spontaneously transformed keratinocytes from histologically normal skin. 293TT cells, generated by introducing SV40 Large T antigen cDNA into 293T cells to increase SV40 Large T antigen expression. All cells were cultured in DMEM with HEPES and L-glutamine, supplemented with 10% fetal bovine serum, and 100 units/mL penicillin-streptomycin at 37° C.in 5% CO2.

The plasmids designated p16sheLL, p18sheLL, and p5sheLL, expressing both L1 and L2 for HPV16, HPV18, and HPV5 pseudovirus production, respectively. pCAG-HcRed reporter plasmid was purchased from Addgene.

HPV PsV was produced by co-transfecting 293TT cells with pCAG-HcRed and a psheLL expression plasmid with or without mutations at the C terminus of L2. The packaged PsV was purified by density gradient centrifugation in Opti Prep. Quality of PsV preparations was confirmed by SDS-PAGE, followed by Coomassie brilliant blue staining for L1 and L2. SV40 was prepared in CVI cells as described.

The infectious multiplicity-of-infection (MOI) of HPV PsV was assessed by flow cytometry for reporter gene expression after infection of HeLa-S3 cells with wild-type HPV16 PsV. The number of packaged reporter plasmids required to achieve the MOI for wild-type PsV was quantified by qPCR, and an equivalent number of genomes in mutant PsV was used to infect cells. For quantifying encapsidated HcRed genomes, purified PsV was treated with DNase I to remove free DNA associated with capsids. Reporter DNA genome was isolated using a DNA purification kit, and the copy number of encapsidated reporter plasmid was determined by qPCR using primers for the HcRed gene in comparison to a standard curve.

Preparation of Peptides

Peptides were purchased from ABclonal Technology at >95% purity. Peptide (sequences shown in FIG. 1A) was resuspended in 30% acetic acid and dimethyl-formamide (~30 µl each, 2.7% stock concentration, 0.02% working concentration), and then dissolved in sterile deionized water with 0.01% sodium azide. Peptide stocks (~5 mg/mL) were aliquoted and stored at −20° C.

Infectivity

To assess the effect of peptides on viral infection, 5×10$^4$ HeLa-S3 in 24-well plates were pretreated with peptides for one hour, followed by infection with wild-type HPV PsV at 37° C. at MOI of ~1 or with mutant PsV containing an equivalent number of encapsidated reporter plasmids. Peptides were left in the medium for the duration of the experiment unless otherwise indicated. As a control, cells were incubated with the solution used to dissolve peptide. Cells were assessed by flow cytometry on a Stratedigm-13 flow cytometer to determine reporter protein expression at 48 h.p.i. unless otherwise indicated. In some experiments, peptides were added at various times after infection and were left in the medium for the duration of the experiment.

To measure the inhibition of infection by authentic HPV16, HeLa cells were infected with 5 µL raft-derived HPV16 (obtained from Craig Meyers, Hershey Medical Center) or with HPV16 PsV in the presence and absence of 14 µM P16/16, and total RNA was isolated 48 h.p.i. by using the RNeasy kit following the manufacturer's instructions. RNA was reverse-transcribed into cDNA by iScript cDNA Synthesis kit. The cDNA was quantified in triplicate by using SYBR Green Supermix real-time PCR detection system and primers for HPV16 E7 or HcRed. Actin mRNA were used for normalization.

```
HcRed forward
                                  (SEQ ID NO: 534)
GCACCCAGAGCATGAGAAT HcRed reverse
                                  (SEQ ID NO: 535)
TCGTAGGTGGTGGTTCTCT HPV16 E7 forward
                                  (SEQ ID NO: 536)
AATGTTTCAGGACCCACAGG HPV16 E7 reverse
                                  (SEQ ID NO: 537)
CTCACGTCGCAGTAACTGTTG Actin forward
                                  (SEQ ID NO: 538)
CTGCTGTCACCTTCACCGTTCC Actin reverse
                                  (SEQ ID NO: 539)
AGTACTCCGTGTGGATCGGC
```

For studies of SV40 infection, 7.5×10$^5$ HeLa-S3 in 6-well plates were incubated with peptides prior to infection. Cells were infected with a crude preparation of SV40 at MOI of ~1 and fixed with 4% paraformaldehyde at 48 h.p.i. Samples were stained with FITC-conjugated anti-large T antigen antibody (Pab101) (Santa Cruz, pSC147 FITC), followed by flow cytometry to determine the mean fluorescent intensity of T antigen staining.

Immunofluorescence Microscopy and Proximity Ligation Assay

For the internalization experiments, 5×10$^4$ HeLa-S3 cells were grown on glass coverslips for 16 hours. After one-hour incubation with or without peptides, PsV at MOI of 50 were added and incubated at 4° C. for 2 hours, washed with PBS three times to remove loosely bound PsV, and shifted to 37° C.to initiate infection. As a control, cells were incubated with the solution used to dissolve peptides alone. At the indicated times post-infection, samples were fixed, permeabilized and stained with anti-L1 and AlexaFluor 488 conjugated secondary antibody. Cells were analyzed by a Leica SP5 confocal microscope.

For the proximity ligation assay, after an hour incubation with peptides, HeLa-S3 cells were infected with wild-type PSV at MOI of 200 or mutant PsV containing the same number of reporter plasmid genomes. Infected cells were fixed at 8 or 16 h.p.i., permeabilized, and incubated with 1:100 dilutions of anti-L1 antibody and an antibody recognizing EEA1, TGN46, or VPS35. PLA was performed with Duolink reagents from Olink Biosciences according to the manufacturer's directions. Briefly, after staining with primary antibody, cells were incubated with a pair of suitable PLA antibody probes at 1:5 in a humidified chamber and processed for ligation and amplification with fluorescent substrate at 37° C.. The nuclei were stained by using Abcam fluorescence mounting medium with DAPI and images were acquired by a Leica SP5 inverted fluorescence microscope. Approximately 200 nuclei in each sample were imaged. The images were processed by Fiji and quantitatively analyzed by BlobFinder software to measure total fluorescence intensity in each sample. The average fluorescence intensity per cell in each sample was normalized to the control sample as indicated in each experiment. All the experiments were done independently three times with similar results.

DMT1-II Localization

3×10$^4$ HeLa-S3 cells were transfected with 0.5 µg of a plasmid expressing a GFP DMT1-II fusion protein. Six hours later, medium was removed. 14 µM P16/16 or PDM/16 was added or cells were left untreated overnight. Medium was replaced with fresh medium containing same concentration of peptide, and cells were fixed and stained overnight with 1:200 dilution of anti-TGN46 antibody and then incubated with secondary antibody that recognized anti-TGN46. Cells were mounted with Abcam mounting medium with DAPI, imaged on a Leica SP5 confocal microscope, and processed with Fiji.

Split GFP Assay

To determine if the cytoplasmic protrusion of L2 of PsV is inhibited by peptides, the split GFP assay was performed. 3×10$^4$ clonal HaCaT/GFP1-10NES expressing GFP1-10NES in the cytoplasm were seeded in eight-chambered glass slides and incubated with peptides for an hour prior to infection at MOI of ~2000 with HPV16 PsV containing wild-type L2 or L2 containing inserted GFP11. Live cells were stained with Hoechst 33342, examined by a Leica SP5 confocal microscope, and processed with Fiji.

The inhibition efficiency of peptides at high MOI was tested by incubating cells with peptides at 30 µM peptide for two hours prior to infection with PsV at MOI of 2,000. At three h.p.i., cells were washed with PBS three times to remove unbound viruses and then incubated at 37° C. in the presence of 30 µM peptide. Forty-eight hours later, cells were assessed by flow cytometry to determine reporter protein expression.

Example 10

Figure 18A:
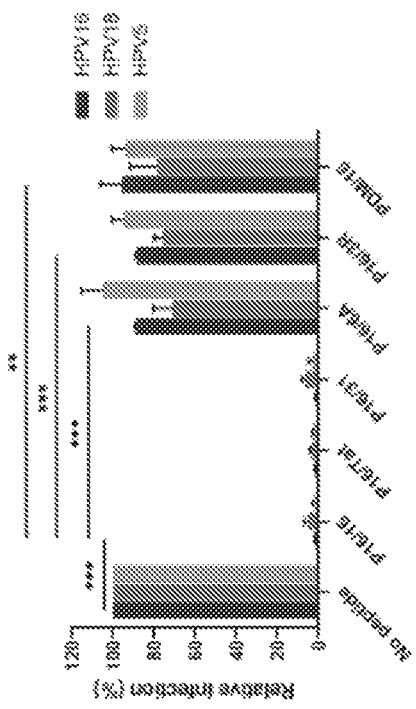
FIGS. 18A-18E depict the identification of peptides that inhibit HPV infection.
Figure 18C:
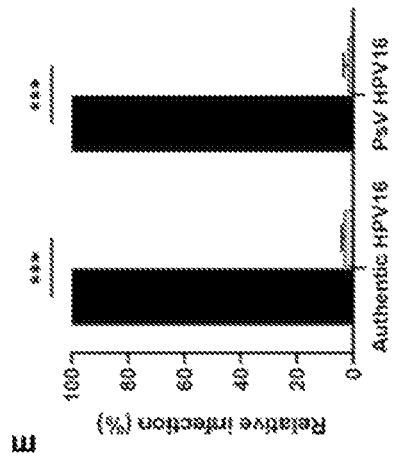
Figure 18D:
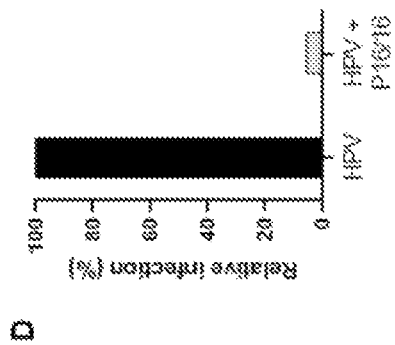
Figure 18E:
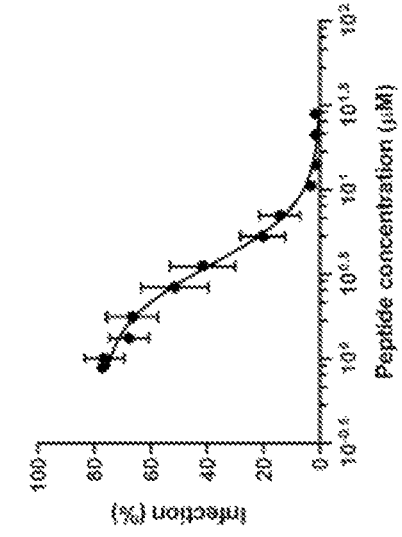
Figure 18B:
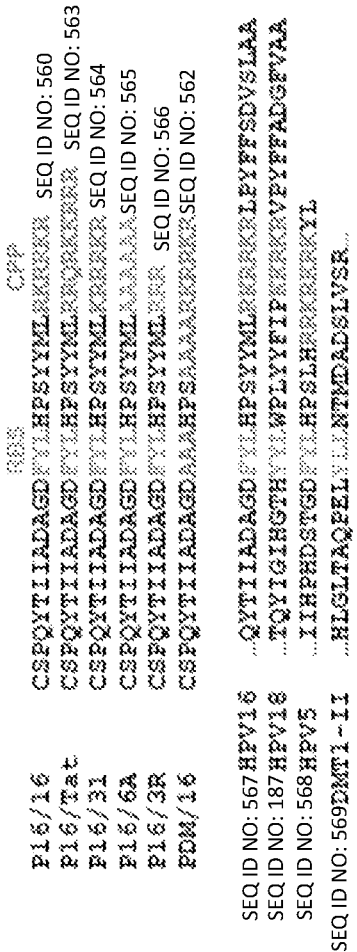
Figure 21:
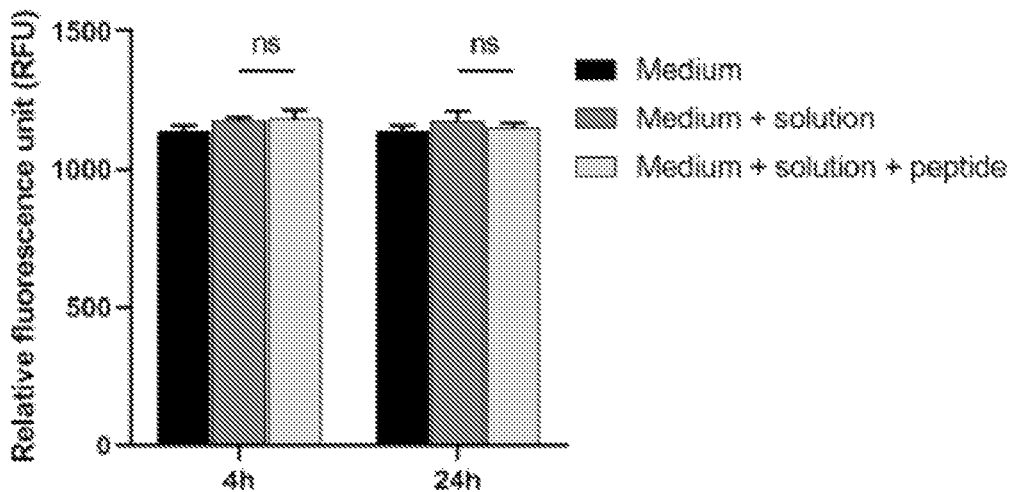
FIG. 21 shows that the L2 peptide does not display toxicity. HeLa-S3 cells were incubated with medium, medium plus vehicle, or medium plus 14 μM P16/16 for 4 or 24 hours. Viability assay was performed by using the CellTiter-Fluor viability assay protocol (Promega, Cat #G6082). Briefly, an equal volume of CellTiter-Fluor reagent was added to each well without removing the medium, mixed briefly, then incubated for one hour at 37° C. Fluorescence was measured by using a GloMax Explorer Multimode Microplate Reader (380-400 nmEx/505 nmEm). n.s., not significant.
Figure 22A:
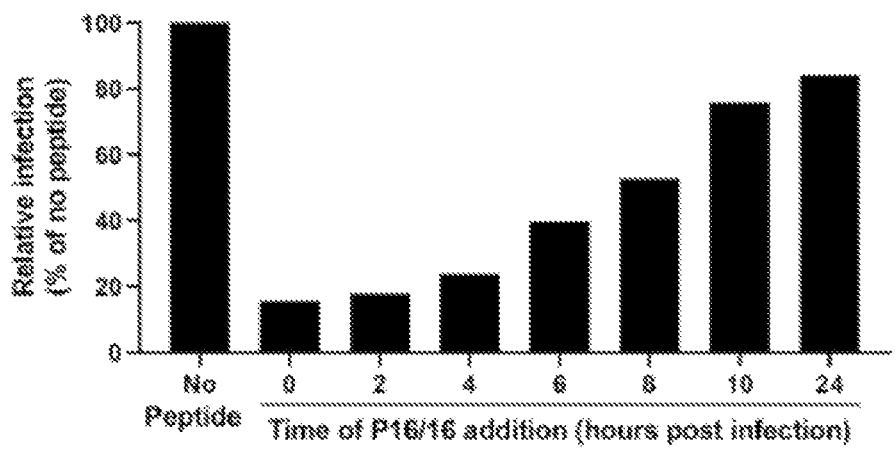
FIG. 22A-22C show the timing of L2 peptide inhibition.
Figure 22B:
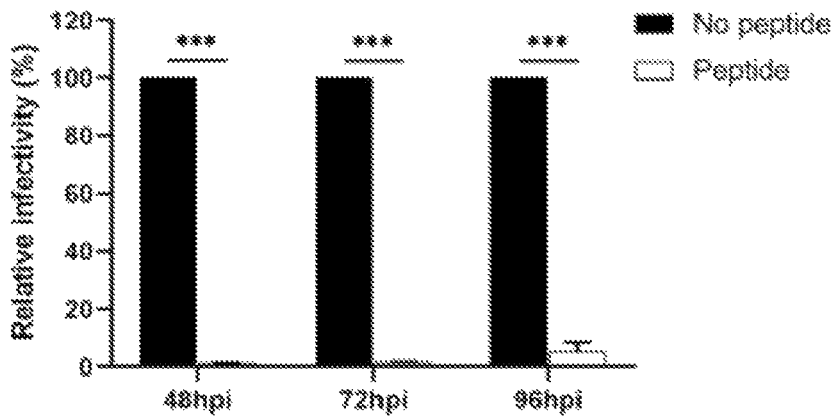
Figure 22C:
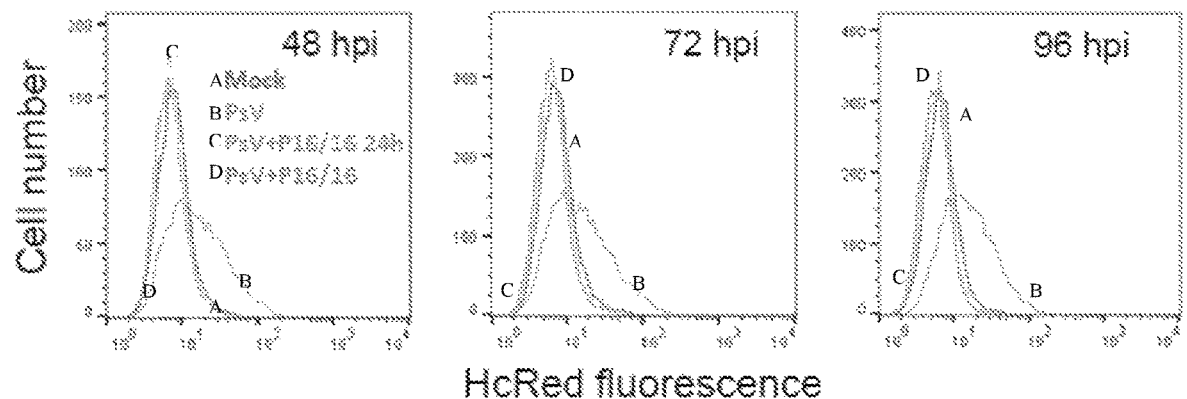

The utility of potential peptide therapeutics with an intracellular site of action is limited by inefficient delivery of the peptide into cells. The L2 CPP can deliver peptides and fusion proteins into cells if added to the culture medium. We reasoned that a segment of L2 containing the CPP would deliver the adjacent RBS into the cytoplasm, sequester retromer from incoming HPV, and block HPV infection. We synthesized a 29-residue peptide, designated P16/16, that contains the RBS and CPP (RKRRKR) (SEQ ID NO: 2), where R represents arginine and K represents lysine) from HPV16 L2 (FIG. 18A). This peptide is competent for retromer binding in vitro. HeLa cells were pre-incubated for one hour in medium containing various concentrations of peptide and then infected at a multiplicity of infection (MOI) of 1 with HPV16 pseudovirus (PsV), which consists of a complete L1 and L2 capsid containing a plasmid that expresses the fluorescent protein, HcRed. As shown in FIG. 18B, the L2 peptide caused a dose-dependent reduction in infection, as assessed by flow cytometry for HcRed fluorescence 48 hours post-infection (h.p.i.). Under these conditions, P16/16 displayed an IC50 of 3.6 µM and caused no apparent toxicity based on morphology and cell viability assay (FIG. 21). For effective inhibition, the peptide needed to be added during the first few hours of infection (FIG. 22A), and inhibition persisted until at least 96 h.p.i. (FIG. 22B). If P16/16 was removed from the medium after 24 hours, infection was not restored over the next three days (FIG. 22C). P16/16 also potently inhibited infection by HPV18 and HPV5 PsV (FIG. 18C). HPV18 is a high-risk oncogenic HPV type that infects genital mucosa like HPV16, and HPV5 is a divergent HPV type associated with skin cancer. All known HPV L2 proteins contain a recognizable RBS, suggesting this strategy will inhibit all HPV types.

Figure 23:
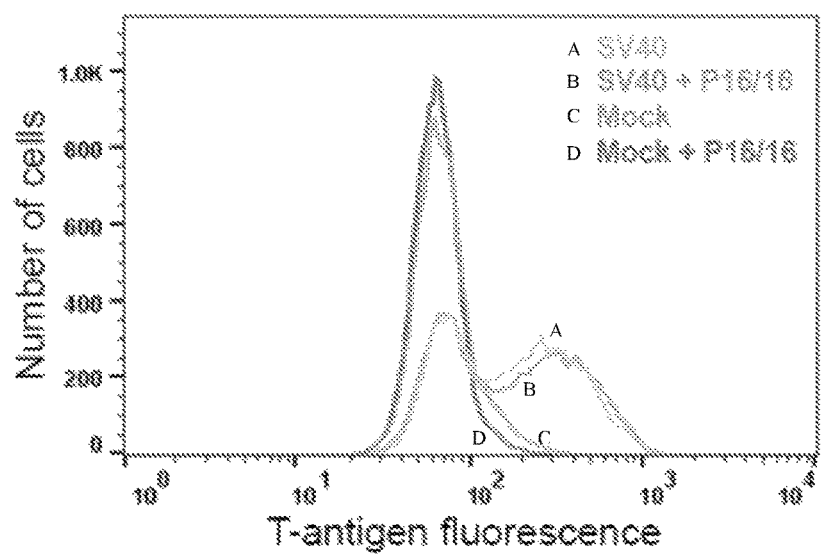
FIG. 23 shows that L2 peptide does not inhibit SV40 infection. HeLa-S3 cells were treated with 14 μM P16/16 peptide or vehicle for one hour then infected with SV40 at MOI of ~1. Forty-eight h.p.i., cells were washed, fixed, and permeabilized with cold methanol for 30 min. Cells were stained for intracellular SV40 large T antigen with fluorophore-conjugated monoclonal antibody PAb101, followed by flow cytometry. The histograms show number of cells and HcRed fluorescence in the absence or presence of peptide. Traces correspond to mock-infected cells (Line C), mock-infected cells in the presence of peptides (Line D), SV40-infected cells (Line A), and SV40-infected cells in the presence of peptides (Line B).

Peptides containing the CPP from HIV Tat (P16/Tat) or HPV31 (P16/31) in place of the HPV16 CPP also markedly inhibited infection of the three HPV PsV types tested (FIGS. 18A and 18C). In addition, P16/16 inhibited infection by HPV16 PsV in HaCaT skin keratinocytes (FIG. 18D). P16/16 also inhibited authentic HPV16 produced in organotypic raft cultures, as assessed by quantitative reverse transcriptase PCR for viral mRNA (FIG. 18E), but did not inhibit SV40, an unrelated non-enveloped small DNA tumor virus that does not require retromer (FIG. 23). Importantly, mutations of the RBS (6A and 3R) or the CPP (DM) in P16/16, which block retromer binding and membrane penetration, respectively, eliminated the inhibitory effect (FIGS. 18A and 18C).

Figure 19A:
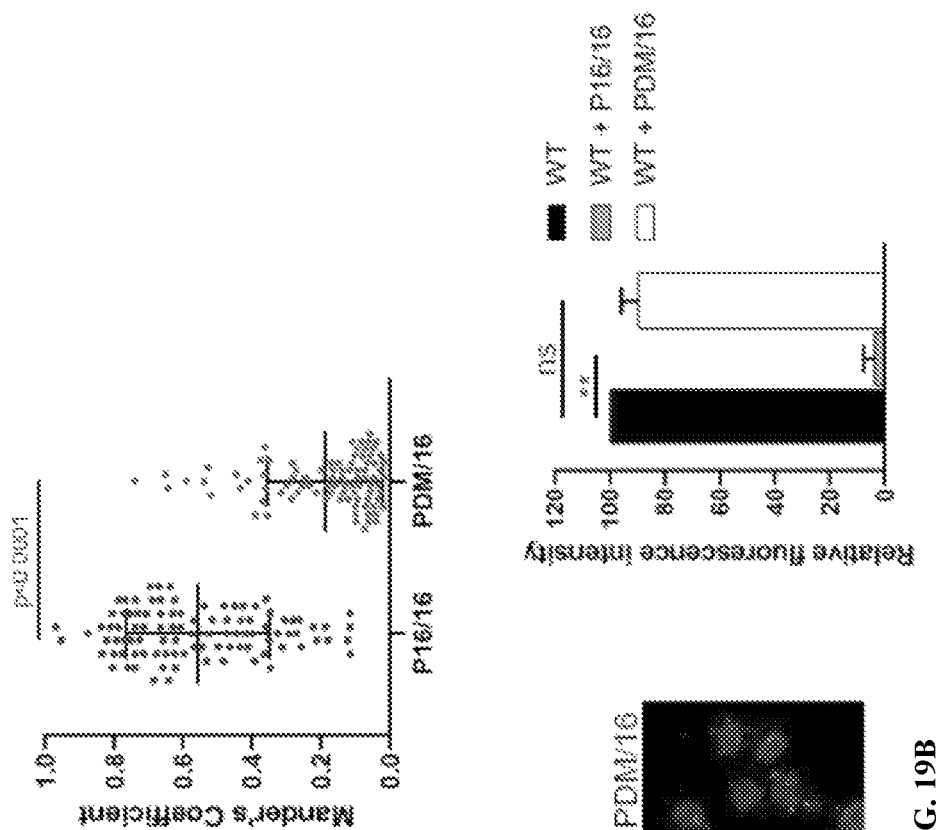
FIGS. 19A-19B show that peptide binds retromer and blocks retromer association with HPV.
Figure 19B:
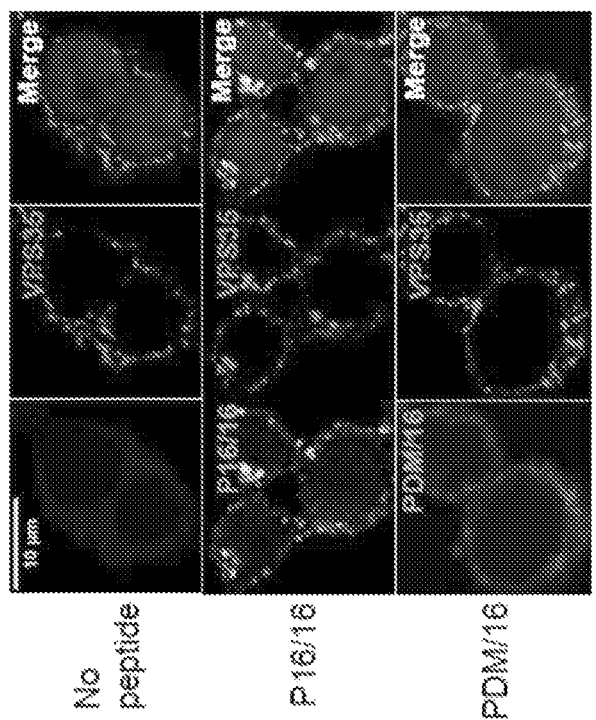
Figure 19B:
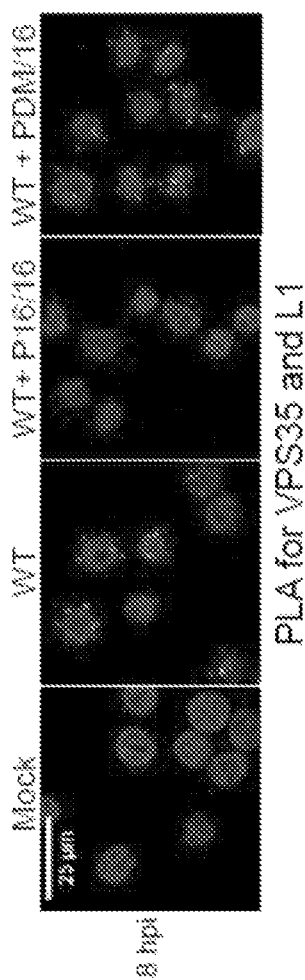
Figure 24:
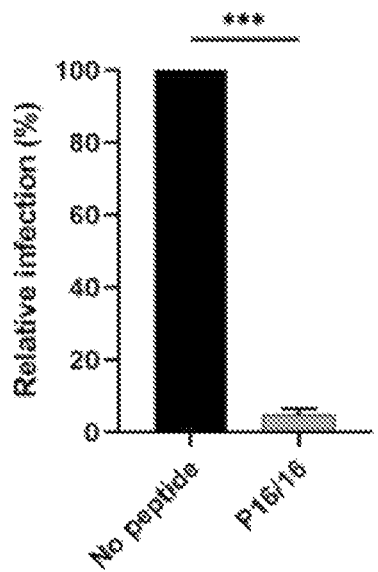
FIG. 24 shows that biotinylated peptides inhibit HPV infection. HeLa cells were infected with HPV16 PsV at MOI of 1 in the presence or absence of 14 μM bP16/16. Infectivity was assessed 48 h.p.i. by flow cytometry for HcRed fluorescence.

We used biotinylated peptides to confirm their transfer into cells and determine their intracellular location. Biotinylation did not affect anti-HPV activity (FIG. 24). Uninfected HeLa cells were incubated with biotinylated P16/16 or PDM/16, a mutant peptide lacking the RBS (designated bP16/16 and bPDM/16, respectively). Three hours later, cells were stained with streptavidin and an antibody that recognizes the retromer subunit, VPS35. bP16/16 was localized to large cytoplasmic puncta superimposed on a more diffuse cytoplasmic distribution (FIG. 19A). Strikingly, the mutant bPDM/16 showed only the diffuse distribution. These results show that the peptides rapidly enter cells and suggest that retromer binding is required for the punctate signal. VPS35 also displayed a punctate distribution in the presence or absence of peptide. Importantly, there was significant colocalization of wild-type bP16/16 and VPS35, which was greatly reduced with PDM/16, showing that the wild-type peptide but not the mutant stably associated with retromer in intact cells. To test whether the L2 peptide inhibited the ability of retromer to bind incoming HPV16 PsV in infected cells, we conducted a proximity ligation assay (PLA) for HPV16 L1 and the retromer subunit VPS35. PLA generates a fluorescent signal when two antigens are within 40 nm. FIG. 19B shows that eight h.p.i., PLA detected interaction of incoming virus with retromer in intact, infected cells. Strikingly, the wild-type P16/16 peptide inhibited the interaction of retromer with HPV, whereas the mutant peptide lacking the RBS did not. Together, these data show that the peptide containing the RBS associates with retromer and inhibits binding of retromer to the incoming virus.

Figure 20A:
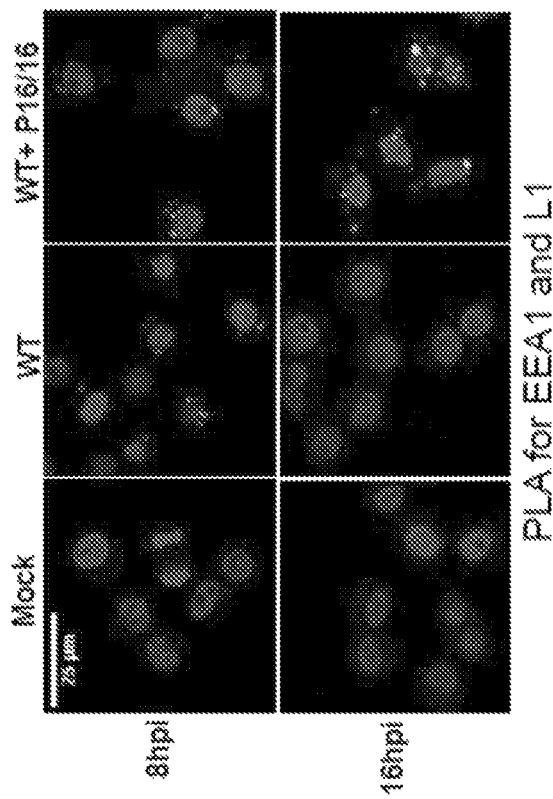
FIGS. 20A and 20B show that the peptide inhibits HPV exit from endosome. HeLa-S3 cells grown on glass coverslips for 16 hours were incubated for one hour with or without 14 μM P16/16, followed by mock-infection or infection with HPV16 PSV at MOI of 200. 8 and 16 h.p.i., cells were processed for PLA with anti-L1 antibody and an antibody recognizing EEA1 (FIG. 20A) or TGN46 (FIG. 20B). PLA was performed as in FIG. 19B. The PLA signal for EEA1/L1 was normalized to that of cells infected with HPV16 PsV in the absence of peptide at 8 h.p.i., while the TGN46/L1 signal was normalized to untreated cells at 16 h.p.i.
Figure 20B:
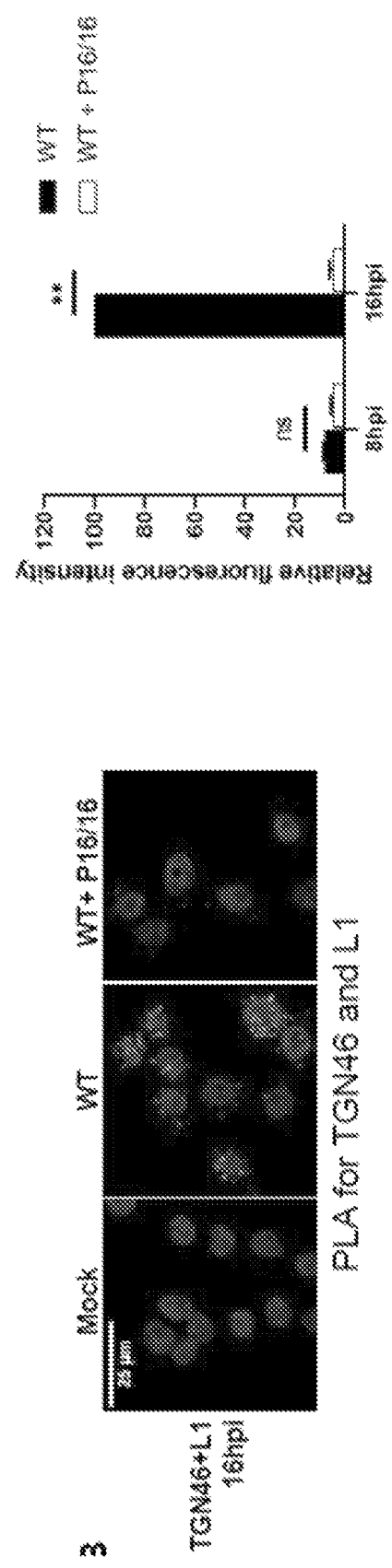
Figure 25:
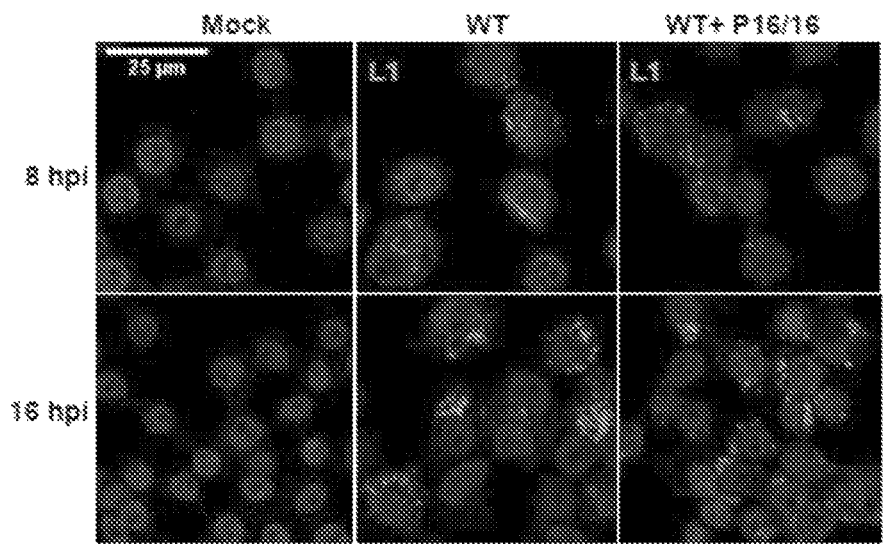
FIG. 25 shows that L2 peptide does not inhibit internalization of HPV PsV. HeLa-S3 cells were incubated with 14 μM P16/16 or vehicle for one hour, followed by infection with HPV16 PsV at MOI of 50 at 4° C. for 2 h. Cells were washed with PBS to remove loosely-bound PsV and then shifted to 37° C. to allow virus internalization. After 8 or 16 h at 37° C., samples were fixed with 4% paraformaldehyde, permeabilized with 1% saponin, and stained with anti-L1 antibody. Cells were also stained with DAPI to visualize nuclei and examined by a Leica SP5 confocal microscope.
Figure 26A:
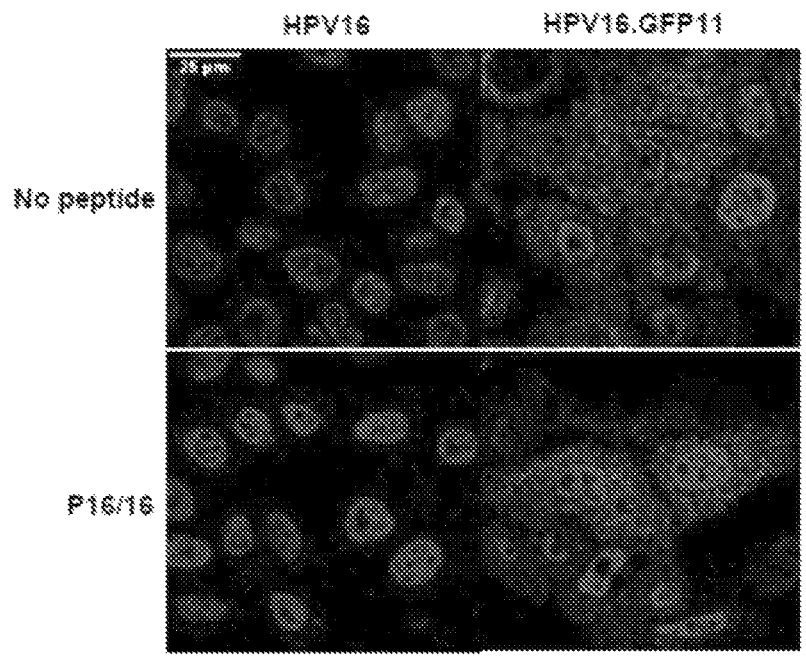
FIGS. 26A-26C show that L2 peptide does not inhibit protrusion of L2 protein into the cytoplasm.
Figure 26B:
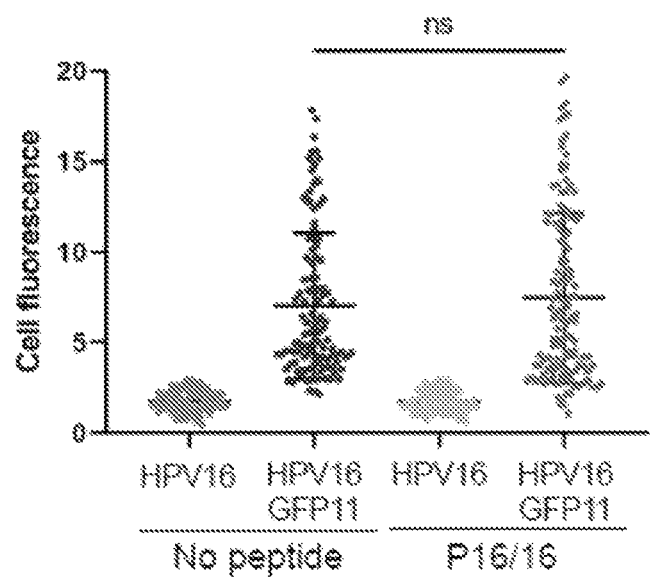
Figure 26C:
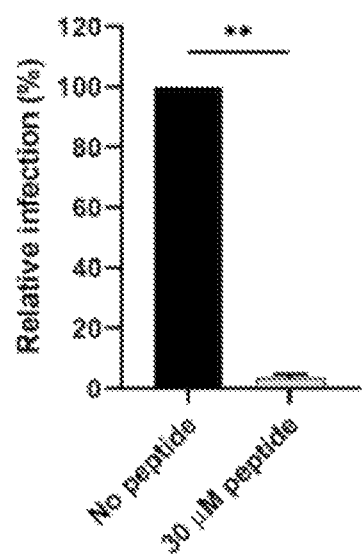

We next identified the step of infection blocked by P16/16. Immunofluorescence studies with antibodies recognizing L1 showed that P16/16 did not inhibit virus internalization (FIG. 25). We then used PLA to examine the localization of incoming HPV16 PsV in cells treated with peptide. PLA for L1 and the endosome marker EEA1 at 8 h.p.i. confirmed arrival of HPV at the endosome regardless of the presence of the peptide (FIG. 20A). However, EEA1/L1 PLA at 16 h.p.i. showed striking accumulation of the virus in the endosome in cells treated with P16/16, a time when the virus had exited the endosome in untreated cells (FIG. 20A). At 16 h.p.i, PLA for L1 and the TGN marker, TGN46, showed that P16/16 inhibited the arrival of HPV in the TGN (FIG. 20B). A split GFP fluorescence reconstitution assay showed that the peptide did not inhibit protrusion of the C terminus of the L2 protein into the cytoplasm (FIG. 26). Thus, P16/16 blocks endosome exit and inhibits intracellular HPV trafficking after protrusion of L2 into the cytoplasm.

Figure 27A:
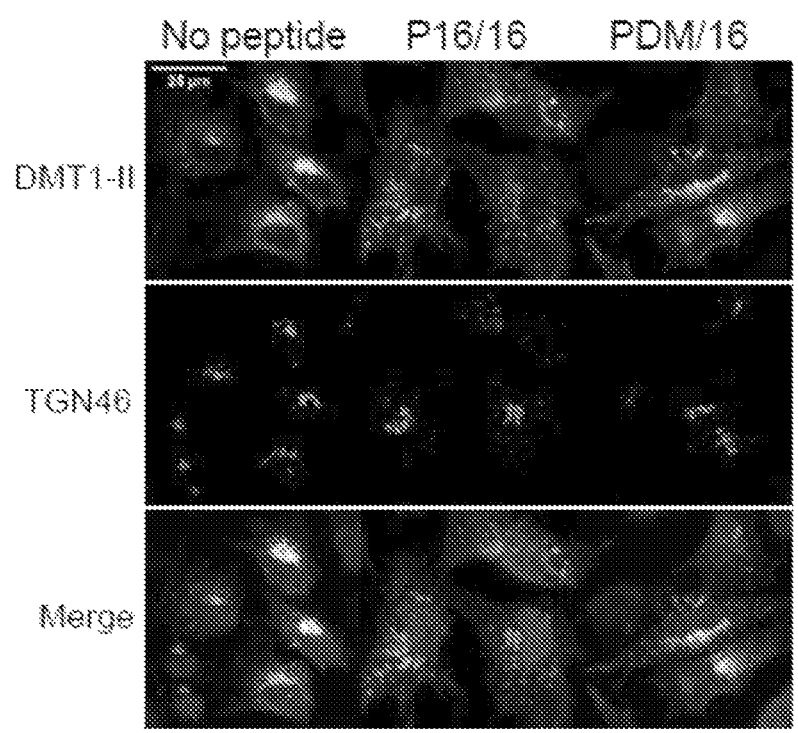
FIGS. 27A and 27B show that L2 peptide causes redistribution of DMT1-II from trans-Golgi network.
Figure 27B:
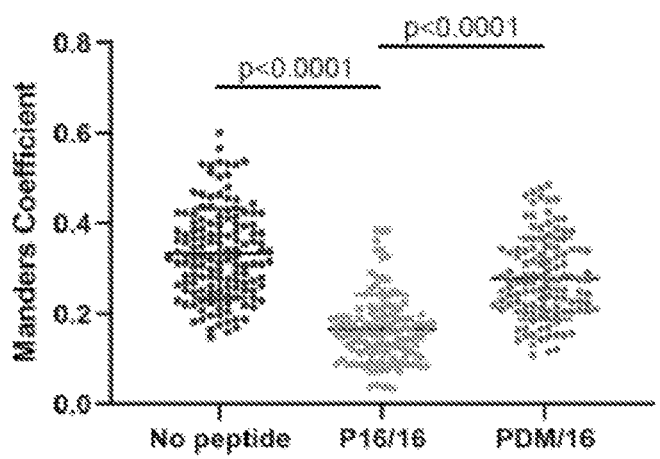

Finally, we tested if the L2 peptide inhibited retrograde transport of a cellular retromer cargo, DMT1-II, which contains a YLL RBS in its cytoplasmic domain required for retromer-mediated transport to the recycling endosome and TGN. We transfected cells with a plasmid expressing GFP fused to DMT1-II, and six hours later, cells were treated with P16/16 or PDM/16 or left untreated. The distribution of GFP fluorescence and anti-TGN46 antibody staining was assessed ~20 hours later by confocal microscopy. As shown in FIG. 27, in untreated cells, DMT1-II and TGN46 showed a concentrated juxtanuclear pattern, with considerable overlap between TGN46 and DMT1-II staining. In contrast, treatment with the wild-type but not the mutant peptide caused DMT1-II to redistribute to a more diffuse localization with less overlap with TGN46. Neither peptide affected the distribution of TGN46. This result shows that a CPP linked to an RBS also affects trafficking of a cellular retromer cargo.

We describe the use of a CPP to deliver soluble peptides containing the HPV16 RBS into the cytoplasm where it sequestered retromer from L2 in the virion and inhibited endosome exit. It may be possible to increase the potency of inhibitory peptides by multimerization of the CPP or the RBS, use of an CPP or RBS from other sources, or other mutation or modification of the peptide sequence. The peptides did not display any obvious toxicity despite the importance of retromer in normal cell physiology, possibly because HPV infection is particularly dependent on retromer function. This might be the case, for example, if incoming HPV must travel via the retromer, whereas cellular cargo is constantly replenished by new synthesis as well as by retrograde transport.

We provide proof-of-principle for a new anti-viral strategy, namely inhibiting virus infection by treating cells with a peptide that enters cells and interferes with the association of the incoming virus with a cellular protein required for virus replication, in this case for proper intracellular trafficking of incoming virus. Because HPV is a localized infection of skin and mucous membranes, topical application of an entry inhibitor might be useful to prevent or limit genital HPV infection. Retromer has also been implicated in supporting the life cycle of other viruses including hepatitis C virus, influenza virus, and HIV, so agents that target retromer, including the peptides described here, may affect these viruses as well. These peptides may also be useful probes of retromer function in non-infected cells. More generally, these results identify intracellular virus trafficking as a potential therapeutic vulnerability The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of delivering a cargo molecule to the cytoplasm of at least one cell, the method comprising contacting the cell with a transport construct comprising the cargo molecule and at least one cell-penetrating peptide selected from SEQ ID NOs: 2 or 360 or a salt thereof.

2. A method of promoting endosomal escape for a cargo molecule, the method comprising contacting at least one cell with a transport construct comprising the cargo molecule and at least one cell-penetrating peptide selected from SEQ ID NO: 360, or a salt thereof.

3. The method according to claim 1, wherein the cell-penetrating peptide is SEQ ID NO: 2.

4. The method according to claim 1, wherein the transport construct further comprises at least one selected from the group consisting of an activity modulating flanking sequence, a temperature modulating flanking sequence, and a pH modulating flanking sequence.

5. The method according to claim 1, wherein the transport construct further comprises a linker connecting the cargo molecule and the cell-penetrating peptide.

6. The method according to claim 1, wherein the cargo molecule is at least one selected from the group consisting of a nucleic acid; peptide; peptide-nucleic acid; protein; oligosaccharide; lipid; glycolipid; lipoprotein; small molecule compound; therapeutic drug; UV-vis, fluorescent or radioactive label; imaging agent; diagnostic agent; prophylactic agent; liposome; and virus.

7. The method according to claim 1, wherein the at least one cell is human.

8. The method according to claim 1, wherein the at least one cell is in a human subject.

9. The method according to claim 8, wherein the contacting comprises administering a pharmaceutical composition comprising an effective amount of the transport construct and at least one pharmaceutically acceptable carrier to the human subject.

10. An isolated transport construct comprising a cargo molecule and at least one cell-penetrating peptide selected from SEQ ID NOs: 2 or 360, or a salt thereof.

11. The transport construct according to claim 10, wherein the cell-penetrating peptide is SEQ ID NO: 2.

12. The transport construct according to claim 10, further comprising at least one selected from the group consisting of an activity modulating flanking sequence, a temperature modulating flanking sequence, and a pH modulating flanking sequence.

13. The transport construct according to claim 10, wherein the transport construct further comprises a linker connecting the cargo molecule and the cell-penetrating peptide.

14. The transport construct according to claim 10, wherein the cargo molecule is at least one selected from the group consisting of a nucleic acid; peptide; peptide-nucleic acid; protein; oligosaccharide; lipid; glycolipid; lipoprotein; small molecule compound; therapeutic drug; UV-vis, fluorescent or radioactive label; imaging agent; diagnostic agent; prophylactic agent; liposome; and virus.

15. A pharmaceutical composition comprising the transport construct according to claim 10 and at least one pharmaceutically acceptable excipient.

* * * * *